(12) United States Patent
Haque et al.

(10) Patent No.: US 10,112,995 B2
(45) Date of Patent: Oct. 30, 2018

(54) HUMAN ANTI-IFN-α ANTIBODIES

(71) Applicant: IMMUNOQURE AG, Dusseldorf (DE)

(72) Inventors: Syeda F. Y. Haque, London (GB); Adrian Hayday, Orpington (GB); Kai Kisand, Tartu (EE); Kai Krohn, Salmentaka (FI); Annalisa Macagno, Schlieren (CH); Steffen Meyer, Munich (DE); Paert Peterson, Tallinn (EE); Mike Rothe, Krailling (DE); Philip Vlaicu, Alling (DE); Martin Woodward, London (GB)

(73) Assignee: ImmunoQure AG, Martinsried (DE)

( * ) Notice: Subject to any disclaimer, the term of this patent is extended or adjusted under 35 U.S.C. 154(b) by 0 days.

(21) Appl. No.: 14/902,409

(22) PCT Filed: Jul. 3, 2014

(86) PCT No.: PCT/EP2014/064167
§ 371 (c)(1),
(2) Date: Dec. 31, 2015

(87) PCT Pub. No.: WO2015/001013
PCT Pub. Date: Jan. 8, 2015

(65) Prior Publication Data
US 2017/0051055 A1    Feb. 23, 2017

(30) Foreign Application Priority Data
Jul. 3, 2013    (EP) ..................................... 13174995

(51) Int. Cl.
| C07K 16/24 | (2006.01) |
| C07H 21/04 | (2006.01) |
| G01N 33/564 | (2006.01) |
| G01N 33/68 | (2006.01) |
| A61K 47/48 | (2006.01) |

(52) U.S. Cl.
CPC ...... *C07K 16/249* (2013.01); *A61K 47/48546* (2013.01); *G01N 33/564* (2013.01); *G01N 33/6866* (2013.01); *C07K 2317/21* (2013.01); *C07K 2317/33* (2013.01); *C07K 2317/34* (2013.01); *C07K 2317/55* (2013.01); *C07K 2317/76* (2013.01); *C07K 2317/92* (2013.01); *G01N 2333/56* (2013.01)

(58) Field of Classification Search
None
See application file for complete search history.

(56) References Cited

U.S. PATENT DOCUMENTS 6,309,636 B1 * 10/2001 do Couto ........... A61K 51/1051
424/133.1

FOREIGN PATENT DOCUMENTS

| WO | WO 2002/066649 A2 | 8/2002 |
| WO | WO 2005/059106 A2 | 6/2005 |
| WO | WO 2006/086586 A2 | 8/2006 |

OTHER PUBLICATIONS

International Search Report and Written Opinion prepared by the European Patent Office dated Dec. 19, 2014, for International Application No. PCT/EP2014/064167.
Meager Anthony et al: "Anti-interferon autoantibodies in autoimmune polyendocrinopathy syndrome type 1", Anti-Interferon Autoantibodies in Autoimmune Polyendocrinopathy Syndrome Type 1, vol. 3, No. 7, May 9, 2012 (May 9, 2012), pp. 1152-1164, XP002675599.
Nolte K-U et al: "Epitopes Recognized by Neutralizing Therapy-Induced Human Anti-Interferon-Alpha Antibodies are Localized within the N-Terminal Functional Domain of Recombinant Interferon-Alpha2", European Journal of Immunology, Wiley—V C H Verlag GMBH & Co. KGAA, DE, vol. 26, No. 9, Jan. 1, 1996 (Jan. 1, 1996), pp. 2155-2159, XP009053227.
International Preliminary Report on Patentability for International Patent Application No. PCT/EP2014/064167, dated Jan. 14, 2016, 6 pages.

* cited by examiner

*Primary Examiner* — Daniel E Kolker
*Assistant Examiner* — Jegatheesan Seharaseyon
(74) *Attorney, Agent, or Firm* — Sheridan Ross P.C.

(57) ABSTRACT

Provided are novel IFB-a binding molecules of human origin, particularly human-derived anti-IFN-α antibodies as well as IFN-α binding fragments, derivatives and variants thereof. In addition, pharmaceutical compositions, kits, and methods for use in diagnosis and therapy are described.

Figure 2:
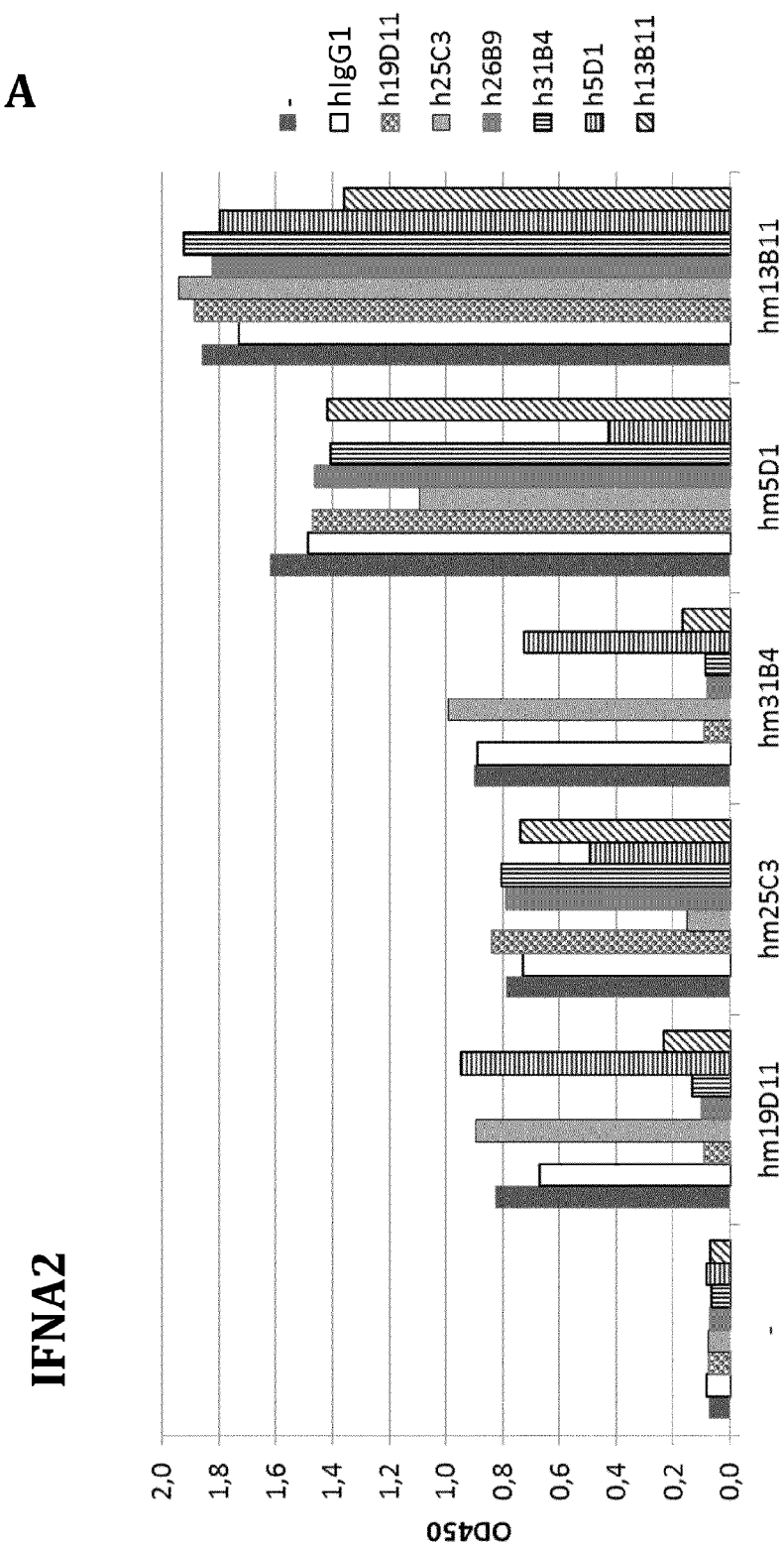
Figure 2:
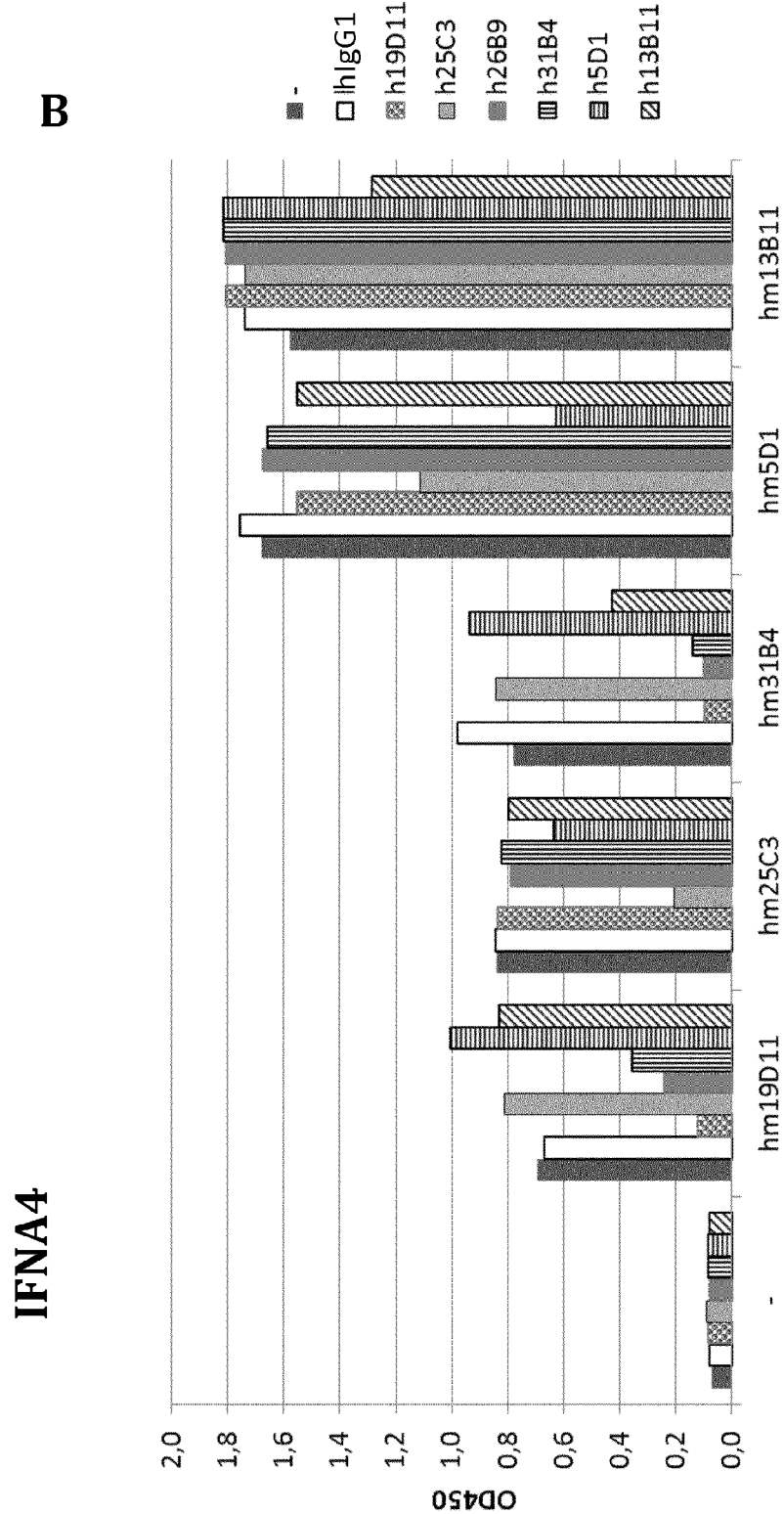
Figure 2:
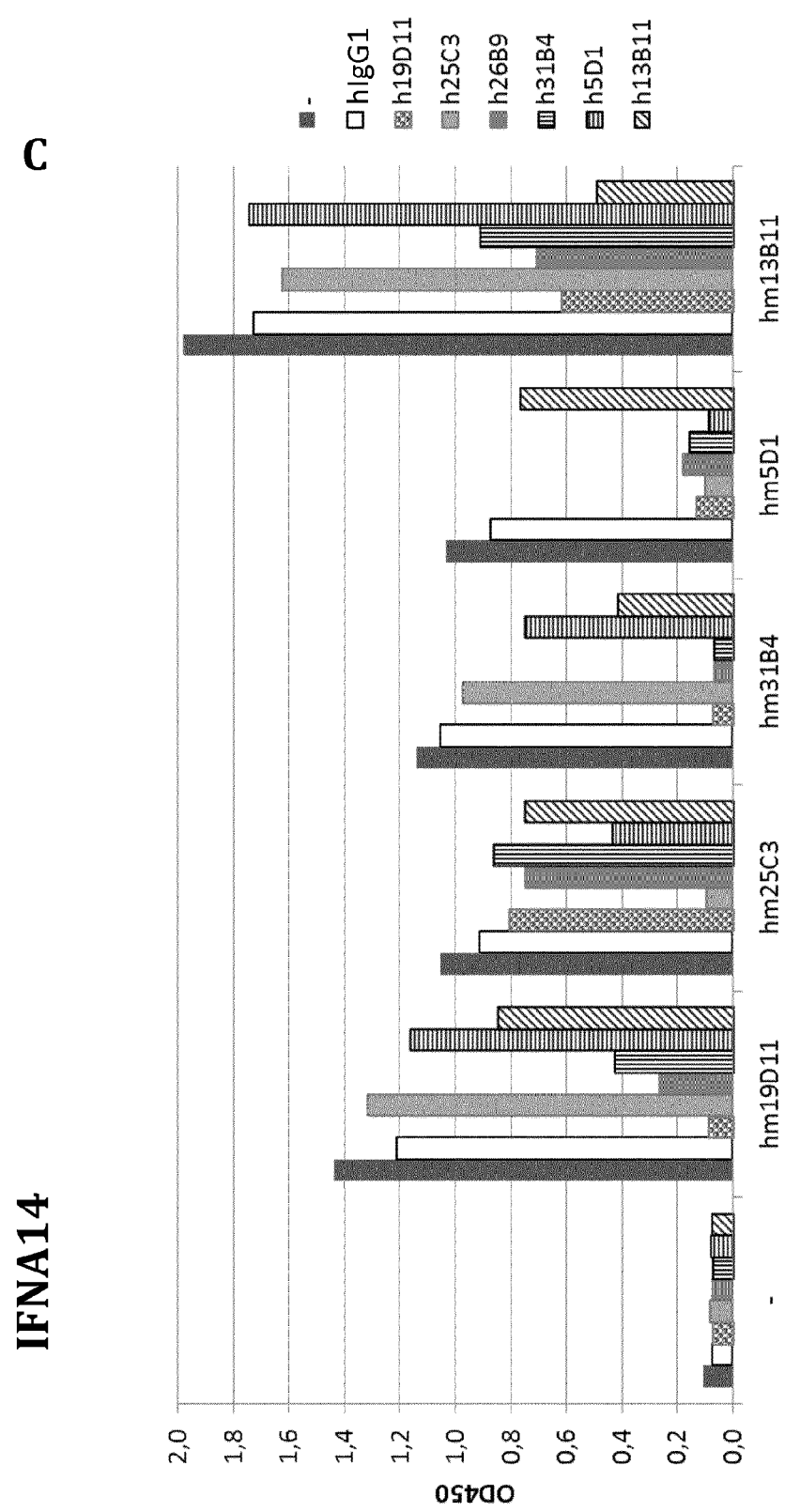
Figure 3:
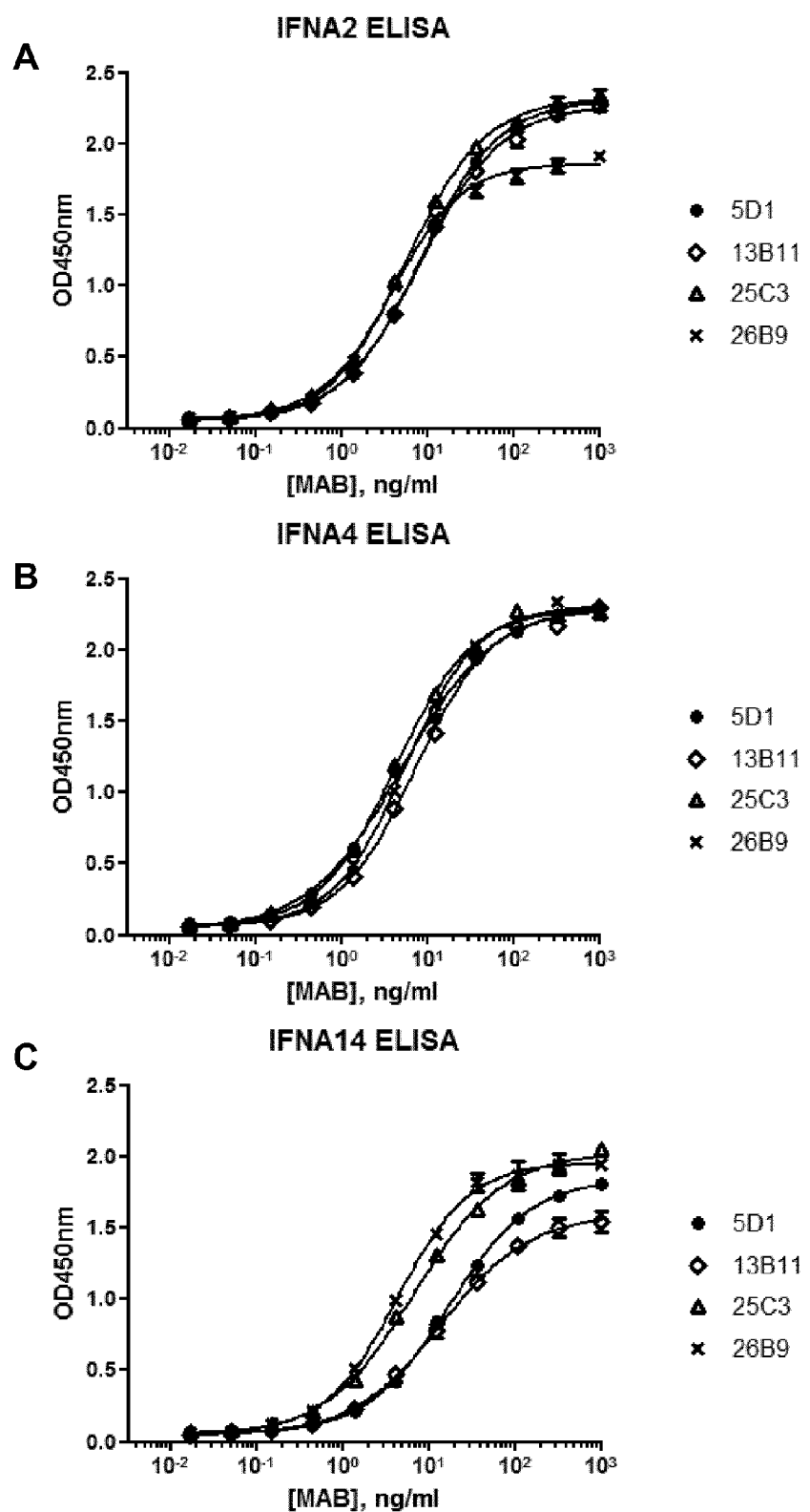
Figure 3:
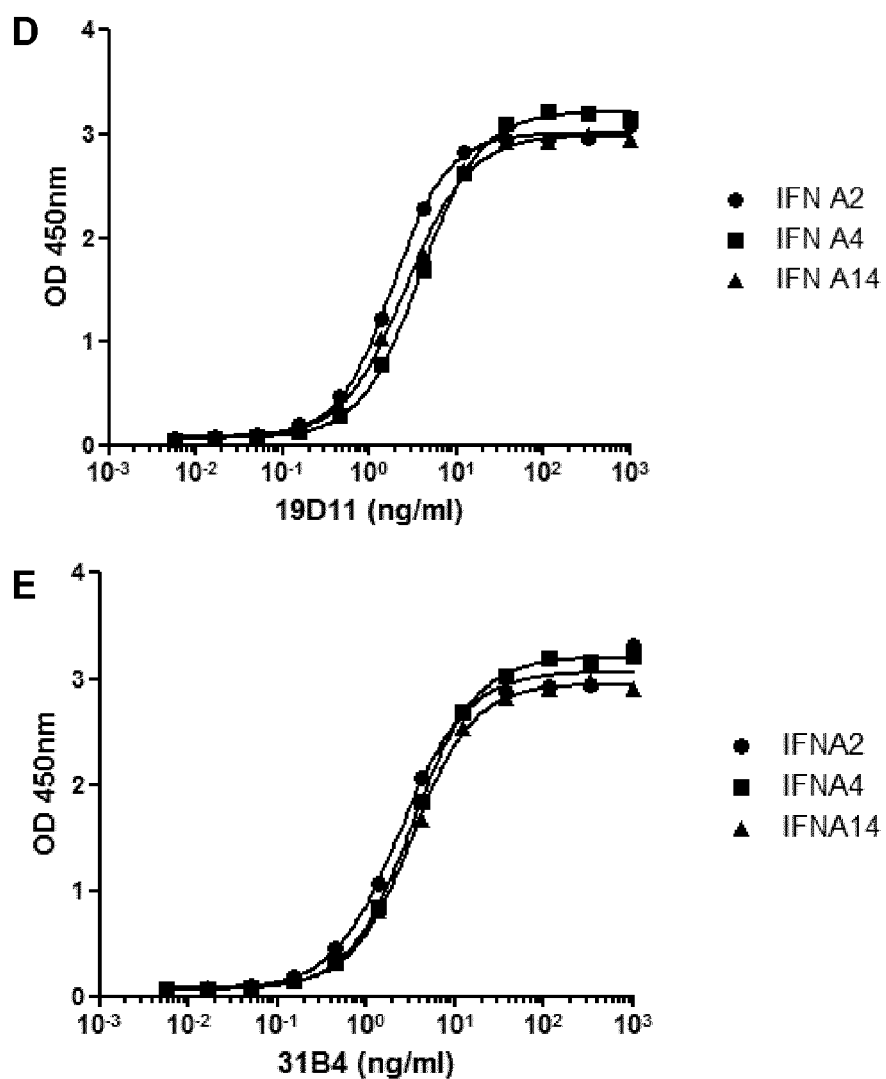

34 Claims, 63 Drawing Sheets
Specification includes a Sequence Listing.

A  5D1 (variable heavy chain sequence VH) – SEQ ID NO: 2
```
FR1---------------------------CDR1-FR2-----------CDR2--------------
EVQLVQAGAEVKAPGESLRISCKVSGYTFTSYWISWVRQIPGKGLEWMVKIDPRDSYTIYNPSFQG FR3------------------------------CDR3---------FR4--------
HVSISVDKSITTVYLQWSSLQASDTAIYYCVRHYLTQSLVDYFDHWGQGTLVAVSS
```

5D1 (variable kappa chain sequence VL) – SEQ ID NO: 4
```
FR1--------------------CDR1-------FR2------------CDR2---
DIQMTQSPSSLSASVGDSVTITCRASQSVSNYFHWYRQKPGKAPELLIYSASNLQT FR3-----------------------------CDR3-----FR4-------
GVPSRFTGSGSGTECTLTITSLQPDDFATYYCQQTHGYPFTFGQGTKLDVR
```

B  13B11 (variable heavy chain sequence VH) – SEQ ID NO: 10
```
FR1---------------------------CDR1-FR2-----------CDR2--------------
DVQLLQSGGGLIQPGGSLRLSCAASGFTFKDYAMSWVRQAPGKGLEWVSVISRSGNIVDYVDSVKG FR3------------------------------CDR3----------FR4--------
RFTVSRDNSNNTLFLQMDGLRADDTAIYYCAKPKDMIVVVPAGFDSWGQGTLVSVSS
```

13B11 (variable kappa chain sequence VL) – SEQ ID NO: 12
```
FR1--------------------CDR1-------FR2------------CDR2---
DIQMTQFPSTLSASVGDSVTITCRASQSISAWLAWYQQKPGKAPKLLIYKGSRLEN FR3-----------------------------CDR3---FR4-------
GVPSRFSGSGSGTEFTLTIGSLQPDDFATYYCQQYKTWTFGQGTKVEIK
```

C  19D11 (variable heavy chain sequence VH) – SEQ ID NO: 18
```
FR1---------------------------CDR1-FR2-----------CDR2--------------
EVQLLESGAEVKRPGSSVRVSCRASGDTFSSYPISWVRQAPGQGLEWMGRILPALGVTNYAQNFRG FR3------------------------------CDR3--------------FR4--------
RITITADKSPLTAYLELSSLRFEDTAVYYCASPSADIIPSILGTTLFAFWGQGSLVTVSS
```

19D11 (variable kappa chain sequence VL) – SEQ ID NO: 20
```
FR1--------------------CDR1--------FR2------------CDR2---
EIVLTQSPGTLSLSPGEGATLSCRASQNVSRHYLTWYQQKPGQSPRLLIYGGSSRAT FR3-----------------------------CDR3-------FR4-------
GVPDRFSGGGSGTDFTLTISRLEPEDFAVFYCQSYHSPPPVYTFGQGTKVEIK
```

Fig. 1

D      25C3 (variable heavy chain sequence VH) – SEQ ID NO: 22

```
FR1----------------------------CDR1-FR2-----------CDR2-------------
EMQLMESGGGLVQPGGSLRLSCVASGFTFKSFAMSWVRQAPGKGLEWVASVGSQGGSKYYAPSVKG

FR3-------------------------------CDR3---------FR4--------
RFSISRDNSNNTLYVQMNSLGVEDTAFYYCVKETDAVATMDALDMWGQGTLVIVST
```

25C3 (variable kappa chain sequence VL) – SEQ ID NO: 24

```
FR1--------------------CDR1-------FR2------------CDR2---
DIRVTQSPSSLSASVGDRVSISCQTSQSVNIYLNWYQQRPGKGPQLLISAASTLQS

FR3-----------------------------CDR3-----FR4-------
GVPSRFSGSGSGTDFILTIISLQPEDSASYYCQQGYITPYTFGQGTKVEIK
```

E      26B9 (variable heavy chain sequence VH) – SEQ ID NO: 30

```
FR1----------------------------CDR1---FR2-----------CDR2-------------
QILLQESGPGLVKPTETLSLTCSVSGDSISDSSHYWAWIRQPPGKGPEWIGSVYFSSMTHYNPSLKS

FR3-------------------------------CDR3----------FR4--------
RVSISVDKPKNQFSLKVTSVTVADTATYYCARQALARVGAMNWFDPWGQGSLVTVSS
```

26B9 (variable lambda chain sequence VL) – SEQ ID NO: 32

```
FR1--------------------CDR1-------------FR2------------CDR2---
DIIMTQSPDSLPVSLGEGVTINCKSSQSVFFTSSNKSCLAWYQQKPGKSPKLLIYWASTRQS

FR3-----------------------------CDR3-----FR4-------
GVPDRFRGSGSGTDFSLTITSLQAEDVAVYFCQQCQTSPPTFGGGTRLEIK
```

F      31B4 (variable heavy chain sequence VH) – SEQ ID NO: 38

```
FR1----------------------------CDR1---FR2-----------CDR2-------------
QIQLQESGPGLVRPTETLSLTCSVSGDSISQSSHYWAWIRQPPGKGPEWIGSVYFSSMTHYNPSLTS

FR3-------------------------------CDR3----FR4--------
RVSISIDKAMNKFSLKVTSVTVADTATYYCARQALARVGAMNWFDPWGQGSLVTVSS
```

31B4 (variable lambda chain sequence VL) – SEQ ID NO: 40

```
FR1--------------------CDR1-------------FR2------------CDR2---
DIIMTQSPESLPVSLGEGVTINCKSSQSVFFTSSNRSCLAWYQQKPGQSPKLLIYWASTRQS

FR3-----------------------------CDR3-----FR4-------
GVPDRFTGSGSGTDFSLTIAGLQVEDVAVYFCQQCHASPPTFGGGTRLELR
```

Fig. 1 (continued)

G     8H1 (variable heavy chain sequence VH) – SEQ ID NO: 76

```
FR1--------------------------CDR1-FR2-----------CDR2-------------
QVQLVQSGAEVKKPGASVKVSCKASGQTFTSDDINWVRQAPGQGLEWMGWRNPNTQDTGYAQKFHG

FR3------------------------------CDR3------------FR4-------
RLTLTSNSSISTSYLELSGLRSEDTAVYYCARAGTSTLTGHYFALGVWGQGTTVIVSS
```

8H1 (variable kappa chain sequence VL) – SEQ ID NO: 78

```
FR1--------------------CDR1-------FR2------------CDR2---
DIQLTQSPSSLSASVGDRVTITCQATQDISKYLNWYQQKPGKVPKLLIYETSNLEV

FR3-----------------------------CDR3-----FR4-------
GVPSRFSGSGSGTHFTLTISSLQAEDFATYYCQQYENFPFTFGGGTKVEIK
```

H     12H5 (variable heavy chain sequence VH) – SEQ ID NO: 84

```
FR1---------------------------CDR1-FR2-----------CDR2-------------
QVQLIQSGPEVKRPGASVKVSCKASENTFDTHYINWVRQAPGQGLTWLGWLNPTTGKTGFPQKFKG

FR3-----------------------------CDR3----------FR4--------
RVILTSDTSLNTAYMEVSRLTSEDTAVYFCARVLKLSDEYNYGFDVWGQGTTVIVSS
```

12H5 (variable kappa chain sequence VL) – SEQ ID NO: 86

```
FR1--------------------CDR1-------FR2------------CDR2---
DIQVTQSPSSLSASIGDRVTITCRASQNILTFINWYQHKPGKAPKLLIYAASVLQN
FR3-----------------------------CDR3------FR4-------
EVPSRFSGSGSGTDFTLTITSLQPDDFGTYYCQQTYLTPQCSFGQGTKVEIK
```

I     50E11 (variable heavy chain sequence VH) – SEQ ID NO: 92

```
FR1---------------------------CDR1-FR2-----------CDR2-------------
QVQLVQSGAEMKKPGSSVKVSCKDFGGTFSVYGVNWVRQAPGQGLEWMGGLIPVIGPANYAQKFQG

FR3-----------------------------CDR3-FR4--------
RITITADESTSTAYMELSSLRFDDTAIYYCVRDDNEYWGQGTLVTVSS
```

50E11 (variable kappa chain sequence VL) – SEQ ID NO: 94

```
FR1--------------------CDR1-------FR2------------CDR2---
EMVLTQSPATLSLSPGERATLSCRASQTVSTFLAWYQQKPGQVPRLLVYDISSRAN

FR3-----------------------------CDR3-------FR4-------
GTPARFSGGGSGTDFTLTISSLELEDFAVYYCQWRSNWPPSLTFGGGTRVEIK
```

Fig. 1 (continued)

| Target | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| dsDNA | o | o | o | o | o | o | o | o | o | o | o |   | o | o | o | o | o | o | o |   |   | o | o |
| IFN-α8 | o | o | o | o | o | o | o | o | o | o | o | o | o | o | o | o | o | o | o | o |   |   |   |
| IFN-α2 | o | o | o | o | o | o | o | o | o | o |   | o | o | o | o | o | o | o | o | o | o | o | o |
| IFN-α4 | o | o | o | o | o | o | o | o | o | o |   | o | o | o | o | o | o | o | o | o | o | o | o |
| IFN-α14 | o | o | o | o | o | o | o | o | o | o |   | o | o | o | o | o | o | o | o | o | o | o | o |
| GAD1 brain |   | o |   | o |   |   |   |   |   | o |   |   |   | o |   | o | o | o |   |   | o |   |   |
| GAD2 |   | o | o | o |   |   | o |   |   | o | o |   |   | o |   | o | o | o |   |   | o |   |   |
| Insulin |   | o |   |   |   |   |   |   |   |   |   |   |   |   |   |   |   |   |   |   |   |   |   |
| IFN-α5 | o |   | o | o | o | o | o | o | o | o |   |   | o | o | o | o | o | o | o |   |   | o | o |
| IFN-α6 | o |   | o | o | o | o | o | o | o | o |   |   | o | o | o | o | o | o | o | o |   | o | o |
| IFN-α21 | o |   | o |   | o | o | o | o | o | o |   |   | o | o | o | o | o | o | o |   |   |   | o |

Fig. 4

Figure 5:
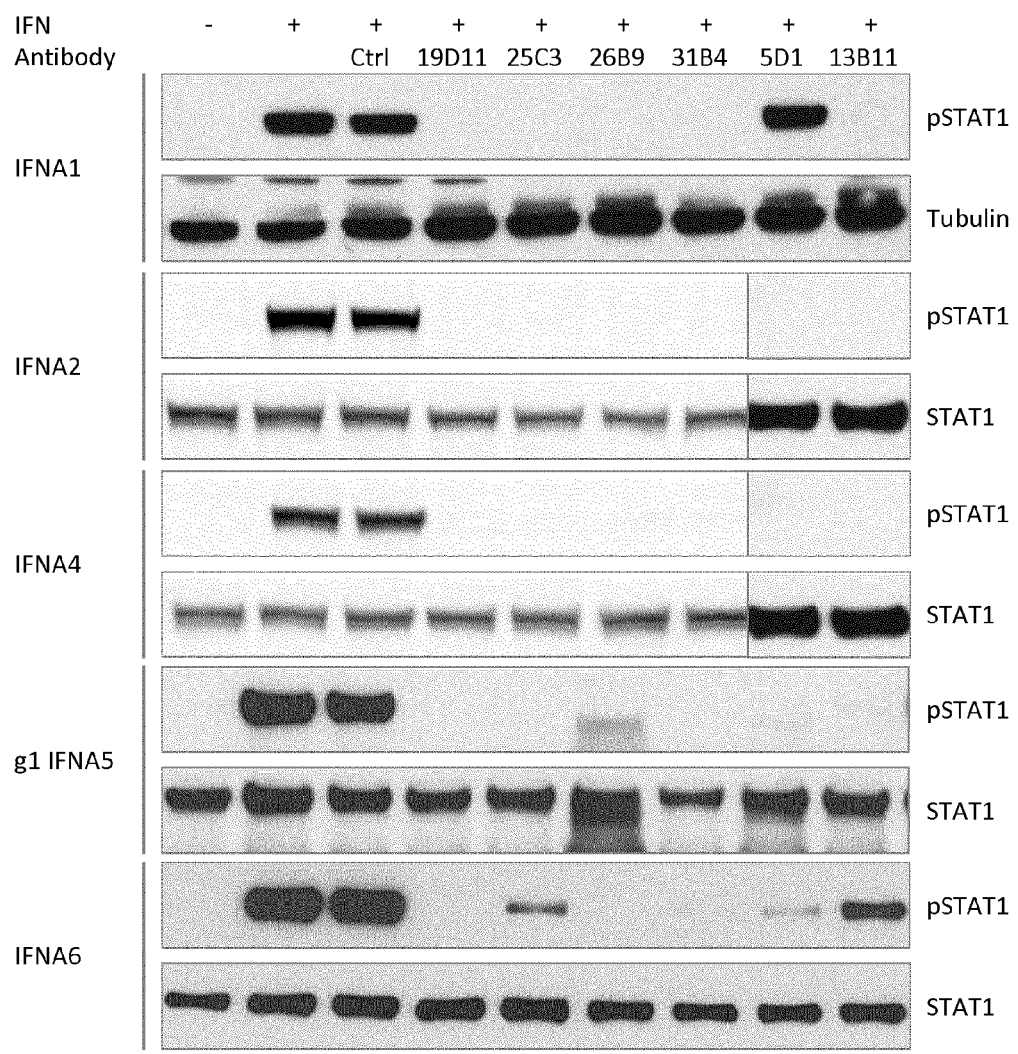
Figure 5:
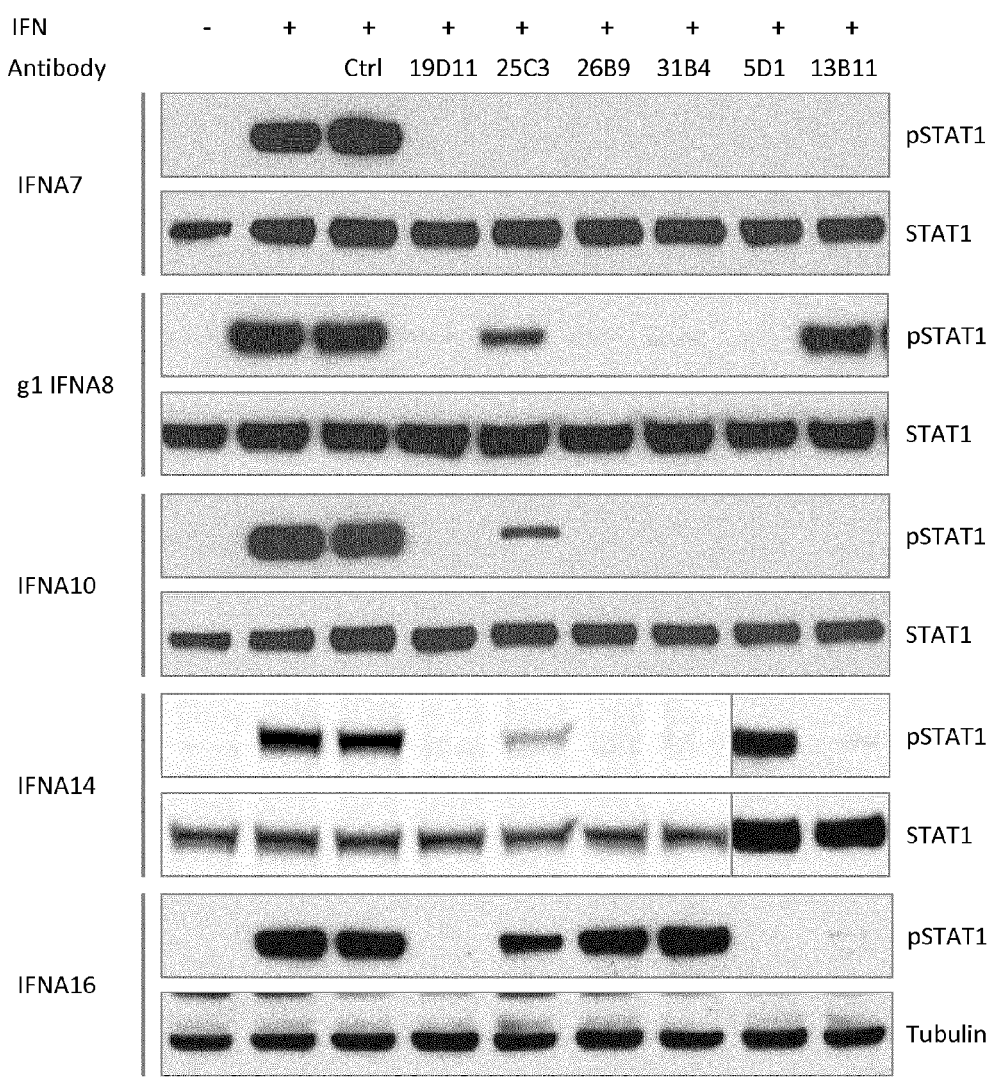
Figure 5:
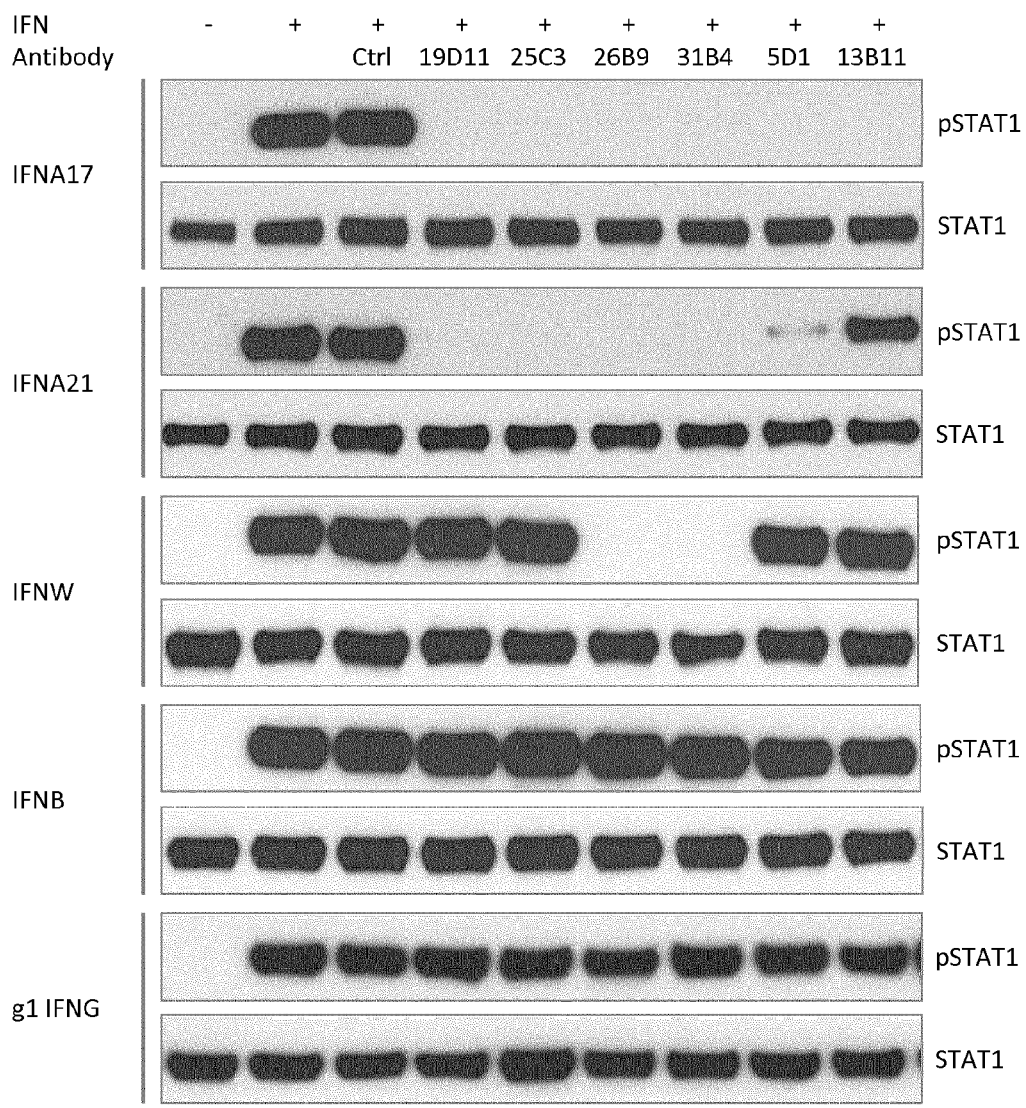

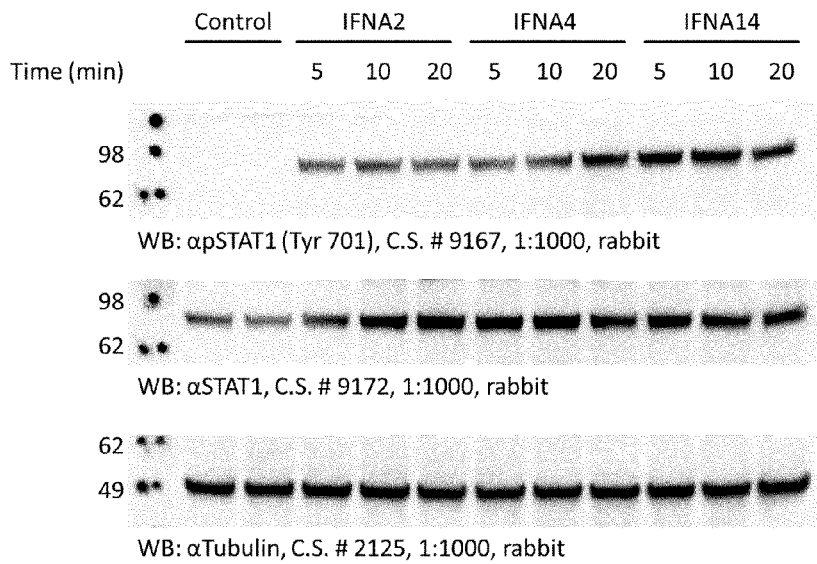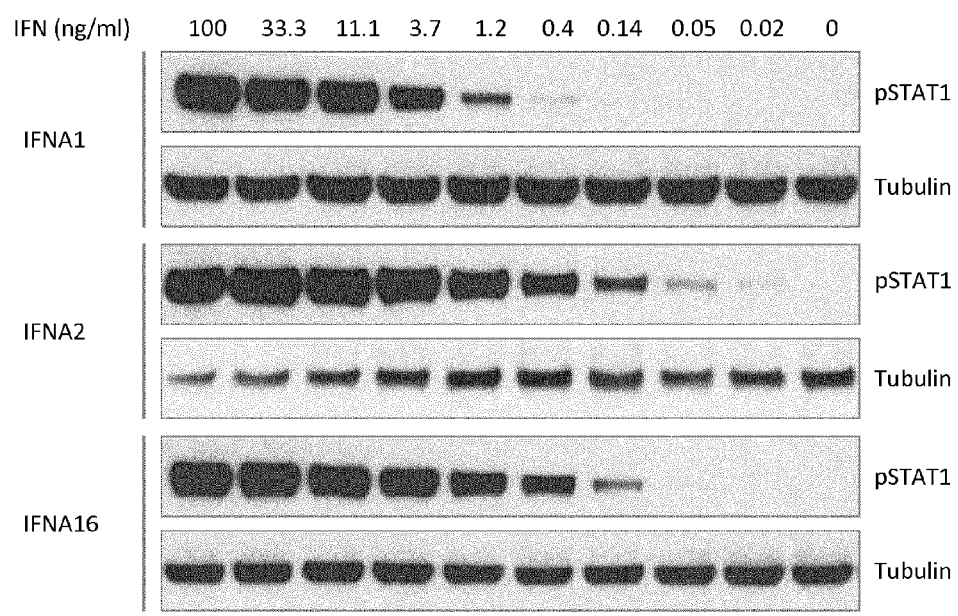
Fig. 5

Figure 11:
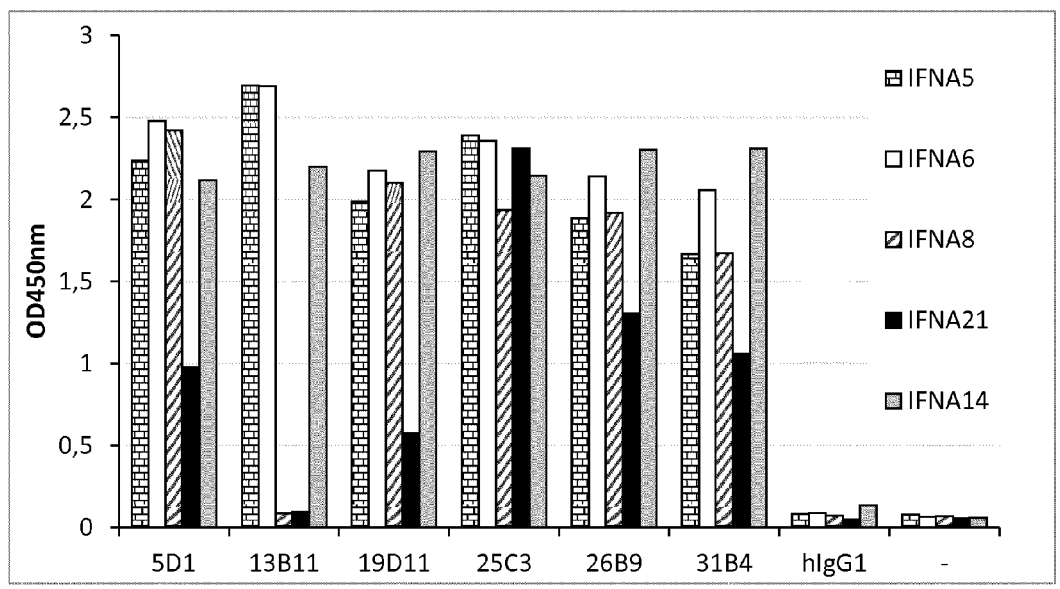

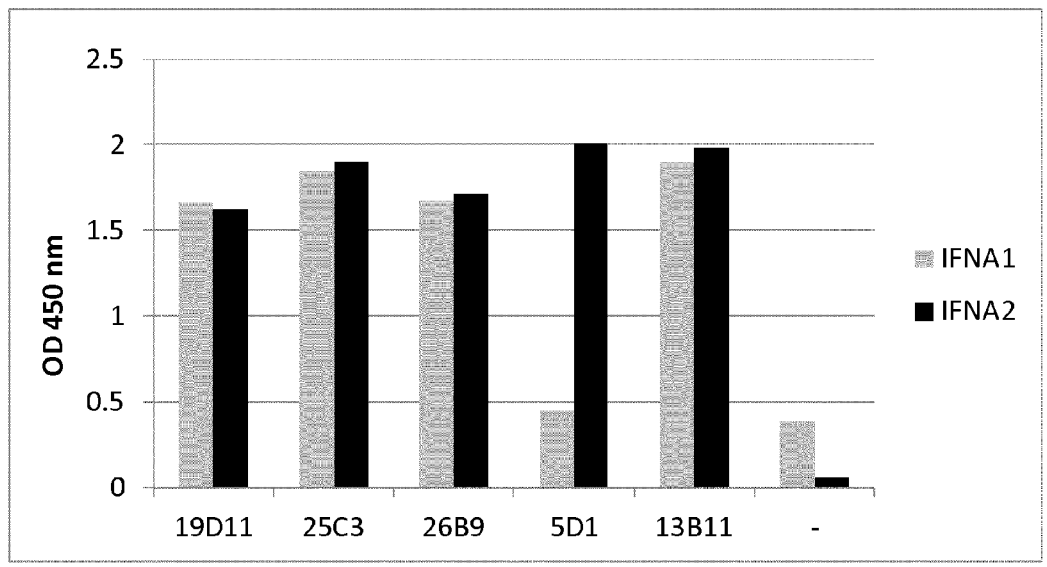
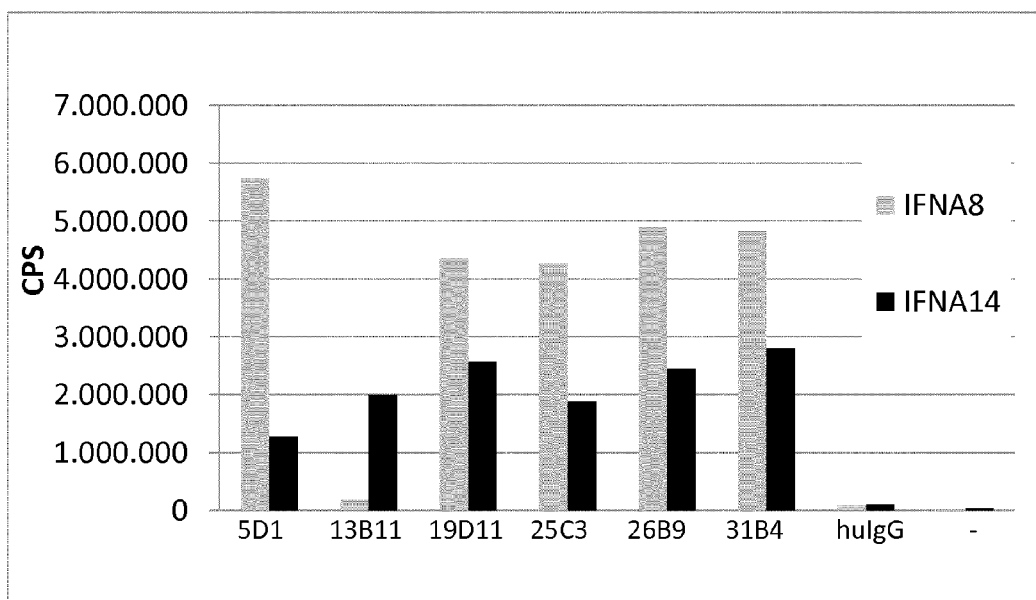
Fig. 11

| Normalisation | 0 | 1 | 2 | 3 | 4 | 5 | 6 |
|---|---|---|---|---|---|---|---|
| A v B<br>PBS a2a | ns | ns | ns | * | * | ** | ** |
| A v C<br>PBS a2b | ns | ns | ns | **** | **** | *** | **** |
| A v D<br>PBS a4 | ns | ns | ns | **** | ** | *** | ** |
| A v E<br>PBS a14 | ns | ** | * | **** | ** | *** | *** |
| B v C<br>a2a a2b | ns | ns | ns | ns | ** | * | * |
| B v D<br>a2a a4 | ns | ns | ns | * | ns | ns | ns |
| B v E<br>a2a a14 | ns | * | ns | ** | * | *** | * |
| C v D<br>a2b a4 | ns | ns | ns | ns | ns | ns | ns |
| C v E<br>a2b a14 | ns | ns | ns | ns | ns | ns | ns |
| D v E<br>a4 a14 | ns | ns | ns | ns | ns | ** | ns |

Fig. 17

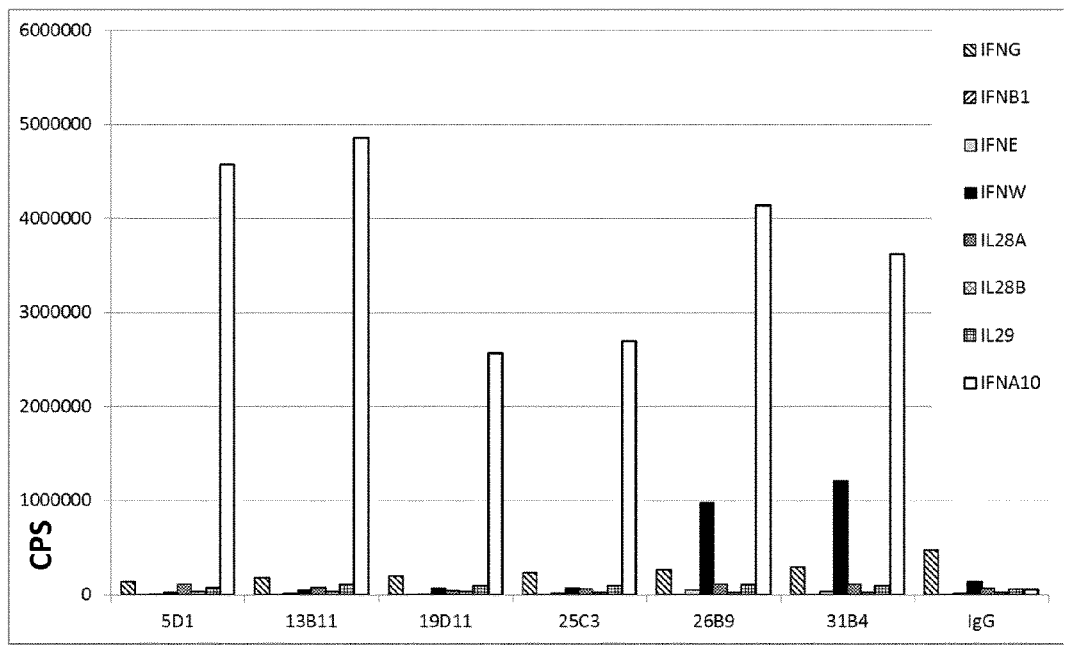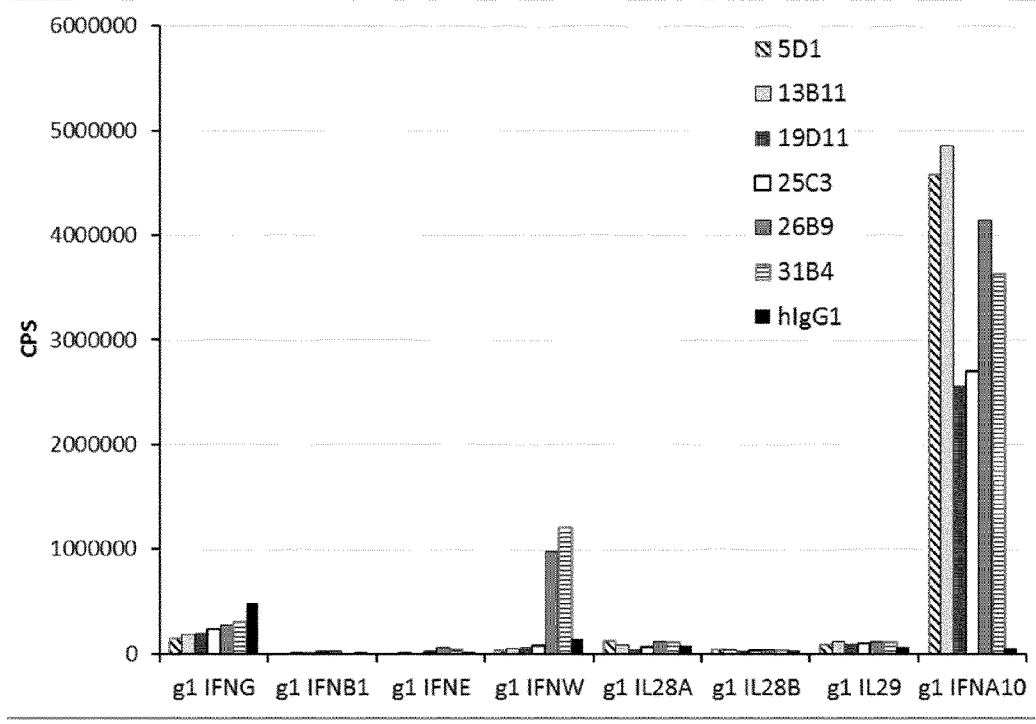
Fig. 18

Figure 23:
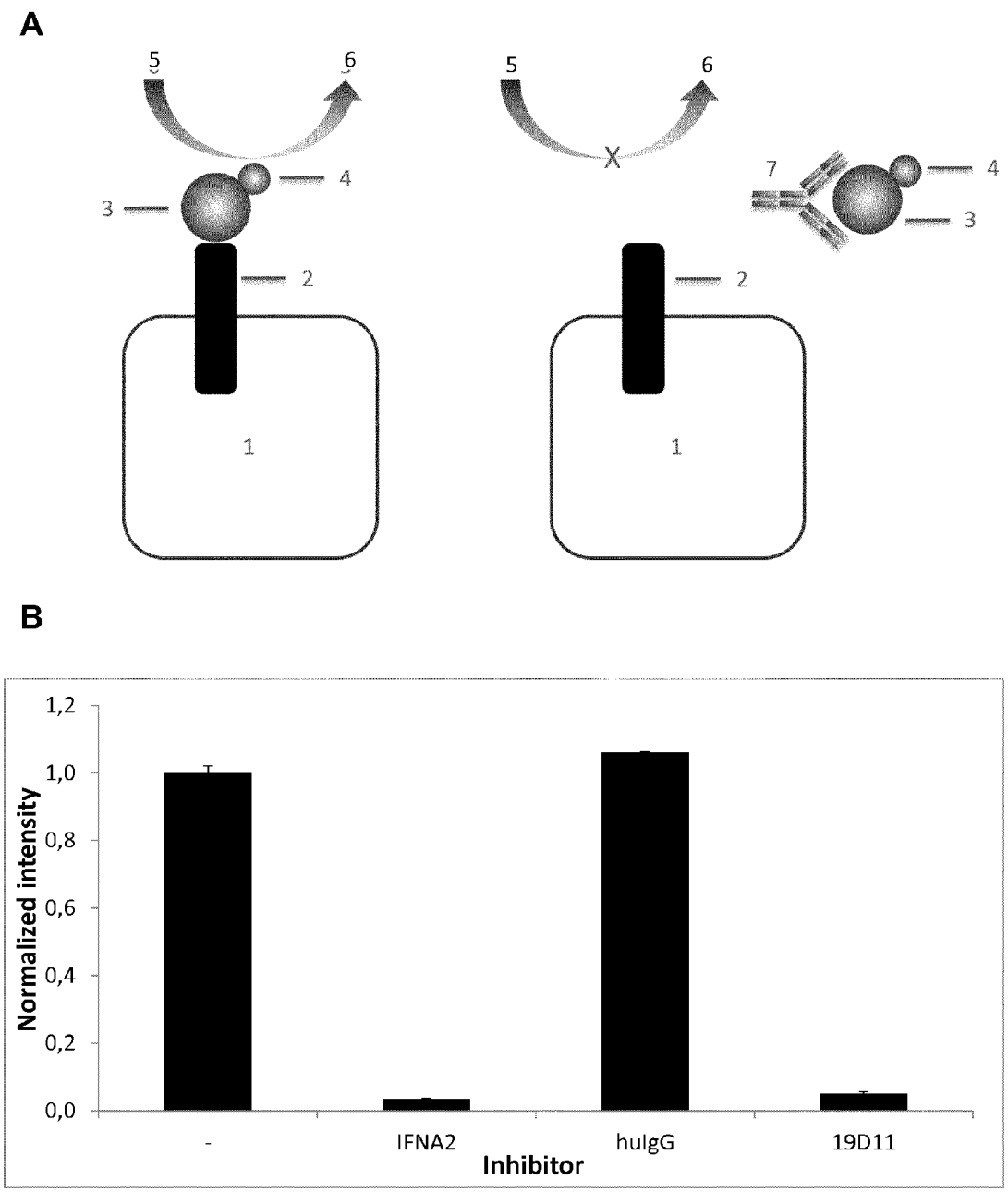

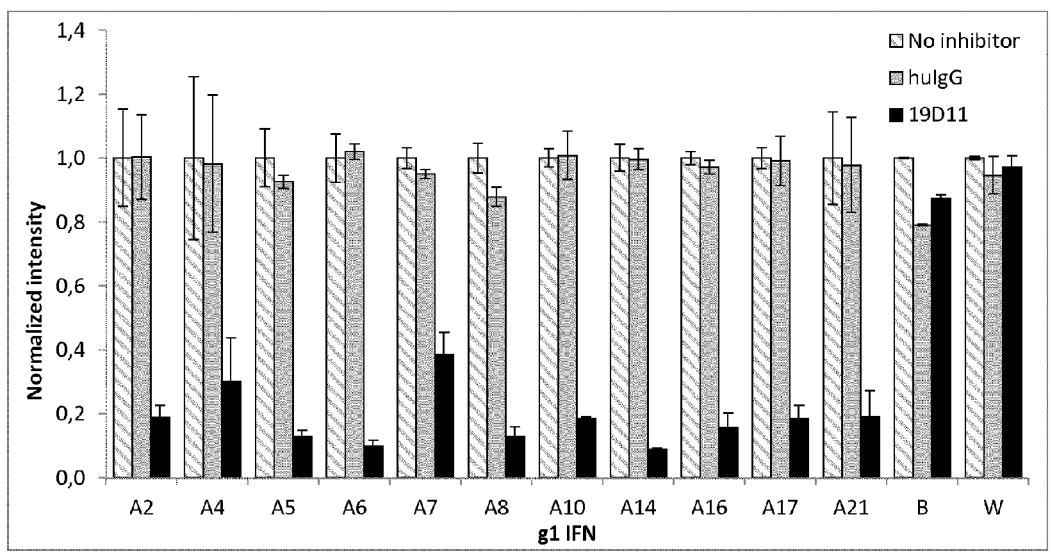
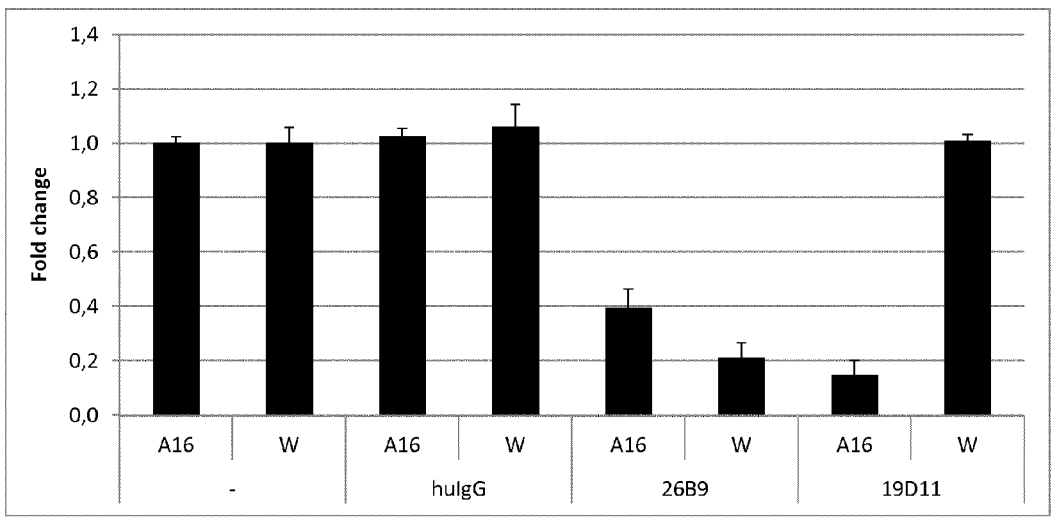
Fig. 23 (continued)

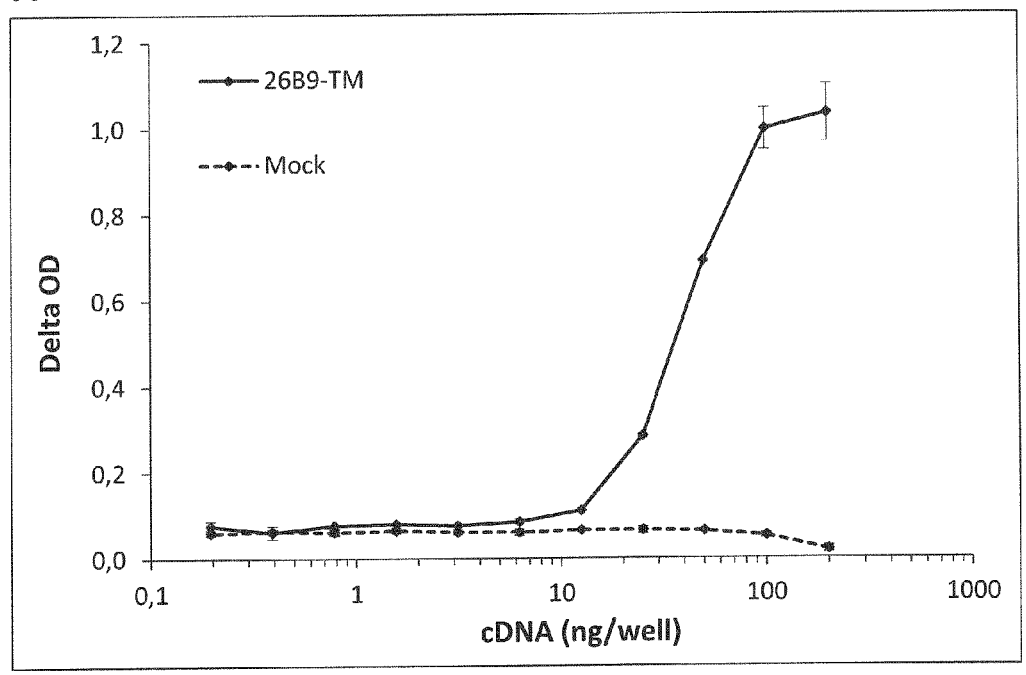
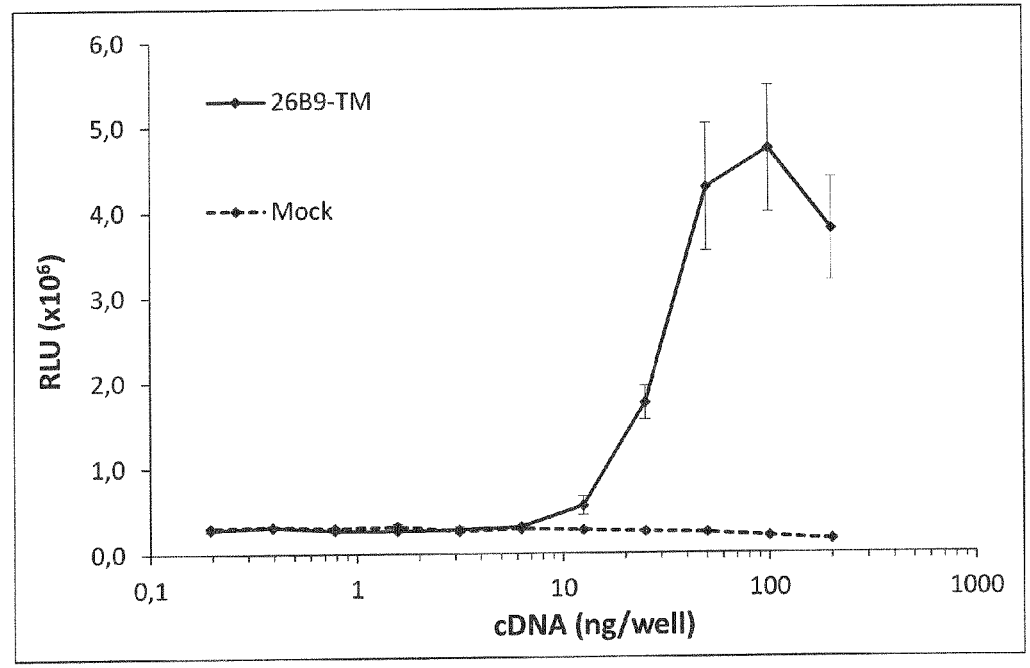
Fig. 24

Figure 29:
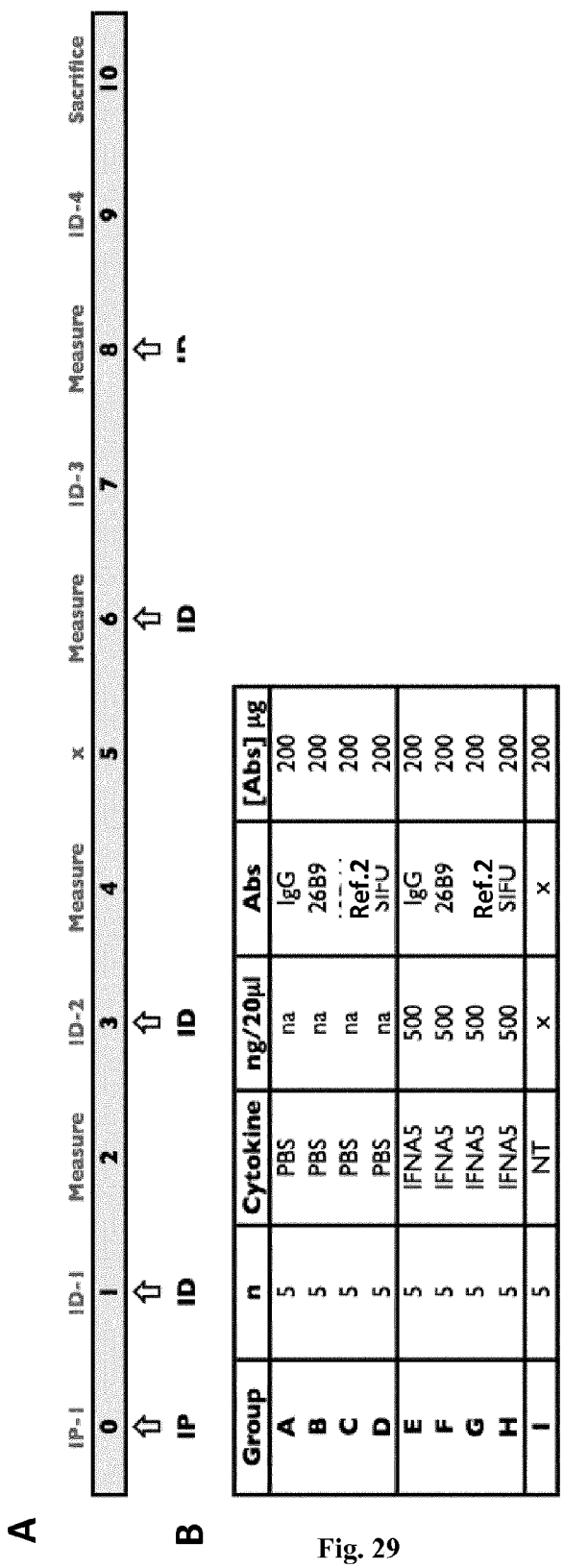

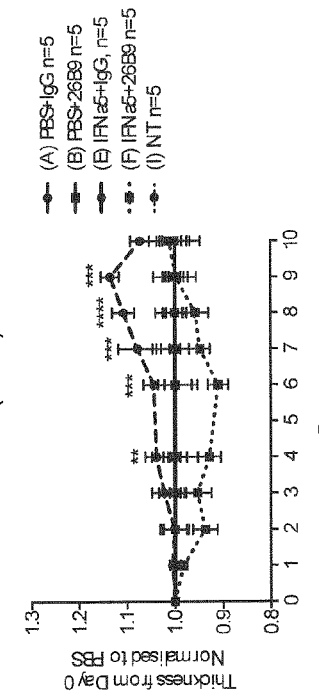
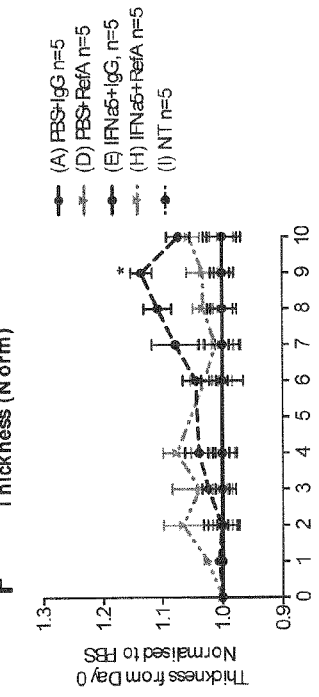
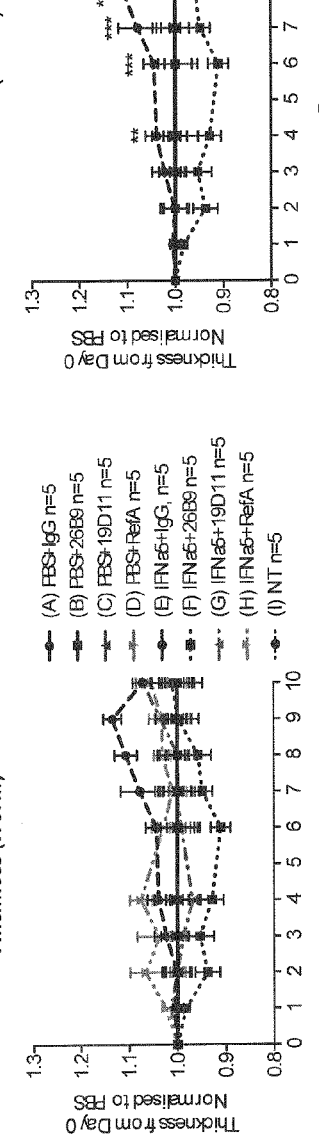
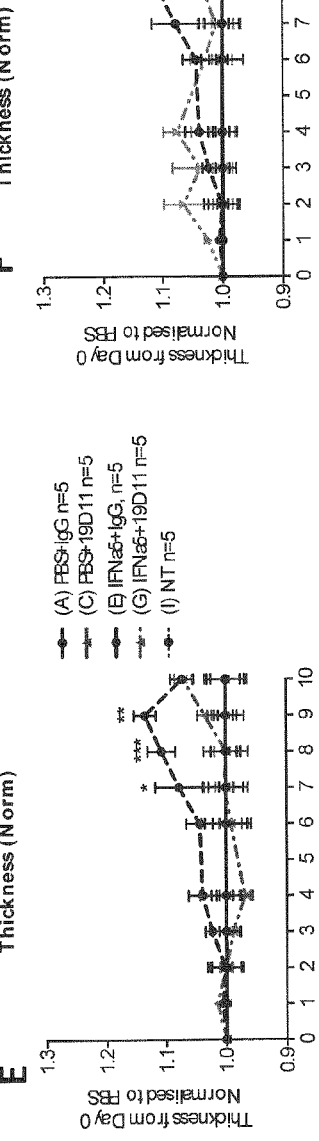
Fig. 29 (continued)

SEQUENCE LISTING

<160> NUMBER OF SEQ ID NOS: 102

<210> SEQ ID NO 1
<211> LENGTH: 366
<212> TYPE: DNA
<213> ORGANISM: Homo sapiens
<220> FEATURE:
<221> NAME/KEY: CDS
<222> LOCATION: (1)..(366)
<223> OTHER INFORMATION: 5D1-VH variable heavy chain (VH) sequence; 5D1:
      IgG1, kappa
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(333)
<223> OTHER INFORMATION: complementarity determining region (CDR)
      VH-CDR3

<400> SEQUENCE: 1

```
gaa gtg caa ctg gtg cag gcc ggc gca gag gtg aaa gcg ccc ggg gag        48
Glu Val Gln Leu Val Gln Ala Gly Ala Glu Val Lys Ala Pro Gly Glu
1               5                   10                  15 tct ctg agg atc tcc tgt aag gtg tct gga tac acc ttt aca agt tat        96
Ser Leu Arg Ile Ser Cys Lys Val Ser Gly Tyr Thr Phe Thr Ser Tyr
            20                  25                  30 tgg atc agt tgg gtg cgc cag att ccc ggg aaa ggc ctg gag tgg atg       144
Trp Ile Ser Trp Val Arg Gln Ile Pro Gly Lys Gly Leu Glu Trp Met
        35                  40                  45 gtg aaa att gat cct aga gac tct tat acc atc tac aac ccg tcc ttc       192
Val Lys Ile Asp Pro Arg Asp Ser Tyr Thr Ile Tyr Asn Pro Ser Phe
    50                  55                  60 caa ggc cac gtc tcc atc tca gtt gac aag tcc atc acc act gtc tac       240
Gln Gly His Val Ser Ile Ser Val Asp Lys Ser Ile Thr Thr Val Tyr
65                  70                  75                  80 ctg cag tgg agc agc ctg cag gcc tcg gac acc gcc att tat tat tgt       288
Leu Gln Trp Ser Ser Leu Gln Ala Ser Asp Thr Ala Ile Tyr Tyr Cys
                85                  90                  95 gtg aga cat tat ctt aca cag tca ttg gtg gac tac ttt gac cac tgg       336
Val Arg His Tyr Leu Thr Gln Ser Leu Val Asp Tyr Phe Asp His Trp
            100                 105                 110 ggc cag gga acg ctg gtc gcc gtc tcc tct                               366
Gly Gln Gly Thr Leu Val Ala Val Ser Ser
        115                 120
```

<210> SEQ ID NO 2
<211> LENGTH: 122
<212> TYPE: PRT
<213> ORGANISM: Homo sapiens

<400> SEQUENCE: 2

```
Glu Val Gln Leu Val Gln Ala Gly Ala Glu Val Lys Ala Pro Gly Glu
1               5                   10                  15

Ser Leu Arg Ile Ser Cys Lys Val Ser Gly Tyr Thr Phe Thr Ser Tyr
            20                  25                  30

Trp Ile Ser Trp Val Arg Gln Ile Pro Gly Lys Gly Leu Glu Trp Met
        35                  40                  45
```

```
Val Lys Ile Asp Pro Arg Asp Ser Tyr Thr Ile Tyr Asn Pro Ser Phe
    50              55                  60

Gln Gly His Val Ser Ile Ser Val Asp Lys Ser Ile Thr Thr Val Tyr
65              70                  75                  80

Leu Gln Trp Ser Ser Leu Gln Ala Ser Asp Thr Ala Ile Tyr Tyr Cys
                85                  90                  95

Val Arg His Tyr Leu Thr Gln Ser Leu Val Asp Tyr Phe Asp His Trp
            100                 105                 110

Gly Gln Gly Thr Leu Val Ala Val Ser Ser
            115                 120

<210> SEQ ID NO 3
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: 5D1-VL variable light chain (VL) sequence,
      kappa type
<220> FEATURE:
<221> NAME/KEY: V_region
<222> LOCATION: (70)..(102)
<223> OTHER INFORMATION: complementarity determining region (CDR)
      VL-CDR1
<220> FEATURE:
<221> NAME/KEY: V_region
<222> LOCATION: (148)..(168)
<223> OTHER INFORMATION: complementarity determining region (CDR)
      VL-CDR2
<220> FEATURE:
<221> NAME/KEY: V_region
<222> LOCATION: (265)..(291)
<223> OTHER INFORMATION: complementarity determining region (CDR)
      VL-CDR3

<400> SEQUENCE: 3 gac att cag atg acc cag tct cca tcc tcc ctg tct gca tct gtg gga     48
Asp Ile Gln Met Thr Gln Ser Pro Ser Ser Leu Ser Ala Ser Val Gly
1               5                   10                  15 gac agt gtc acc atc act tgc cgg gca agt cag agc gta tcc aac tac     96
Asp Ser Val Thr Ile Thr Cys Arg Ala Ser Gln Ser Val Ser Asn Tyr
                20                  25                  30 ttc cat tgg tat cga cag aag ccc ggg aaa gcc cct gaa ctc ctg atc    144
Phe His Trp Tyr Arg Gln Lys Pro Gly Lys Ala Pro Glu Leu Leu Ile
            35                  40                  45 tat tct gca tcc aat ttg caa act ggg gtc cca tca aga ttc act ggc    192
Tyr Ser Ala Ser Asn Leu Gln Thr Gly Val Pro Ser Arg Phe Thr Gly
        50                  55                  60 agt ggg tct ggg aca gaa tgc act ctc acc atc acc agt ctg cag cct    240
Ser Gly Ser Gly Thr Glu Cys Thr Leu Thr Ile Thr Ser Leu Gln Pro
65                  70                  75                  80 gat gat ttc gca act tac tac tgt caa cag act cac ggt tac ccg ttc    288
Asp Asp Phe Ala Thr Tyr Tyr Cys Gln Gln Thr His Gly Tyr Pro Phe
                85                  90                  95 act ttt ggc cag ggg acc aag ctg gac gtc aga                        321
Thr Phe Gly Gln Gly Thr Lys Leu Asp Val Arg
            100                 105

<210> SEQ ID NO 4
<211> LENGTH: 107
<212> TYPE: PRT
<213> ORGANISM: Homo sapiens

<400> SEQUENCE: 4
```

```
Asp Ile Gln Met Thr Gln Ser Pro Ser Ser Leu Ser Ala Ser Val Gly
  1               5                  10                  15

Asp Ser Val Thr Ile Thr Cys Arg Ala Ser Gln Ser Val Ser Asn Tyr
             20                  25                  30

Phe His Trp Tyr Arg Gln Lys Pro Gly Lys Ala Pro Glu Leu Leu Ile
         35                  40                  45

Tyr Ser Ala Ser Asn Leu Gln Thr Gly Val Pro Ser Arg Phe Thr Gly
     50                  55                  60

Ser Gly Ser Gly Thr Glu Cys Thr Leu Thr Ile Thr Ser Leu Gln Pro
 65                  70                  75                  80

Asp Asp Phe Ala Thr Tyr Tyr Cys Gln Gln Thr His Gly Tyr Pro Phe
                 85                  90                  95

Thr Phe Gly Gln Gly Thr Lys Leu Asp Val Arg
            100                 105

<210> SEQ ID NO 5
<211> LENGTH: 993
<212> TYPE: DNA
<213> ORGANISM: Homo sapiens
<220> FEATURE:
<221> NAME/KEY: CDS
<222> LOCATION: (1)..(993)
<223> OTHER INFORMATION: 5D1-CH constant heavy chain (CH) sequence

<400> SEQUENCE: 5 gcc tcc acc aag ggc cca tcg gtc ttc ccc ctg gca ccc tcc tcc aag      48
Ala Ser Thr Lys Gly Pro Ser Val Phe Pro Leu Ala Pro Ser Ser Lys
  1               5                  10                  15 agc acc tct ggg ggc aca gcg gcc ctg ggc tgc ctg gtc aag gac tac      96
Ser Thr Ser Gly Gly Thr Ala Ala Leu Gly Cys Leu Val Lys Asp Tyr
             20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
         35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
     50                  55                  60 ctc agc agc gtg gtg acc gtg ccc tcc agc agc ttg ggc acc cag acc     240
Leu Ser Ser Val Val Thr Val Pro Ser Ser Ser Leu Gly Thr Gln Thr
 65                  70                  75                  80 tac atc tgc aac gtg aat cac aag ccc agc aac acc aag gtg gac aag     288
Tyr Ile Cys Asn Val Asn His Lys Pro Ser Asn Thr Lys Val Asp Lys
                 85                  90                  95 aaa gtt gag ccc aaa tct tgt gac aaa act cac aca tgc cca ccg tgc     336
Lys Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca     384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc     432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg     480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag     528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg     576
Glu Gln Tyr Asn Ser Thr Tyr Arg Val Val Ser Val Leu Thr Val Leu
```

```
                180                 185                 190
cac cag gac tgg ctg aat ggc aag gag tac aag tgc aag gtc tcc aac       624
His Gln Asp Trp Leu Asn Gly Lys Glu Tyr Lys Cys Lys Val Ser Asn
            195                 200                 205 aaa gcc ctc cca gcc ccc atc gag aaa acc atc tcc aaa gcc aaa ggg       672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gat gag       720
Gln Pro Arg Glu Pro Gln Val Tyr Thr Leu Pro Pro Ser Arg Asp Glu
225                 230                 235                 240 ctg acc aag aac cag gtc agc ctg acc tgc ctg gtc aaa ggc ttc tat       768
Leu Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac       816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc       864
Asn Tyr Lys Thr Thr Pro Pro Val Leu Asp Ser Asp Gly Ser Phe Phe
    275                 280                 285 ctc tac agc aag ctc acc gtg gac aag agc agg tgg cag cag ggg aac       912
Leu Tyr Ser Lys Leu Thr Val Asp Lys Ser Arg Trp Gln Gln Gly Asn
290                 295                 300 gtc ttc tca tgc tcc gtg atg cat gag gct ctg cac aac cac tac acg       960
Val Phe Ser Cys Ser Val Met His Glu Ala Leu His Asn His Tyr Thr
                305                 310                 315                 320 cag aag agc ctc tcc ctg tct ccg ggt aaa tga                           993
Gln Lys Ser Leu Ser Leu Ser Pro Gly Lys
            325                 330

<210> SEQ ID NO 6
<211> LENGTH: 330
<212> TYPE: PRT
<213> ORGANISM: Homo sapiens

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 7
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: 5D1-CL constant kappa chain (CL) sequence
<220> FEATURE:
<221> NAME/KEY: misc_feature
<222> LOCATION: (268)..(324)
<223> OTHER INFORMATION: not sequenced but obtained from database

<400> SEQUENCE: 7 cga act gtg gct gca cca tct gtc ttc atc ttc ccg cca tct gat gag        48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc        96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa       144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc       192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag       240
Thr Tyr Ser Leu Ser Ser Thr Leu Thr Leu Ser Lys Ala Asp Tyr Glu
65                  70                  75                  80 aaa cac aaa gtc tac gcc tgc gaa gtc acc cat cag ggc ctg agc tcg       288
Lys His Lys Val Tyr Ala Cys Glu Val Thr His Gln Gly Leu Ser Ser
                85                  90                  95 ccc gtc aca aag agc ttc aac agg gga gag tgt tag                       324
Pro Val Thr Lys Ser Phe Asn Arg Gly Glu Cys
            100                 105

<210> SEQ ID NO 8
<211> LENGTH: 107
<212> TYPE: PRT
<213> ORGANISM: Homo sapiens
```

<400> SEQUENCE: 8

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 9
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION: 13B11-VH variable heavy chain (VH) sequence;
      13B11: IgG1, kappa
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(336)
<223> OTHER INFORMATION: complementarity determining region (CDR)
      VH-CDR3

<400> SEQUENCE: 9 gac gta cag ctg ttg cag tct ggg gga ggc ttg ata cag ccg ggg ggg     48
Asp Val Gln Leu Leu Gln Ser Gly Gly Gly Leu Ile Gln Pro Gly Gly
1               5                   10                  15 tcc ctg aga ctc tcc tgt gca gcc tct ggc ttt act ttt aag gac tat     96
Ser Leu Arg Leu Ser Cys Ala Ala Ser Gly Phe Thr Phe Lys Asp Tyr
            20                  25                  30 gcc atg agt tgg gtc cgc cag gct cca ggg aag ggc ctg gag tgg gtc    144
Ala Met Ser Trp Val Arg Gln Ala Pro Gly Lys Gly Leu Glu Trp Val
        35                  40                  45 tca gta ata agt cgt agt ggt aat att gta gac tat gtc gac tcc gtg    192
Ser Val Ile Ser Arg Ser Gly Asn Ile Val Asp Tyr Val Asp Ser Val
    50                  55                  60 aag ggc cgg ttc acc gtc tcc aga gac aat tcc aac aac aca ctc ttt    240
Lys Gly Arg Phe Thr Val Ser Arg Asp Asn Ser Asn Asn Thr Leu Phe
65                  70                  75                  80 ctg caa atg gac ggc ctg aga gcc gac gac acg gcc att tat tac tgt    288
Leu Gln Met Asp Gly Leu Arg Ala Asp Asp Thr Ala Ile Tyr Tyr Cys
                85                  90                  95 gcg aaa ccc aag gat atg att gtc gtg gtc cct gcg ggc ttt gac tcc    336
Ala Lys Pro Lys Asp Met Ile Val Val Val Pro Ala Gly Phe Asp Ser
            100                 105                 110

-continued

```
tgg ggc cag gga acc ctt gtc tcc gtc tcc tca                          369
Trp Gly Gln Gly Thr Leu Val Ser Val Ser Ser
        115                 120

<210> SEQ ID NO 10
<211> LENGTH: 123
<212> TYPE: PRT
<213> ORGANISM: Homo sapiens

<400> SEQUENCE: 10

Asp Val Gln Leu Leu Gln Ser Gly Gly Gly Leu Ile Gln Pro Gly Gly
1               5                   10                  15

Ser Leu Arg Leu Ser Cys Ala Ala Ser Gly Phe Thr Phe Lys Asp Tyr
            20                  25                  30

Ala Met Ser Trp Val Arg Gln Ala Pro Gly Lys Gly Leu Glu Trp Val
        35                  40                  45

Ser Val Ile Ser Arg Ser Gly Asn Ile Val Asp Tyr Val Asp Ser Val
    50                  55                  60

Lys Gly Arg Phe Thr Val Ser Arg Asp Asn Ser Asn Asn Thr Leu Phe
65                  70                  75                  80

Leu Gln Met Asp Gly Leu Arg Ala Asp Asp Thr Ala Ile Tyr Tyr Cys
                85                  90                  95

Ala Lys Pro Lys Asp Met Ile Val Val Pro Ala Gly Phe Asp Ser
            100                 105                 110

Trp Gly Gln Gly Thr Leu Val Ser Val Ser Ser
        115                 120

<210> SEQ ID NO 11
<211> LENGTH: 315
<212> TYPE: DNA
<213> ORGANISM: Homo sapiens
<220> FEATURE:
<221> NAME/KEY: CDS
<222> LOCATION: (1)..(315)
<223> OTHER INFORMATION: 13B11-VL variable light chain (VL) sequence,
      kappa type
<220> FEATURE:
<221> NAME/KEY: V_region
<222> LOCATION: (70)..(102)
<223> OTHER INFORMATION: complementarity determining region (CDR)
      VL-CDR1
<220> FEATURE:
<221> NAME/KEY: V_region
<222> LOCATION: (148)..(168)
<223> OTHER INFORMATION: complementarity determining region (CDR)
      VL-CDR2
<220> FEATURE:
<221> NAME/KEY: V_region
<222> LOCATION: (265)..(285)
<223> OTHER INFORMATION: complementarity determining region (CDR)
      VL-CDR3

<400> SEQUENCE: 11 gac atc cag atg acc cag ttt cca tcc acc ctg tct gca tct gtt gga    48
Asp Ile Gln Met Thr Gln Phe Pro Ser Thr Leu Ser Ala Ser Val Gly
1               5                   10                  15 gac agc gtc acc atc act tgc cgg gcc agt cag agc att agt gcc tgg    96
Asp Ser Val Thr Ile Thr Cys Arg Ala Ser Gln Ser Ile Ser Ala Trp
            20                  25                  30 ttg gcc tgg tat cag cag aaa cca ggg aaa gcc cct aaa ctc ctg atc    144
Leu Ala Trp Tyr Gln Gln Lys Pro Gly Lys Ala Pro Lys Leu Leu Ile
        35                  40                  45 tat aag ggg tct aga tta gaa aac ggg gtc cca tcg agg ttc agc ggc    192
Tyr Lys Gly Ser Arg Leu Glu Asn Gly Val Pro Ser Arg Phe Ser Gly
```

| | | | | | | | | | | | | | | | |
|---|---|---|---|---|---|---|---|---|---|---|---|---|---|---|---|
| | | 50 | | | 55 | | | | 60 | | | | | | |
| agt | gga | tct | ggg | aca | gaa | ttc | act | ctc | acc | atc | ggc | agc | ctg | cag | cct | 240 |
| Ser | Gly | Ser | Gly | Thr | Glu | Phe | Thr | Leu | Thr | Ile | Gly | Ser | Leu | Gln | Pro | |
| 65 | | | | 70 | | | | | 75 | | | | | 80 | | |
| gat | gat | ttt | gca | act | tat | tac | tgc | caa | caa | tat | aag | act | tgg | acg | ttc | 288 |
| Asp | Asp | Phe | Ala | Thr | Tyr | Tyr | Cys | Gln | Gln | Tyr | Lys | Thr | Trp | Thr | Phe | |
| | | | | 85 | | | | | 90 | | | | | 95 | | |
| ggc | caa | ggg | acc | aag | gtg | gaa | atc | aaa | | | | | | | | 315 |
| Gly | Gln | Gly | Thr | Lys | Val | Glu | Ile | Lys | | | | | | | | |
| | | 100 | | | | | 105 | | | | | | | | | |

<210> SEQ ID NO 12
<211> LENGTH: 105
<212> TYPE: PRT
<213> ORGANISM: Homo sapiens

<400> SEQUENCE: 12

Asp Ile Gln Met Thr Gln Phe Pro Ser Thr Leu Ser Ala Ser Val Gly
1               5                   10                  15

Asp Ser Val Thr Ile Thr Cys Arg Ala Ser Gln Ser Ile Ser Ala Trp
            20                  25                  30

Leu Ala Trp Tyr Gln Gln Lys Pro Gly Lys Ala Pro Lys Leu Leu Ile
        35                  40                  45

Tyr Lys Gly Ser Arg Leu Glu Asn Gly Val Pro Ser Arg Phe Ser Gly
    50                  55                  60

Ser Gly Ser Gly Thr Glu Phe Thr Leu Thr Ile Gly Ser Leu Gln Pro
65                  70                  75                  80

Asp Asp Phe Ala Thr Tyr Tyr Cys Gln Gln Tyr Lys Thr Trp Thr Phe
                85                  90                  95

Gly Gln Gly Thr Lys Val Glu Ile Lys
            100                 105

<210> SEQ ID NO 13
<211> LENGTH: 993
<212> TYPE: DNA
<213> ORGANISM: Homo sapiens
<220> FEATURE:
<221> NAME/KEY: CDS
<222> LOCATION: (1)..(993)
<223> OTHER INFORMATION: 13B11-CH constant heavy chain (CH) sequence

<400> SEQUENCE: 13

| | | | | | | | | | | | | | | | |
|---|---|---|---|---|---|---|---|---|---|---|---|---|---|---|---|
| gcc | tcc | acc | aag | ggc | cca | tcg | gtc | ttc | ccc | ctg | gca | ccc | tcc | tcc | aag | 48 |
| Ala | Ser | Thr | Lys | Gly | Pro | Ser | Val | Phe | Pro | Leu | Ala | Pro | Ser | Ser | Lys | |
| 1 | | | | 5 | | | | | 10 | | | | | 15 | | |
| agc | acc | tct | ggg | ggc | aca | gcg | gcc | ctg | ggc | tgc | ctg | gtc | aag | gac | tac | 96 |
| Ser | Thr | Ser | Gly | Gly | Thr | Ala | Ala | Leu | Gly | Cys | Leu | Val | Lys | Asp | Tyr | |
| | | | 20 | | | | | 25 | | | | | 30 | | | |
| ttc | ccc | gaa | ccg | gtg | acg | gtg | tcg | tgg | aac | tca | ggc | gcc | ctg | acc | agc | 144 |
| Phe | Pro | Glu | Pro | Val | Thr | Val | Ser | Trp | Asn | Ser | Gly | Ala | Leu | Thr | Ser | |
| | | 35 | | | | | 40 | | | | | 45 | | | | |
| ggc | gtg | cac | acc | ttc | ccg | gct | gtc | cta | cag | tcc | tca | gga | ctc | tac | tcc | 192 |
| Gly | Val | His | Thr | Phe | Pro | Ala | Val | Leu | Gln | Ser | Ser | Gly | Leu | Tyr | Ser | |
| | 50 | | | | | 55 | | | | | 60 | | | | | |
| ctc | agc | agc | gtg | gtg | acc | gtg | ccc | tcc | agc | agc | ttg | ggc | acc | cag | acc | 240 |
| Leu | Ser | Ser | Val | Val | Thr | Val | Pro | Ser | Ser | Ser | Leu | Gly | Thr | Gln | Thr | |
| 65 | | | | 70 | | | | | 75 | | | | | 80 | | |
| tac | atc | tgc | aac | gtg | aat | cac | aag | ccc | agc | aac | acc | aag | gtg | gac | aag | 288 |
| Tyr | Ile | Cys | Asn | Val | Asn | His | Lys | Pro | Ser | Asn | Thr | Lys | Val | Asp | Lys | |
| | | | | 85 | | | | | 90 | | | | | 95 | | |

| | | |
|---|---|---|
| aaa gtt gag ccc aaa tct tgt gac aaa act cac aca tgc cca ccg tgc<br>Lys Val Glu Pro Lys Ser Cys Asp Lys Thr His Thr Cys Pro Pro Cys<br>                    100                      105                  110 | 336 |
| cca gca cct gaa ctc ctg ggg gga ccg tca gtc ttc ctc ttc ccc cca<br>Pro Ala Pro Glu Leu Leu Gly Gly Pro Ser Val Phe Leu Phe Pro Pro<br>         115                      120                    125 | 384 |
| aaa ccc aag gac acc ctc atg atc tcc cgg acc cct gag gtc aca tgc<br>Lys Pro Lys Asp Thr Leu Met Ile Ser Arg Thr Pro Glu Val Thr Cys<br>130                      135                      140 | 432 |
| gtg gtg gtg gac gtg agc cac gaa gac cct gag gtc aag ttc aac tgg<br>Val Val Val Asp Val Ser His Glu Asp Pro Glu Val Lys Phe Asn Trp<br>145                      150                      155                  160 | 480 |
| tac gtg gac ggc gtg gag gtg cat aat gcc aag aca aag ccg cgg gag<br>Tyr Val Asp Gly Val Glu Val His Asn Ala Lys Thr Lys Pro Arg Glu<br>                    165                      170                    175 | 528 |
| gag cag tac aac agc acg tac cgt gtg gtc agc gtc ctc acc gtc ctg<br>Glu Gln Tyr Asn Ser Thr Tyr Arg Val Val Ser Val Leu Thr Val Leu<br>                  180                      185                    190 | 576 |
| cac cag gac tgg ctg aat ggc aag gag tac aag tgc aag gtc tcc aac<br>His Gln Asp Trp Leu Asn Gly Lys Glu Tyr Lys Cys Lys Val Ser Asn<br>         195                      200                    205 | 624 |
| aaa gcc ctc cca gcc ccc atc gag aaa acc atc tcc aaa gcc aaa ggg<br>Lys Ala Leu Pro Ala Pro Ile Glu Lys Thr Ile Ser Lys Ala Lys Gly<br>210                      215                      220 | 672 |
| cag ccc cga gaa cca cag gtg tac acc ctg ccc cca tcc cgg gat gag<br>Gln Pro Arg Glu Pro Gln Val Tyr Thr Leu Pro Pro Ser Arg Asp Glu<br>225                      230                      235                  240 | 720 |
| ctg acc aag aac cag gtc agc ctg acc tgc ctg gtc aaa ggc ttc tat<br>Leu Thr Lys Asn Gln Val Ser Leu Thr Cys Leu Val Lys Gly Phe Tyr<br>                  245                      250                    255 | 768 |
| ccc agc gac atc gcc gtg gag tgg gag agc aat ggg cag ccg gag aac<br>Pro Ser Asp Ile Ala Val Glu Trp Glu Ser Asn Gly Gln Pro Glu Asn<br>                    260                      265                    270 | 816 |
| aac tac aag acc acg cct ccc gtg ctg gac tcc gac ggc tcc ttc ttc<br>Asn Tyr Lys Thr Thr Pro Pro Val Leu Asp Ser Asp Gly Ser Phe Phe<br>         275                      280                    285 | 864 |
| ctc tac agc aag ctc acc gtg gac aag agc agg tgg cag cag ggg aac<br>Leu Tyr Ser Lys Leu Thr Val Asp Lys Ser Arg Trp Gln Gln Gly Asn<br>290                      295                      300 | 912 |
| gtc ttc tca tgc tcc gtg atg cat gag gct ctg cac aac cac tac acg<br>Val Phe Ser Cys Ser Val Met His Glu Ala Leu His Asn His Tyr Thr<br>305                      310                      315                  320 | 960 |
| cag aag agc ctc tcc ctg tct ccg ggt aaa tga<br>Gln Lys Ser Leu Ser Leu Ser Pro Gly Lys<br>                  325                      330 | 993 |

<210> SEQ ID NO 14
<211> LENGTH: 330
<212> TYPE: PRT
<213> ORGANISM: Homo sapiens

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 15
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: 13B11-CL constant kappa chain (CL) sequence

<400> SEQUENCE: 15 cga act gtg gct gca cca tct gtc ttc atc ttc ccg cca tct gat gag        48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc        96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa        144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc        192
Ser Gly Asn Ser Gln Glu Ser Val Thr Glu Gln Asp Ser Lys Asp Ser
    50                  55                  60

```
acc tac agc ctc agc agc acc ctg acg ctg agc aaa gca gac tac gag    240
Thr Tyr Ser Leu Ser Ser Thr Leu Thr Leu Ser Lys Ala Asp Tyr Glu
65                  70                  75                  80 aaa cac aaa gtc tac gcc tgc gaa gtc acc cat cag ggc ctg agc tcg    288
Lys His Lys Val Tyr Ala Cys Glu Val Thr His Gln Gly Leu Ser Ser
                85                  90                  95 ccc gtc aca aag agc ttc aac agg gga gag tgt tag                    324
Pro Val Thr Lys Ser Phe Asn Arg Gly Glu Cys
            100                 105
```

<210> SEQ ID NO 16
<211> LENGTH: 107
<212> TYPE: PRT
<213> ORGANISM: Homo sapiens

<400> SEQUENCE: 16

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 17
<211> LENGTH: 378
<212> TYPE: DNA
<213> ORGANISM: Homo sapiens
<220> FEATURE:
<221> NAME/KEY: CDS
<222> LOCATION: (1)..(378)
<223> OTHER INFORMATION: 19D11-VH variable heavy chain (VH) sequence;
      19D11: IgG1, kappa
<220> FEATURE:
<221> NAME/KEY: misc_feature
<222> LOCATION: (1)..(18)
<223> OTHER INFORMATION: not sequenced but obtained from database
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(345)
<223> OTHER INFORMATION: complementarity determining region (CDR)
      VH-CDR3
<220> FEATURE:
<221> NAME/KEY: misc_feature
<222> LOCATION: (361)..(378)
<223> OTHER INFORMATION: not sequenced but obtained from database

<400> SEQUENCE: 17

```
gag gtg cag ctg ttg gag tct ggg gct gag gtg aag agg cct ggg tcg    48
```

```
                                   Glu Val Gln Leu Leu Glu Ser Gly Ala Glu Val Lys Arg Pro Gly Ser
                                   1               5                   10                  15 tcg gtg agg gtc tcc tgc agg gct tct gga gac acc ttc agc agt tac          96
Ser Val Arg Val Ser Cys Arg Ala Ser Gly Asp Thr Phe Ser Ser Tyr
                20                  25                  30 cct atc agt tgg gtg cga cag gcc cct gga caa ggc ctt gag tgg atg         144
Pro Ile Ser Trp Val Arg Gln Ala Pro Gly Gln Gly Leu Glu Trp Met
            35                  40                  45 gga agg atc ctc cct gcc ctt ggt gtc aca aac tac gct cag aac ttc         192
Gly Arg Ile Leu Pro Ala Leu Gly Val Thr Asn Tyr Ala Gln Asn Phe
        50                  55                  60 cgg ggc aga atc acg att acc gcg gac aag tcg ccc ctc aca gcc tac         240
Arg Gly Arg Ile Thr Ile Thr Ala Asp Lys Ser Pro Leu Thr Ala Tyr
65                  70                  75                  80 ttg gaa ctg agt agc ctc aga ttt gag gac acg gcc gtg tat tac tgt         288
Leu Glu Leu Ser Ser Leu Arg Phe Glu Asp Thr Ala Val Tyr Tyr Cys
                    85                  90                  95 gcg agt ccc agt gcg gac ata att cct tcg att ttg ggg acg acc ctc         336
Ala Ser Pro Ser Ala Asp Ile Ile Pro Ser Ile Leu Gly Thr Thr Leu
                100                 105                 110 ttt gcc ttc tgg ggc cag gga agc ctg gtc acc gtc tcc tca                 378
Phe Ala Phe Trp Gly Gln Gly Ser Leu Val Thr Val Ser Ser
            115                 120                 125
```

<210> SEQ ID NO 18
<211> LENGTH: 126
<212> TYPE: PRT
<213> ORGANISM: Homo sapiens

<400> SEQUENCE: 18

```
Glu Val Gln Leu Leu Glu Ser Gly Ala Glu Val Lys Arg Pro Gly Ser
1               5                   10                  15

Ser Val Arg Val Ser Cys Arg Ala Ser Gly Asp Thr Phe Ser Ser Tyr
                20                  25                  30

Pro Ile Ser Trp Val Arg Gln Ala Pro Gly Gln Gly Leu Glu Trp Met
            35                  40                  45

Gly Arg Ile Leu Pro Ala Leu Gly Val Thr Asn Tyr Ala Gln Asn Phe
        50                  55                  60

Arg Gly Arg Ile Thr Ile Thr Ala Asp Lys Ser Pro Leu Thr Ala Tyr
65                  70                  75                  80

Leu Glu Leu Ser Ser Leu Arg Phe Glu Asp Thr Ala Val Tyr Tyr Cys
                    85                  90                  95

Ala Ser Pro Ser Ala Asp Ile Ile Pro Ser Ile Leu Gly Thr Thr Leu
                100                 105                 110

Phe Ala Phe Trp Gly Gln Gly Ser Leu Val Thr Val Ser Ser
            115                 120                 125
```

<210> SEQ ID NO 19
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: 19D11-VL variable light chain (VL) sequence,
      kappa type
<220> FEATURE:
<221> NAME/KEY: misc_feature
<222> LOCATION: (1)..(18)
<223> OTHER INFORMATION: not sequenced but obtained from database
<220> FEATURE:
<221> NAME/KEY: V_region

```
<222> LOCATION: (70)..(105)
<223> OTHER INFORMATION: complementarity determining region (CDR)
      VL-CDR1
<220> FEATURE:
<221> NAME/KEY: V_region
<222> LOCATION: (151)..(171)
<223> OTHER INFORMATION: complementarity determining region (CDR)
      VL-CDR2
<220> FEATURE:
<221> NAME/KEY: V_region
<222> LOCATION: (268)..(300)
<223> OTHER INFORMATION: complementarity determining region (CDR)
      VL-CDR3
<220> FEATURE:
<221> NAME/KEY: misc_feature
<222> LOCATION: (312)..(330)
<223> OTHER INFORMATION: not sequenced but obtained from database

<400> SEQUENCE: 19 gaa att gtg ttg acg cag tct cca ggc acc ctg tct ctg tct ccg ggg      48
Glu Ile Val Leu Thr Gln Ser Pro Gly Thr Leu Ser Leu Ser Pro Gly
1               5                   10                  15 gaa ggg gcc acc ctc tcc tgc agg gcc agt cag aat gtt agc aga cac      96
Glu Gly Ala Thr Leu Ser Cys Arg Ala Ser Gln Asn Val Ser Arg His
            20                  25                  30 tac tta acc tgg tac cag cag aaa cct ggc cag tct ccc cgg ctc ctc     144
Tyr Leu Thr Trp Tyr Gln Gln Lys Pro Gly Gln Ser Pro Arg Leu Leu
        35                  40                  45 atc tat ggt ggc tcc agc agg gcc act ggc gtc cca gac agg ttc agt     192
Ile Tyr Gly Gly Ser Ser Arg Ala Thr Gly Val Pro Asp Arg Phe Ser
    50                  55                  60 ggc ggt ggg tct ggg aca gac ttc act ctc acc atc agc agg ctg gag     240
Gly Gly Gly Ser Gly Thr Asp Phe Thr Leu Thr Ile Ser Arg Leu Glu
65                  70                  75                  80 cct gaa gac ttt gca gtg ttt tac tgc cag agc tat cat agc cca cct     288
Pro Glu Asp Phe Ala Val Phe Tyr Cys Gln Ser Tyr His Ser Pro Pro
                85                  90                  95 cct gtg tac act ttc ggc cag ggg acc aag gtg gag atc aaa             330
Pro Val Tyr Thr Phe Gly Gln Gly Thr Lys Val Glu Ile Lys
            100                 105                 110

<210> SEQ ID NO 20
<211> LENGTH: 110
<212> TYPE: PRT
<213> ORGANISM: Homo sapiens

<400> SEQUENCE: 20

Glu Ile Val Leu Thr Gln Ser Pro Gly Thr Leu Ser Leu Ser Pro Gly
1               5                   10                  15

Glu Gly Ala Thr Leu Ser Cys Arg Ala Ser Gln Asn Val Ser Arg His
            20                  25                  30

Tyr Leu Thr Trp Tyr Gln Gln Lys Pro Gly Gln Ser Pro Arg Leu Leu
        35                  40                  45

Ile Tyr Gly Gly Ser Ser Arg Ala Thr Gly Val Pro Asp Arg Phe Ser
    50                  55                  60

Gly Gly Gly Ser Gly Thr Asp Phe Thr Leu Thr Ile Ser Arg Leu Glu
65                  70                  75                  80

Pro Glu Asp Phe Ala Val Phe Tyr Cys Gln Ser Tyr His Ser Pro Pro
                85                  90                  95

Pro Val Tyr Thr Phe Gly Gln Gly Thr Lys Val Glu Ile Lys
            100                 105                 110

<210> SEQ ID NO 21
```

<211> LENGTH: 366
<212> TYPE: DNA
<213> ORGANISM: Homo sapiens
<220> FEATURE:
<221> NAME/KEY: CDS
<222> LOCATION: (1)..(366)
<223> OTHER INFORMATION: 25C3-VH variable heavy chain (VH) sequence;
      25C3: IgG1, kappa
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(333)
<223> OTHER INFORMATION: complementarity determining region (CDR)
      VH-CDR3

<400> SEQUENCE: 21

```
gag atg cag ctg atg gag tct ggg gga ggt ttg gta caa ccg ggg ggg       48
Glu Met Gln Leu Met Glu Ser Gly Gly Gly Leu Val Gln Pro Gly Gly
1               5                   10                  15 tcc ctg aga ctc tcc tgt gta gcc tct ggt ttc acc ttt aaa agt ttt       96
Ser Leu Arg Leu Ser Cys Val Ala Ser Gly Phe Thr Phe Lys Ser Phe
            20                  25                  30 gcg atg agt tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45 gct agt gtc ggc tct cag ggt ggc agc aaa tac tat gca ccc tcc gtg      192
Ala Ser Val Gly Ser Gln Gly Gly Ser Lys Tyr Tyr Ala Pro Ser Val
    50                  55                  60 aag ggc cgg ttc tcc atc tcc aga gac aat tcc aac aac act ctc tat      240
Lys Gly Arg Phe Ser Ile Ser Arg Asp Asn Ser Asn Asn Thr Leu Tyr
65                  70                  75                  80 gtg caa atg aac agc ctg gga gtc gag gac acg gcc ttt tat tat tgt      288
Val Gln Met Asn Ser Leu Gly Val Glu Asp Thr Ala Phe Tyr Tyr Cys
                85                  90                  95 gtt aaa gag acc gat gca gtg gcg acg atg gac gct ctt gac atg tgg      336
Val Lys Glu Thr Asp Ala Val Ala Thr Met Asp Ala Leu Asp Met Trp
            100                 105                 110 ggc caa ggg acc ctg gtc atc gtc tct acc                              366
Gly Gln Gly Thr Leu Val Ile Val Ser Thr
        115                 120
```

<210> SEQ ID NO 22
<211> LENGTH: 122
<212> TYPE: PRT
<213> ORGANISM: Homo sapiens

<400> SEQUENCE: 22

```
Glu Met Gln Leu Met Glu Ser Gly Gly Gly Leu Val Gln Pro Gly Gly
1               5                   10                  15

Ser Leu Arg Leu Ser Cys Val Ala Ser Gly Phe Thr Phe Lys Ser Phe
            20                  25                  30

Ala Met Ser Trp Val Arg Gln Ala Pro Gly Lys Gly Leu Glu Trp Val
        35                  40                  45

Ala Ser Val Gly Ser Gln Gly Gly Ser Lys Tyr Tyr Ala Pro Ser Val
    50                  55                  60

Lys Gly Arg Phe Ser Ile Ser Arg Asp Asn Ser Asn Asn Thr Leu Tyr
```

```
                65                  70                  75                  80
Val Gln Met Asn Ser Leu Gly Val Glu Asp Thr Ala Phe Tyr Tyr Cys
                        85                  90                  95

Val Lys Glu Thr Asp Ala Val Ala Thr Met Asp Ala Leu Asp Met Trp
                        100                 105                 110

Gly Gln Gly Thr Leu Val Ile Val Ser Thr
                        115                 120

<210> SEQ ID NO 23
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: 25C3-VL variable light chain (VL) sequence,
      kappa type
<220> FEATURE:
<221> NAME/KEY: V_region
<222> LOCATION: (70)..(102)
<223> OTHER INFORMATION: complementarity determining region (CDR)
      VL-CDR1
<220> FEATURE:
<221> NAME/KEY: V_region
<222> LOCATION: (148)..(168)
<223> OTHER INFORMATION: complementarity determining region (CDR)
      VL-CDR2
<220> FEATURE:
<221> NAME/KEY: V_region
<222> LOCATION: (265)..(291)
<223> OTHER INFORMATION: complementarity determining region (CDR)
      VL-CDR3

<400> SEQUENCE: 23 gac atc cgg gtg acc cag tct cca tcc tcc ctg tct gca tct gtc gga      48
Asp Ile Arg Val Thr Gln Ser Pro Ser Ser Leu Ser Ala Ser Val Gly
1               5                   10                  15 gac agg gtc tcc atc tct tgc cag aca agt cag agt gtt aac ata tat      96
Asp Arg Val Ser Ile Ser Cys Gln Thr Ser Gln Ser Val Asn Ile Tyr
            20                  25                  30 cta aat tgg tat caa cag aga cca ggg aaa ggc cct cag ctc ctg atc     144
Leu Asn Trp Tyr Gln Gln Arg Pro Gly Lys Gly Pro Gln Leu Leu Ile
        35                  40                  45 tct gct gct tcc act ttg cag agt ggg gtc cca tca agg ttc agt ggc     192
Ser Ala Ala Ser Thr Leu Gln Ser Gly Val Pro Ser Arg Phe Ser Gly
    50                  55                  60 agt gga tct ggg aca gac ttc atc ctc acc atc atc agt cta caa cct     240
Ser Gly Ser Gly Thr Asp Phe Ile Leu Thr Ile Ile Ser Leu Gln Pro
65                  70                  75                  80 gaa gat tct gca tcc tac tac tgt caa cag ggt tac att acc ccg tac     288
Glu Asp Ser Ala Ser Tyr Tyr Cys Gln Gln Gly Tyr Ile Thr Pro Tyr
                85                  90                  95 act ttt ggc cag ggg acc aag gtg gag atc aaa                         321
Thr Phe Gly Gln Gly Thr Lys Val Glu Ile Lys
                100                 105

<210> SEQ ID NO 24
<211> LENGTH: 107
<212> TYPE: PRT
<213> ORGANISM: Homo sapiens

<400> SEQUENCE: 24

Asp Ile Arg Val Thr Gln Ser Pro Ser Ser Leu Ser Ala Ser Val Gly
1               5                   10                  15

Asp Arg Val Ser Ile Ser Cys Gln Thr Ser Gln Ser Val Asn Ile Tyr
```

```
                20                  25                  30
Leu Asn Trp Tyr Gln Gln Arg Pro Gly Lys Gly Pro Gln Leu Leu Ile
         35                  40                  45

Ser Ala Ala Ser Thr Leu Gln Ser Gly Val Pro Ser Arg Phe Ser Gly
 50                  55                  60

Ser Gly Ser Gly Thr Asp Phe Ile Leu Thr Ile Ser Leu Gln Pro
 65                  70                  75                  80

Glu Asp Ser Ala Ser Tyr Tyr Cys Gln Gln Gly Tyr Ile Thr Pro Tyr
                 85                  90                  95

Thr Phe Gly Gln Gly Thr Lys Val Glu Ile Lys
             100                 105

<210> SEQ ID NO 25
<211> LENGTH: 993
<212> TYPE: DNA
<213> ORGANISM: Homo sapiens
<220> FEATURE:
<221> NAME/KEY: CDS
<222> LOCATION: (1)..(993)
<223> OTHER INFORMATION: 25C3-constant heavy chain (CH) sequence

<400> SEQUENCE: 25 gcc tcc acc aag ggc cca tcg gtc ttc ccc ctg gca ccc tcc tcc aag      48
Ala Ser Thr Lys Gly Pro Ser Val Phe Pro Leu Ala Pro Ser Ser Lys
 1               5                  10                  15 agc acc tct ggg ggc aca gcg gcc ctg ggc tgc ctg gtc aag gac tac      96
Ser Thr Ser Gly Gly Thr Ala Ala Leu Gly Cys Leu Val Lys Asp Tyr
             20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
         35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
 50                  55                  60 ctc agc agc gtg gtg acc gtg ccc tcc agc agc ttg ggc acc cag acc     240
Leu Ser Ser Val Val Thr Val Pro Ser Ser Ser Leu Gly Thr Gln Thr
 65                  70                  75                  80 tac atc tgc aac gtg aat cac aag ccc agc aac acc aag gtg gac aag     288
Tyr Ile Cys Asn Val Asn His Lys Pro Ser Asn Thr Lys Val Asp Lys
                 85                  90                  95 aga gtt gag ccc aaa tct tgt gac aaa act cac aca tgc cca ccg tgc     336
Arg Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca     384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc     432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg     480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag     528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg     576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac     624
His Gln Asp Trp Leu Asn Gly Lys Glu Tyr Lys Cys Lys Val Ser Asn
```

```
aaa gcc ctc cca gcc ccc atc gag aaa acc atc tcc aaa gcc aaa ggg      672
Lys Ala Leu Pro Ala Pro Ile Glu Lys Thr Ile Ser Lys Ala Lys Gly
    210             215                 220 cag ccc cga gaa cca cag gtg tac acc ctg ccc cca tcc cgg gag gag      720
Gln Pro Arg Glu Pro Gln Val Tyr Thr Leu Pro Pro Ser Arg Glu Glu
225             230                 235                 240 atg acc aag aac cag gtc agc ctg acc tgc ctg gtc aaa ggc ttc tat      768
Met Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac      816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc      864
Asn Tyr Lys Thr Thr Pro Pro Val Leu Asp Ser Asp Gly Ser Phe Phe
        275                 280                 285 ctc tat agc aag ctc acc gtg gac aag agc agg tgg cag cag ggg aac      912
Leu Tyr Ser Lys Leu Thr Val Asp Lys Ser Arg Trp Gln Gln Gly Asn
    290                 295                 300 gtc ttc tca tgc tcc gtg atg cat gag gct ctg cac aac cac tac acg      960
Val Phe Ser Cys Ser Val Met His Glu Ala Leu His Asn His Tyr Thr
305             310                 315                 320 cag aag agc ctc tcc ctg tcc ccg ggt aaa tga                          993
Gln Lys Ser Leu Ser Leu Ser Pro Gly Lys
                325                 330

<210> SEQ ID NO 26
<211> LENGTH: 330
<212> TYPE: PRT
<213> ORGANISM: Homo sapiens

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
              195                 200                 205
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 27
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: 25C3-constant kappa chain (CL) sequence
<220> FEATURE:
<221> NAME/KEY: misc_feature
<222> LOCATION: (268)..(324)
<223> OTHER INFORMATION: not sequenced but obtained from database

<400> SEQUENCE: 27 cga act gtg gct gca cca tct gtc ttc atc ttc ccg cca tct gat gag      48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ctc      96
Gln Leu Lys Ser Gly Thr Ala Ser Val Val Cys Leu Leu Asn Asn Leu
            20                  25                  30 tat ccc aga gag gcc aaa gta cag tgg aag gtg gat aac gcc ctc caa     144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc     192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag     240
Thr Tyr Ser Leu Ser Ser Thr Leu Thr Leu Ser Lys Ala Asp Tyr Glu
65                  70                  75                  80 aaa cac aaa gtc tac gcc tgc gaa gtc acc cat cag ggc ctg agc tcg     288
Lys His Lys Val Tyr Ala Cys Glu Val Thr His Gln Gly Leu Ser Ser
                85                  90                  95 ccc gtc aca aag agc ttc aac agg gga gag tgt tag                     324
Pro Val Thr Lys Ser Phe Asn Arg Gly Glu Cys
            100                 105

<210> SEQ ID NO 28
<211> LENGTH: 107
<212> TYPE: PRT
<213> ORGANISM: Homo sapiens

<400> SEQUENCE: 28

Arg Thr Val Ala Ala Pro Ser Val Phe Ile Phe Pro Pro Ser Asp Glu
```

```
              1               5                  10                 15
              Gln Leu Lys Ser Gly Thr Ala Ser Val Val Cys Leu Leu Asn Asn Leu
                      20                  25                  30
              Tyr Pro Arg Glu Ala Lys Val Gln Trp Lys Val Asp Asn Ala Leu Gln
                      35                  40                  45
              Ser Gly Asn Ser Gln Glu Ser Val Thr Glu Gln Asp Ser Lys Asp Ser
                      50                  55                  60
              Thr Tyr Ser Leu Ser Ser Thr Leu Thr Leu Ser Lys Ala Asp Tyr Glu
               65                  70                  75                  80
              Lys His Lys Val Tyr Ala Cys Glu Val Thr His Gln Gly Leu Ser Ser
                              85                  90                  95
              Pro Val Thr Lys Ser Phe Asn Arg Gly Glu Cys
                          100                 105

<210> SEQ ID NO 29
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: 26B9-VH variable heavy chain (VH) sequence;
      26B9: IgG1, kappa
<220> FEATURE:
<221> NAME/KEY: V_region
<222> LOCATION: (91)..(111)
<223> OTHER INFORMATION: complementarity determining region (CDR)
      VH-CDR1
<220> FEATURE:
<221> NAME/KEY: V_region
<222> LOCATION: (154)..(201)
<223> OTHER INFORMATION: complementarity determining region (CDR)
      VH-CDR2
<220> FEATURE:
<221> NAME/KEY: V_region
<222> LOCATION: (298)..(339)
<223> OTHER INFORMATION: complementarity determining region (CDR)
      VH-CDR3

<400> SEQUENCE: 29 cag ata cta ctg cag gag tcg ggc cca gga ctg gtg aag ccc acg gag       48
Gln Ile Leu Leu Gln Glu Ser Gly Pro Gly Leu Val Lys Pro Thr Glu
 1               5                  10                  15 acc ctg tcc ctc acc tgt agt gtc tct ggt gac tcc atc agt gat agt       96
Thr Leu Ser Leu Thr Cys Ser Val Ser Gly Asp Ser Ile Ser Asp Ser
              20                  25                  30 agt cac tac tgg gcc tgg att cgc cag ccc cca ggg aag gga cca gag      144
Ser His Tyr Trp Ala Trp Ile Arg Gln Pro Pro Gly Lys Gly Pro Glu
          35                  40                  45 tgg att ggc agt gtc tat ttt agt tcg atg acc cac tac aac ccg tcc      192
Trp Ile Gly Ser Val Tyr Phe Ser Ser Met Thr His Tyr Asn Pro Ser
      50                  55                  60 ctc aaa agt cgc gtc agc atc tcc gtt gac aag ccc aag aac cag ttc      240
Leu Lys Ser Arg Val Ser Ile Ser Val Asp Lys Pro Lys Asn Gln Phe
 65                  70                  75                  80 tcc tta aaa gtg acc tct gtg act gtc gcc gac acg gcc aca tat tac      288
Ser Leu Lys Val Thr Ser Val Thr Val Ala Asp Thr Ala Thr Tyr Tyr
                  85                  90                  95 tgt gcg aga caa gcc ctt gcc cga gtc gga gcc atg aat tgg ttc gac      336
Cys Ala Arg Gln Ala Leu Ala Arg Val Gly Ala Met Asn Trp Phe Asp
             100                 105                 110 ccc tgg ggc cag gga tct ctg gtc aca gtc tcc tca                      372
Pro Trp Gly Gln Gly Ser Leu Val Thr Val Ser Ser
         115                 120
```

<210> SEQ ID NO 30
<211> LENGTH: 124
<212> TYPE: PRT
<213> ORGANISM: Homo sapiens

<400> SEQUENCE: 30

Gln Ile Leu Leu Gln Glu Ser Gly Pro Gly Leu Val Lys Pro Thr Glu
1               5                   10                  15

Thr Leu Ser Leu Thr Cys Ser Val Ser Gly Asp Ser Ile Ser Asp Ser
            20                  25                  30

Ser His Tyr Trp Ala Trp Ile Arg Gln Pro Pro Gly Lys Gly Pro Glu
        35                  40                  45

Trp Ile Gly Ser Val Tyr Phe Ser Ser Met Thr His Tyr Asn Pro Ser
    50                  55                  60

Leu Lys Ser Arg Val Ser Ile Ser Val Asp Lys Pro Lys Asn Gln Phe
65                  70                  75                  80

Ser Leu Lys Val Thr Ser Val Thr Val Ala Asp Thr Ala Thr Tyr Tyr
                85                  90                  95

Cys Ala Arg Gln Ala Leu Ala Arg Val Gly Ala Met Asn Trp Phe Asp
            100                 105                 110

Pro Trp Gly Gln Gly Ser Leu Val Thr Val Ser Ser
        115                 120

<210> SEQ ID NO 31
<211> LENGTH: 339
<212> TYPE: DNA
<213> ORGANISM: Homo sapiens
<220> FEATURE:
<221> NAME/KEY: CDS
<222> LOCATION: (1)..(339)
<223> OTHER INFORMATION: 26B9-VL variable light chain (VL) sequence,
      kappa type
<220> FEATURE:
<221> NAME/KEY: V_region
<222> LOCATION: (70)..(120)
<223> OTHER INFORMATION: complementarity determining region (CDR)
      VL-CDR1
<220> FEATURE:
<221> NAME/KEY: V_region
<222> LOCATION: (166)..(186)
<223> OTHER INFORMATION: complementarity determining region (CDR)
      VL-CDR2
<220> FEATURE:
<221> NAME/KEY: V_region
<222> LOCATION: (283)..(309)
<223> OTHER INFORMATION: complementarity determining region (CDR)
      VL-CDR3

<400> SEQUENCE: 31 gac atc ata atg acc cag tct cca gac tcc ctg cct gtg tct ctg ggc      48
Asp Ile Ile Met Thr Gln Ser Pro Asp Ser Leu Pro Val Ser Leu Gly
1               5                   10                  15 gag ggg gtc acc atc aac tgc aag tcc agc cag agc gtc ttt ttc acc      96
Glu Gly Val Thr Ile Asn Cys Lys Ser Ser Gln Ser Val Phe Phe Thr
            20                  25                  30 tcc agt aat aag agt tgt tta gct tgg tat cag cag aag cca gga aag     144
Ser Ser Asn Lys Ser Cys Leu Ala Trp Tyr Gln Gln Lys Pro Gly Lys
        35                  40                  45 tct ccc aaa ttg ctc att tac tgg gca tca ccc gc caa tcc ggg gtc     192
Ser Pro Lys Leu Leu Ile Tyr Trp Ala Ser Thr Arg Gln Ser Gly Val
    50                  55                  60 cct gac cga ttc aga ggc agc ggg tct ggg aca gat ttc tct ctc acc     240
Pro Asp Arg Phe Arg Gly Ser Gly Ser Gly Thr Asp Phe Ser Leu Thr

```
                    65                  70                  75                  80 atc acc agt ctg cag gct gaa gat gtg gct gtt tat ttc tgt cag cag          288
Ile Thr Ser Leu Gln Ala Glu Asp Val Ala Val Tyr Phe Cys Gln Gln
                85                  90                  95 tgt cag aca tcc cct ccc act ttc ggc gga ggg acc agg ttg gag atc          336
Cys Gln Thr Ser Pro Pro Thr Phe Gly Gly Gly Thr Arg Leu Glu Ile
            100                 105                 110 aaa                                                                      339
Lys <210> SEQ ID NO 32
<211> LENGTH: 113
<212> TYPE: PRT
<213> ORGANISM: Homo sapiens

<400> SEQUENCE: 32

Asp Ile Ile Met Thr Gln Ser Pro Asp Ser Leu Pro Val Ser Leu Gly
1               5                   10                  15

Glu Gly Val Thr Ile Asn Cys Lys Ser Ser Gln Ser Val Phe Phe Thr
            20                  25                  30

Ser Ser Asn Lys Ser Cys Leu Ala Trp Tyr Gln Gln Lys Pro Gly Lys
        35                  40                  45

Ser Pro Lys Leu Leu Ile Tyr Trp Ala Ser Thr Arg Gln Ser Gly Val
    50                  55                  60

Pro Asp Arg Phe Arg Gly Ser Gly Ser Gly Thr Asp Phe Ser Leu Thr
65                  70                  75                  80

Ile Thr Ser Leu Gln Ala Glu Asp Val Ala Val Tyr Phe Cys Gln Gln
                85                  90                  95

Cys Gln Thr Ser Pro Pro Thr Phe Gly Gly Gly Thr Arg Leu Glu Ile
            100                 105                 110

Lys

<210> SEQ ID NO 33
<211> LENGTH: 993
<212> TYPE: DNA
<213> ORGANISM: Homo sapiens
<220> FEATURE:
<221> NAME/KEY: CDS
<222> LOCATION: (1)..(993)
<223> OTHER INFORMATION: 26B9-CH constant heavy chain (CH) sequence

<400> SEQUENCE: 33 gcc tcc acc aag ggc cca tcg gtc ttc ccc ctg gca ccc tcc tcc aag          48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac          96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc          144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc          192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc          240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag          288
Tyr Ile Cys Asn Val Asn His Lys Pro Ser Asn Thr Lys Val Asp Lys
                85                  90                  95
```

```
aga gtt gag ccc aaa tct tgt gac aaa act cac aca tgc cca ccg tgc    336
Arg Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca    384
Pro Ala Pro Glu Leu Leu Gly Gly Pro Ser Val Phe Leu Phe Pro Pro
    115                 120                 125 aaa ccc aag gac acc ctc atg atc tcc cgg acc cct gag gtc aca tgc    432
Lys Pro Lys Asp Thr Leu Met Ile Ser Arg Thr Pro Glu Val Thr Cys
130                 135                 140 gtg gtg gtg gac gtg agc cac gaa gac cct gag gtc aag ttc aac tgg    480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag    528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg    576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac    624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg    672
Lys Ala Leu Pro Ala Pro Ile Glu Lys Thr Ile Ser Lys Ala Lys Gly
210                 215                 220 cag ccc cga gaa cca cag gtg tac acc ctg ccc cca tcc cgg gag gag    720
Gln Pro Arg Glu Pro Gln Val Tyr Thr Leu Pro Pro Ser Arg Glu Glu
225                 230                 235                 240 atg acc aag aac cag gtc agc ctg acc tgc ctg gtc aaa ggc ttc tat    768
Met Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac    816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc    864
Asn Tyr Lys Thr Thr Pro Pro Val Leu Asp Ser Asp Gly Ser Phe Phe
        275                 280                 285 ctc tat agc aag ctc acc gtg gac aag agc agg tgg cag cag ggg aac    912
Leu Tyr Ser Lys Leu Thr Val Asp Lys Ser Arg Trp Gln Gln Gly Asn
    290                 295                 300 gtc ttc tca tgc tcc gtg atg cat gag gct ctg cac aac cac tac acg    960
Val Phe Ser Cys Ser Val Met His Glu Ala Leu His Asn His Tyr Thr
305                 310                 315                 320 cag aag agc ctc tcc ctg tcc ccg ggt aaa tga                        993
Gln Lys Ser Leu Ser Leu Ser Pro Gly Lys
                325                 330

<210> SEQ ID NO 34
<211> LENGTH: 330
<212> TYPE: PRT
<213> ORGANISM: Homo sapiens

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
```

```
                50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 35
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: 26B9-CL constant kappa chain (CL) sequence

<400> SEQUENCE: 35 cga act gtg gct gca cca tct gtc ttc atc ttc ccg cca tct gat gag      48
Arg Thr Val Ala Ala Pro Ser Val Phe Ile Phe Pro Pro Ser Asp Glu
 1               5                  10                  15 cag ttg aaa tct gga act gcc tct gtt gtg tgc ctg ctg aat aac ttc      96
Gln Leu Lys Ser Gly Thr Ala Ser Val Val Cys Leu Leu Asn Asn Phe
                20                  25                  30 tat ccc aga gag gcc aaa gta cag tgg aag gtg gat aac gcc ctc caa     144
Tyr Pro Arg Glu Ala Lys Val Gln Trp Lys Val Asp Asn Ala Leu Gln
            35                  40                  45 tcg ggt aac tcc cag gag agt gtc aca gag cag gac agc aag gac agc     192
Ser Gly Asn Ser Gln Glu Ser Val Thr Glu Gln Asp Ser Lys Asp Ser
```

```
acc tac agc ctc agc agc acc ctg acg ctg agc aaa gca gac tac gag      240
Thr Tyr Ser Leu Ser Ser Thr Leu Thr Leu Ser Lys Ala Asp Tyr Glu
 65                  70                  75                  80 aaa cac aaa gtc tac gcc tgc gaa gtc acc cat cag ggc ctg agc tcg      288
Lys His Lys Val Tyr Ala Cys Glu Val Thr His Gln Gly Leu Ser Ser
                 85                  90                  95 ccc gtc aca aag agc ttc aac agg gga gag tgt tag                      324
Pro Val Thr Lys Ser Phe Asn Arg Gly Glu Cys
            100                 105
```

<210> SEQ ID NO 36
<211> LENGTH: 107
<212> TYPE: PRT
<213> ORGANISM: Homo sapiens

<400> SEQUENCE: 36

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 37
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: 31B4-VH variable heavy chain (VH) sequence;
      31B4: IgG1, kappa
<220> FEATURE:
<221> NAME/KEY: V_region
<222> LOCATION: (91)..(111)
<223> OTHER INFORMATION: complementarity determining region (CDR)
      VH-CDR1
<220> FEATURE:
<221> NAME/KEY: V_region
<222> LOCATION: (154)..(201)
<223> OTHER INFORMATION: complementarity determining region (CDR)
      VH-CDR2
<220> FEATURE:
<221> NAME/KEY: V_region
<222> LOCATION: (298)..(339)
<223> OTHER INFORMATION: complementarity determining region (CDR)
      VH-CDR3

<400> SEQUENCE: 37

```
cag ata cag ctg cag gag tcg ggc cca gga ctg gtg agg ccc acg gag       48
Gln Ile Gln Leu Gln Glu Ser Gly Pro Gly Leu Val Arg Pro Thr Glu
 1               5                  10                  15 acc ctg tcc ctc act tgt agt gtc tct ggt gac tcc atc agt cag agt       96
Thr Leu Ser Leu Thr Cys Ser Val Ser Gly Asp Ser Ile Ser Gln Ser
            20                  25                  30
```

```
agt cat tac tgg gcc tgg att cgc cag ccc cca ggg aag gga cca gaa    144
Ser His Tyr Trp Ala Trp Ile Arg Gln Pro Pro Gly Lys Gly Pro Glu
        35                  40                  45 tgg att ggc agt gtc tat ttt agc tcg atg acc cac tac aac ccg tcc    192
Trp Ile Gly Ser Val Tyr Phe Ser Ser Met Thr His Tyr Asn Pro Ser
    50                  55                  60 ctc aca agt cgc gtc agc atc tcc att gac aag gcc atg aat aag ttc    240
Leu Thr Ser Arg Val Ser Ile Ser Ile Asp Lys Ala Met Asn Lys Phe
65                  70                  75                  80 tcc tta aaa gtg acc tct gtg act gtc gcc gac acg gcc aca tat tac    288
Ser Leu Lys Val Thr Ser Val Thr Val Ala Asp Thr Ala Thr Tyr Tyr
                85                  90                  95 tgt gcg aga cag gcc ctt gcc cga gtc gga gcc atg aat tgg ttc gac    336
Cys Ala Arg Gln Ala Leu Ala Arg Val Gly Ala Met Asn Trp Phe Asp
            100                 105                 110 ccc tgg ggc cag gga tct ctg gtc aca gtc tcc tca                    372
Pro Trp Gly Gln Gly Ser Leu Val Thr Val Ser Ser
        115                 120
```

<210> SEQ ID NO 38
<211> LENGTH: 124
<212> TYPE: PRT
<213> ORGANISM: Homo sapiens

<400> SEQUENCE: 38

```
Gln Ile Gln Leu Gln Glu Ser Gly Pro Gly Leu Val Arg Pro Thr Glu
1               5                   10                  15

Thr Leu Ser Leu Thr Cys Ser Val Ser Gly Asp Ser Ile Ser Gln Ser
            20                  25                  30

Ser His Tyr Trp Ala Trp Ile Arg Gln Pro Pro Gly Lys Gly Pro Glu
        35                  40                  45

Trp Ile Gly Ser Val Tyr Phe Ser Ser Met Thr His Tyr Asn Pro Ser
    50                  55                  60

Leu Thr Ser Arg Val Ser Ile Ser Ile Asp Lys Ala Met Asn Lys Phe
65                  70                  75                  80

Ser Leu Lys Val Thr Ser Val Thr Val Ala Asp Thr Ala Thr Tyr Tyr
                85                  90                  95

Cys Ala Arg Gln Ala Leu Ala Arg Val Gly Ala Met Asn Trp Phe Asp
            100                 105                 110

Pro Trp Gly Gln Gly Ser Leu Val Thr Val Ser Ser
        115                 120
```

<210> SEQ ID NO 39
<211> LENGTH: 339
<212> TYPE: DNA
<213> ORGANISM: Homo sapiens
<220> FEATURE:
<221> NAME/KEY: CDS
<222> LOCATION: (1)..(339)
<223> OTHER INFORMATION: 31B4-VL variable light chain (VL) sequence,
      kappa type
<220> FEATURE:
<221> NAME/KEY: V_region
<222> LOCATION: (70)..(120)
<223> OTHER INFORMATION: complementarity determining region (CDR)
      VL-CDR1
<220> FEATURE:
<221> NAME/KEY: V_region
<222> LOCATION: (166)..(186)
<223> OTHER INFORMATION: complementarity determining region (CDR)
      VL-CDR2
<220> FEATURE:
<221> NAME/KEY: V_region
<222> LOCATION: (283)..(309)

<223> OTHER INFORMATION: complementarity determining region (CDR)
      VL-CDR3

<400> SEQUENCE: 39

```
gac atc ata atg acc cag tct cca gag tcc ctg cct gtg tct ctg ggc      48
Asp Ile Ile Met Thr Gln Ser Pro Glu Ser Leu Pro Val Ser Leu Gly
1               5                   10                  15 gag ggg gtc acc atc aac tgc aag tcc agc cag agc gtc ttt ttc acc      96
Glu Gly Val Thr Ile Asn Cys Lys Ser Ser Gln Ser Val Phe Phe Thr
            20                  25                  30 tcc agt aat agg agt tgt tta gct tgg tat cag cag aag cca gga cag     144
Ser Ser Asn Arg Ser Cys Leu Ala Trp Tyr Gln Gln Lys Pro Gly Gln
        35                  40                  45 tct ccc aaa ttg ctc att tac tgg gca tca acc cgc caa tcc ggg gtc     192
Ser Pro Lys Leu Leu Ile Tyr Trp Ala Ser Thr Arg Gln Ser Gly Val
    50                  55                  60 cct gac cga ttc aca ggc agc ggg tct ggg aca gat ttc tct ctc acc     240
Pro Asp Arg Phe Thr Gly Ser Gly Ser Gly Thr Asp Phe Ser Leu Thr
65                  70                  75                  80 atc gcc ggt ctg cag gtt gaa gat gtg gct gtt tat ttc tgt cag cag     288
Ile Ala Gly Leu Gln Val Glu Asp Val Ala Val Tyr Phe Cys Gln Gln
                85                  90                  95 tgt cac gca tcc cct ccc act ttc ggc ggc ggg acc agg ttg gag ctc     336
Cys His Ala Ser Pro Pro Thr Phe Gly Gly Gly Thr Arg Leu Glu Leu
            100                 105                 110 aga                                                                  339
Arg
```

<210> SEQ ID NO 40
<211> LENGTH: 113
<212> TYPE: PRT
<213> ORGANISM: Homo sapiens

<400> SEQUENCE: 40

```
Asp Ile Ile Met Thr Gln Ser Pro Glu Ser Leu Pro Val Ser Leu Gly
1               5                   10                  15

Glu Gly Val Thr Ile Asn Cys Lys Ser Ser Gln Ser Val Phe Phe Thr
            20                  25                  30

Ser Ser Asn Arg Ser Cys Leu Ala Trp Tyr Gln Gln Lys Pro Gly Gln
        35                  40                  45

Ser Pro Lys Leu Leu Ile Tyr Trp Ala Ser Thr Arg Gln Ser Gly Val
    50                  55                  60

Pro Asp Arg Phe Thr Gly Ser Gly Ser Gly Thr Asp Phe Ser Leu Thr
65                  70                  75                  80

Ile Ala Gly Leu Gln Val Glu Asp Val Ala Val Tyr Phe Cys Gln Gln
                85                  90                  95

Cys His Ala Ser Pro Pro Thr Phe Gly Gly Gly Thr Arg Leu Glu Leu
            100                 105                 110

Arg
```

<210> SEQ ID NO 41
<211> LENGTH: 993
<212> TYPE: DNA
<213> ORGANISM: Homo sapiens
<220> FEATURE:
<221> NAME/KEY: CDS
<222> LOCATION: (1)..(993)
<223> OTHER INFORMATION: 31B4-CH constant heavy chain (CH) sequence

<400> SEQUENCE: 41

```
gcc tcc acc aag ggc cca tcg gtc ttc ccc ctg gca ccc tcc tcc aag      48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac      96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc     240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag     288
Tyr Ile Cys Asn Val Asn His Lys Pro Ser Asn Thr Lys Val Asp Lys
                85                  90                  95 aga gtt gag ccc aaa tct tgt gac aaa act cac aca tgc cca ccg tgc     336
Arg Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca     384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc     432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg     480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag     528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg     576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac     624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg     672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gag gag     720
Gln Pro Arg Glu Pro Gln Val Tyr Thr Leu Pro Pro Ser Arg Glu Glu
225                 230                 235                 240 atg acc aag aac cag gtc agc ctg acc tgc ctg gtc aaa ggc ttc tat     768
Met Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac     816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc     864
Asn Tyr Lys Thr Thr Pro Pro Val Leu Asp Ser Asp Gly Ser Phe Phe
        275                 280                 285 ctc tat agc aag ctc acc gtg gac aag agc agg tgg cag cag ggg aac     912
Leu Tyr Ser Lys Leu Thr Val Asp Lys Ser Arg Trp Gln Gln Gly Asn
    290                 295                 300 gtc ttc tca tgc tcc gtg atg cat gag gct ctg cac aac cac tac acg     960
Val Phe Ser Cys Ser Val Met His Glu Ala Leu His Asn His Tyr Thr
305                 310                 315                 320
```

```
cag aag agc ctc tcc ctg tcc ccg ggt aaa tga                              993
Gln Lys Ser Leu Ser Leu Ser Pro Gly Lys
            325                 330
```

<210> SEQ ID NO 42
<211> LENGTH: 330
<212> TYPE: PRT
<213> ORGANISM: Homo sapiens

<400> SEQUENCE: 42

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 43
<211> LENGTH: 324

<212> TYPE: DNA
<213> ORGANISM: Homo sapiens
<220> FEATURE:
<221> NAME/KEY: CDS
<222> LOCATION: (1)..(324)
<223> OTHER INFORMATION: 31B4-CL constant kappa chain (CL) sequence
<220> FEATURE:
<221> NAME/KEY: misc_feature
<222> LOCATION: (268)..(324)
<223> OTHER INFORMATION: not sequenced but obtained from database

<400> SEQUENCE: 43

```
cga act gtg gct gca cca tct gtc ttc atc ttc ccg cca tct gat gag      48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc      96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa     144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc     192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag     240
Thr Tyr Ser Leu Ser Ser Thr Leu Thr Leu Ser Lys Ala Asp Tyr Glu
65                  70                  75                  80 aaa cac aaa gtc tac gcc tgc gaa gtc acc cat cag ggc ctg agc tcg     288
Lys His Lys Val Tyr Ala Cys Glu Val Thr His Gln Gly Leu Ser Ser
                85                  90                  95 ccc gtc aca aag agc ttc aac agg gga gag tgt tag                     324
Pro Val Thr Lys Ser Phe Asn Arg Gly Glu Cys
            100                 105
```

<210> SEQ ID NO 44
<211> LENGTH: 107
<212> TYPE: PRT
<213> ORGANISM: Homo sapiens

<400> SEQUENCE: 44

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 45
<211> LENGTH: 40
<212> TYPE: DNA
<213> ORGANISM: Artificial Sequence
<220> FEATURE:
<223> OTHER INFORMATION: Forward oligonucleotide/primer IFNA1F for amplification of a fragment encoding aa 24-189 of IFNA1

<400> SEQUENCE: 45
tttggatcct atgtgatctc cctgagaccc acagcctgga        40

<210> SEQ ID NO 46
<211> LENGTH: 44
<212> TYPE: DNA
<213> ORGANISM: Artificial Sequence
<220> FEATURE:
<223> OTHER INFORMATION: Reverse oligonucleotide/primer IFNA1R for
      amplification of a fragment encoding aa 24-189 of IFNA1

<400> SEQUENCE: 46
tttgcggccg cgaccagatg ttattccttc ctccttaatc tttc        44

<210> SEQ ID NO 47
<211> LENGTH: 34
<212> TYPE: DNA
<213> ORGANISM: Artificial Sequence
<220> FEATURE:
<223> OTHER INFORMATION: Forward oligonucleotide/primer IFNA2F for
      amplification of a fragment encoding aa 24-188 of IFNA2

<400> SEQUENCE: 47
tttgggatcc tctgtgatct gcctcaaacc caca        34

<210> SEQ ID NO 48
<211> LENGTH: 33
<212> TYPE: DNA
<213> ORGANISM: Artificial Sequence
<220> FEATURE:
<223> OTHER INFORMATION: Reverse oligonucleotide/primer IFNA2R for
      amplification of a fragment encoding aa 24-188 of IFNA2

<400> SEQUENCE: 48
tttgcggccg cttacttctt aaactttctt gca        33

<210> SEQ ID NO 49
<211> LENGTH: 39
<212> TYPE: DNA
<213> ORGANISM: Artificial Sequence
<220> FEATURE:
<223> OTHER INFORMATION: Forward oligonucleotide/primer IFNA4F for
      amplification of a fragment encoding aa 24-189 of IFNA4

<400> SEQUENCE: 49
tttggatcct atgtgatctg cctcagaccc acagcctgg        39

<210> SEQ ID NO 50
<211> LENGTH: 54
<212> TYPE: DNA
<213> ORGANISM: Artificial Sequence
<220> FEATURE:
<223> OTHER INFORMATION: Reverse oligonucleotide/primer IFNA4R for
      amplification of a fragment encoding aa 24-189 of IFNA4 and for
      amplification of a fragment encoding aa 24-189 of IFNA10

<400> SEQUENCE: 50
tttgcggccg ctcaatcctt cctccttaat cttttttgca agtttgttga aaac        54

<210> SEQ ID NO 51
<211> LENGTH: 46
<212> TYPE: DNA
<213> ORGANISM: Artificial Sequence
<220> FEATURE:
<223> OTHER INFORMATION: Forward oligonucleotide/primer IFNA5F for
      amplification of a fragment encoding aa 22-189 of IFNA5

<400> SEQUENCE: 51
tttggatcct actgggctgt gatctgcctc agacccacag cctgag    46

<210> SEQ ID NO 52
<211> LENGTH: 47
<212> TYPE: DNA
<213> ORGANISM: Artificial Sequence
<220> FEATURE:
<223> OTHER INFORMATION: Reverse oligonucleotide/primer IFNA5R for
      amplification of a fragment encoding aa 22-189 of IFNA5

<400> SEQUENCE: 52
tttgcggccg ctcattcctt cctccttaat ctttcttgca agtttgc    47

<210> SEQ ID NO 53
<211> LENGTH: 51
<212> TYPE: DNA
<213> ORGANISM: Artificial Sequence
<220> FEATURE:
<223> OTHER INFORMATION: Forward oligonucleotide/primer IFNA6F for
      amplification of a fragment encoding aa 21-189 of IFNA6

<400> SEQUENCE: 53
tttggatcct atctctggac tgtgatctgc ctcagaccca cagcctgggt c    51

<210> SEQ ID NO 54
<211> LENGTH: 46
<212> TYPE: DNA
<213> ORGANISM: Artificial Sequence
<220> FEATURE:
<223> OTHER INFORMATION: Reverse oligonucleotide/primer IFNA6R for
      amplification of a fragment encoding aa 21-189 of IFNA6

<400> SEQUENCE: 54
tttgcggccg cttattcctt cctccttaac ctttcttgca agtttc    46

<210> SEQ ID NO 55
<211> LENGTH: 39
<212> TYPE: DNA
<213> ORGANISM: Artificial Sequence
<220> FEATURE:
<223> OTHER INFORMATION: Forward oligonucleotide/primer IFNA7F for
      amplification of a fragment encoding aa 24-189 of IFNA7

<400> SEQUENCE: 55
tttggatcct atgtgatctg cctcagaccc acagcctgc    39

<210> SEQ ID NO 56
<211> LENGTH: 48
<212> TYPE: DNA
<213> ORGANISM: Artificial Sequence
<220> FEATURE:
<223> OTHER INFORMATION: Reverse oligonucleotide/primer IFNA7R for
      amplification of a fragment encoding aa 24-189 of IFNA7

<400> SEQUENCE: 56
tttgcggccg cgaaccagtt ttcaatcctt cctccttaat ccttttt    48

<210> SEQ ID NO 57
<211> LENGTH: 34
<212> TYPE: DNA
<213> ORGANISM: Artificial Sequence
<220> FEATURE:
<223> OTHER INFORMATION: Forward oligonucleotide/primer IFNA8F for
      amplification of a fragment encoding aa 23-189 of IFNA8

<400> SEQUENCE: 57
tttgggatcc tctgtgatct gcctcagact caca                34

<210> SEQ ID NO 58
<211> LENGTH: 33
<212> TYPE: DNA
<213> ORGANISM: Artificial Sequence
<220> FEATURE:
<223> OTHER INFORMATION: Reverse oligonucleotide/primer IFNA8R for
      amplification of a fragment encoding aa 23-189 of IFNA8

<400> SEQUENCE: 58
tttgcggccg ctcattcctt actcttcaat ctt                 33

<210> SEQ ID NO 59
<211> LENGTH: 40
<212> TYPE: DNA
<213> ORGANISM: Artificial Sequence
<220> FEATURE:
<223> OTHER INFORMATION: Forward oligonucleotide/primer IFNA17F for
      amplification of a fragment encoding aa 24-189 of IFNA10 and for
      amplification of a fragment encoding aa 24-189 of IFNA17

<400> SEQUENCE: 59
tttggatcct atgtgatctg cctcagaccc acagcctggg          40

<210> SEQ ID NO 60
<211> LENGTH: 40
<212> TYPE: DNA
<213> ORGANISM: Artificial Sequence
<220> FEATURE:
<223> OTHER INFORMATION: Forward oligonucleotide/primer IFNA14F for
      amplification of a fragment encoding aa 24-189 of IFNA14

<400> SEQUENCE: 60
tttggatcct atgtaatctg tctcaaaccc acagcctgaa          40

<210> SEQ ID NO 61
<211> LENGTH: 47
<212> TYPE: DNA
<213> ORGANISM: Artificial Sequence
<220> FEATURE:
<223> OTHER INFORMATION: Reverse oligonucleotide/primer IFNA14R for
      amplification of a fragment encoding aa 24-189 of IFNA14

<400> SEQUENCE: 61
tttgcggccg ctcaatcctt cctccttaat ctttttgca agtttgt   47

<210> SEQ ID NO 62
<211> LENGTH: 29
<212> TYPE: DNA
<213> ORGANISM: Artificial Sequence
<220> FEATURE:
<223> OTHER INFORMATION: Forward oligonucleotide/primer IFNA16F for
      amplification of a fragment encoding aa 24-189 of IFNA16

<400> SEQUENCE: 62
tttggatcct atgtgatctg cctcagact                      29

<210> SEQ ID NO 63
<211> LENGTH: 32
<212> TYPE: DNA
<213> ORGANISM: Artificial Sequence
<220> FEATURE:
<223> OTHER INFORMATION: Reverse oligonucleotide/primer IFNA16R for
      amplification of a fragment encoding aa 24-189 of IFNA16

<400> SEQUENCE: 63
tttgcggccg ctcaatcctt ccttcttaat cc                                    32

<210> SEQ ID NO 64
<211> LENGTH: 44
<212> TYPE: DNA
<213> ORGANISM: Artificial Sequence
<220> FEATURE:
<223> OTHER INFORMATION: Reverse oligonucleotide/primer IFNA17R for
      amplification of a fragment encoding aa 24-189 of IFNA17

<400> SEQUENCE: 64
tttgcggccg cgttgaacca gttttcaatc cttcctcctt aata                       44

<210> SEQ ID NO 65
<211> LENGTH: 37
<212> TYPE: DNA
<213> ORGANISM: Artificial Sequence
<220> FEATURE:
<223> OTHER INFORMATION: Forward oligonucleotide/primer IFNA21F for
      amplification of a fragment encoding aa 24-189 of IFNA21

<400> SEQUENCE: 65
tttggatcct atgtgatctg cctcagaccc acagcct                               37

<210> SEQ ID NO 66
<211> LENGTH: 43
<212> TYPE: DNA
<213> ORGANISM: Artificial Sequence
<220> FEATURE:
<223> OTHER INFORMATION: Reverse oligonucleotide/primer IFNA21R for
      amplification of a fragment encoding aa 24-189 of IFNA21

<400> SEQUENCE: 66
tttgcggccg ctcattcctt cctccttaat ctttcttgaa aaa                        43

<210> SEQ ID NO 67
<211> LENGTH: 39
<212> TYPE: DNA
<213> ORGANISM: Artificial Sequence
<220> FEATURE:
<223> OTHER INFORMATION: Forward oligonucleotide/primer IFNB1F for
      amplification of a fragment encoding aa 22-187 of IFN-Beta 1

<400> SEQUENCE: 67
tttggatcct aatgagctac aacttgcttg gattcctac                             39

<210> SEQ ID NO 68
<211> LENGTH: 38
<212> TYPE: DNA
<213> ORGANISM: Artificial Sequence
<220> FEATURE:
<223> OTHER INFORMATION: Reverse oligonucleotide/primer IFNB1R for
      amplification of a fragment encoding aa 22-187 of IFN-Beta 1

<400> SEQUENCE: 68
tttgcggccg ctcagtttcg gaggtaacct gtaagtct                              38

<210> SEQ ID NO 69
<211> LENGTH: 41
<212> TYPE: DNA
<213> ORGANISM: Artificial Sequence
<220> FEATURE:
<223> OTHER INFORMATION: Forward oligonucleotide/primer IFNGF for
      amplification of a fragment encoding aa 24-166 of IFN-Gamma

<400> SEQUENCE: 69

```
tttggatcct acaggaccca tatgtaaaag aagcagaaaa c                           41
```

<210> SEQ ID NO 70
<211> LENGTH: 36
<212> TYPE: DNA
<213> ORGANISM: Artificial Sequence
<220> FEATURE:
<223> OTHER INFORMATION: Reverse oligonucleotide/primer IFNGR for
      amplification of a fragment encoding aa 24-166 of IFN-Gamma

<400> SEQUENCE: 70

```
tttgcggccg cccattactg ggatgctctt cgacct                                36
```

<210> SEQ ID NO 71
<211> LENGTH: 993
<212> TYPE: DNA
<213> ORGANISM: Homo sapiens
<220> FEATURE:
<221> NAME/KEY: CDS
<222> LOCATION: (1)..(993)
<223> OTHER INFORMATION: 19D11-CH constant heavy chain (CH) sequence
<220> FEATURE:
<221> NAME/KEY: Unsure
<222> LOCATION: (1)..(35)
<223> OTHER INFORMATION: not sequenced but obtained from database
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (968)..(968)
<223> OTHER INFORMATION: n is a, c, g, or t

<400> SEQUENCE: 71

```
gcc tcc acc aag ggc cca tcg gtc ttc ccc ctg gca ccc tcc tcc aag        48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac        96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc       144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc       192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc       240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag       288
Tyr Ile Cys Asn Val Asn His Lys Pro Ser Asn Thr Lys Val Asp Lys
                85                  90                  95 aga gtt gag ccc aaa tct tgt gac aaa act cac aca tgc cca ccg tgc       336
Arg Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca       384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc       432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg       480
Val Val Val Asp Val Ser His Glu Asp Pro Glu Val Lys Phe Asn Trp
145                 150                 155                 160
```

```
tac gtg gac ggc gtg gag gtg cat aat gcc aag aca aag ccg cgg gag     528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg     576
Glu Gln Tyr Asn Ser Thr Tyr Arg Val Val Ser Val Leu Thr Val Leu
                180                 185                 190 cac cag gac tgg ctg aat ggc aag gag tac aag tgc aag gtc tcc aac     624
His Gln Asp Trp Leu Asn Gly Lys Glu Tyr Lys Cys Lys Val Ser Asn
                195                 200                 205 aaa gcc ctc cca gcc ccc atc gag aaa acc atc tcc aaa gcc aaa ggg     672
Lys Ala Leu Pro Ala Pro Ile Glu Lys Thr Ile Ser Lys Ala Lys Gly
                210                 215                 220 cag ccc cga gaa cca cag gtg tac acc ctg ccc cca tcc cgg gag gag     720
Gln Pro Arg Glu Pro Gln Val Tyr Thr Leu Pro Pro Ser Arg Glu Glu
225                 230                 235                 240 atg acc aag aac cag gtc agc ctg acc tgc ctg gtc aaa ggc ttc tat     768
Met Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac     816
Pro Ser Asp Ile Ala Val Glu Trp Glu Ser Asn Gly Gln Pro Glu Asn
                260                 265                 270 aac tac aag acc acg cct ccc gtg ctg gac tcc gac ggc tcc ttc ttc     864
Asn Tyr Lys Thr Thr Pro Pro Val Leu Asp Ser Asp Gly Ser Phe Phe
                275                 280                 285 ctc tat agc aag ctc acc gtg gac aag agc agg tgg cag cag ggg aac     912
Leu Tyr Ser Lys Leu Thr Val Asp Lys Ser Arg Trp Gln Gln Gly Asn
                290                 295                 300 gtc ttc tca tgc tcc gtg atg cat gag gct ctg cac aac cac tac acg     960
Val Phe Ser Cys Ser Val Met His Glu Ala Leu His Asn His Tyr Thr
305                 310                 315                 320 cag aan anc ctc tcc ctg tcc ccg ggt aaa tga                         993
Gln Xaa Xaa Leu Ser Leu Ser Pro Gly Lys
                325                 330
```

<210> SEQ ID NO 72
<211> LENGTH: 330
<212> TYPE: PRT
<213> ORGANISM: Homo sapiens
<220> FEATURE:
<221> NAME/KEY: misc_feature
<222> LOCATION: (322)..(322)
<223> OTHER INFORMATION: The 'Xaa' at location 322 stands for Lys, or
      Asn.
<220> FEATURE:
<221> NAME/KEY: misc_feature
<222> LOCATION: (323)..(323)
<223> OTHER INFORMATION: The 'Xaa' at location 323 stands for Asn, Ser,
      Thr, or Ile.

<400> SEQUENCE: 72

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Xaa Xaa Leu Ser Leu Ser Pro Gly Lys
                325                 330

<210> SEQ ID NO 73
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: 19D11-CL constant kappa chain (CL) sequence

<400> SEQUENCE: 73 cga act gtg gct gca cca tct gtc ttc atc ttc ccg cca tct gat gag       48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc       96
Gln Leu Lys Ser Gly Thr Ala Ser Val Val Cys Leu Leu Asn Asn Phe
                20                  25                  30 tat ccc aga gag gcc aaa gta cag tgg aag gtg gat aac gcc ctc caa      144
Tyr Pro Arg Glu Ala Lys Val Gln Trp Lys Val Asp Asn Ala Leu Gln
            35                  40                  45 tcg ggt aac tcc cag gag agt gtc aca gag cag gac agc aag gac agc      192
Ser Gly Asn Ser Gln Glu Ser Val Thr Glu Gln Asp Ser Lys Asp Ser
        50                  55                  60 acc tac agc ctc agc agc acc ctg acg ctg agc aaa gca gac tac gag      240
Thr Tyr Ser Leu Ser Ser Thr Leu Thr Leu Ser Lys Ala Asp Tyr Glu
65                  70                  75                  80 aaa cac aaa gtc tac gcc tgc gaa gtc acc cat cag ggc ctg agc tcg      288
Lys His Lys Val Tyr Ala Cys Glu Val Thr His Gln Gly Leu Ser Ser

```
Lys His Lys Val Tyr Ala Cys Glu Val Thr His Gln Gly Leu Ser Ser
            85                  90                  95 ccc gtc aca aag agc ttc aac agg gga gag tgt tag                    324
Pro Val Thr Lys Ser Phe Asn Arg Gly Glu Cys
        100                 105
```

<210> SEQ ID NO 74
<211> LENGTH: 107
<212> TYPE: PRT
<213> ORGANISM: Homo sapiens

<400> SEQUENCE: 74

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 75
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: 8H1-VH variable heavy chain (VH) sequence; 8H1: kappa
<220> FEATURE:
<221> NAME/KEY: V_region
<222> LOCATION: (91)..(105)
<223> OTHER INFORMATION: complementarity determining region (CDR) VH-CDR1
<220> FEATURE:
<221> NAME/KEY: V_region
<222> LOCATION: (148)..(198)
<223> OTHER INFORMATION: complementarity determining region (CDR) VH-CDR2
<220> FEATURE:
<221> NAME/KEY: V_region
<222> LOCATION: (295)..(339)
<223> OTHER INFORMATION: complementarity determining region (CDR) VH-CDR3

<400> SEQUENCE: 75

```
cag gtg cag ctg gtg cag tct ggg gct gag gtg aag aag cct ggg gcc    48
Gln Val Gln Leu Val Gln Ser Gly Ala Glu Val Lys Lys Pro Gly Ala
1               5                   10                  15 tca gtg aag gtc tcc tgc aag gct tct gga cag acc ttc acc agt gat    96
Ser Val Lys Val Ser Cys Lys Ala Ser Gly Gln Thr Phe Thr Ser Asp
            20                  25                  30 gat atc aac tgg gtg cga cag gcc cct gga cag ggg cta gag tgg atg   144
Asp Ile Asn Trp Val Arg Gln Ala Pro Gly Gln Gly Leu Glu Trp Met
        35                  40                  45 gga tgg agg aac cct aac act cag gac acg ggc tat gca cag aag ttc   192
Gly Trp Arg Asn Pro Asn Thr Gln Asp Thr Gly Tyr Ala Gln Lys Phe
    50                  55                  60
```

```
cac ggc aga ctc acc ttg acc agc aac agt tcc ata agt aca tcc tat      240
His Gly Arg Leu Thr Leu Thr Ser Asn Ser Ser Ile Ser Thr Ser Tyr
 65                  70                  75                  80 ctg gag ttg agc ggc ctg aga tct gag gac acg gcc gtg tat tac tgt      288
Leu Glu Leu Ser Gly Leu Arg Ser Glu Asp Thr Ala Val Tyr Tyr Cys
                 85                  90                  95 gcg aga gcg ggg act tcg acc ttg acc ggc cac tac ttc gct ttg ggg      336
Ala Arg Ala Gly Thr Ser Thr Leu Thr Gly His Tyr Phe Ala Leu Gly
            100                 105                 110 gtc tgg ggc cag ggg acc acg gtc atc gtc tcc tca                      372
Val Trp Gly Gln Gly Thr Thr Val Ile Val Ser Ser
        115                 120

<210> SEQ ID NO 76
<211> LENGTH: 124
<212> TYPE: PRT
<213> ORGANISM: Homo sapiens

<400> SEQUENCE: 76

Gln Val Gln Leu Val Gln Ser Gly Ala Glu Val Lys Lys Pro Gly Ala
 1               5                  10                  15

Ser Val Lys Val Ser Cys Lys Ala Ser Gly Gln Thr Phe Thr Ser Asp
                20                  25                  30

Asp Ile Asn Trp Val Arg Gln Ala Pro Gly Gln Gly Leu Glu Trp Met
            35                  40                  45

Gly Trp Arg Asn Pro Asn Thr Gln Asp Thr Gly Tyr Ala Gln Lys Phe
        50                  55                  60

His Gly Arg Leu Thr Leu Thr Ser Asn Ser Ser Ile Ser Thr Ser Tyr
 65                  70                  75                  80

Leu Glu Leu Ser Gly Leu Arg Ser Glu Asp Thr Ala Val Tyr Tyr Cys
                 85                  90                  95

Ala Arg Ala Gly Thr Ser Thr Leu Thr Gly His Tyr Phe Ala Leu Gly
            100                 105                 110

Val Trp Gly Gln Gly Thr Thr Val Ile Val Ser Ser
        115                 120

<210> SEQ ID NO 77
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: 8H1-VL variable light chain (VL) sequence,
      kappa type
<220> FEATURE:
<221> NAME/KEY: V_region
<222> LOCATION: (70)..(102)
<223> OTHER INFORMATION: complementarity determining region (CDR)
      VL-CDR1
<220> FEATURE:
<221> NAME/KEY: V_region
<222> LOCATION: (148)..(165)
<223> OTHER INFORMATION: complementarity determining region (CDR)
      VL-CDR2
<220> FEATURE:
<221> NAME/KEY: V_region
<222> LOCATION: (265)..(291)
<223> OTHER INFORMATION: complementarity determining region (CDR)
      VL-CDR3

<400> SEQUENCE: 77 gac atc cag ctg acc cag tct cca tcc tcc ctg tct gca tct gta gga       48
Asp Ile Gln Leu Thr Gln Ser Pro Ser Ser Leu Ser Ala Ser Val Gly
```

```
1               5                   10                  15
gac aga gtc acc atc act tgt cag gcg act cag gat att agc aaa tat      96
Asp Arg Val Thr Ile Thr Cys Gln Ala Thr Gln Asp Ile Ser Lys Tyr
            20                  25                  30 tta aat tgg tat cag cag aaa cca ggg aaa gtc cct aaa ctc ctg atc      144
Leu Asn Trp Tyr Gln Gln Lys Pro Gly Lys Val Pro Lys Leu Leu Ile
        35                  40                  45 tac gaa aca tcc aat ttg gaa gta ggg gtc cca tca agg ttc agt gga      192
Tyr Glu Thr Ser Asn Leu Glu Val Gly Val Pro Ser Arg Phe Ser Gly
    50                  55                  60 agt ggg tct ggg aca cat ttt act ctc acc atc agc agc ctg cag gct      240
Ser Gly Ser Gly Thr His Phe Thr Leu Thr Ile Ser Ser Leu Gln Ala
65                  70                  75                  80 gaa gat ttt gca aca tat tac tgt caa cag tat gag aat ttc ccg ttc      288
Glu Asp Phe Ala Thr Tyr Tyr Cys Gln Gln Tyr Glu Asn Phe Pro Phe
                85                  90                  95 act ttc ggc gga ggg acc aag gtg gag atc aaa                          321
Thr Phe Gly Gly Gly Thr Lys Val Glu Ile Lys
            100                 105
```

<210> SEQ ID NO 78
<211> LENGTH: 107
<212> TYPE: PRT
<213> ORGANISM: Homo sapiens

<400> SEQUENCE: 78

```
Asp Ile Gln Leu Thr Gln Ser Pro Ser Ser Leu Ser Ala Ser Val Gly
1               5                   10                  15

Asp Arg Val Thr Ile Thr Cys Gln Ala Thr Gln Asp Ile Ser Lys Tyr
            20                  25                  30

Leu Asn Trp Tyr Gln Gln Lys Pro Gly Lys Val Pro Lys Leu Leu Ile
        35                  40                  45

Tyr Glu Thr Ser Asn Leu Glu Val Gly Val Pro Ser Arg Phe Ser Gly
    50                  55                  60

Ser Gly Ser Gly Thr His Phe Thr Leu Thr Ile Ser Ser Leu Gln Ala
65                  70                  75                  80

Glu Asp Phe Ala Thr Tyr Tyr Cys Gln Gln Tyr Glu Asn Phe Pro Phe
                85                  90                  95

Thr Phe Gly Gly Gly Thr Lys Val Glu Ile Lys
            100                 105
```

<210> SEQ ID NO 79
<211> LENGTH: 990
<212> TYPE: DNA
<213> ORGANISM: Homo sapiens
<220> FEATURE:
<221> NAME/KEY: CDS
<222> LOCATION: (1)..(990)
<223> OTHER INFORMATION: 8H1-CH constant heavy chain (CH) sequence

<400> SEQUENCE: 79

```
gcc tcc acc aag ggc cca tcg gtc ttc ccc ctg gca ccc tcc tcc aag      48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac      96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc      144
Phe Pro Glu Pro Val Thr Val Ser Trp Asn Ser Gly Ala Leu Thr Ser
        35                  40                  45
```

```
ggc gtg cac acc ttc ccg gct gtc cta cag tcc tca gga ctc tac tcc      192
Gly Val His Thr Phe Pro Ala Val Leu Gln Ser Ser Gly Leu Tyr Ser
 50              55                  60 ctc agc agc gtg gtg acc gtg ccc tcc agc agc ttg ggc acc cag acc      240
Leu Ser Ser Val Val Thr Val Pro Ser Ser Ser Leu Gly Thr Gln Thr
 65              70                  75                  80 tac atc tgc aac gtg aat cac aag ccc agc aac acc aag gtg gac aag      288
Tyr Ile Cys Asn Val Asn His Lys Pro Ser Asn Thr Lys Val Asp Lys
                 85                  90                  95 aga gtt gag ccc aaa tct tgt gac aaa act cac aca tgc cca ccg tgc      336
Arg Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca      384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc      432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg      480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag      528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg      576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac      624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg      672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gag gag      720
Gln Pro Arg Glu Pro Gln Val Tyr Thr Leu Pro Pro Ser Arg Glu Glu
225                 230                 235                 240 atg acc aag aac cag gtc agc ctg acc tgc ctg gtc aaa ggc ttc tat      768
Met Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac      816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc      864
Asn Tyr Lys Thr Thr Pro Pro Val Leu Asp Ser Asp Gly Ser Phe Phe
        275                 280                 285 ctc tat agc aag ctc acc gtg gac aag agc agg tgg cag cag ggg aac      912
Leu Tyr Ser Lys Leu Thr Val Asp Lys Ser Arg Trp Gln Gln Gly Asn
    290                 295                 300 gtc ttc tca tgc tcc gtg atg cat gag gct ctg cac aac cac tac acg      960
Val Phe Ser Cys Ser Val Met His Glu Ala Leu His Asn His Tyr Thr
305                 310                 315                 320 cag aag agc ctc tcc ctg tcc ccg ggt aaa                              990
Gln Lys Ser Leu Ser Leu Ser Pro Gly Lys
                325                 330

<210> SEQ ID NO 80
<211> LENGTH: 330
<212> TYPE: PRT
<213> ORGANISM: Homo sapiens

<400> SEQUENCE: 80
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 81
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: 8H1-CL constant kappa chain (CL) sequence

<400> SEQUENCE: 81

```
cga act gtg gct gca cca tct gtc ttc atc ttc ccg cca tct gat gag       48
Arg Thr Val Ala Ala Pro Ser Val Phe Ile Phe Pro Pro Ser Asp Glu
1               5                   10                  15
```

```
cag ttg aaa tct gga act gcc tct gtt gtg tgc ctg ctg aat aac ttc      96
Gln Leu Lys Ser Gly Thr Ala Ser Val Val Cys Leu Leu Asn Asn Phe
        20                  25                  30 tat ccc aga gag gcc aaa gta cag tgg aag gtg gat aac gcc ctc caa     144
Tyr Pro Arg Glu Ala Lys Val Gln Trp Lys Val Asp Asn Ala Leu Gln
            35                  40                  45 tcg ggt aac tcc cag gag agt gtc aca gag cag gac agc aag gac agc     192
Ser Gly Asn Ser Gln Glu Ser Val Thr Glu Gln Asp Ser Lys Asp Ser
 50                  55                  60 acc tac agc ctc agc agc acc ctg acg ctg agc aaa gca gac tac gag     240
Thr Tyr Ser Leu Ser Ser Thr Leu Thr Leu Ser Lys Ala Asp Tyr Glu
 65                  70                  75                  80 aaa cac aaa gtc tac gcc tgc gaa gtc acc cat cag ggc ctg agc tcg     288
Lys His Lys Val Tyr Ala Cys Glu Val Thr His Gln Gly Leu Ser Ser
                85                  90                  95 ccc gtc aca aag agc ttc aac agg gga gag tgt tag                     324
Pro Val Thr Lys Ser Phe Asn Arg Gly Glu Cys
            100                 105
```

<210> SEQ ID NO 82
<211> LENGTH: 107
<212> TYPE: PRT
<213> ORGANISM: Homo sapiens

<400> SEQUENCE: 82

```
Arg Thr Val Ala Ala Pro Ser Val Phe Ile Phe Pro Pro Ser Asp Glu
 1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 83
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION: 12H5-VH variable heavy chain (VH) sequence;
      12H5, kappa
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(336)
<223> OTHER INFORMATION: complementarity determining region (CDR)
      VH-CDR3

<400> SEQUENCE: 83

```
caa gtg caa ctg ata cag tct ggg cct gag gtg aag agg cct ggg gcc      48
Gln Val Gln Leu Ile Gln Ser Gly Pro Glu Val Lys Arg Pro Gly Ala
 1               5                  10                  15 tca gtg aag gtc tcc tgc aag gcg tct gaa aac acc ttc gac act cat      96
Ser Val Lys Val Ser Cys Lys Ala Ser Glu Asn Thr Phe Asp Thr His
             20                  25                  30 tat att aat tgg gtg cga cag gcc cct gga caa ggg ctt act tgg ctg     144
Tyr Ile Asn Trp Val Arg Gln Ala Pro Gly Gln Gly Leu Thr Trp Leu
         35                  40                  45 gga tgg ctg aac cct acc act ggt aaa aca ggc ttt cca caa aag ttt     192
Gly Trp Leu Asn Pro Thr Thr Gly Lys Thr Gly Phe Pro Gln Lys Phe
     50                  55                  60 aag ggc aga gtc att ctg acc agc gac acc tcc cta aat act gcc tat     240
Lys Gly Arg Val Ile Leu Thr Ser Asp Thr Ser Leu Asn Thr Ala Tyr
 65                  70                  75                  80 atg gaa gtg agc cgc ctg aca tct gag gac acg gcc gtt tat ttc tgt     288
Met Glu Val Ser Arg Leu Thr Ser Glu Asp Thr Ala Val Tyr Phe Cys
                 85                  90                  95 gcc aga gtt ttg aag ttg tct gat gag tac aac tat ggt ttc gac gtc     336
Ala Arg Val Leu Lys Leu Ser Asp Glu Tyr Asn Tyr Gly Phe Asp Val
            100                 105                 110 tgg ggc caa ggg acc acg gtc atc gtc tcc tca                         369
Trp Gly Gln Gly Thr Thr Val Ile Val Ser Ser
        115                 120
```

<210> SEQ ID NO 84
<211> LENGTH: 123
<212> TYPE: PRT
<213> ORGANISM: Homo sapiens

<400> SEQUENCE: 84

```
Gln Val Gln Leu Ile Gln Ser Gly Pro Glu Val Lys Arg Pro Gly Ala
 1               5                  10                  15

Ser Val Lys Val Ser Cys Lys Ala Ser Glu Asn Thr Phe Asp Thr His
             20                  25                  30

Tyr Ile Asn Trp Val Arg Gln Ala Pro Gly Gln Gly Leu Thr Trp Leu
         35                  40                  45

Gly Trp Leu Asn Pro Thr Thr Gly Lys Thr Gly Phe Pro Gln Lys Phe
     50                  55                  60

Lys Gly Arg Val Ile Leu Thr Ser Asp Thr Ser Leu Asn Thr Ala Tyr
 65                  70                  75                  80

Met Glu Val Ser Arg Leu Thr Ser Glu Asp Thr Ala Val Tyr Phe Cys
                 85                  90                  95

Ala Arg Val Leu Lys Leu Ser Asp Glu Tyr Asn Tyr Gly Phe Asp Val
            100                 105                 110

Trp Gly Gln Gly Thr Thr Val Ile Val Ser Ser
        115                 120
```

<210> SEQ ID NO 85
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: 12H5-VL variable light chain (VL) sequence,
      kappa type
<220> FEATURE:
<221> NAME/KEY: V_region
<222> LOCATION: (70)..(102)
<223> OTHER INFORMATION: complementarity determining region (CDR)
       VL-CDR1
<220> FEATURE:
<221> NAME/KEY: V_region
<222> LOCATION: (148)..(168)
<223> OTHER INFORMATION: complementarity determining region (CDR)
       VL-CDR2
<220> FEATURE:
<221> NAME/KEY: V_region
<222> LOCATION: (265)..(294)
<223> OTHER INFORMATION: complementarity determining region (CDR)
       VL-CDR3

<400> SEQUENCE: 85

```
gac atc cag gtg acc cag tct cca tcc tcc ctg tct gca tct att ggg         48
Asp Ile Gln Val Thr Gln Ser Pro Ser Ser Leu Ser Ala Ser Ile Gly
1               5                   10                  15 gac aga gtc acc atc acg tgc cgg gca agt cag aac att ctc acc ttt         96
Asp Arg Val Thr Ile Thr Cys Arg Ala Ser Gln Asn Ile Leu Thr Phe
            20                  25                  30 ata aat tgg tat cag cac aaa cca ggg aaa gcc cct aaa ctc ctg atc        144
Ile Asn Trp Tyr Gln His Lys Pro Gly Lys Ala Pro Lys Leu Leu Ile
        35                  40                  45 tat gct gca tcc gtt tta caa aat gaa gtc cca tca agg ttc agt ggc        192
Tyr Ala Ala Ser Val Leu Gln Asn Glu Val Pro Ser Arg Phe Ser Gly
50                  55                  60 agt gga tct ggg aca gat ttc act ctc acc atc acc agt ctg caa cct        240
Ser Gly Ser Gly Thr Asp Phe Thr Leu Thr Ile Thr Ser Leu Gln Pro
65                  70                  75                  80 gac gat ttt gga act tac tac tgt cag cag act tac ctt acc cct caa        288
Asp Asp Phe Gly Thr Tyr Tyr Cys Gln Gln Thr Tyr Leu Thr Pro Gln
                85                  90                  95 tgc agt ttt ggc cag ggg acc aag gtg gag atc aaa                        324
Cys Ser Phe Gly Gln Gly Thr Lys Val Glu Ile Lys
            100                 105
```

<210> SEQ ID NO 86
<211> LENGTH: 108
<212> TYPE: PRT
<213> ORGANISM: Homo sapiens

<400> SEQUENCE: 86

Asp Ile Gln Val Thr Gln Ser Pro Ser Ser Leu Ser Ala Ser Ile Gly
1               5                   10                  15

Asp Arg Val Thr Ile Thr Cys Arg Ala Ser Gln Asn Ile Leu Thr Phe
            20                  25                  30

Ile Asn Trp Tyr Gln His Lys Pro Gly Lys Ala Pro Lys Leu Leu Ile
        35                  40                  45

Tyr Ala Ala Ser Val Leu Gln Asn Glu Val Pro Ser Arg Phe Ser Gly
50                  55                  60

Ser Gly Ser Gly Thr Asp Phe Thr Leu Thr Ile Thr Ser Leu Gln Pro
65                  70                  75                  80

Asp Asp Phe Gly Thr Tyr Tyr Cys Gln Gln Thr Tyr Leu Thr Pro Gln
                85                  90                  95

Cys Ser Phe Gly Gln Gly Thr Lys Val Glu Ile Lys
            100                 105

<210> SEQ ID NO 87
<211> LENGTH: 993
<212> TYPE: DNA
<213> ORGANISM: Homo sapiens
<220> FEATURE:

<221> NAME/KEY: CDS
<222> LOCATION: (1)..(993)
<223> OTHER INFORMATION: 12H5-CH constant heavy chain (CH) sequence

<400> SEQUENCE: 87

```
gcc tcc acc aag ggc cca tcg gtc ttc ccc ctg gca ccc tcc tcc aag      48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac      96
Ser Thr Ser Gly Gly Thr Ala Ala Leu Gly Cys Leu Val Lys Asp Tyr
                20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
            35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
        50                  55                  60 ctc agc agc gtg gtg acc gtg ccc tcc agc agc ttg ggc acc cag acc     240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag     288
Tyr Ile Cys Asn Val Asn His Lys Pro Ser Asn Thr Lys Val Asp Lys
                85                  90                  95 aaa gtt gag ccc aaa tct tgt gac aaa act cac aca tgc cca ccg tgc     336
Lys Val Glu Pro Lys Ser Cys Asp Lys Thr His Thr Cys Pro Pro Cys
                100                 105                 110 cca gca cct gaa ctc ctg ggg gga ccg tca gtc ttc ctc ttc ccc cca     384
Pro Ala Pro Glu Leu Leu Gly Gly Pro Ser Val Phe Leu Phe Pro Pro
            115                 120                 125 aaa ccc aag gac acc ctc atg atc tcc cgg acc cct gag gtc aca tgc     432
Lys Pro Lys Asp Thr Leu Met Ile Ser Arg Thr Pro Glu Val Thr Cys
        130                 135                 140 gtg gtg gtg gac gtg agc cac gaa gac cct gag gtc aag ttc aac tgg     480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag     528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg     576
Glu Gln Tyr Asn Ser Thr Tyr Arg Val Val Ser Val Leu Thr Val Leu
                180                 185                 190 cac cag gac tgg ctg aat ggc aag gag tac aag tgc aag gtc tcc aac     624
His Gln Asp Trp Leu Asn Gly Lys Glu Tyr Lys Cys Lys Val Ser Asn
            195                 200                 205 aaa gcc ctc cca gcc ccc atc gag aaa acc atc tcc aaa gcc aaa ggg     672
Lys Ala Leu Pro Ala Pro Ile Glu Lys Thr Ile Ser Lys Ala Lys Gly
        210                 215                 220 cag ccc cga gaa cca cag gtg tac acc ctg ccc cca tcc cgg gat gag     720
Gln Pro Arg Glu Pro Gln Val Tyr Thr Leu Pro Pro Ser Arg Asp Glu
225                 230                 235                 240 ctg acc aag aac cag gtc agc ctg acc tgc ctg gtc aaa ggc ttc tat     768
Leu Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac     816
Pro Ser Asp Ile Ala Val Glu Trp Glu Ser Asn Gly Gln Pro Glu Asn
                260                 265                 270 aac tac aag acc acg cct ccc gtg ctg gac tcc gac ggc tcc ttc ttc     864
Asn Tyr Lys Thr Thr Pro Pro Val Leu Asp Ser Asp Gly Ser Phe Phe
            275                 280                 285 ctc tac agc aag ctc acc gtg gac aag agc agg tgg cag cag ggg aac     912
```

```
Leu Tyr Ser Lys Leu Thr Val Asp Lys Ser Arg Trp Gln Gln Gly Asn
    290                 295                 300 gtc ttc tca tgc tcc gtg atg cat gag gct ctg cac aac cac tac acg      960
Val Phe Ser Cys Ser Val Met His Glu Ala Leu His Asn His Tyr Thr
305                 310                 315                 320 cag aag agc ctc tcc ctg tct ccg ggt aaa tga                          993
Gln Lys Ser Leu Ser Leu Ser Pro Gly Lys
                325                 330
```

<210> SEQ ID NO 88
<211> LENGTH: 330
<212> TYPE: PRT
<213> ORGANISM: Homo sapiens

<400> SEQUENCE: 88

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

```
Gln Lys Ser Leu Ser Leu Ser Pro Gly Lys
            325                 330

<210> SEQ ID NO 89
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: 12H5-CL variable light chain (VL) sequence,
      kappa type

<400> SEQUENCE: 89 cga act gtg gct gca cca tct gtc ttc atc ttc ccg cca tct gat gag      48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc      96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa     144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc     192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag     240
Thr Tyr Ser Leu Ser Ser Thr Leu Thr Leu Ser Lys Ala Asp Tyr Glu
65                  70                  75                  80 aaa cac aaa gtc tac gcc tgc gaa gtc acc cat cag ggc ctg agc tcg     288
Lys His Lys Val Tyr Ala Cys Glu Val Thr His Gln Gly Leu Ser Ser
                85                  90                  95 ccc gtc aca aag agc ttc aac agg gga gag tgt tag                     324
Pro Val Thr Lys Ser Phe Asn Arg Gly Glu Cys
            100                 105

<210> SEQ ID NO 90
<211> LENGTH: 107
<212> TYPE: PRT
<213> ORGANISM: Homo sapiens

<400> SEQUENCE: 90

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 91
<211> LENGTH: 342
<212> TYPE: DNA
<213> ORGANISM: Homo sapiens
<220> FEATURE:
```

```
<221> NAME/KEY: CDS
<222> LOCATION: (1)..(342)
<223> OTHER INFORMATION: 50E11-VH variable heavy chain (VH) sequence;
      50E1, kappa
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(309)
<223> OTHER INFORMATION: complementarity determining region (CDR)
      VH-CDR3

<400> SEQUENCE: 91 cag gtg cag ctg gtg cag tct ggg gca gag atg aag aag cct ggg tcc        48
Gln Val Gln Leu Val Gln Ser Gly Ala Glu Met Lys Lys Pro Gly Ser
1               5                   10                  15 tcg gtg aag gtc tcc tgc aag gat ttt gga ggc acc ttc agc gtc tat        96
Ser Val Lys Val Ser Cys Lys Asp Phe Gly Gly Thr Phe Ser Val Tyr
            20                  25                  30 ggt gtc aac tgg gtg cga cag gcc cct gga caa ggg ctt gag tgg atg       144
Gly Val Asn Trp Val Arg Gln Ala Pro Gly Gln Gly Leu Glu Trp Met
        35                  40                  45 ggg ggg ctc atc cct gtc att ggg cca gct aac tac gca cag aag ttc       192
Gly Gly Leu Ile Pro Val Ile Gly Pro Ala Asn Tyr Ala Gln Lys Phe
    50                  55                  60 cag ggc aga atc acc att act gcg gac gaa tcc acg agc aca gcc tat       240
Gln Gly Arg Ile Thr Ile Thr Ala Asp Glu Ser Thr Ser Thr Ala Tyr
65                  70                  75                  80 atg gag ttg agc agc ctg aga ttt gac gac acg gcc att tat tat tgt       288
Met Glu Leu Ser Ser Leu Arg Phe Asp Asp Thr Ala Ile Tyr Tyr Cys
                85                  90                  95 gtg aga gac gac aac gaa tat tgg ggc cag gga acc ctg gtc acc gtc       336
Val Arg Asp Asp Asn Glu Tyr Trp Gly Gln Gly Thr Leu Val Thr Val
            100                 105                 110 tcc tcg                                                                342
Ser Ser <210> SEQ ID NO 92
<211> LENGTH: 114
<212> TYPE: PRT
<213> ORGANISM: Homo sapiens

<400> SEQUENCE: 92

Gln Val Gln Leu Val Gln Ser Gly Ala Glu Met Lys Lys Pro Gly Ser
1               5                   10                  15

Ser Val Lys Val Ser Cys Lys Asp Phe Gly Gly Thr Phe Ser Val Tyr
            20                  25                  30

Gly Val Asn Trp Val Arg Gln Ala Pro Gly Gln Gly Leu Glu Trp Met
        35                  40                  45

Gly Gly Leu Ile Pro Val Ile Gly Pro Ala Asn Tyr Ala Gln Lys Phe
    50                  55                  60

Gln Gly Arg Ile Thr Ile Thr Ala Asp Glu Ser Thr Ser Thr Ala Tyr
65                  70                  75                  80

Met Glu Leu Ser Ser Leu Arg Phe Asp Asp Thr Ala Ile Tyr Tyr Cys
                85                  90                  95
```

```
Val Arg Asp Asp Asn Glu Tyr Trp Gly Gln Gly Thr Leu Val Thr Val
            100                 105                 110

Ser Ser

<210> SEQ ID NO 93
<211> LENGTH: 327
<212> TYPE: DNA
<213> ORGANISM: Homo sapiens
<220> FEATURE:
<221> NAME/KEY: CDS
<222> LOCATION: (1)..(327)
<223> OTHER INFORMATION: 50E11-VL variable light chain (VL) sequence,
      kappa type
<220> FEATURE:
<221> NAME/KEY: V_region
<222> LOCATION: (70)..(102)
<223> OTHER INFORMATION: complementarity determining region (CDR)
      VL-CDR1
<220> FEATURE:
<221> NAME/KEY: V_region
<222> LOCATION: (148)..(168)
<223> OTHER INFORMATION: complementarity determining region (CDR)
      VL-CDR2
<220> FEATURE:
<221> NAME/KEY: V_region
<222> LOCATION: (265)..(297)
<223> OTHER INFORMATION: complementarity determining region (CDR)
      VL-CDR3

<400> SEQUENCE: 93 gaa atg gtg ctg aca cag tct cca gcc acc ctg tct ttg tct cca gga        48
Glu Met Val Leu Thr Gln Ser Pro Ala Thr Leu Ser Leu Ser Pro Gly
1               5                   10                  15 gaa aga gcc acc ctc tcc tgt agg gcc agt cag act gtt agc acc ttc        96
Glu Arg Ala Thr Leu Ser Cys Arg Ala Ser Gln Thr Val Ser Thr Phe
                20                  25                  30 tta gcc tgg tac caa cag aaa cct ggc cag gtt ccc agg ctc ctc gtc       144
Leu Ala Trp Tyr Gln Gln Lys Pro Gly Gln Val Pro Arg Leu Leu Val
            35                  40                  45 tac gat atc tcc tcc agg gcc aat ggc act cca gcc agg ttc agt ggc       192
Tyr Asp Ile Ser Ser Arg Ala Asn Gly Thr Pro Ala Arg Phe Ser Gly
        50                  55                  60 ggt ggg tct ggg aca gac ttc act ctc acc atc agc agc cta gaa ctt       240
Gly Gly Ser Gly Thr Asp Phe Thr Leu Thr Ile Ser Ser Leu Glu Leu
65                  70                  75                  80 gaa gat ttt gcg gtt tat tac tgt cag tgg cgt agc aac tgg cct ccc       288
Glu Asp Phe Ala Val Tyr Tyr Cys Gln Trp Arg Ser Asn Trp Pro Pro
                85                  90                  95 tcg ctc act ttc ggc gga ggg acc agg gtg gag atc aaa                   327
Ser Leu Thr Phe Gly Gly Gly Thr Arg Val Glu Ile Lys
            100                 105

<210> SEQ ID NO 94
<211> LENGTH: 109
<212> TYPE: PRT
<213> ORGANISM: Homo sapiens

<400> SEQUENCE: 94

Glu Met Val Leu Thr Gln Ser Pro Ala Thr Leu Ser Leu Ser Pro Gly
1               5                   10                  15

Glu Arg Ala Thr Leu Ser Cys Arg Ala Ser Gln Thr Val Ser Thr Phe
                20                  25                  30

Leu Ala Trp Tyr Gln Gln Lys Pro Gly Gln Val Pro Arg Leu Leu Val
            35                  40                  45

Tyr Asp Ile Ser Ser Arg Ala Asn Gly Thr Pro Ala Arg Phe Ser Gly
```

```
                50              55                  60
Gly Gly Ser Gly Thr Asp Phe Thr Leu Thr Ile Ser Ser Leu Glu Leu
 65                  70                  75                  80

Glu Asp Phe Ala Val Tyr Tyr Cys Gln Trp Arg Ser Asn Trp Pro Pro
                 85                  90                  95

Ser Leu Thr Phe Gly Gly Gly Thr Arg Val Glu Ile Lys
            100                 105

<210> SEQ ID NO 95
<211> LENGTH: 993
<212> TYPE: DNA
<213> ORGANISM: Homo sapiens
<220> FEATURE:
<221> NAME/KEY: CDS
<222> LOCATION: (1)..(993)
<223> OTHER INFORMATION: 50E11-CH constant heavy chain (CH) sequence

<400> SEQUENCE: 95 gcc tcc acc aag ggc cca tcg gtc ttc ccc ctg gca ccc tcc tcc aag        48
Ala Ser Thr Lys Gly Pro Ser Val Phe Pro Leu Ala Pro Ser Ser Lys
 1               5                  10                  15 agc acc tct ggg ggc aca gcg gcc ctg ggc tgc ctg gtc aag gac tac        96
Ser Thr Ser Gly Gly Thr Ala Ala Leu Gly Cys Leu Val Lys Asp Tyr
                20                  25                  30 ttc ccc gaa ccg gtg acg gtg tcg tgg aac tca ggc gcc ctg acc agc       144
Phe Pro Glu Pro Val Thr Val Ser Trp Asn Ser Gly Ala Leu Thr Ser
             35                  40                  45 ggc gtg cac acc ttc ccg gct gtc cta cag tcc tca gga ctc tac tcc       192
Gly Val His Thr Phe Pro Ala Val Leu Gln Ser Ser Gly Leu Tyr Ser
         50                  55                  60 ctc agc agc gtg gtg acc gtg ccc tcc agc agc ttg ggc acc cag acc       240
Leu Ser Ser Val Val Thr Val Pro Ser Ser Leu Gly Thr Gln Thr
 65                  70                  75                  80 tac atc tgc aac gta aat cac aag ccc agc aac acc aag gtg gac aag       288
Tyr Ile Cys Asn Val Asn His Lys Pro Ser Asn Thr Lys Val Asp Lys
                 85                  90                  95 aaa gtt gag ccc aaa tct tgt gac aaa act cac aca tgc cca ccg tgc       336
Lys Val Glu Pro Lys Ser Cys Asp Lys Thr His Thr Cys Pro Pro Cys
                100                 105                 110 cca gca cct gaa ctc ctg ggg gga ccg tca gtc ttc ctc ttc ccc cca       384
Pro Ala Pro Glu Leu Leu Gly Gly Pro Ser Val Phe Leu Phe Pro Pro
             115                 120                 125 aaa ccc aag gac acc ctc atg atc tcc cgg acc cct gag gtc aca tgc       432
Lys Pro Lys Asp Thr Leu Met Ile Ser Arg Thr Pro Glu Val Thr Cys
         130                 135                 140 gtg gtg gtg gac gtg agc cac gaa gac cct gag gtc aag ttc aac tgg       480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag       528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg       576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac       624
His Gln Asp Trp Leu Asn Gly Lys Glu Tyr Lys Cys Lys Val Ser Asn
         195                 200                 205 aaa gcc ctc cca gcc ccc atc gag aaa acc atc tcc aaa gcc aaa ggg       672
Lys Ala Leu Pro Ala Pro Ile Glu Lys Thr Ile Ser Lys Ala Lys Gly
        210                 215                 220
```

```
cag ccc cga gaa cca cag gtg tac acc ctg ccc cca tcc cgg gat gag        720
Gln Pro Arg Glu Pro Gln Val Tyr Thr Leu Pro Pro Ser Arg Asp Glu
225                 230                 235                 240 ctg acc aag aac cag gtc agc ctg acc tgc ctg gtc aaa ggc ttc tat        768
Leu Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac        816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc        864
Asn Tyr Lys Thr Thr Pro Pro Val Leu Asp Ser Asp Gly Ser Phe Phe
        275                 280                 285 ctc tac agc aag ctc acc gtg gac aag agc agg tgg cag cag ggg aac        912
Leu Tyr Ser Lys Leu Thr Val Asp Lys Ser Arg Trp Gln Gln Gly Asn
    290                 295                 300 gtc ttc tca tgc tcc gtg atg cat gag ggt ctg cac aac cac tac acg        960
Val Phe Ser Cys Ser Val Met His Glu Gly Leu His Asn His Tyr Thr
305                 310                 315                 320 cag aag agc ctc tcc ctg tct ccg ggt aaa tga                            993
Gln Lys Ser Leu Ser Leu Ser Pro Gly Lys
                325                 330

<210> SEQ ID NO 96
<211> LENGTH: 330
<212> TYPE: PRT
<213> ORGANISM: Homo sapiens

<400> SEQUENCE: 96

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
```

```
                225                 230                 235                 240
Leu Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Gly Leu His Asn His Tyr Thr
305                 310                 315                 320

Gln Lys Ser Leu Ser Leu Ser Pro Gly Lys
                325                 330

<210> SEQ ID NO 97
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: 50E11-CL constant kappa chain (CL) sequence

<400> SEQUENCE: 97 cga act gtg gct gca cca tct gtc ttc atc ttc ccg cca tct gat gag       48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc       96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa      144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc      192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag      240
Thr Tyr Ser Leu Ser Ser Thr Leu Thr Leu Ser Lys Ala Asp Tyr Glu
65                  70                  75                  80 aaa cac aaa gtc tac gcc tgc gaa gtc acc cat cag ggc ctg agc tcg      288
Lys His Lys Val Tyr Ala Cys Glu Val Thr His Gln Gly Leu Ser Ser
                85                  90                  95 ccc gtc aca aag agc ttc aac agg gga gag tgt tag                      324
Pro Val Thr Lys Ser Phe Asn Arg Gly Glu Cys
            100                 105

<210> SEQ ID NO 98
<211> LENGTH: 107
<212> TYPE: PRT
<213> ORGANISM: Homo sapiens

<400> SEQUENCE: 98

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60
```

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 99
<211> LENGTH: 18
<212> TYPE: PRT
<213> ORGANISM: Homo sapiens
<220> FEATURE:
<221> NAME/KEY: BINDING
<222> LOCATION: (1)..(18)
<223> OTHER INFORMATION: IFNA2-peptide 19 bound specifically by mAB
      19D11

<400> SEQUENCE: 99

Ser Ala Ala Trp Asp Glu Thr Leu Leu Asp Lys Phe Tyr Thr Glu Leu
1               5                   10                  15

Tyr Gln

<210> SEQ ID NO 100
<211> LENGTH: 18
<212> TYPE: PRT
<213> ORGANISM: Homo sapiens
<220> FEATURE:
<221> NAME/KEY: BINDING
<222> LOCATION: (1)..(18)
<223> OTHER INFORMATION: IFNA2-peptide 32 bound specifically by mAB
      19D11

<400> SEQUENCE: 100

Arg Ile Thr Leu Tyr Leu Lys Glu Lys Lys Tyr Ser Pro Cys Ala Trp
1               5                   10                  15

Glu Val

<210> SEQ ID NO 101
<211> LENGTH: 18
<212> TYPE: PRT
<213> ORGANISM: Homo sapiens
<220> FEATURE:
<221> NAME/KEY: BINDING
<222> LOCATION: (1)..(18)
<223> OTHER INFORMATION: IFNA2-peptide 22 bound specifically by mAB 26B9

<400> SEQUENCE: 101

Tyr Thr Glu Leu Tyr Gln Gln Leu Asn Asp Leu Glu Ala Cys Val Ile
1               5                   10                  15

Gln Gly

<210> SEQ ID NO 102
<211> LENGTH: 18
<212> TYPE: PRT
<213> ORGANISM: Homo sapiens
<220> FEATURE:
<221> NAME/KEY: BINDING
<222> LOCATION: (1)..(18)
<223> OTHER INFORMATION: IFNW-peptide 23 bound specifically by mAB 26B9

```
<400> SEQUENCE: 102

Thr Gly Leu His Gln Gln Leu Gln His Leu Glu Thr Cys Leu Leu Gln
1               5                   10                  15

Val Val
```

HUMAN ANTI-IFN-α ANTIBODIES

CROSS REFERENCE TO RELATED APPLICATIONS

This application is a U.S. national stage application under 35 U.S.C. 371 and claims the benefit of PCT Application No. PCT/EP2014/064167 having an international filing date of Jul. 3, 2014, which designated the United States, which PCT application claimed the benefit of European Patent Application No. 13174995.4 filed Jul. 3, 2013, the disclosures of each of which are incorporated herein by reference.

REFERENCE TO SEQUENCE LISTING

This application contains a Sequence Listing submitted as an electronic text file named "WO2015001013SequenceListing.txt", having a size in bytes of 162 KB, and created on Jul. 30, 2014. The sequence listing information recorded in computer readable form is identical to the written (on paper or compact disc) sequence listing and includes no new matter. The information contained in this electronic file is hereby incorporated by reference in its entirety pursuant to 37 CFR § 1.52(e)(5).

FIELD OF THE INVENTION

The present invention generally relates to novel molecules binding IFN-α of mammal, preferably human origin, particularly human monoclonal antibodies as well as fragments, derivatives and variants thereof that recognize different subtypes of IFN-α. In particular, recombinant human patient-derived anti-IFN-α antibodies and methods of making the same are provided. In addition, compositions comprising such binding molecules, antibodies and mimics thereof useful in the treatment and diagnosis of disorders are described. Furthermore, the present invention relates to autoantibodies as agents for use in immunotherapy as well as targets in the therapeutic intervention of autoimmune and autoinflammatory disorders as well as malignancies, such as systemic lupus erythematosus (SLE) and type 1 diabetes mellitus (TIDM). More specifically, the present invention relates to monoclonal autoantibodies which have been isolated from B cells derived from subjects affected with an impaired central and/or peripheral tolerance or loss of self-tolerance typically due to a mutation in a gene involved in immune regulation.

BACKGROUND OF THE INVENTION

Inappropriate responses of the immune system may cause stressful symptoms to the involved organism. Exaggerated immune answers to foreign substances or physical states which usually do not have a significant effect on the health of an animal or human may lead to allergies with symptoms ranging from mild reactions, such as skin irritations to life-threatening situations such as an anaphylactic shock or various types of vasculitis. Immune answers to endogenous antigens may cause autoimmune disorders such as systemic lupus erythematosus (SLE), type for insulin dependent diabetes mellitus (TIDM or IDDM) and different forms of arthritis.

Immune responses occur in a coordinated manner, involving several cells and requiring communication by signaling molecules such as cytokines between the cells involved. This communication may be influenced or inhibited by, e.g., interception of the signals or block of the respective receptors.

Cytokines are secreted soluble proteins, peptides and glycoproteins acting as humoral regulators at nano- to picomolar concentrations behaving like classical hormones in that they act at a systemic level and which, either under normal or pathological conditions, modulate the functional activities of individual cells and tissues. Cytokines differ from hormones in that they are not produced by specialized cells organized in specialized glands, i.e. there is not a single organ or cellular source for these mediators as they are expressed by virtually all cells involved in innate and adaptive immunity such as epithelial cells, macrophages, dendritic cells (DC), natural killer (NK) cells and especially by T cells, prominent among which are T helper (Th) lymphocytes.

Depending on their respective functions, cytokines may be classified into three functional categories: regulating innate immune responses, regulating adaptive immune responses and stimulating hematopoiesis. Due to their pleiotropic activities within said three categories, e.g., concerning cell activation, proliferation, differentiation, recruitment, or other physiological responses, e.g., secretion of proteins characteristic for inflammation by target cells, disturbances of the cell signaling mediated by aberrantly regulated cytokine production have been found as a cause of many disorders associated with defective immune response, for example, inflammation and cancer.

Interferons (IFN), consisting from three known protein families, type I, II and III interferons constitute one of the most important classes of cytokines. All human type I interferons bind to a cell surface receptor (IFN alpha receptor, IFN-αR) consisting of two transmembrane proteins, IFN-αR-1 and IFN-αR-2 leading to JAK-STAT activation, the formation of ISGF3 and subsequent onset of gene expression (Platanias and Fish, *Exp. Hematol.* (1999), 1583-1592). The composition, receptors and signaling pathways of type I IFNs have been reviewed, e.g., in Stark et al., *Annu. Rev. Biochem.* (1998), 227-64; Pestka S., *Biopolymers* (2000), 254-87. Type I interferons build a structurally related family (IFN-α (alpha), IFN-(beta), IFN-K (kappa), IFN-8 (delta), IFN-£ (epsilon), IFN-T (tau), IFN-ω (omega), and IFN-s (zeta)), of which IFN-8 and IFN-T do not occur in humans. Human type I interferon (IFN) genes are clustered on human chromosome 9p21 and the mouse genes are located in the region of conserved synteny on mouse chromosome 4. So far, 14 IFN-α genes and 3 pseudogenes have been identified in the mouse. In humans 13 IFN-α (or IFN-α) genes (IFN-α1, IFN-α2, IFN-α4, IFN-α5, IFN-α6, IFN-α7, IFN-α8, IFN-α10, IFN-α13, IFN-α14, IFN-α16, IFN-α17 and IFN-α21) and 1 pseudogene have been identified, wherein two human IFN-α genes (IFN-α1/IFN-α1 and IFN-α13/IFN-α13) encode for identical proteins (van Pesch et al., *J Viral.* (2004), 8219-8228). IFN-γ is the sole Type II interferon. It is mainly involved in the induction of antimicrobial and antitumor mechanisms by macrophage stimulation. The IFN-γ receptor (IFNGR) is a heterodimeric receptor comprised of two ligand-binding IFNGRI chains associated with two signal-transducing IFNGR2 chains (Schroder et al., *J Leukoc. Biol.* 75 (2004), 163-189; Bach et al., *Annu. Rev. Immunol.* 15 (1997), 563-591). Type III interferons consist of three subtypes and are also termed IFN-α (IFN11,1 or IL-29, IFN-α2 or IL-28A and IFN-α3 or IL-28B) and have antiviral, antitumor, and immunoregulatory activity. The IFN-A receptor is also a heterodimeric complex consisting of a unique ligand-binding chain, IFN- 11,R1 (also designated IL-28Ra), and an accessory chain IL-I OR2, which is shared with receptors for IL-I 0-related cytokines (Li et al., *J Leukoc. Biol.* 86 (2009), 23-32)

Type I interferons are pleiotropic cytokines with antiviral, antitumor and immunoregulatory functions. Depending on context, they can be anti-inflammatory and tissue protective or proinflammatory and promote autoimmunity. IFN-1a or 1b is used for the treatment of multiple sclerosis and IFN-α2b therapy for many cancers (melanoma, hemat. malig.). Elevated IFN-α activity has been frequently detected in the sera of patients with systemic lupus erythematosus (SLE) indicating that IFN-α plays a central role in SLE development (R6nnblom and Alm, *J Exp. Med.* (2001), F59-F63; Crow M K, *Arthritis Rheum.* (2003), 2396-2401; Crow M K., *Curr Top Microbial. Immunol.* (2007), 359-386; Crow M K. *Rheum Dis Clin North Am.* (2010), 173-186).

On the other side, a specific expression pattern of interferon-dependent genes (termed the "interferon signature") is displayed in the leukocytes of patients with various autoimmune disorders such as SLE, TIDM, Sj6gren's syndrome, Dermatomyositis, Multiple Sclerosis (MS), Psoriasis and rheumatic arthritis (RA) patients. In addition, development of inflammatory arthritis, MS and TIDM has been repeatedly observed during IFN-α therapy indicating that IFN-α at least promotes those diseases (Crow M K., *Arthritis Res Ther.* (2010), Suppl 1:S5). Further data suggest an involvement of IFN-α in myositis, systemic scleroderma, chronic psoriasis (Higgs et al., *Eur Muse Rev* (2012), 22-28; Bissonnette et al., J Am Acad Dermatol (2009), 427-436; Greenberg S A, *Arth Res Ther* (2010): S4) and autoimmune thyroiditis (Prummel and Laurberg, *Thyroid* (2003), 547-551).

Accordingly, wherein depending on the context situation, treatment with Type I interferons, as in RA, MS and different leukemia or treatment with antibodies neutralizing Type I interferons, e.g., in SLE may be indicated, the very same treatment may be detrimental to the patient by promoting autoimmunity, inflammation and interferon-treatment related toxicities or even leading to the development of diseases such as MS and TIDM. One factor in these different effects may arise from the fact that, despite that different IFN subtypes activate the same cell surface receptor complex, they mediate variable responses which are also cell type dependent (van Pesch et al., *J Viral* 78 (2004), 8219-8228; Antonelli G., *New Microbial.* 31 (2008), 305-318; Gibbert et al., *PLoS Pathog.* 8 (2012), e1002868). The treatment therefore, should preferably be performed in a selective manner, wherein only particular IFN-α subtypes are administered to a patient, or particular IFN-α subtypes are neutralized, which are associated with a given pathological condition. Regarding IFN-α treatment such selectivity may be obtained by usage of highly purified IFN-α preparations for therapeutic purposes (Antonelli G., New Microbiol. 31 (2008), 305-318). However, regarding the use of IFN-α antibodies it is more difficult to obtain selectivity in respect of specific IFN-α subtypes, because there is a high degree of homology at the amino acid level with 80-95% homology between the IFN-α subtypes and 50% homology with IFN-β. It would be desirable therefore to provide a pool of IFN-α antibodies tolerable in humans of varying specificity towards all, selected or particular human IFN-α subtypes, which might be selectively used depending on the therapeutic and/or diagnostic indication.

First attempts to achieve this aim have already been made. For example, patent application US 2009/0214565 A1 describes isolation of several mouse anti-human IFN-α antibodies which neutralize between three and thirteen different subtypes of human IFN-α and U.S. Pat. No. 7,087,726 B2 describes a murine anti-human IFN-α antibody and its humanized version which recognize seven subtypes of human IFN-α. However, most if not all anti-IFN-antibodies provided so far are of murine origin and thus prone to an adverse reaction in humans.

Due to immunological responses to foreign antibodies, as mouse antibodies in humans (RAMA-response; Schroff et al., *Cancer Res.* 45 (1985), 879-885; Shawler et al., *J Immunol.* 135 (1985), 1530-1535), mostly humanized versions of antibodies are used in present therapeutic approaches (Chan and Carter, *Nature Reviews Immunology* 10 (2010), 301-316; Nelson et al., *Nature Reviews Drug Discovery* 9 (2010), 767-774). One approach to gain such antibodies was to transplant the complementarity determining regions (CDR) into a completely human framework, a process known as antibody humanization (Jones et al., *Nature* 321 (1986), 522-525). This approach is often complicated by the fact that mouse CDR do not easily transfer to a human variable domain framework, resulting in lower affinity of the humanized antibody over their parental murine antibody. Therefore, additional and elaborate mutagenesis experiments are often required, to increase the affinity of the so engineered antibodies. Another approach for achieving humanized antibodies is to immunize mice which have had their innate antibody genes replaced with human antibody genes and to isolate the antibodies produced by these animals. However, this method still requires immunization with an antigen, which is not possible with all antigens because of the toxicity of some of them. Furthermore, this method is limited to the production of transgenic mice of a specific strain.

Another method is to use libraries of human antibodies, such as phage display, as described, for example, for the generation of IL-13 specific antibodies in international application WO 2005/007699. Here, bacteriophages are engineered to display human scFv/Fab fragments on their surface by inserting a human antibody gene into the phage population. Unfortunately, there is a number of disadvantages of this method as well, including size limitation of the protein sequence for polyvalent display, the requirement of secretion of the proteins, i.e. antibody scFv/Fab fragments, from bacteria, the size limits of the library, limited number of possible antibodies produced and tested, a reduced proportion of antibodies with somatic hypermutations produced by natural immunization and that all phage-encoded proteins are fusion proteins, which may limit the activity or accessibility for the binding of some proteins. Similarly, European patent application EP O 616 640 A1 describes the production of autoantibodies from antibody segment repertoires displayed on phage. Phage libraries are generated from unimmunized humans in this respect (see, e.g., Example 1; page 16, lines 43-51; Example 2, at page 17, paragraph [0158], lines 57-58). However, also the methods described in this patent application suffer from above mentioned general disadvantages of antibodies generated from phage libraries, in comparison to antibodies produced and matured in a mammalian, i.e. human body.

The same applies to the most prominent anti-IFNa monoclonal antibody Sifalimumab (formerly, MEDI-545) that binds to and specifically neutralizes most IFN-α subtypes, preventing signaling through the type I IFN receptor. Sifalimumab is said to be a "human" anti-IFNa monoclonal antibody but actually has been derived from humanized mice, i.e. from the former company Medarex' UltiMab platform which is based on transgenic mice in which the largest fraction of the human germline repertoire was introduced. Nevertheless, though the amino acid sequences of the antibodies derived from humanized mice are of human origin these antibodies are artificial and not truly human as they have not undergone immunization, recombination, selection and affinity maturation in a human being for which reason there is still the risk of their being immunogenic and less effective, in particular compared to human-derived antibodies.

In view of the above, there is still a need for additional and new compounds like binding molecules of high specificity for particular human IFN-α subtypes, specific for a selected range or for all IFN-α subtypes which are tolerable in humans either for monotherapy or combinatorial approaches.

The solution to this problem is provided by the embodiments of the present invention as characterized in the claims and disclosed in the description and illustrated in the Examples and Figures further below.

SUMMARY OF THE INVENTION

The present invention relates to IFN-α specific human monoclonal antibodies and IFN-α binding fragments thereof. In particular, human monoclonal anti-IFN-α antibodies are provided with a selective binding profile towards IFN-α subtypes and displaying binding and neutralizing activity as shown in the Examples and the Figures. Due to their neutralizing property, the antibodies of the present invention have therapeutic, prognostic and diagnostic utility, which make them in particular valuable for applications in relationship with diverse autoimmune or autoinflammatory disorders and conditions associated with/involving IFN-α activity in initiation and/or maintenance of undesired immune responses, such as systemic lupus erythematosus (SLE), various forms of arthritis including but not limited to rheumatoid arthritis (RA), type 1 or insulin dependent diabetes mellitus (TIDM or IDDM), Sjögren's syndrome, Dermatomyositis, Multiple Sclerosis (MS), psoriasis, chronic psoriasis, myositis, systemic scleroderma, autoimmune thyroiditis and cancer including leukemia (ALL; Einav et al., Oncogene 24 (2005), 6367-6375); see as well the section "Background of the invention" above, describing the IFN-α subtypes and their possible involvement disorders and implications towards possible indications of the antibodies of the present invention in related therapeutic, diagnostic and/or prognostic applications.

The antibodies of the present invention are preferably isolated from mammals, in particular humans, which are affected with an impaired central and/or peripheral tolerance or loss of self-tolerance which may be due to or associated with a disrupted or deregulated genesis of self-tolerance, preferably caused by a monogenic autoimmune disorder. Examples of mammals which provide a particularly suitable source for autoantibodies in accordance with the present invention are mammals, e.g., humans having a disorder associated with a mutation in the AIRE (Autoimmune Regulator) gene such as Autoimmune polyendocrinopathy syndrome type 1 (APS1) (Peterson et al., *Nat. Rev. Immunol.* 8 (2008), 948-957), Autoimmune polyendocrinopathy syndrome type 2 (APS2) (Baker et al., *J Clin. Endocrinol. Metab.* 95 (2010), E263-E270) and immunodysregulation polyendocrinopathy enteropathy X-linked syndrome (IPEX) (Powell et al., *J Pediatr.* 100 (1982), 731-737; Ochs et al., *Immunol. Rev.* 203 (2005), 156-164). Preferably, the patients from whom the antibodies were isolated are APS1 patients characterized by being symptom-free for Lupus erythematodes (SLE) and displaying seroreactivity against dsDNA and at least one at least one of the human IFN-α subtypes.

In particular, in accordance with the present invention for the first time human and human patient derived anti-IFN-α antibodies are provided with different IFN-α binding profiles and IFN-α neutralizing activity, thereby alone or in combination covering substantially all IFN-α subtypes.

Therefore, in one aspect the present invention generally relates to high affinity neutralizing monoclonal antibodies to several IFN-α subtypes. In a further aspect, the present invention relates to human monoclonal antibodies (mAbs, or MABs) against several IFN-α subtypes, i.e. at least one of the human IFN-α subtypes IFN-α1/13 (¹/₁₃ IFN-α1 b), IFN-α2, IFN-α4, IFN-α5, IFN-α6, IFN-α8, IFN-α10, IFN-α14 or IFN-α21, described in detail below, which are considered to be safe and effective therapeutics for disorders in which those cytokines are involved. In one embodiment, the IFN-α binding molecule of the present invention does not bind and/or neutralize to any significant extent IFN-(beta interferon, IFNB), IFN-γ (gamma interferon, IFNG) or IFN-ω (interferon omega, IFN-ω).

In another embodiment, in accordance with the present invention anti-IFN-α antibodies are provided, which in addition bind to and neutralize the activity of IFN-ω, respectively, hitherto described to be unrelated to IFN-α in its antigenic properties, as it usually does not cross-react with antisera or monoclonal antibodies in immunoassays or antiviral neutralization bioassays. Thus, in one aspect the present invention relates to novel IFN binding molecules, preferably human-derived monoclonal antibodies as well as fragments and biotechnological derivatives thereof which are capable of binding to/and or neutralizing the activity of at least one human IFN-α subtype and of human IFN-ω. Preferably, the binding and neutralizing activity, respectively, of the IFN-binding molecule is essentially the same or at least in the same order of magnitude for IFN-α subtype(s) and IFN-ω.

Naturally, the present invention extends to nucleic acids, in particular cDNA encoding at least one variable, constant and/or complementarity determining region of the antibodies of the present invention, vectors comprising such nucleic acids, antibody producing cell lines and recombinant cells. The present invention further relates to pharmaceutical compositions, diagnostic assays and kits that comprise the binding molecules or peptides recognized by the antibodies isolated in accordance with the present invention and to therapeutic methods based thereon.

In addition, the present invention relates to a process for the manufacture of a human-derived anti-IFN-α and anti-IFN-α/IFN-ω monoclonal antibody, respectively, or an IFN-binding fragment or biotechnological derivative thereof or of a composition comprising the anti-IFN-α and anti-IFN-α/IFN-ω monoclonal antibody, respectively, or an IFN-binding fragment or biotechnological derivative thereof, which manufacture comprises the step of preparation of the antibody, IFN-binding fragment or biotechnological derivative thereof by expression in a recombinant host organism of transforming DNA encoding the antibody, IFN-binding fragment or biotechnological derivative thereof. In one embodiment, the composition is a pharmaceutical composition, wherein the step of preparation of the antibody, IFN-binding fragment or biotechnological derivative thereof is followed by admixing the antibody, IFN-binding fragment or biotechnological derivative thereof with a pharmaceutically acceptable carrier in the manufacture of a pharmaceutical composition.

While the invention is illustrated and described by way of reference to the human-derived antibody originally obtained in the experiments performed in accordance with the present invention and described in the Examples it is to be understood that the antibody or antibody fragment of the present invention include synthetic and biotechnological derivatives of an antibody which means any engineered antibody or antibody-like IFN binding molecule, synthesized by chemical or recombinant techniques, which retains one or more of the functional properties of the subject antibody, in particular its neutralizing activity towards IFN-α and IFN-ω. Thus, while the present invention may be described for the sake of conciseness by way of reference to an antibody, unless stated otherwise synthetic and biotechnological derivatives thereof as well as equivalent IFN binding molecules are meant and included with the meaning of the term antibody.

Further embodiments of the present invention will be apparent from the description and examples that follow.

BRIEF DESCRIPTION OF THE DRAWINGS

FIG. 1: Amino acid sequences of the variable region, i.e. heavy chain and kappa/lambda light chain (VH, VL) of anti-IFN-α specific human antibodies of the present invention. IgG1, kappa, anti-IFN-α specific antibodies A: 5D1; B: 13B11; C: 19D11; D: 25C3; E: 26B9; F: 31B4, G: 8H1, H: 12H5 and I: 50E11. Framework (FR) and complementarity determining regions (CDRs) are indicated with the CDRs being underlined. Italic amino acids indicate sequences which have not been sequenced but obtained from database. Due to the cloning strategy the amino acid sequence at the N-terminus of the heavy chain and light chain may potentially contain primer-induced alterations in FR1, which however do not substantially affect the biological activity of the antibody.

FIG. 2: Cross-competition—Epitope mapping. Differential binding of exemplary anti-IFN-α MABs of the present invention to distinct binding sites was investigated in cross-competition experiments on A: IFN-α2, B: IFN-α4 and C: IFN-α14. As an IFN-α non-binding control (hlgG1) a human antibody binding to an unrelated antigen has been used.

FIG. 3: EC50 ELISA determination. EC50 binding of hMABs 5D1, 13B11, 25C3 and 26B9 to A: IFN-α2, B: IFN-α4 and C: IFN-α14. EC50 binding to IFN-α2/-4/-14 of hMABs D: 19D11 and E: 31B4.

FIG. 4: Correlating the presence of known disease-associated and protective autoantibodies in APS1 patients indicates that IFN-α autoantibodies prevent the onset of lupus erythematosus in APS1 patients (columns dsDNA to IFNα14). Target: Coding number of the particular APS1-patient examined in the correlation study. Anti-dsDNA antibodies are highly specific for SLE and used in the diagnosis of the disease. No APS1 patients have lupus despite the frequent presence of anti-dsDNA antibodies as assessed by ProtoArray analysis (Life Technologies). APS1 patients display pronounced seroreactivity against several IFN-α subtypes which are clinically-relevant drug targets involved in many lupus-implicated molecular mechanisms. Circles indicate the presence, empty cells the absence of particular antibodies. Patients 2, 4, 13 and 21 (black arrows) are T1DMs. Patients 10, 14, 16, 17 and 18 (white arrows) have characteristics of being T1DM but are not. The results suggest differential neutralizing activity in serum of APS1 patients suffering from T1DM and these who are not. As can be inferred from FIGS. 31 and 32 this difference observed here seems to be due to differences in titers of anti-IFN antibodies in both patient classes, with much higher antibody titers in APS1 patients not suffering from T1DM, rather than differences in the neutralizing activity of individual anti-IFN antibodies.

FIG. 5: Human-derived anti-IFN-α monoclonal antibodies neutralize rhIFN-α-mediated STAT1 activation in HEK 293T cells. HEK 293T cells were either left untreated (–) or stimulated (+) with recombinant human rhIFN-αs or IFN-*Gaussia* luciferase fusion proteins (g1 IFNs), in the absence of antibodies or in the presence of human-derived IFN-α monoclonal antibodies or a human control IgG as indicated (Ctrl). Cell lysates were subjected to SDS-PAGE and phosphorylated STAT1 levels (pSTAT1) were visualized in Western blots. Total STAT1 levels or tubulin levels serve as loading control. Antibody concentration: 5 μg/ml. rhIFN-α concentration: 10 ng/ml (rhIFN-α1), 2 ng/ml (all other rhIFNs); g1 IFN-α-containing supernatants of 293T cells transiently expressing IFN-*Gaussia* luciferase fusion proteins were used at their respective EC80 dilutions. A1: Control: detection of total and phosphorylated STAT1 (pSTAT1) by Western Blots (WB) in 293T cells after 100 ng/ml IFN-α2/-4/-14 stimulation. 293T-cells stimulation by IFN-α2/-4/-14. (i): phosphorylated STAT1, (ii): total STAT1, (iii): Tubulin loading control. Time: indicates treatment duration of the cells with the respective IFN. After stimulation phosphorylated STAT1 can be observed for all three IFN-α subtypes. Positions of respective molecular weight (kDa) standard bands are indicated on the left of the blot for comparison. A2: Control: detection of total and phosphorylated STAT1 (pSTAT1) by Western Blots (WB) in 293T cells after stimulation with different doses of rhIFN-α1, rhIFN-α2 and rhIFN-α16. B: IFN-α1, IFN-α2, IFN-α4, g1 IFN-α5 and IFN-α6 stimulation. All exemplary antibodies except 5D1 neutralize IFN-α1 efficiently, and all exemplary antibodies neutralize IFN-α2, IFN-α4 and g1 IFN-α5. Exemplary antibodies 25C3, 5D1 and 13B11 display weaker neutralization of IFN-α6. C: IFN-α7, g1 IFN-α8, IFN-α10, IFN-α14 and IFN-α16 stimulation. All exemplary antibodies neutralize IFN-α7. All exemplary antibodies except 25C3 and 13B11 neutralize g1 IFN-α8 efficiently. IFN-α10 is efficiently neutralized by all exemplary antibodies except 25C3, while IFN-α16 is efficiently neutralized only by exemplary antibodies 19D11, 5D1 and 13B11. D: IFN-α17, IFN-α21, IFNB and g1 IFNG stimulation. All exemplary antibodies neutralize IFN-α17, and all exemplary antibodies except 13B11 efficiently neutralize IFN-α21. IFN-ω is apparently only efficiently neutralized by exemplary antibodies 26B9 and 31B4. None of the exemplary antibodies neutralizes IFNB or g1 IFNG.

FIG. 6: Schematic representation of the Firefly-Luciferase reporter construct and the *Renilla*-Luciferase construct used as internal normalization control. TRETranscription response element; CMV-cytomegalovirus.

FIG. 7: Human-derived anti-IFN-α monoclonal antibodies neutralize rhIFN-α-induced ISRE-Luciferase reporter gene activation in HEK 293T cells. A and B: Testing of exemplary anti-IFN-α antibodies 19D11, 25C3, 26B9 and 31B4. HEK 293T cells transiently expressing ISRE dual luciferase reporter constructs were either left untreated (–) or stimulated with rhIFNs (+), in the absence of antibodies or in the presence of human-derived IFN-α monoclonal antibodies or a human control IgG as indicated. rhIFN concentration: 2 ng/ml; antibody concentration: 5 μg/ml, C and D: Testing of exemplary anti-IFN-α antibodies 5D1 and 13B11. HEK 293T cells transiently expressing ISRE dual luciferase reporter constructs were treated as in (A/B) and ISRE reporter activity was analyzed after 24 hours. rhIFN-α concentration: 1 ng/ml; antibody concentration: 5 μg/ml.) A/C: measurements of the relative luciferase units, B/D: calculation of the expressional fold change. E: Neutralization of rhIFN-α1, A2, A4, A5, A6, A7, A8, A10, A14, A16, A17, A21, rhIFN-ω and rhIFNB by exemplary human-derived monoclonal antibodies of the present invention 8H1 and 12H5. Exemplary antibody 8H1 fully neutralizes IFN-ω, together with IFN-α1, A4, A5, A6, A7, A10, A16, A17 and A21, while displaying slightly weaker neutralization of IFN-α2, A8 and A14. Exemplary antibody 12H5 neutralizes all IFN-α subtypes and not IFN-ω. Neither exemplary antibody 8H1 nor 12H5 neutralizes IFNB. HEK 293T MSR were treated as in A and ISRE reporter activity was analyzed after 24 hours. rhIFN concentration: 10 ng/ml (IFN-α1), 1.3 ng/ml (IFN-α16), 4 ng/ml (IFN-α21), 1 ng/ml (IFNB) and 2 ng/ml (all other IFNs). Antibody concentration: 5 μg/ml.

Figure 8:
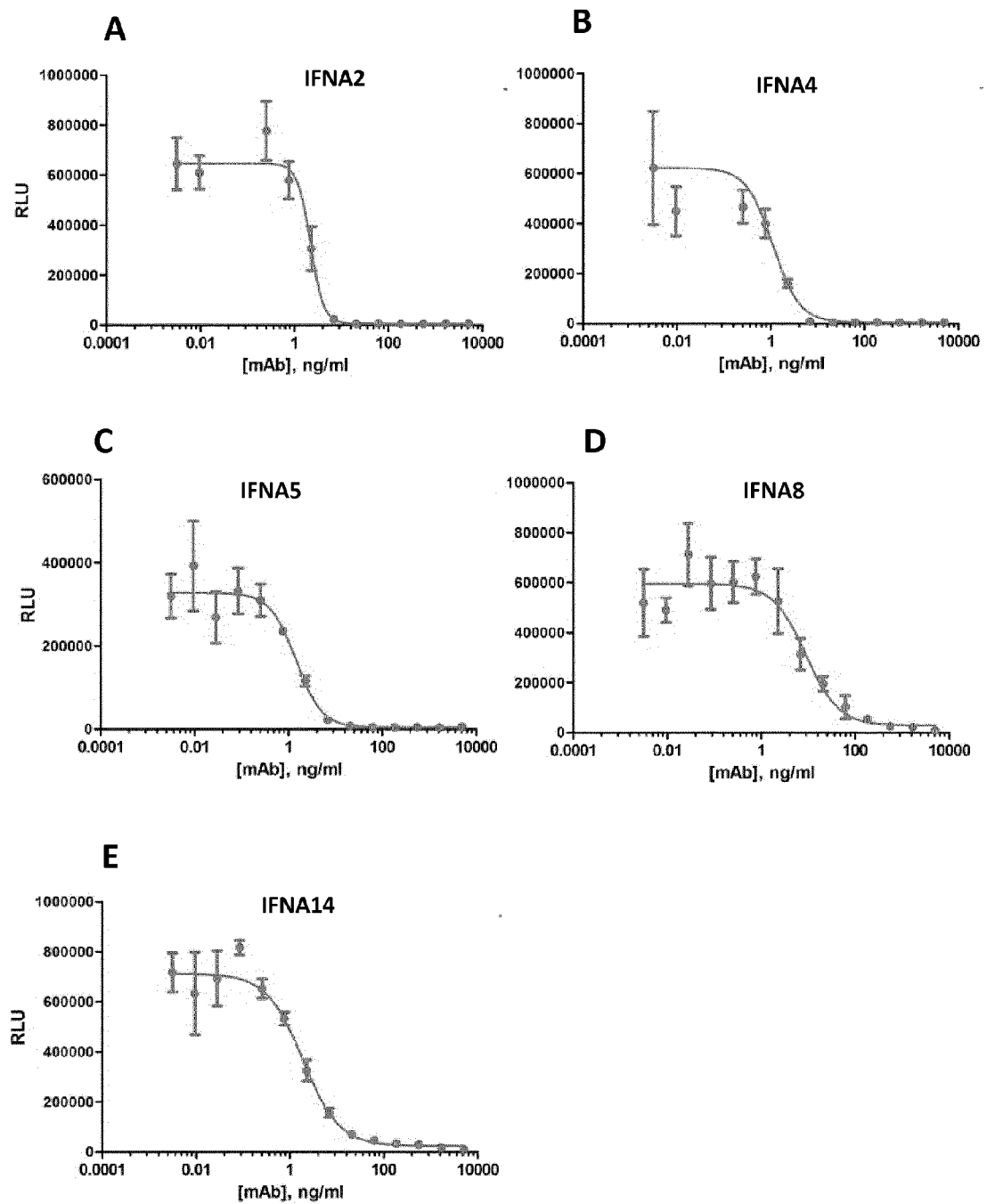
Figure 8:
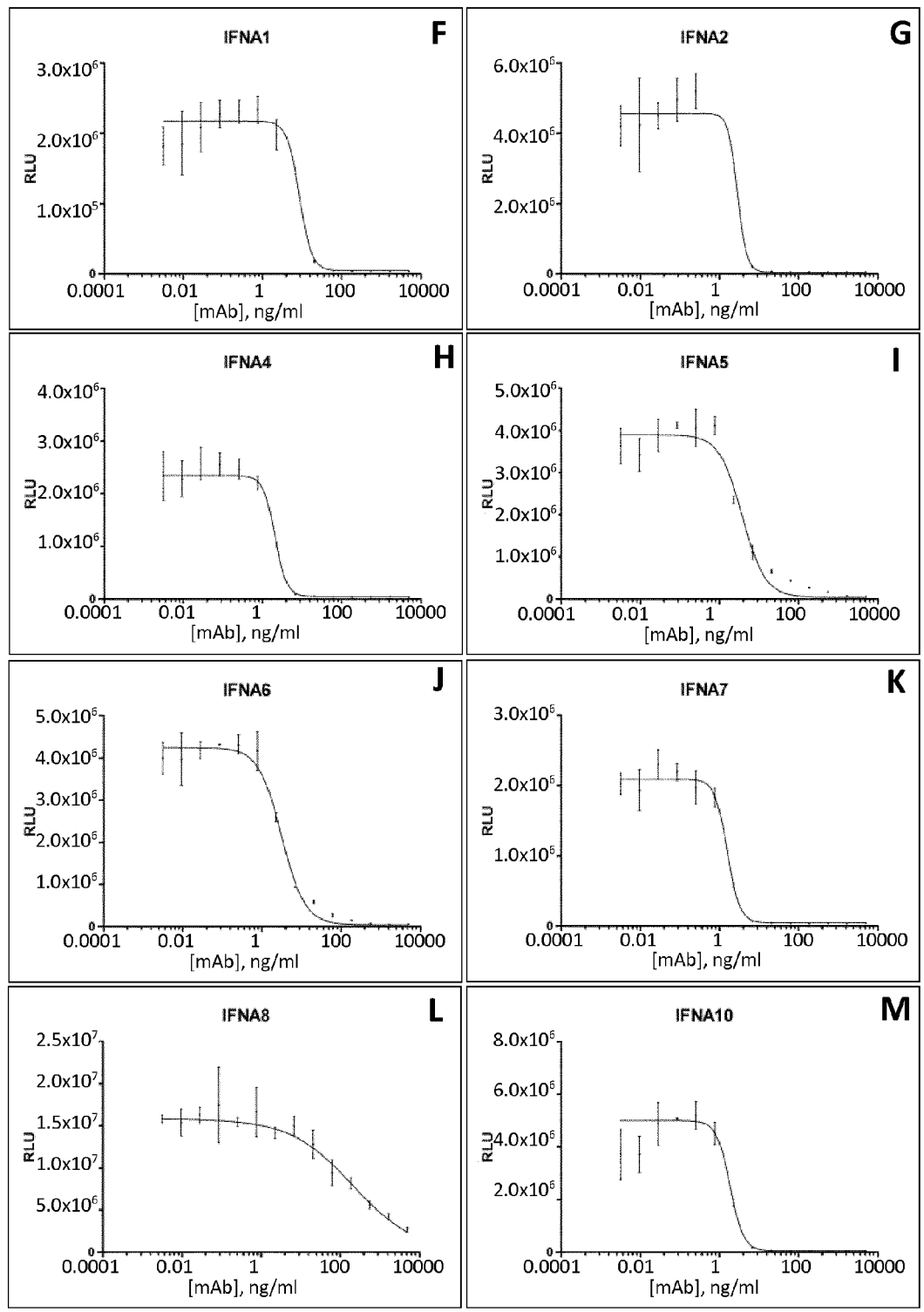
Figure 8:
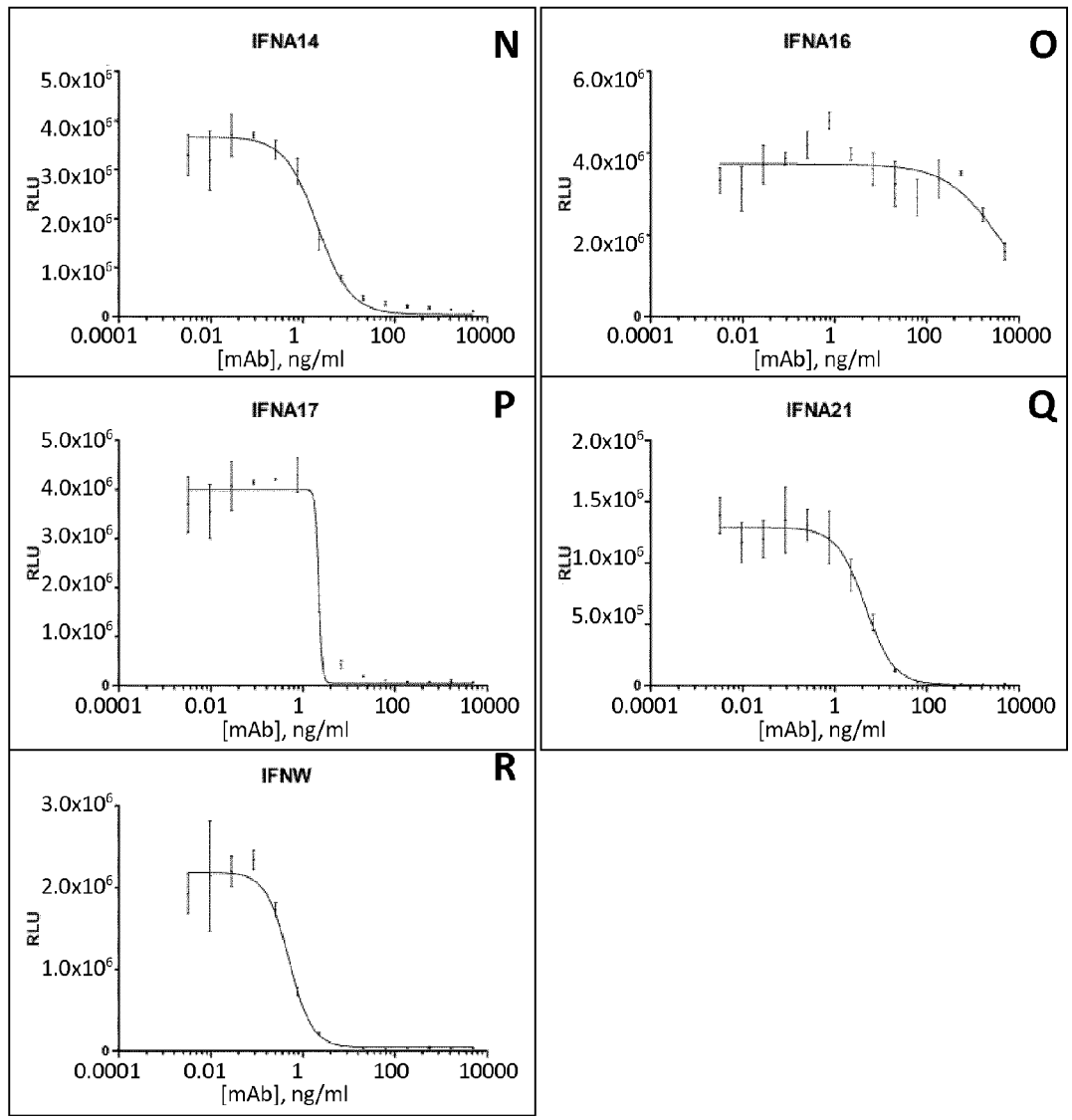

FIG. 8: IC 50 analysis of exemplary human-derived IFN-α mAb 26B9 by ISRE-Luciferase reporter neutralization assay. IC 50 neutralization graphs by exemplary antibody 26B9 of A: IFN-α2; B: IFN-α4; C: IFN-α5; D: IFN-α8; E: IFN-α14. IC 50 analysis results of a confirmative round of neutralization assays for the exemplary antibody 26B9 are shown of F: IFN-α1, G: IFN-α2, H: IFN-α4, I: IFN-α5, J: IFN-α6, K: IFN-α7, L: IFN-α8, M: IFN-α10, N: IFN-α14, 0: IFN-α16, P: IFN-α17, Q: IFN-α21 and R: IFN-ω. IC 50 data is summarized in Table 4. RLU at the Y-axis=relative light units, as in foregoing figures.

Figure 9:
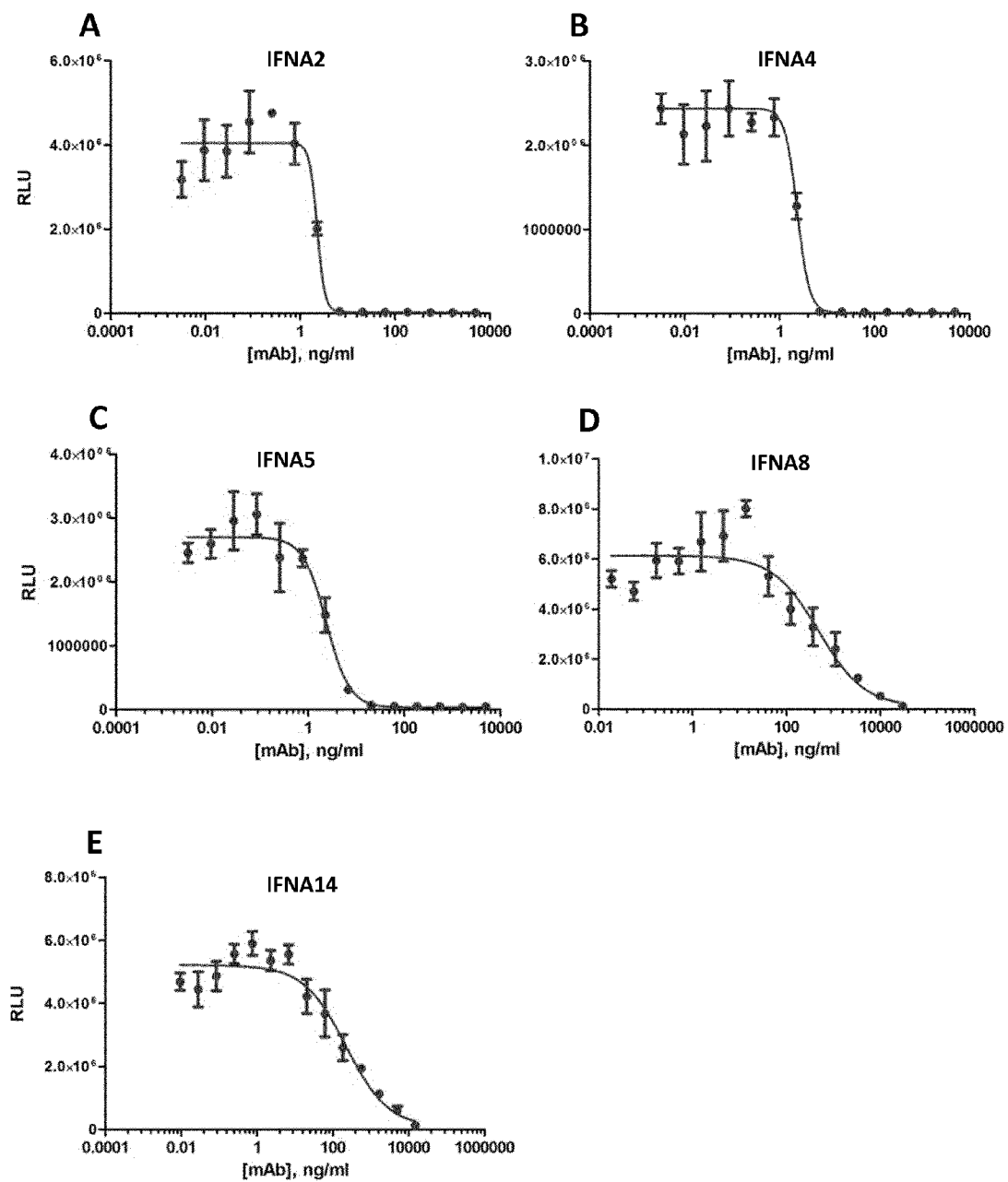

FIG. 9: IC50 analysis of exemplary human-derived anti-IFN-α mAb 25C3 by ISRE Luciferase reporter neutralization assay. Assay performed as described in FIG. 8. IC50 neutralization graphs by exemplary antibody 26B9 of: A: IFN-α2; B: IFN-α4; C: IFN-α5; D: IFN-α8 and E: IFN-α14.

Figure 10:
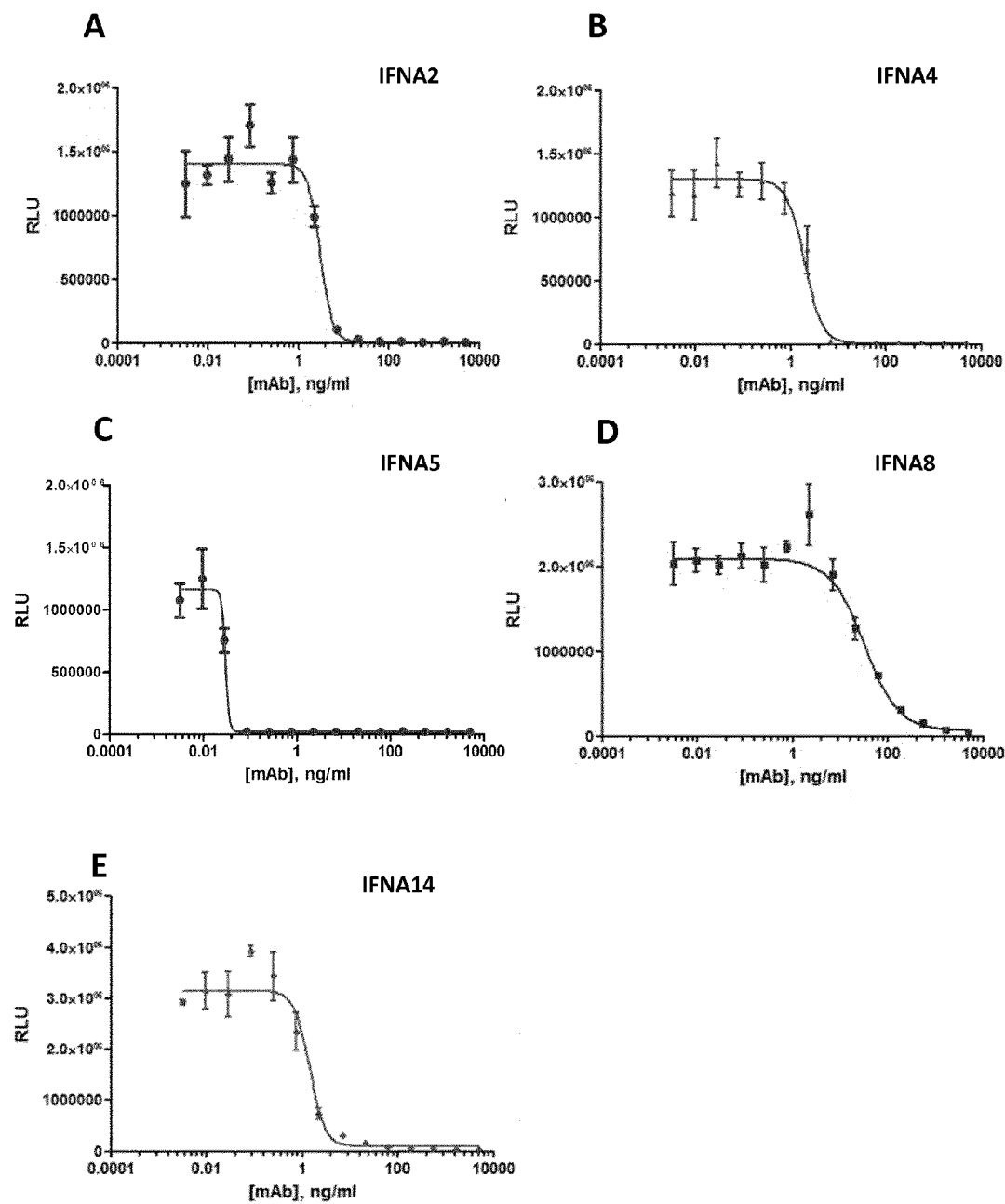
Figure 10:
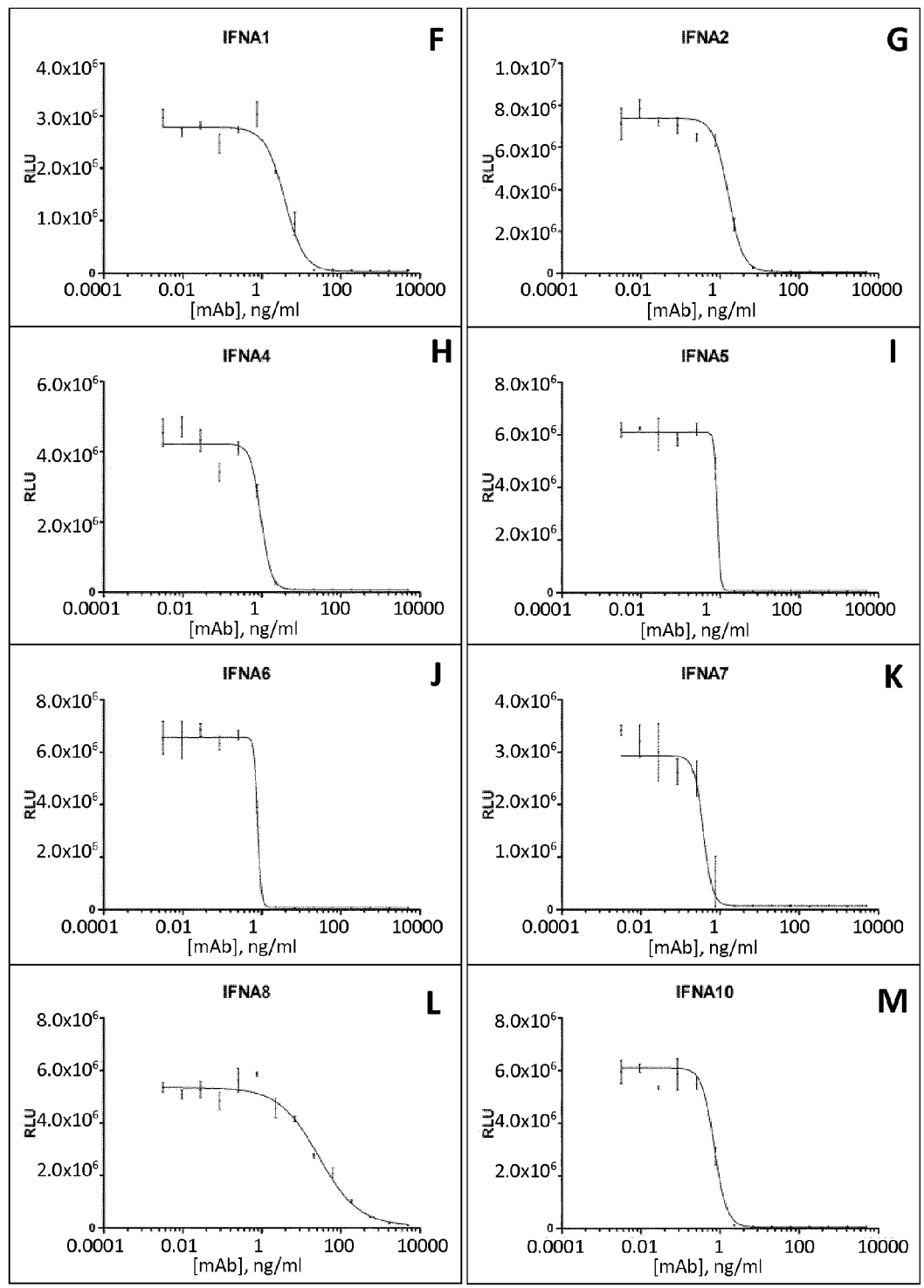
Figure 10:
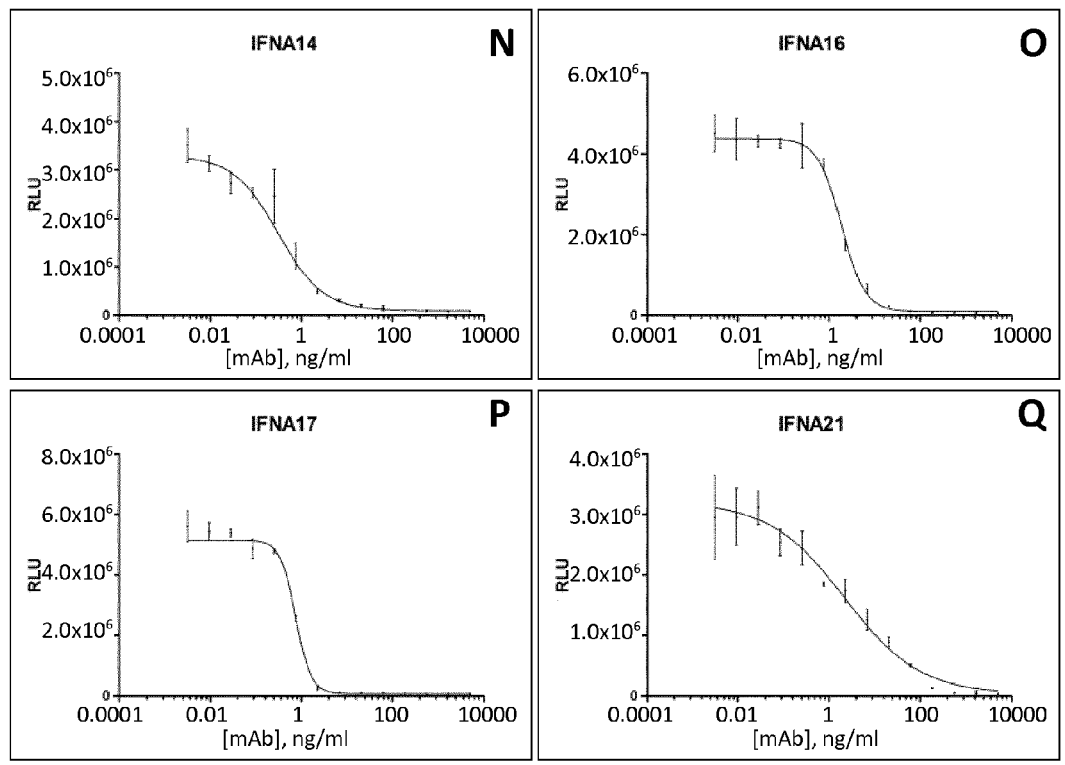

FIG. 10: IC50 analysis of exemplary human-derived anti-IFN-α mAb 19D11 by ISRE Luciferase reporter neutralization assay. Assay performed as described in FIG. 8. IC50 graphs of neutralization by exemplary antibody 19D11 of: A: IFN-α2; B: IFN-α4; C: IFN-α5; D: IFN-α8; E: IFN-α14. IC 50 neutralization graphs of a confirmative experimental round by exemplary antibody 19D11 of F: IFN-α1, G: IFN-α2, H: IFN-α4, I: IFN-α5, J: IFN-α6, K: IFN-α7, L: IFN-α8, M: IFN-α10, N: IFN-α14, 0: IFN-α16, P: IFN-α17 and Q: IFN-α21. IC 50 data is summarized in Table 4.

FIG. 11: A: Determination and comparison of binding of exemplary MABs 19D11, 25C3, 26B9, 5D1 and 13B11 of the present invention to IFN-α1 and IFN-α2 (ImmunoTools) by ELISA. Exemplary anti-IFN-α-α antibody 5D1 does not cross-react with IFN-α1. B: Determination and comparison of binding of exemplary MABs 5D1, 13B11, 19D11, 25C3, 26B9 and 31B4 of the present invention to IFN-α8 and IFN-α14 (IFN-*Gaussia* luciferase fusion proteins) by LIPS. Exemplary MAB 13B11 does not have cross-reactivity with IFN-α8 (g1IFN-α8). C: Determination and comparison of binding of exemplary MABs 5D1, 13B11 19D11, 25C3, 26B9 and 31B4 of the present invention to IFN-α5, IFN-α6, IFN-α8, IFN-α21 (all from PBL) and IFN-α14 (ATGen). Exemplary anti-IFN-α-α antibody 13B1 does not cross-react with IFN-α8 and IFN-α21. Antibody 19D11 cross-reacts with a lower affinity with IFN-α21 than with the other IFN-α subtypes. MABs were tested at 1 μg/ml in (C).

Figure 12:
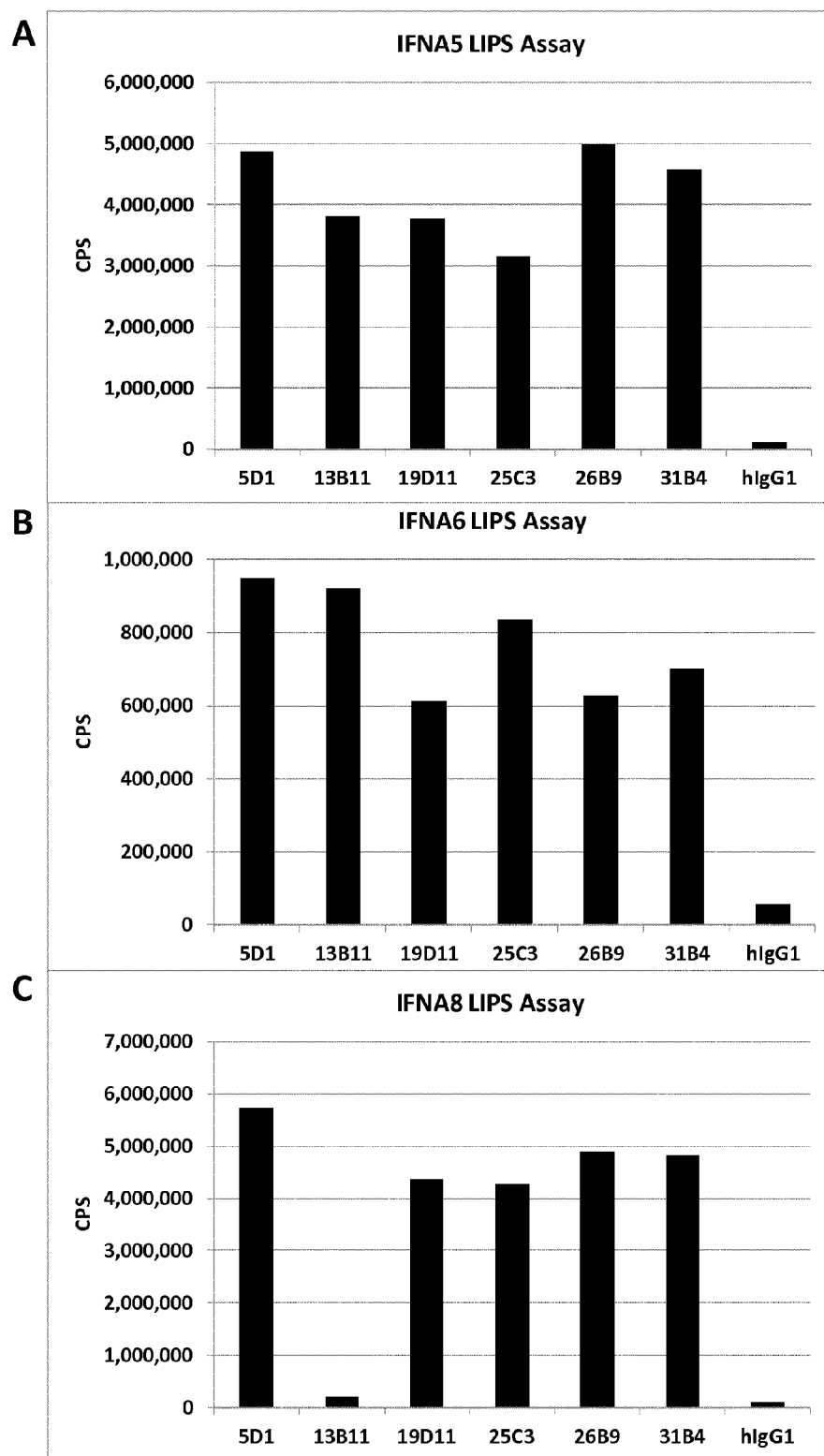

FIG. 12: LIPS assay-determination of binding of the antibodies of the present invention to different IFN-α subtypes (IFN-*Gaussia* luciferase fusion proteins). Binding of the exemplary antibodies of the present invention to A: IFN-α5; B: IFN-α6 and C: INFA8. Exemplary anti-IFN-α antibody 13B11 shows no substantial cross-reactivity with IFN-α8. As an IFN-α non-binding control (hIgG1) an human antibody binding to an unrelated antigen was used.

Figure 13:
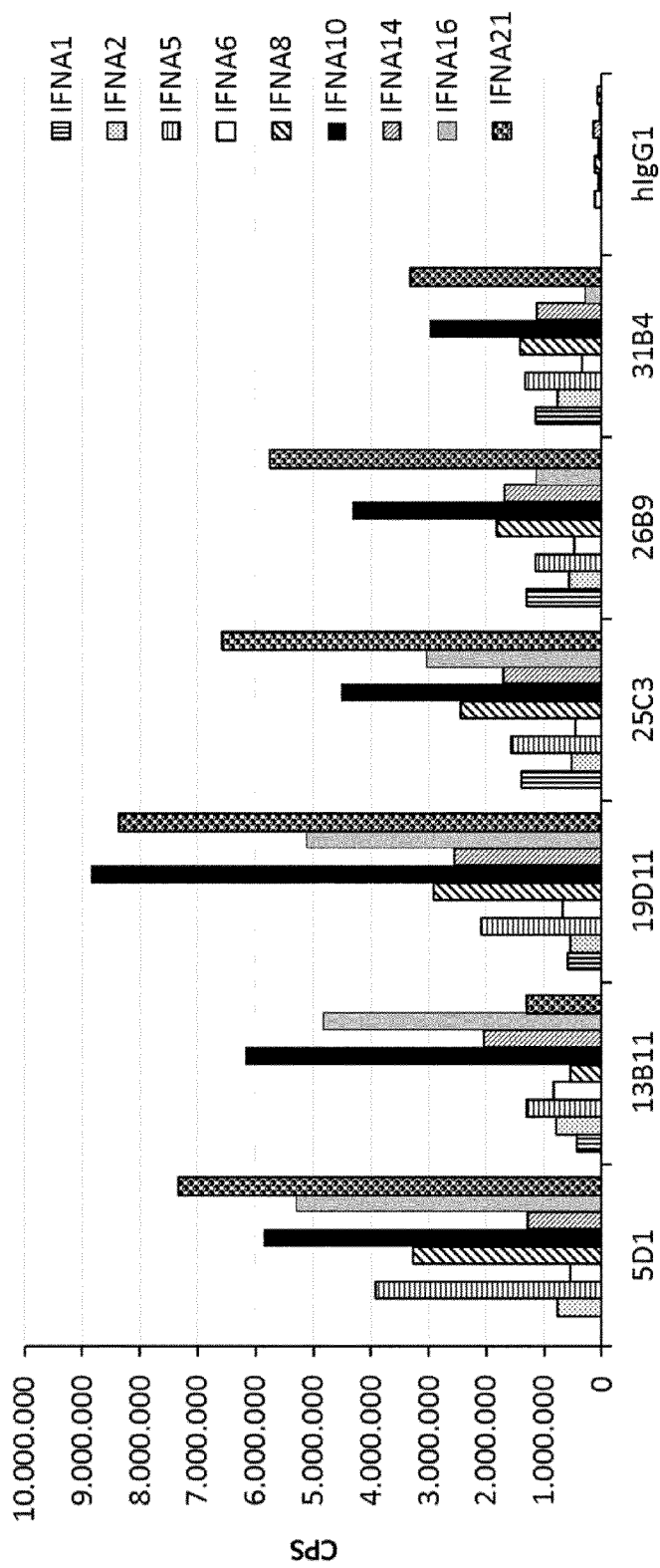

FIG. 13: LIPS assay—determination of binding characteristics of the exemplary antibodies 5D1, 13B11, 19D11, 25C3, 26B9 and 31B4 of the present invention towards IFN-α1, IFN-α2, IFN-α5, IFN-α6, IFN-α8, IFN-α10, IFN-α14, IFN-α16 and IFN-α 21 (IFN-*Gaussia* luciferase fusion proteins). As an IFN-α non-binding control (hIgG1) a human antibody binding to an unrelated antigen was used. All antibodies were tested at 0.5 μg/ml. All IFN-α subtypes used in FIGS. 12 and 13 are IFN-α-*Gaussia* luciferase fusion proteins (g1IFN-αs).

Figure 14:
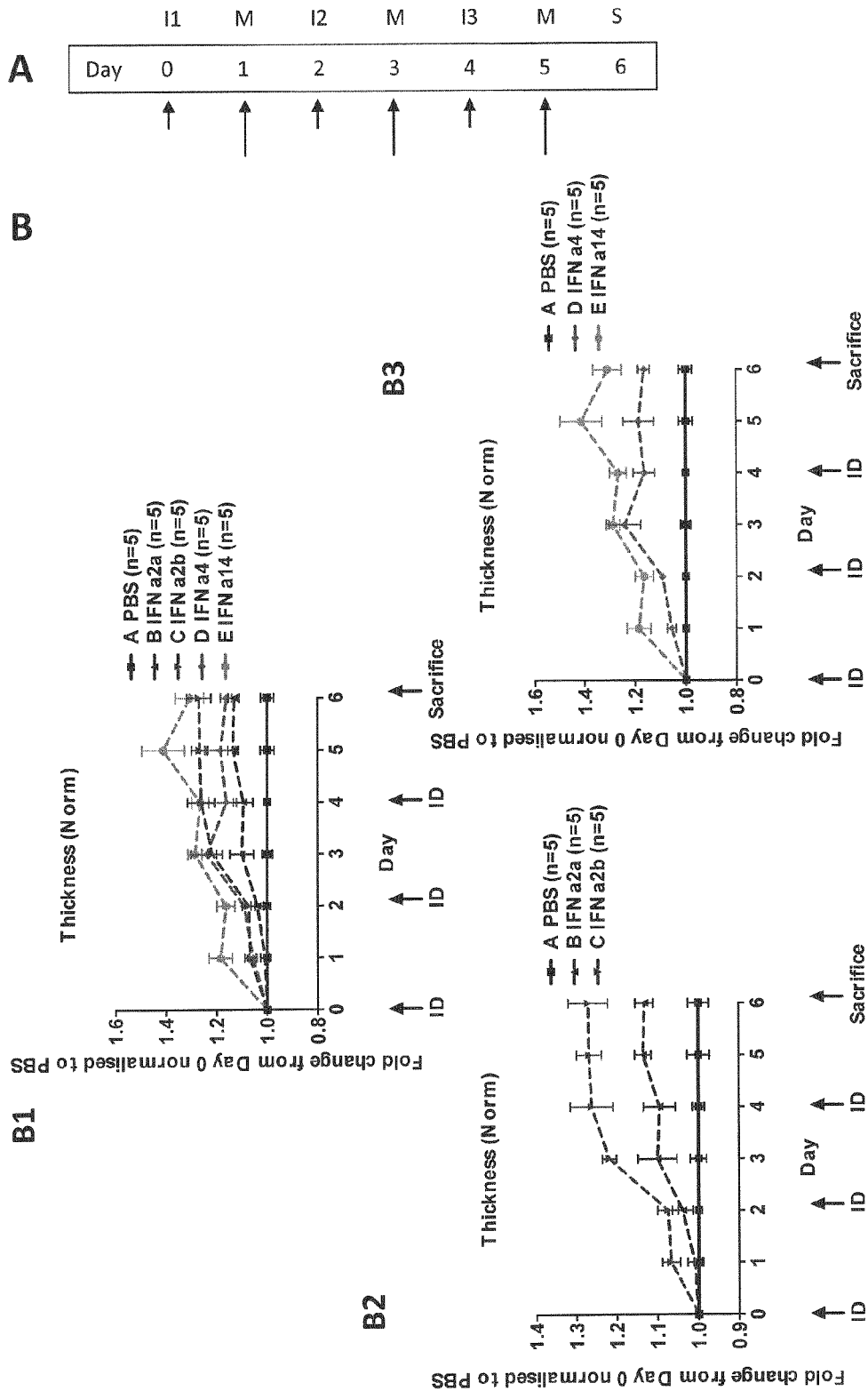

FIG. 14: Ear inflammation assay-test of the proinflammatory effect of human IFN subtypes in mice. A: Exemplary 6-day experimental timeline. B: CytoEar ear thickness measurements calculated as fold change relative to day 0 measurements than normalized to relevant PBS controls, for each cohort. B1: Overview of the effect of all normalized measurements. B2: Effects of the IFNa2a and IFNa2b injections. B3: Effects of the IFNa4 and IFNa14 injections. All four human IFN-α subtypes tested were able to significantly induce ear swelling following ID. All ears were markedly thicker than PBS treated ears. IFNa14 was the most potent proinflammatory agent. Mean+/−SEM, 11-3 or ID=intradermal cytokine injections, M=Measurements—ear thickness and animal weight, S=Sacrifice of the animals; short arrows—cytokine injections; long arrows—exemplary days of anti-IFN-α antibody injections.

Figure 15:
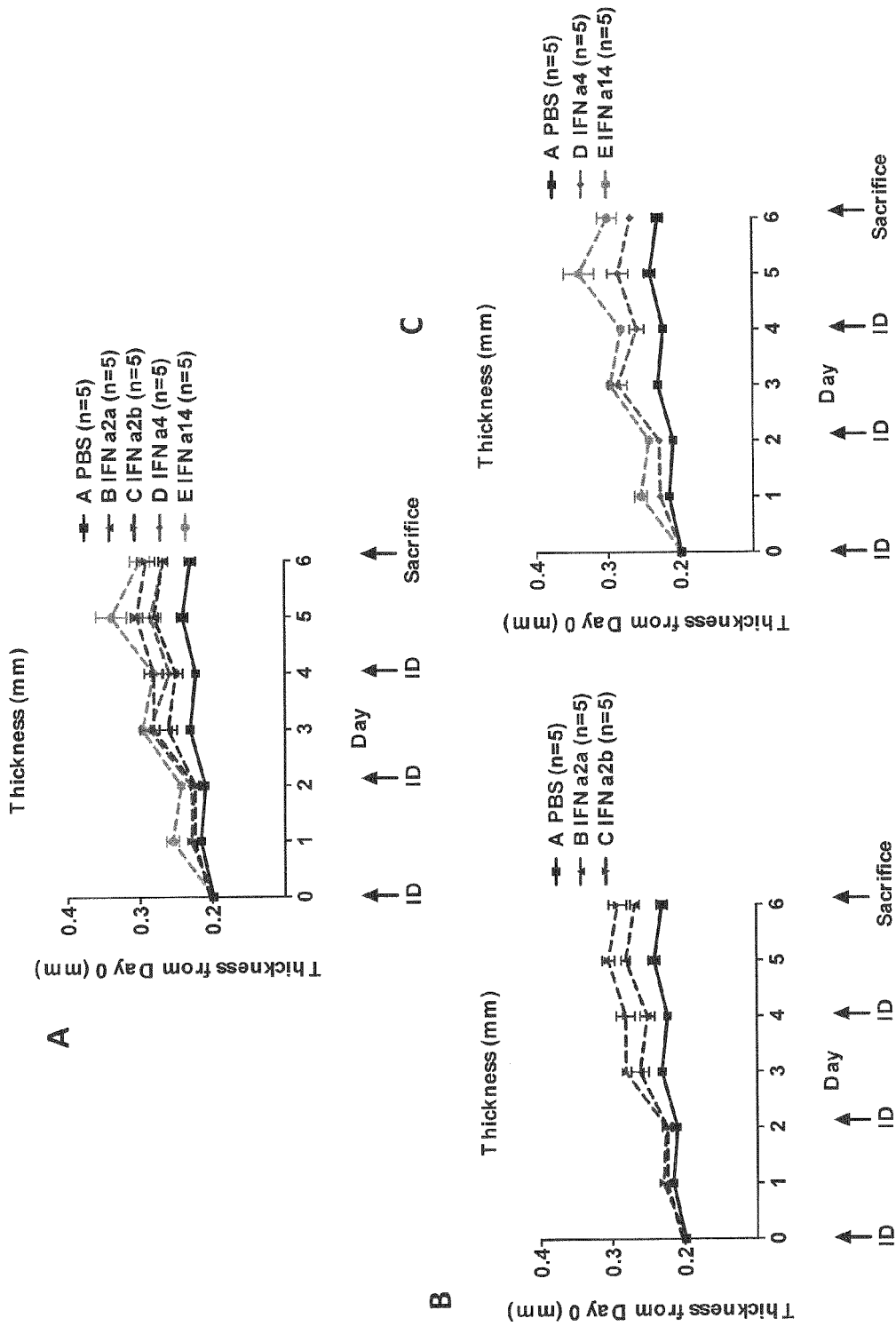

FIG. 15: Ear inflammation assay-test of the proinflammatory effect of human IFN subtypes in mice. CytoEar ear thickness measurements are shown as absolute values (mm) for each cohort. A: Overview of the effect of all measurements. B: Effects of the IFNa2a and IFNa2b injections. C: Effects of the IFNa4 and IFNa14 injections. All indications as in FIG. 14.

Figure 16:
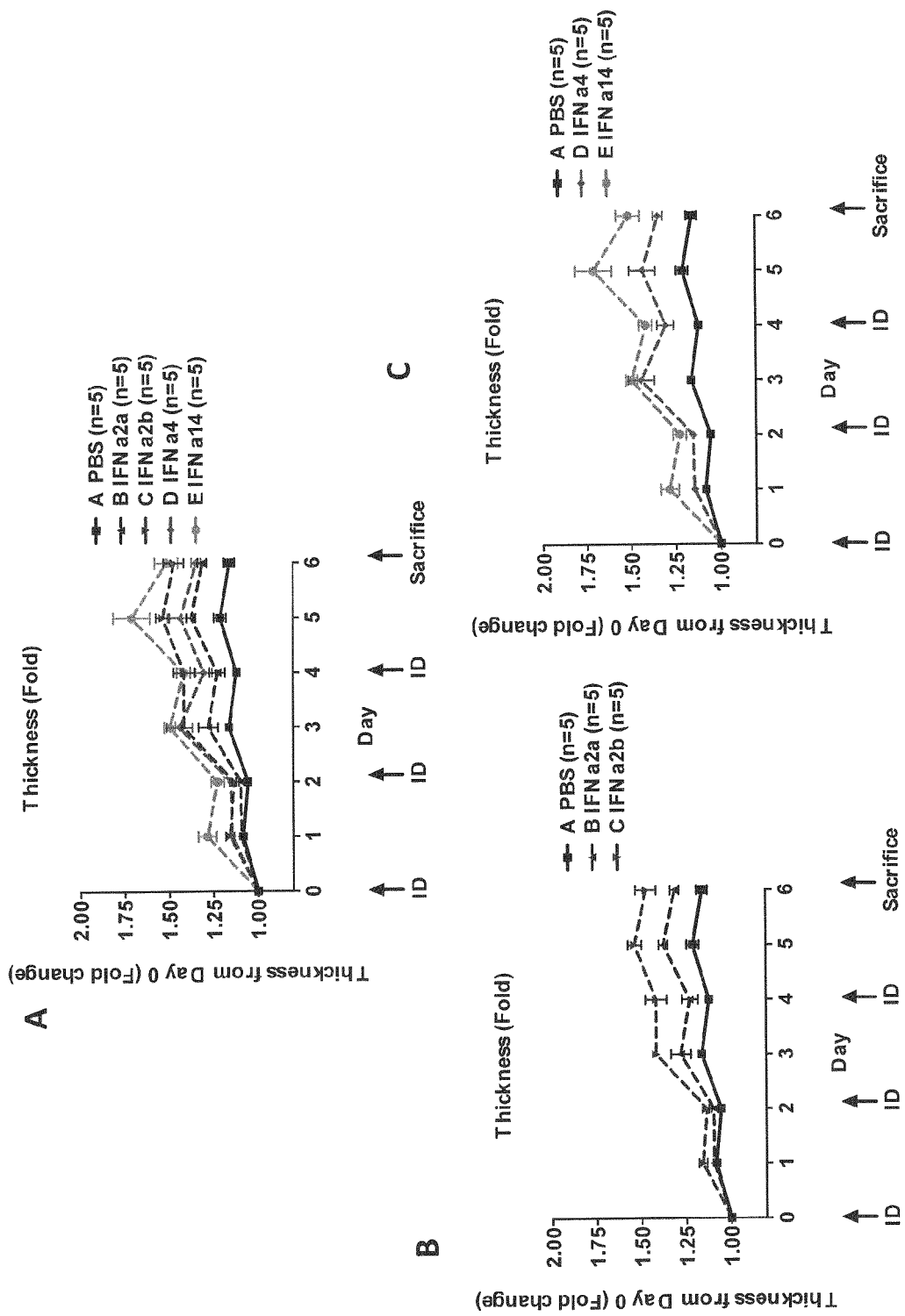

FIG. 16: Ear inflammation assay-test of the proinflammatory effect of human IFN subtypes in mice. CytoEar ear thickness measurements are shown fold change from Day 0 for each cohort. The thickness on Day 0 has been set as 1. A: Overview of the effect of all measurements. B: Effects of the IFNa2a and IFNa2b injections. C: Effects of the IFNa4 and IFNa14 injections. All indications as in FIG. 14.

FIG. 17: Summary of the ear inflammation assay in respect of human IFN-α subtype capabilities for induction of ear inflammation. P values obtained by 2-way ANOVA testing, ns (not significant)=P>0.05; *=P≤0.05; =P≤0.01; *=P<0.001, ****=p<0.0001. All ears were markedly thicker than PBS treated ears; this was significant in all groups after the 2nd ID, from Day 3 until the end of the experiment.

FIG. 18: LIPS assay—determination and comparison of binding characteristics of the exemplary anti-IFN-α antibodies 5D1, 13B11, 19D11, 25C3, 26B9 and 31B4 of the present invention towards IFNγ (IFNG), IFN-β1 (IFNB1), IFNε (IFNE), IFN-ω (IFN-ω), three IFNλ. (IL28A, IL28B and IL29) and IFN-α10 (all IFN-*Gaussia* luciferase fusion proteins). A: Binding of the antibodies towards the different IFN-types. B: Reciprocal diagram, binding of the IFNs by the antibodies. Exemplary antibodies 26B9 and 31B4 show binding of IFN-ω(IFN-ω) besides their affinity towards IFN-α10. No substantial binding of the exemplary antibodies of IFNβ1 (IFNB1), IFNε (IFNE), the three IFNλ and IFNγ (IFNG) could be observed.

Figure 19:
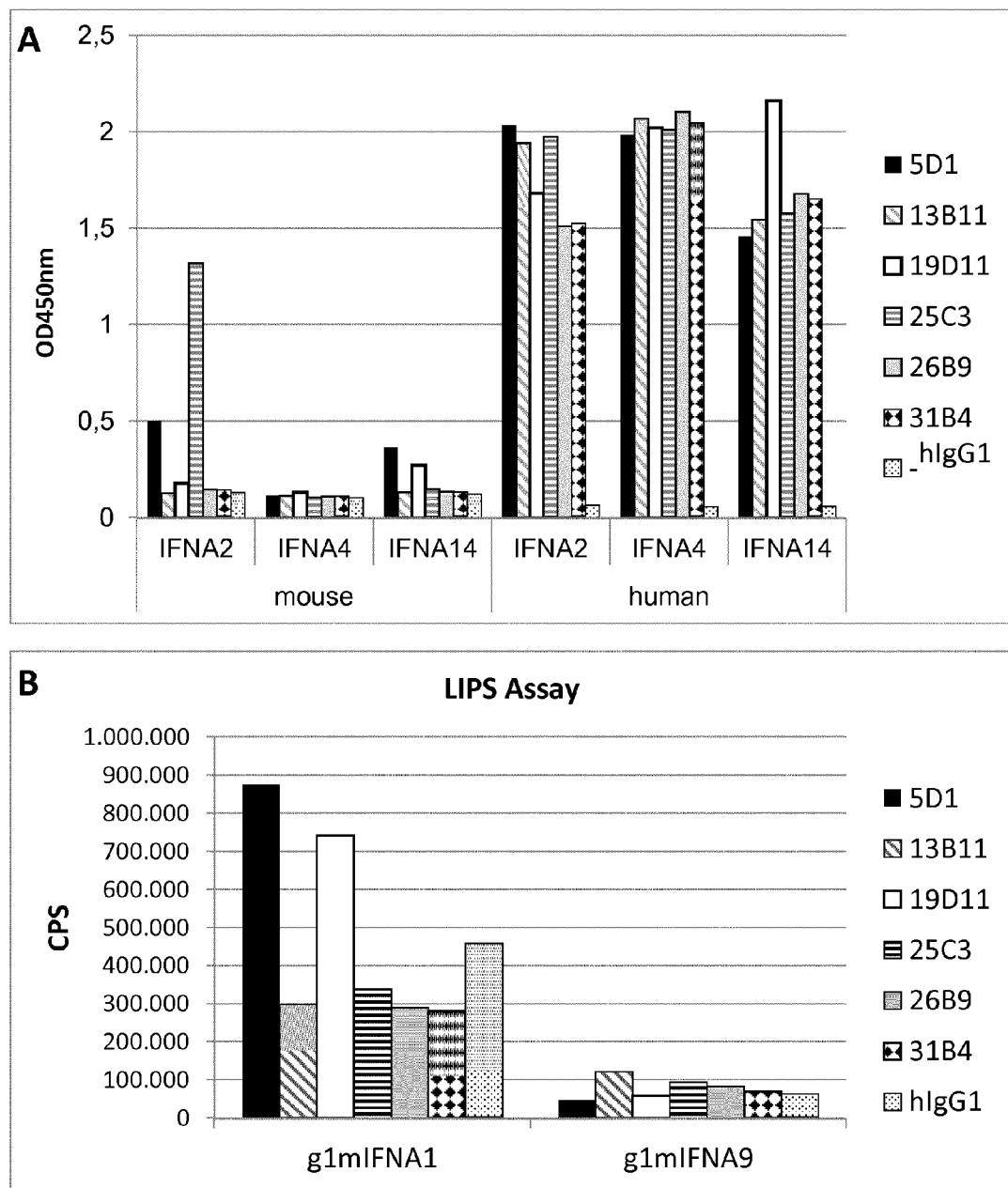

FIG. 19: Cross-reactivity of MABs towards mouse IFN-αs (ELISA). hIgG1=antibody of non-IFN-α related specificity (negative control). A: Test of cross-reactivity of the exemplary antibodies 5D1, 13B11, 19D11, 25C3, 26B9 and 31B4 against human and murine IFN-α2, IFN-α4 and IFN-α14 in an ELISA assay. Except antibody 25C3 showing cross-reactivity towards murine IFN-α2, the other antibodies show no or only residual binding specificity towards the murine IFN-α subtypes tested. B: Cross-reactivity of MABs on mouse IFN-αs (LIPS-assay). Antibodies 5D1 and 19D11 show cross-reactivity towards murine g1mIFN-α1, wherein the other antibodies only show reactivity below the level observed for the negative control. None of the antibodies shows cross-reactivity towards murine IFN-α subtype g1mIFN-α9.

Figure 20:
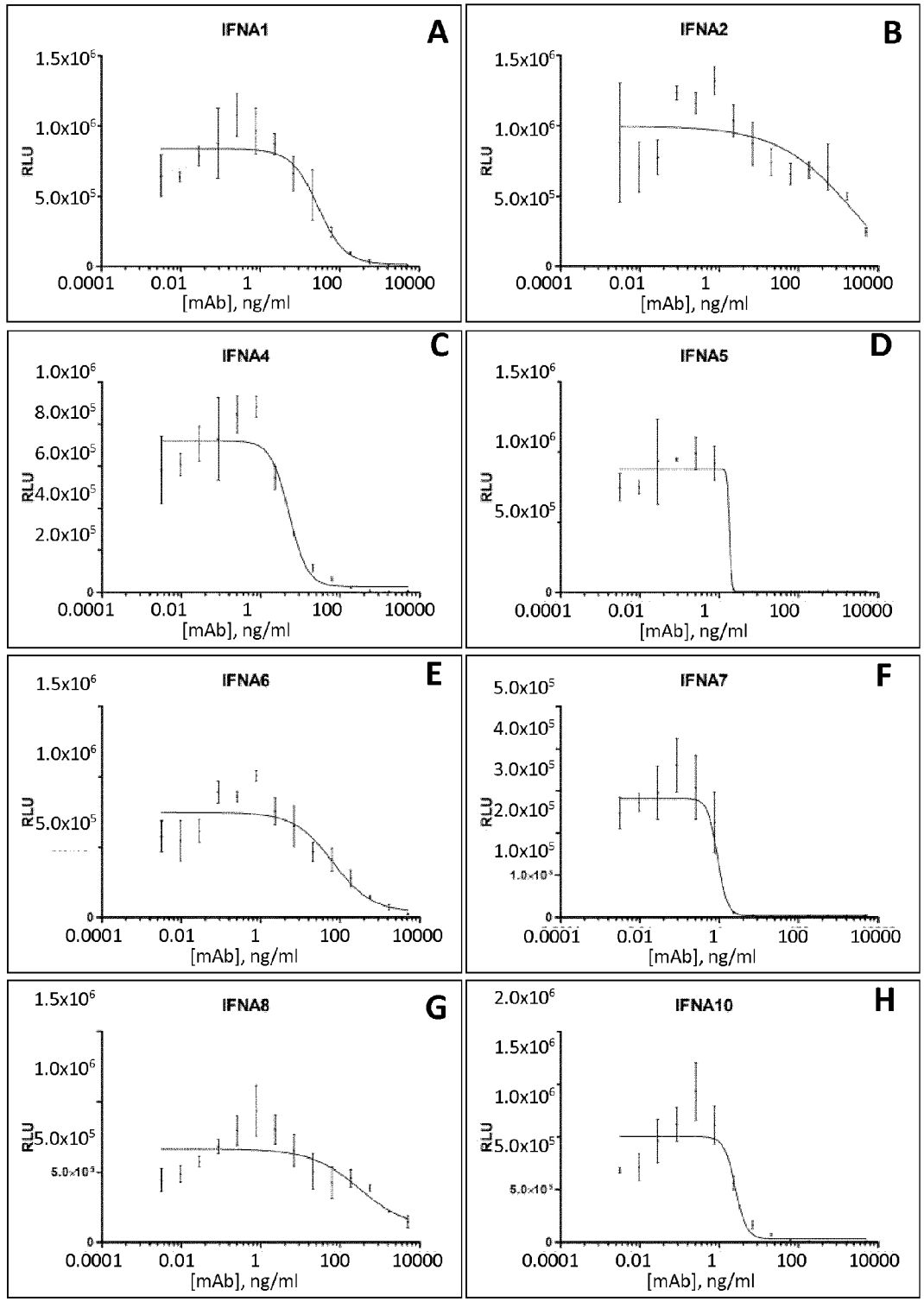
Figure 20:
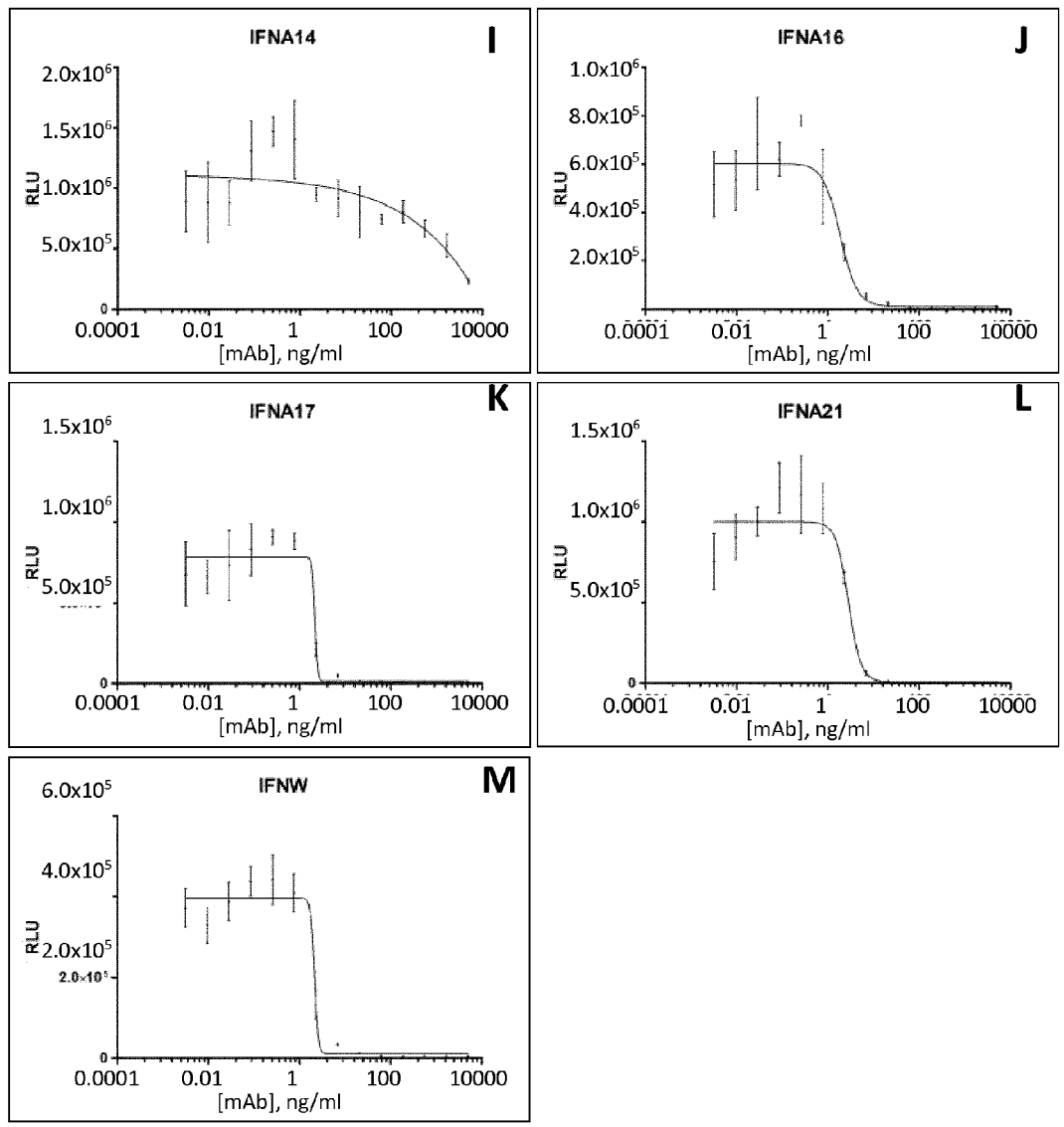

FIG. 20: IC 50 analysis of exemplary human-derived anti-IFN-α mAb 8H1 by ISRE Luciferase reporter neutralization assay. IC 50 neutralization graphs of exemplary antibody 8H1. A: IFN-α1, B: IFN-α2, C: IFN-α4, D: IFN-α5, E: IFN-α6, F: IFN-α7, G: IFN-α8, H: IFN-α10, I: IFN-α14, J: IFN-α16, K: IFN-α17, L: IFN-α21 and M: 20 IFN-ω. IC 50 data is summarized in Table 4.

Figure 21:
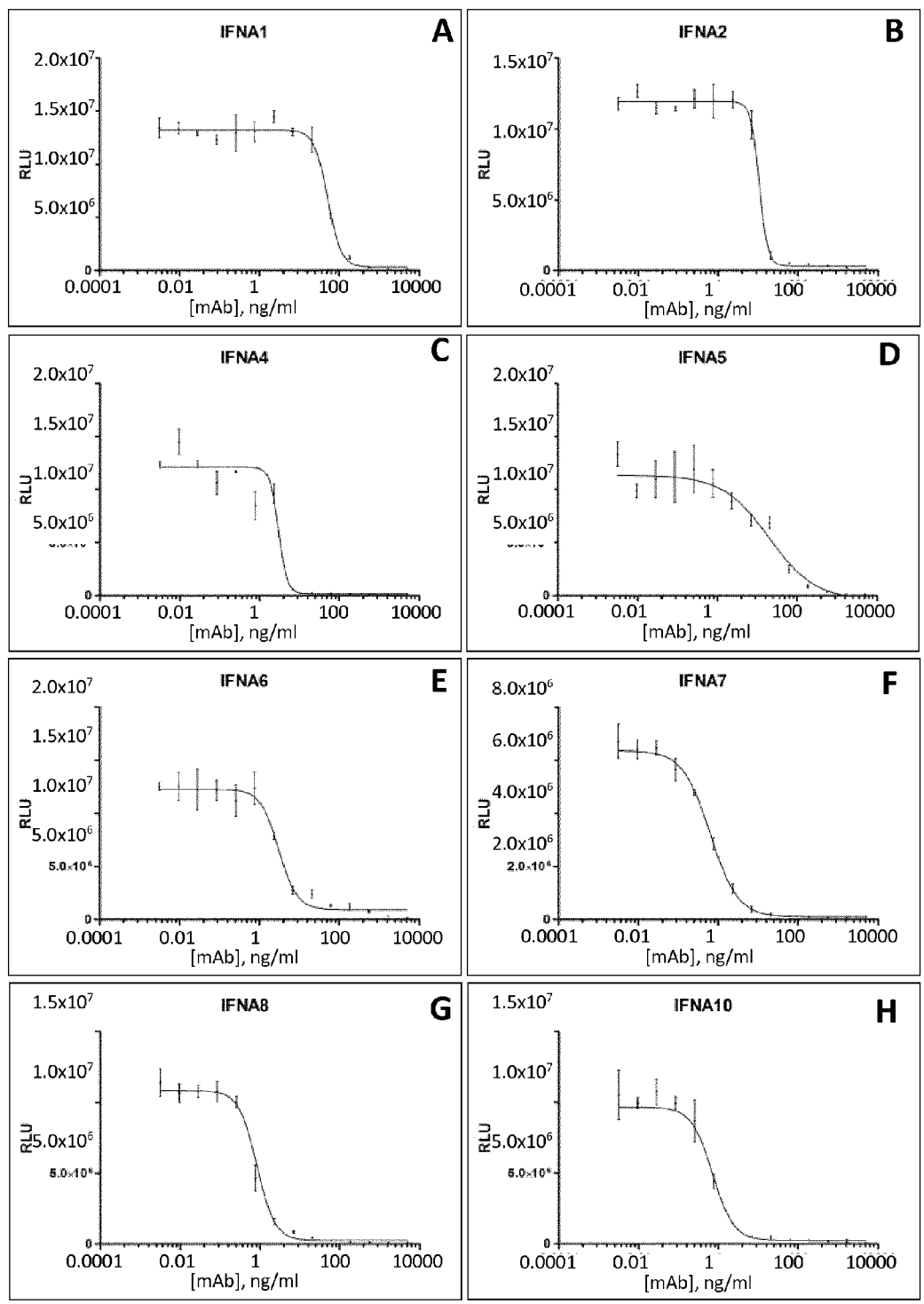
Figure 21:
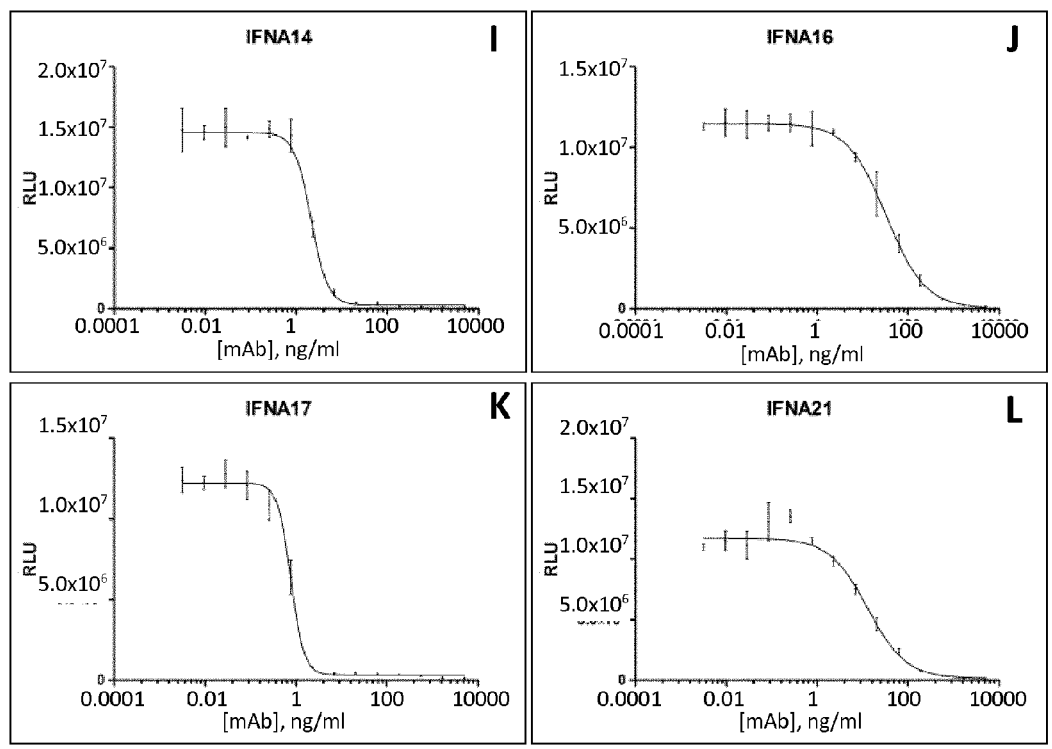

FIG. 21: IC 50 analysis of exemplary human-derived anti-IFN-α mAb 12H5 by ISRE Luciferase reporter neutralization assay. IC 50 neutralization graphs of exemplary antibody 12H5. A: IFN-α1, B: IFN-α2, C: IFN-α4, D: IFN-α5, E: IFN-α6, F: IFN-α7, 25 G: IFN-α8, H: IFN-α10, I: IFN-α14, J: IFN-α16, K: IFN-α17 and L: IFN-α21. IC 50 data is summarized in Table 4.

Figure 22:
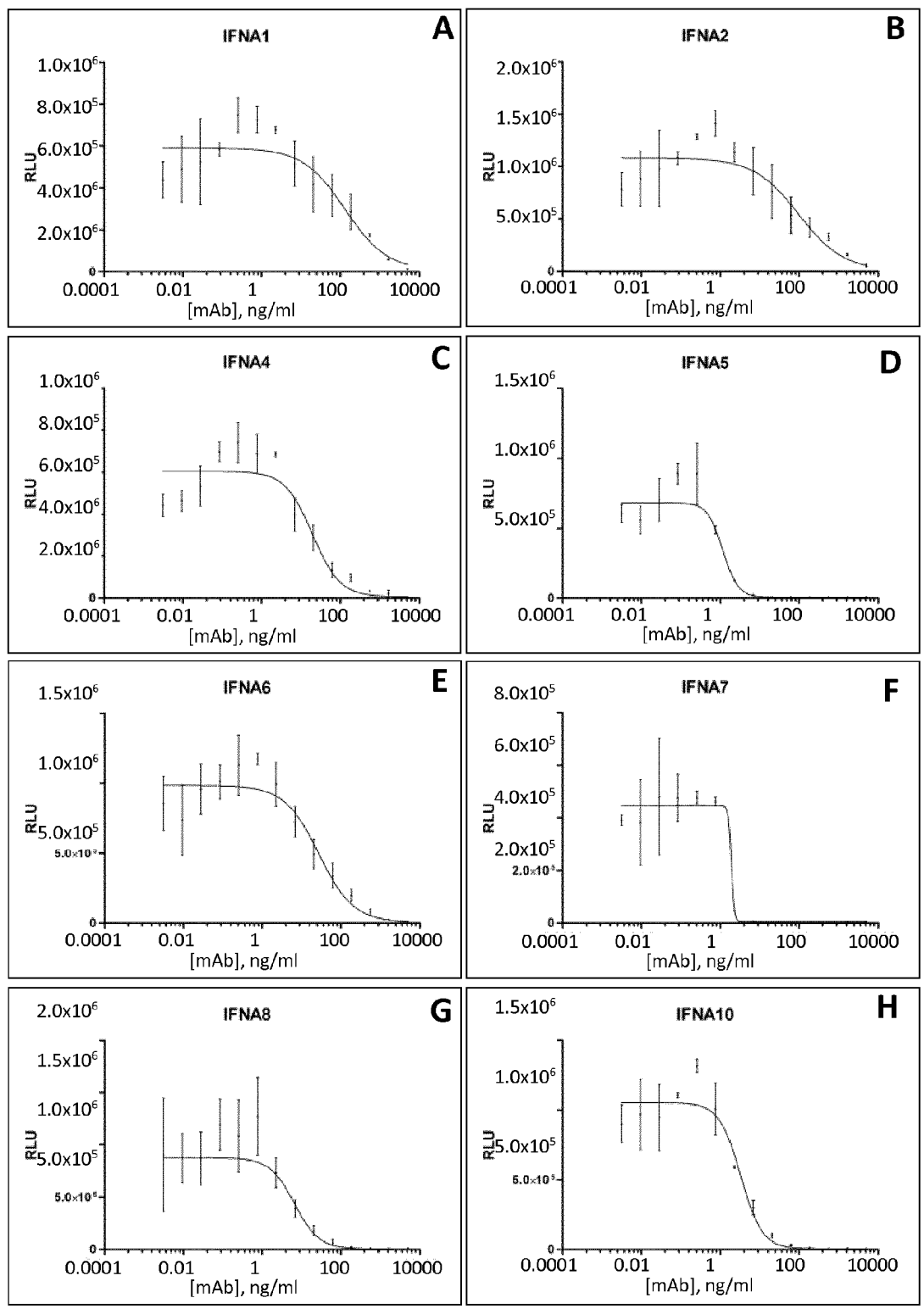
Figure 22:
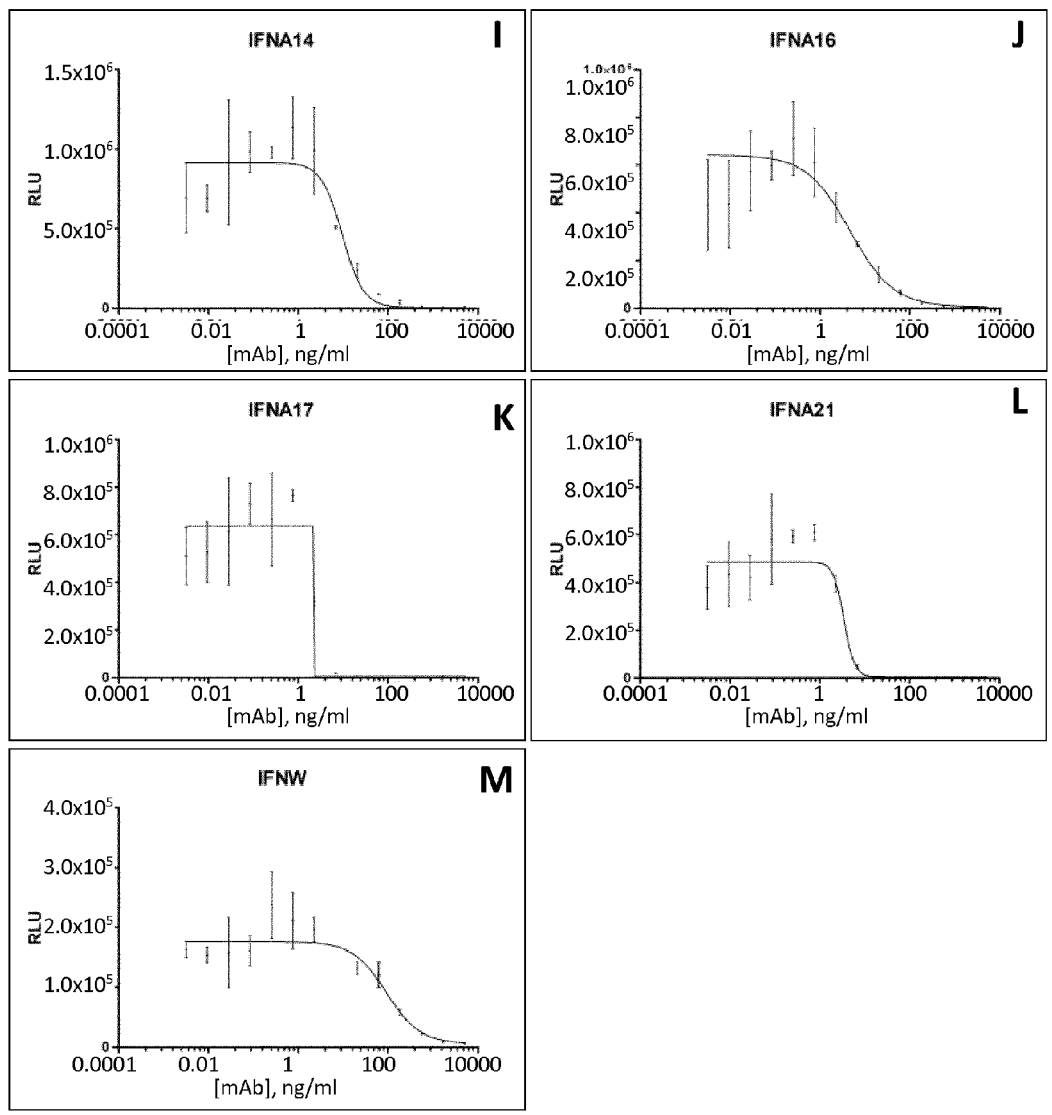

FIG. 22: IC 50 analysis of exemplary human-derived anti-IFN-α mAb 50E11 1 by ISRE Luciferase reporter neutralization assay. IC 50 neutralization graphs of exemplary antibody 50E11. A: IFN-α1, B: IFN-α2, C: IFN-α4, D: IFN-α5, E: IFN-α6, F: IFN-α7, G: IFN-α8, H: IFN-α10, I: IFN-α14, J: IFN-α16, K: IFN-α17, L: IFN-α21 and M: IFN-α. IC 50 data is summarized in Table 4.

FIG. 23: Human-derived anti-IFN-α monoclonal antibodies neutralize binding of IFN-Gaussia luciferase fusion proteins to HEK 293T MSR cells endogenously expressing IFN receptors in the luminescent cellular binding assay. Cells were incubated with supernatants of HEK 293T cells expressing Interferon-Gaussia luciferase fusion proteins in the absence of inhibitors (−) or in the presence of competitive inhibitors as indicated. A: Schematic representation of the luciferase-based chemiluminescent cellular binding assay. A ligand of interest (3) is fused to Gaussia luciferase (4). The fusion protein is bound to cells (1) expressing receptors for the ligand of interest (2). After removal of unbound fusion proteins a luciferase substrate is added (5) and light emission is recorded (6). The light output is proportional to the amount of bound fusion protein. Anti-ligand antibodies that compete with the receptors for binding of the ligand of interest (7) lead to a decrease in bound ligand and reduced light output. B: Control: Human IFN-α-Gaussia luciferase fusion proteins bind specifically to HEK 293T MSR cells. Binding of IFN-α5-Gaussia luciferase fusion proteins (g1 IFN-α5) to HEK 293T MSR cells is inhibited by unlabeled rhIFN-α2 (3 μg/ml) and by exemplary human-derived monoclonal IFN-α antibody 19D11 (1.7 μg/ml). A human control antibody (huIgG, 15 μg/ml) shows no effect. C: Binding of g1 IFN-α2, A4, A5, A6, A7, A8, A10, A14, A16, A17 and A21 fusion proteins to HEK 293T MSR cells is inhibited by exemplary human-derived monoclonal IFN antibody 19D11. Binding of g1 IFNB and IFN-ω is unaffected by 19D11. Binding of all g1 IFNs is unaffected by a control human antibody (huIgG). Antibody concentration: 5 D: Binding neutralization of g1 IFN-α16 and g1 IFN-ω by exemplary antibodies 19D11 and 26B9. Cells were treated with g1 IFN-α16 or g1 IFN-ω as indicated in the absence of antibodies (−) or in the presence of exemplary antibodies 19D11, 26B9 or of a control human antibody (huIgG). Antibody concentration: 10 μg/ml. Exemplary antibody 19D11 is more potent than 26B9 at neutralizing g1 IFN-α16. Exemplar antibody 26B9 efficiently blocks binding of g1 IFN-ω to its receptors on 293T MSR cells, while exemplary antibody 19D 11 shows no apparent effect against this ligand.

FIG. 24: Human IFN-ω-*Gaussia* luciferase fusion proteins bind specifically to HEK 293T MSR cells expressing a transmembrane anti-IFN-αmAb. HEK 293T MSR cells were reverse-transfected with the indicated amounts of cDNA encoding a membrane-bound version of anti-IFN-ω mAb 26B9 (26B9-TM) or empty vector (Mock). Forty-eight hours after transfection, IFN-ω-*Gaussia* luciferase was added (g1 IFN-ω) and binding was analysed in the chemiluminescent cellular binding assay. A: Control: 26B9-TM is expressed at the cell surface of transfected HEK 293T MSR cells. Surface antibody expression was analysed 48 hours after transfection in a cell-based ELISA. B: g1 IFN-ω specifically binds to cells expressing 26B9-TM in the luminescent cellular binding assay.

FIG. 25: Crosscompetition assay of anti-IFN-ω antibodies. Binding of g1 IFN-ω to 26B9-TM is competed dose-dependently by soluble 26B9 and by the clonally related 31B4 antibody. In contrast, binding is not affected by a control IgG or by exemplary anti-IFN-ω antibody 8H1.

FIG. 26: SPR analysis. A: Detailed analysis of the sensograms concerning of the binding of human A1/B1: IFN-α2b, A2/B2: IFN-α4, A3/B3: IFN14 and A4/B4: IFNω to exemplary antibodies 19D11 (A1-A4) and 26B9 (B1-B4) of the present invention. A 1:1 binding kinetic was observed. The antigens were injected in concentrations of 1 nM, 2.5 nM, 5 nM, 10 nM, 15 nM, 25 nM, 50 nM and 100 nM. Calculated Affinities (KD values [M]) are indicated in the diagrams. C: The plot shows the kinetic parameters derived from the fitted curves for the association (on-rate ka) and dissociation (off-rate kd) of all tested antibodies. Dashed diagonals indicate affinities (KD). D: KD values of exemplary antibodies of this invention in comparison with SPR literature value of Biotin-Straptavidin binding. The affinities towards human IFN-α4 and IFN-α14 are in the sub-picomolar range and in sub-nanomolar range for IFN2b, respectively. 26B9 also binds human IFNω with a sub-picomolar affinity.

FIG. 27: Epitope mapping. A: Binding of antibodies of the present invention to full length antigens coupled to the microarray. The Y-axis indicated the fluorescence intensity (RFU) upon detection with a Cy5-conjugated secondary antibody. B: Primary peptide array of 18mer peptides of human IFN-α2 against the antibody 19D11 of the present invention. In the lower panel the peptides covering the sequence from Asparagine 65 to Lysine 98 and from Lysine 117 to Serine 150 are depicted. The antibody 19D11 binds specifically to peptides 19 and 32. C: Primary peptide array of 18mer peptides of human IFN-α2 against the antibody 26B9 of the present invention. In the lower panel the peptides covering the sequence from Aspartic acid 77 to Lysine 110 are depicted. The antibody 26B9 binds specifically to peptide 22. D: Primary peptide array of 18mer peptides of human IFN-αW against the antibody 26B9 of the present invention. In the lower panel the peptides covering the sequence from Methionine 102 to Alanine 135 are depicted. The antibody 26B9 binds specifically to peptide 23.

FIG. 28: Ear inflammation assay CytoEar IFN-α14. Testing the effect of different IFN-α blocking antibodies of the present invention following hIFN-α14 induced inflammation. To induce inflammation 20 μl IFNa14 was injected per ear at a concentration of 25 μg/ml. Measurement of thickness was also performed before giving the injection, and with two measurements per ear. A: Exemplary 10-day experimental timeline. B: Overview of the experimental treatment of the experimental animal groups A to I. Ref. A-IFN-α-specific reference antibody. CytoEar ear thickness measurements calculated as fold change relative to day 0 measurements than normalized to relevant PBS controls, for each cohort. C: Overview of the effect of all normalized measurements. D: Effects of 26B9 treatment following IFNa14 injections. E: Effects of 19D11 treatment following IFNa14 injections. F: Effect of the treatment with reference anti-IFN-α antibody Ref. A following IFNa14 injections. Treatment with antibodies 26B9 and 19D11 (significant reduction of ear thickness at days 7, 9, 10, respective at days 4, 7-10 for 19D11) of the present invention leads to pronounced reduction of the ear thickness resulting from IFNa14 injections compared to the control treatment with IgG (of IFN-α non-related binding specificity) and of treatment with Ref. A. Mean+/−SEM, ID=intradermal cytokine injections, M=Measurements—ear thickness, S=Sacrifice of the animals; ID-cytokine injections; tested antibodies 26B9, 19D11, Ref.A and the control IgG were injected at day 0 (IP).

FIG. 29: Ear inflammation assay CytoEar IFN-α5. Testing the effect of different IFN-α blocking antibodies of the present invention following hIFN-α5 induced inflammation. To induce inflammation 20 μl IFNa5 was injected per ear at a concentration of 25 μg/ml. Measurement of thickness was also performed before giving the injection, and with two measurements per ear. A: Exemplary 10-day experimental timeline. B: Overview of the experimental treatment of the experimental animal groups A to I. Ref. A—reference IFN-α-specific antibody. CytoEar ear thickness measurements calculated as fold change relative to day 0 measurements than normalized to relevant PBS controls, for each cohort. C: Overview of the effect of all normalized measurements. D: Effects of 26B9 treatment following IFNa5 injections. E: Effects of 19D11 treatment following IFNa5 injections. F: Effect of the treatment with reference anti-IFN-α antibody Ref. A following IFNa5 injections. Treatment with antibodies 26B9 and 19D11 of the present invention leads to a reduction of the ear thickness resulting from IFNa5 injections (significant reduction for 26B9 at days 4, 6, 7, 8 and 9: for 19B11 at days 7-9). See description of FIG. 26 for further details. Tested antibodies 26B9, 19D11, Ref.A and the control IgG were injected at day 0 (IP).

Figure 30:
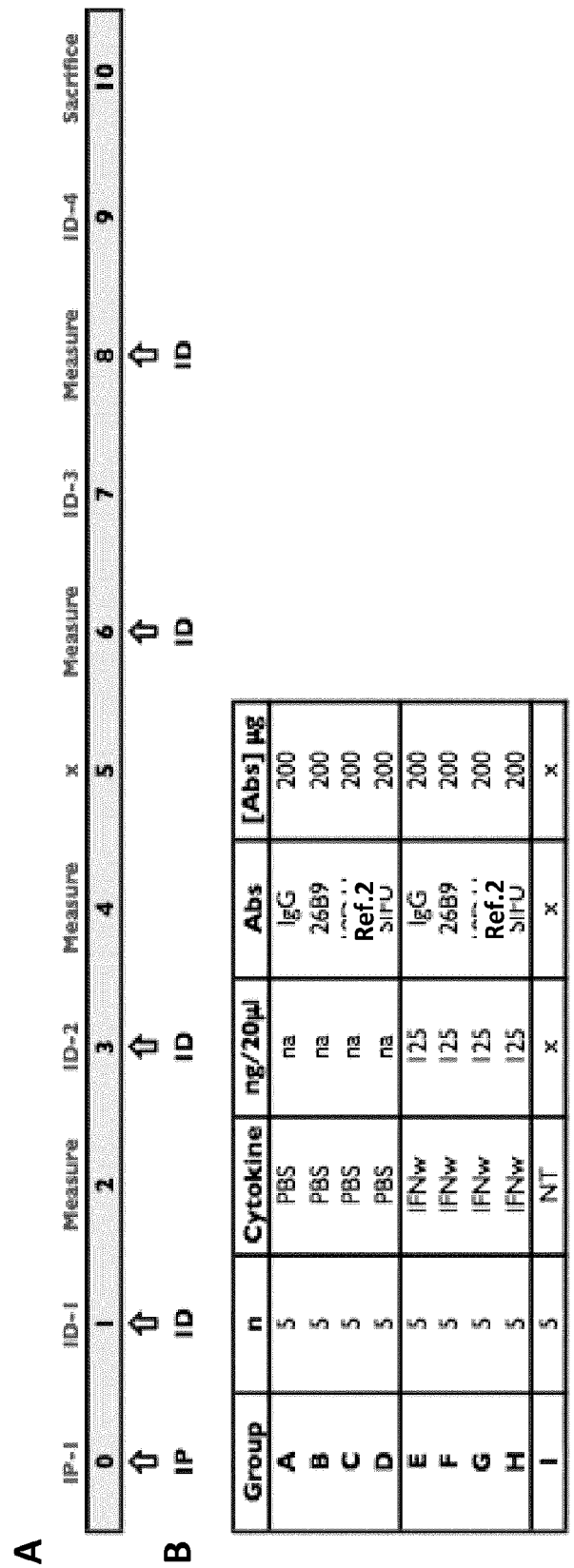
Figure 30:
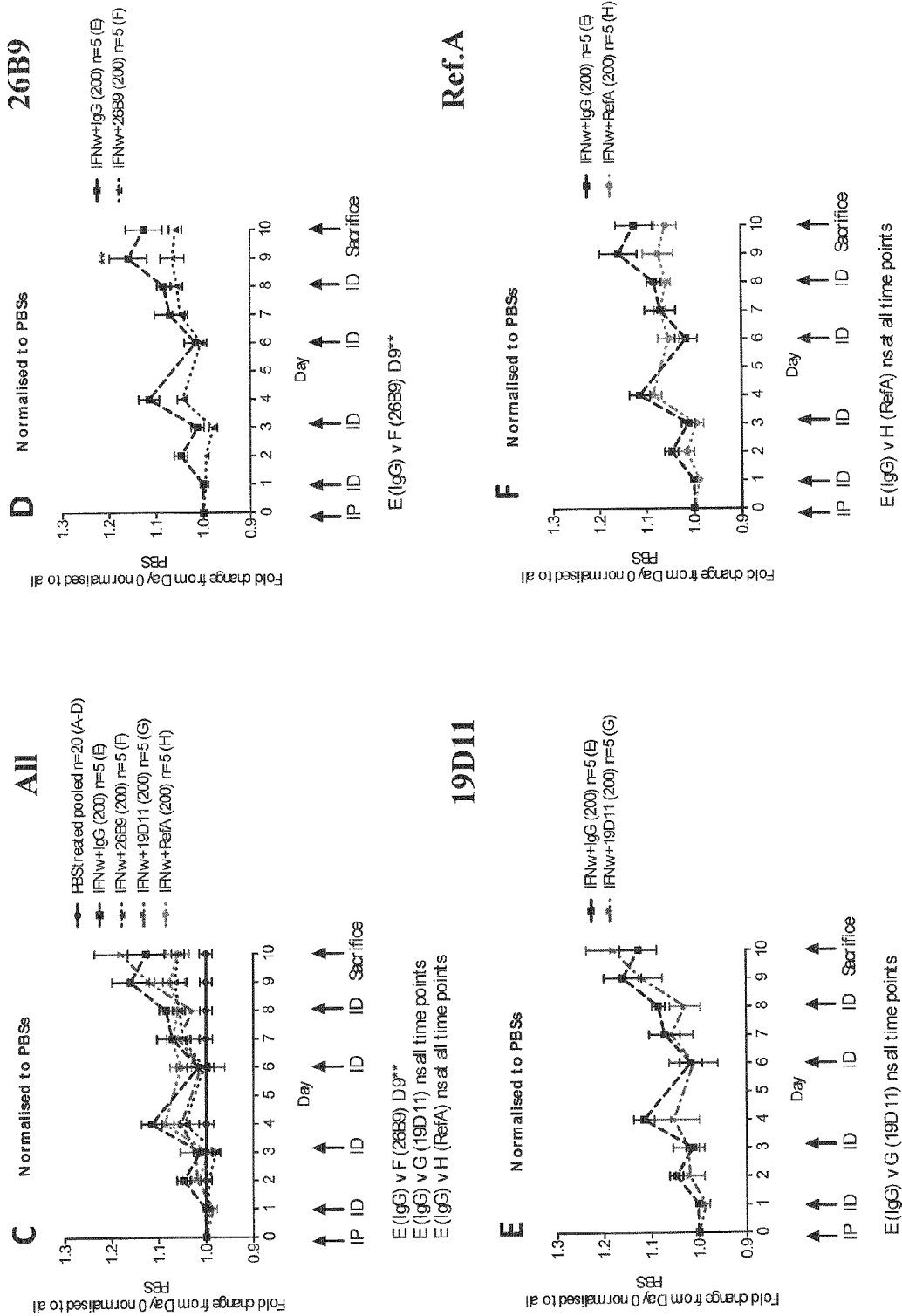

FIG. 30: Ear inflammation assay CytoEar IFNω. Testing the effect of different IFN-α blocking antibodies of the present invention following hIFNω (IFNω) induced inflammation To induce inflammation 20 μl IFNω was injected per ear at a concentration of 6.25 μg/ml, 125 ng/ear. Measurement of thickness was also performed before giving the injection, and with two measurements per ear. A: Exemplary 10-day experimental timeline. B: Overview of the experimental treatment of the experimental animal groups A to I. Ref. A—reference IFN-α specific antibody. CytoEar ear thickness measurements calculated as fold change relative to day 0 measurements than normalized to relevant PBS controls, for each cohort. C: Overview of the effect of all normalized measurements. D: Effects of 26B9 treatment following IFNω injections. E: Effects of 19D11 treatment following IFNω injections. F: Effect of the treatment with reference anti-IFN-α antibody Ref.A following IFNω injections. Treatment with antibody 26B9 of the present invention leads to a significant reduction of the ear thickness resulting from IFNω injections at experimental Day 9. Treatment with 19D11 or Ref.A leads to apparently none or very slight reduction of the ear thickness (not significant (ns) compared to control IgG injections at all days). See description of FIG. 26 for further details. Tested antibodies 26B9, 19D11, Ref.A and the control IgG were injected at day 0 (IP).

Figure 31:
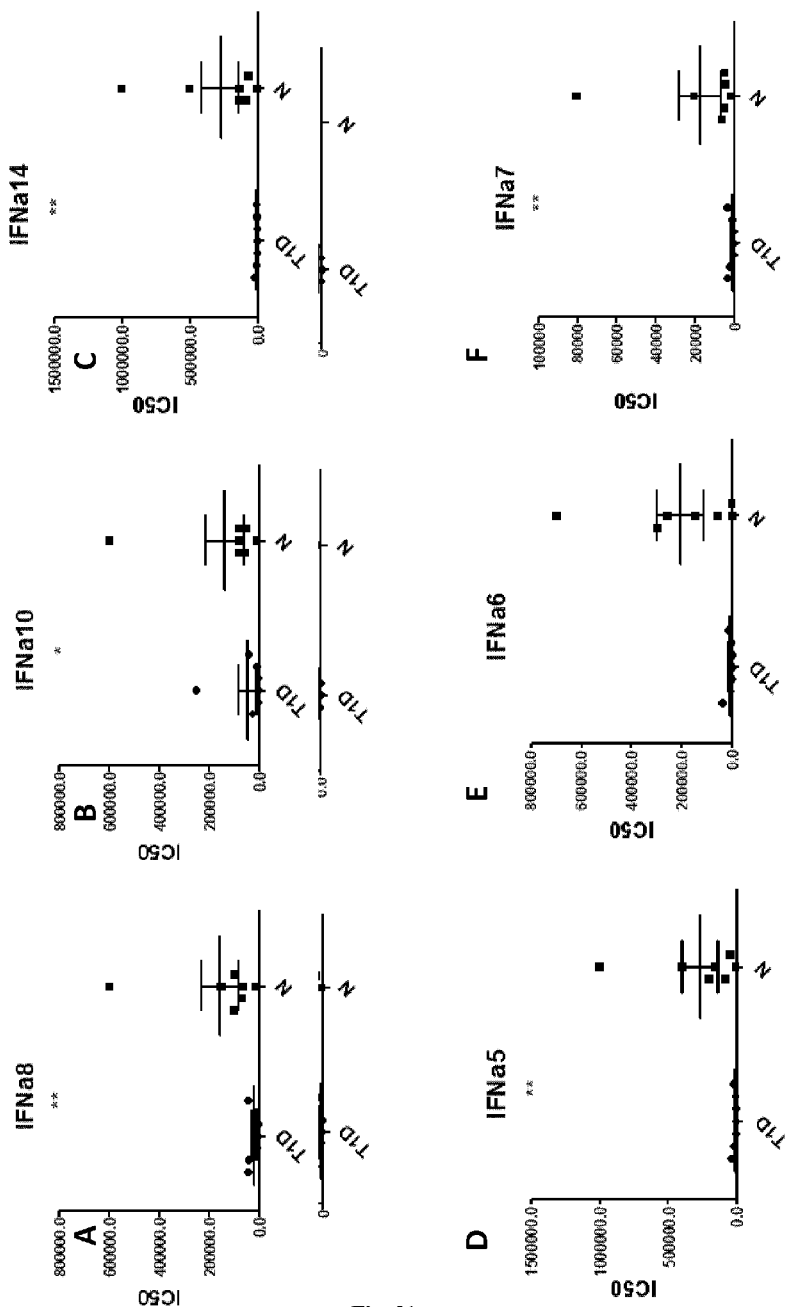
Figure 31:
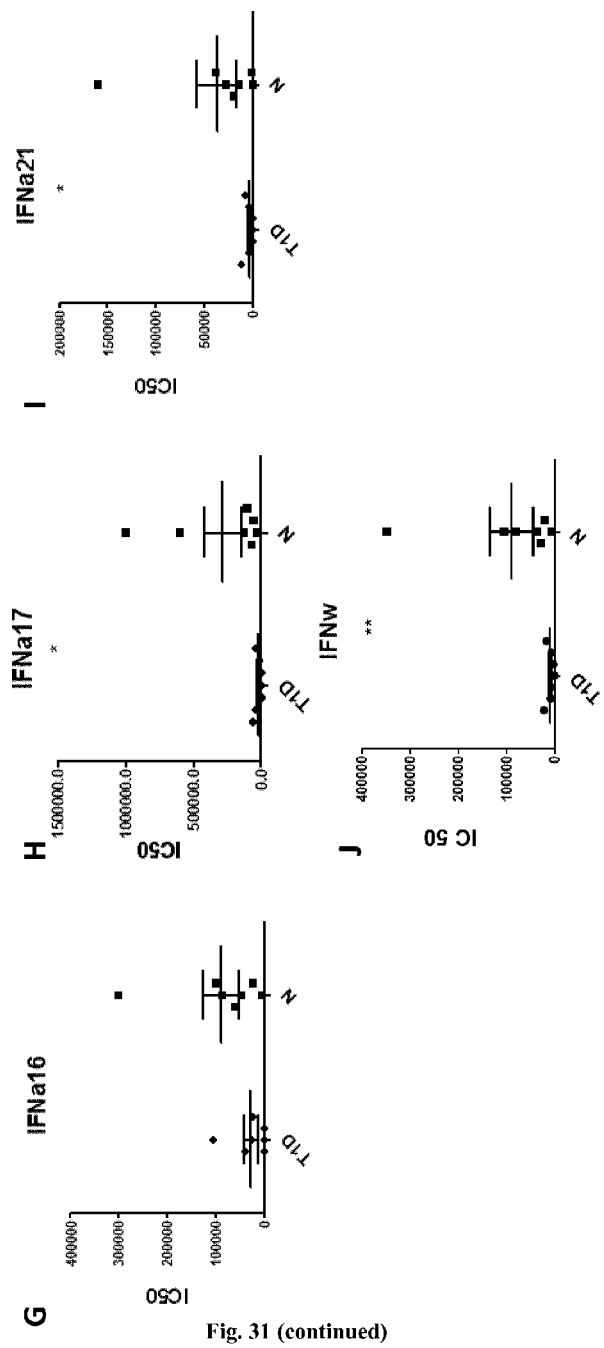

FIG. 31: Comparison of IFN neutralizing activity in serum of APS1/APECED patients with type 1 diabetes (T1D) or without (N). A: IFN-α1, B: IFN-α2a, C: IFN-α4, D: IFN-α5, E: IFN-α6, F: IFN-α7, G: IFN-α16, H: IFN-α17, I: IFN-α21 and J: IFN-ω.

Figure 32:
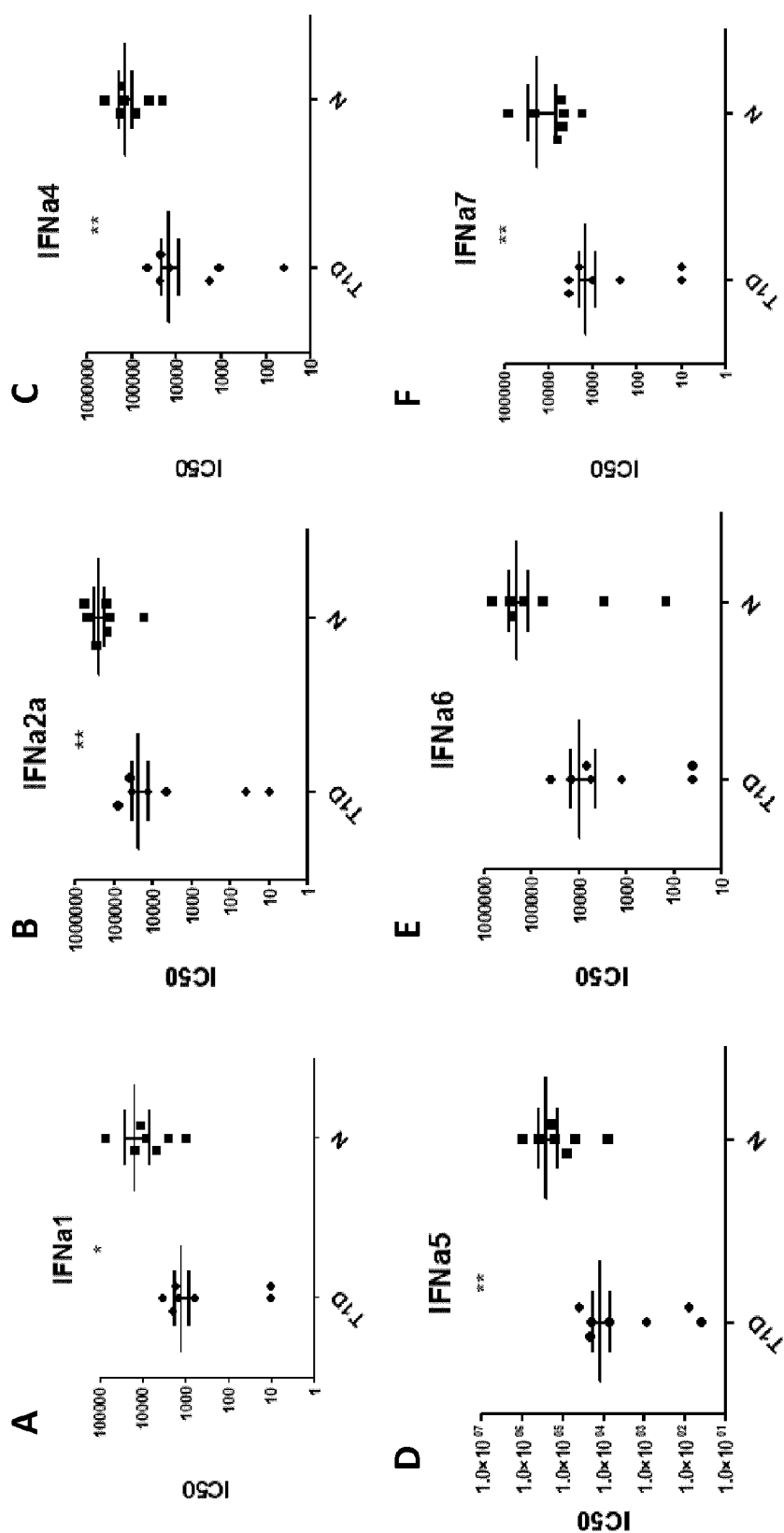
Figure 32:
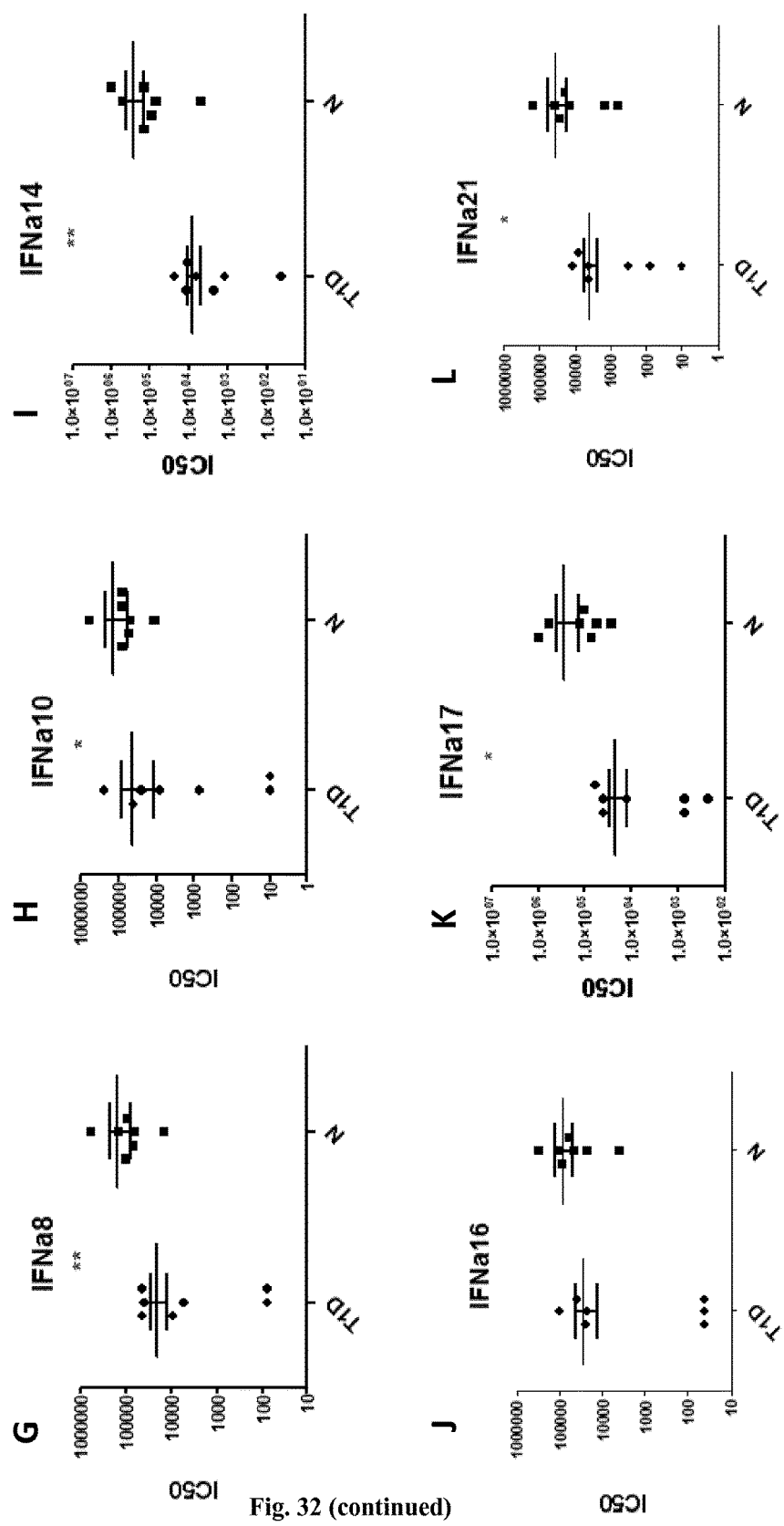

FIG. 32: Comparison of IFN neutralizing activity in serum of APS1/APECED patients with type 1 diabetes (T1D) or without (N). As in FIG. 31 however with logarithmic scale at the Y-axis for a better visualization of the neutralizing activity measured in serum of APS1/APECED patients with TID. A: IFN-α1, B: IFN-α2a, C: IFN-α4, D: IFN-α5, E: IFN-α6, F: IFN-α7, G: IFN-α8, H: IFN-αIO, I: IFN-α14, J: IFN-α16, K: IFN-α17, and L: IFN-α21. APS1 patients not suffering from T1D (N) show for all antibodies a higher titer in their serum than T1D-APS1-patients. This titer difference may indicate differential therapeutic requirements in both patient groups.

DETAILED DESCRIPTION OF THE INVENTION

The present invention generally relates to novel molecules binding IFN-α of mammal, preferably human origin, particularly patient-derived human monoclonal antibodies as well as fragments, derivatives and variants thereof that recognize and more importantly are capable of neutralizing the activity of different subtypes of IFN-α; see also the background section supra for description of the IFN-α subtypes, including IFN-α1, IFN-α2, IFN-α4, IFN-α5, IFN-α6, IFN-α7, IFN-α8, IFN-α10, IFN-α13, IFN-α14, IFN-α16, IFN-α17 and IFN-α21, wherein the IFN-α1 and IFN-α13 genes encode for the same IFN-α1/13 subtype.

As described in the Examples, the exemplary antibodies of the present invention have been isolated by a method subject of and disclosed in applicant's international application WO2013/098419 A1, based on screening the sera of patients with an impaired central and/or peripheral tolerance or loss of self-tolerance, such as APECED/APS1 patients for autoantibodies against IFN-α proteins as well as using a novel method of isolating antibodies from B cells of subject suffering from an autoimmune disorder od auto-inflammatory disease, which is subject of and disclosed in applicant's international application WO2013/098420 A1.

Experiments performed in accordance with the present invention were directed towards the provision of IFN-α binding molecules of selective IFN-α subtype specificities, i.e. antibodies and IFN-α binding fragments thereof which immunoreactivity has been shown in APECED/APS1 patients as protective against the onset of, e.g., SLE or at least reducing manifestation of SLE symptoms.

Accordingly, in a first general aspect the present invention provides a human-derived anti-interferon-alpha (IFN-α) antibody or an IFN-α binding fragment, synthetic or biotechnological derivative thereof showing a binding specificity and preferably neutralizing activity towards all or only a sub-range or particular IFN-α subtypes. In a preferred embodiment of the present invention the anti-IFN-α antibody or IFN-α binding fragment
(i) binds to human IFN-α subtypes IFN-α2, IFN-α4, IFN-α5, IFN-α6, IFN-α10 and IFN-α14;

(ii) binds to at least one human IFN-α subtype IFN-α1/13 (IFN-α1b), IFN-α8, IFN-α16 and/or IFN-α21; and/or (iii) is capable of neutralizing a biological activity of at least one of the human IFN-α subtypes. Accordingly, the present invention provides a pool of antibodies of different IFNa subtype specificity different from and providing a broader application profile than antibodies known in the art.

All IFNα subtypes utilize the heterodimeric IFNα/receptor (IFN-αR) and generate a signal in the receiving cell via cytoplasmic tyrosine kinases Tyk2 and Jak1 performed phosphorylation and concomitant activation of STAT1 and STAT2 (signal transducers and activators of transcription). The STAT proteins translocate to the nucleus and activate the expression of genes that have either GAS or ISRE sites, or both, in their promoters (Borden et al., Nat. Rev. Drug Discov. 6 (2007), 975-990; Hu et al., Immunol. Rev. 226 (2008), 41-56; van Boxel-Dezaire et al., Immunity 25 (2006), 361-372). This activation mechanism has been used within the present invention as well as for designing IFN-activity measurement in vitro methods, such as the cell based STAT (signal transducers and activators of transcription) activation assay and the ISRE (Interferon stimulated response element) reporter gene assay as described and used herein (Cignal Reporter Assay, Qiagen), e.g., in Example 3 and in FIGS. 5 to 7 to monitor the neutralizing abilities of the antibodies of the present invention. As described in detail therein, the antibodies of the present invention have been found to have a potent neutralizing activity towards several IFN-α subtypes as specified in detail further below.

Therefore, in one embodiment of the present invention, the biological activity neutralized by the antibody or IFN-α binding fragment of the present invention is IFN-α signaling in a cell based STAT (signal transducers and activators of transcription) activation assay, in an ISRE (Interferon stimulated response element) reporter gene assay, and/or in an cellular binding assay (see Example 9).

Furthermore, the binding affinities of the antibodies of the present invention have been tested by ELISA, LIPS and cellular binding assays as described herein, e.g., in Examples 1, 2, 6 and 9 and shown in FIGS. 3, 7 to 13, and 18 to 27. In accordance with the results of these experiments, the present invention provides several exemplary anti-IFN-α antibodies showing differential binding affinities towards distinct IFN-α subtypes, which exemplify the binding and neutralization characteristics of the IFN-α binding molecules provided herein.

Figure 6:
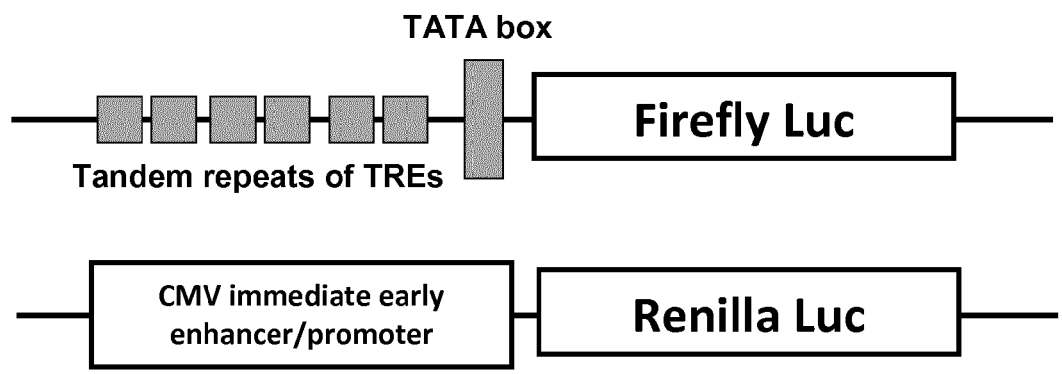
Figure 7:
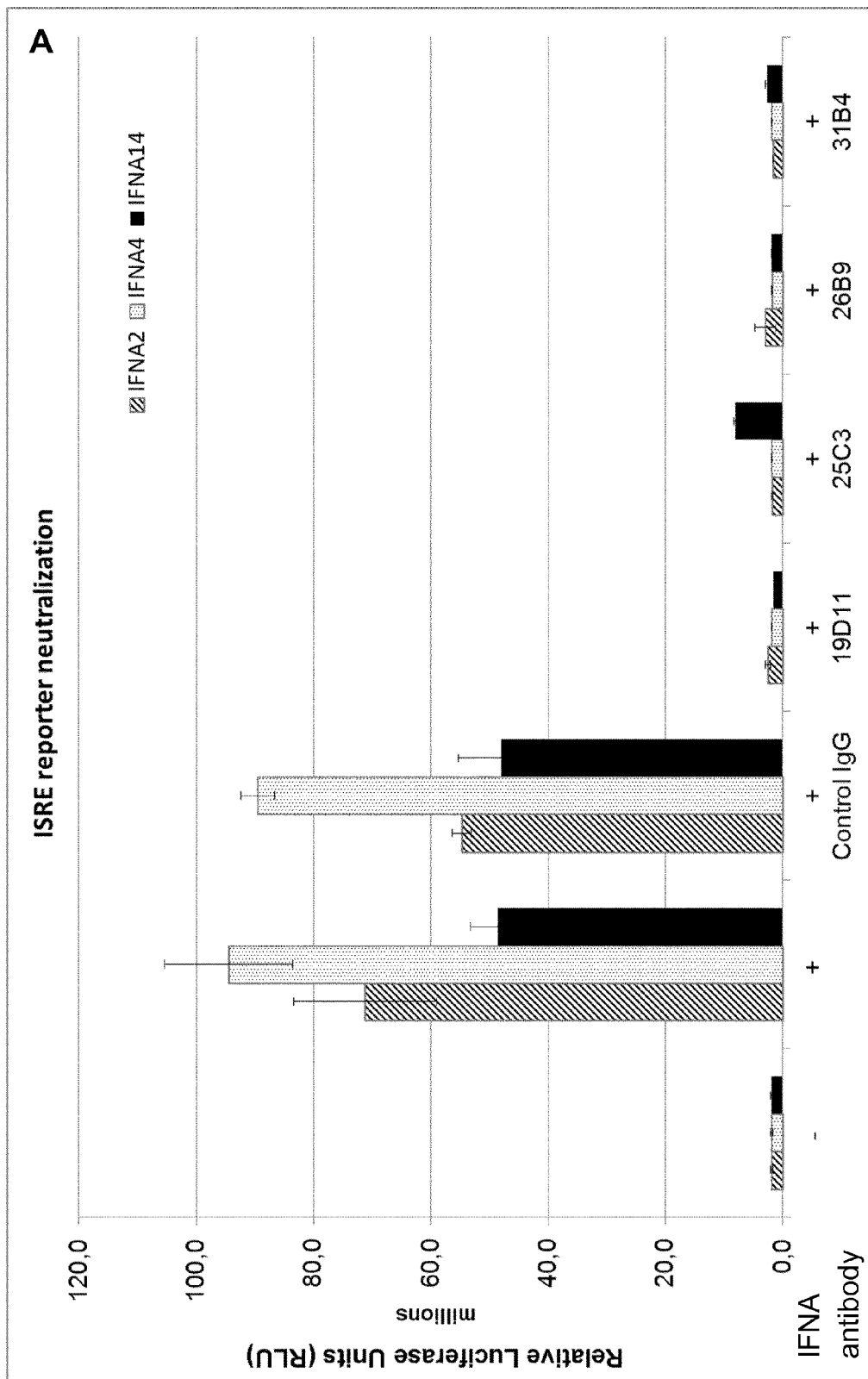
Figure 7:
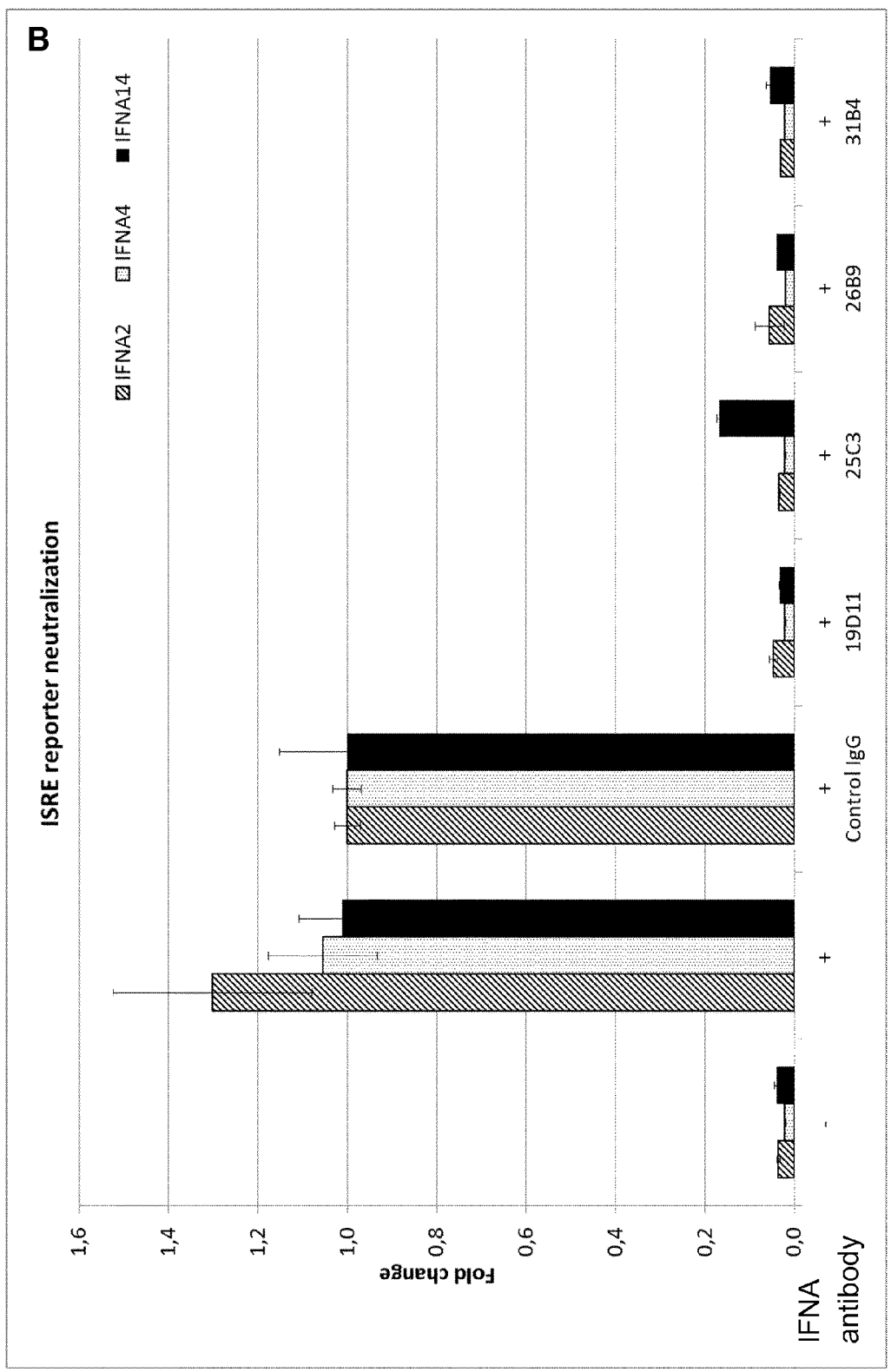
Figure 7:
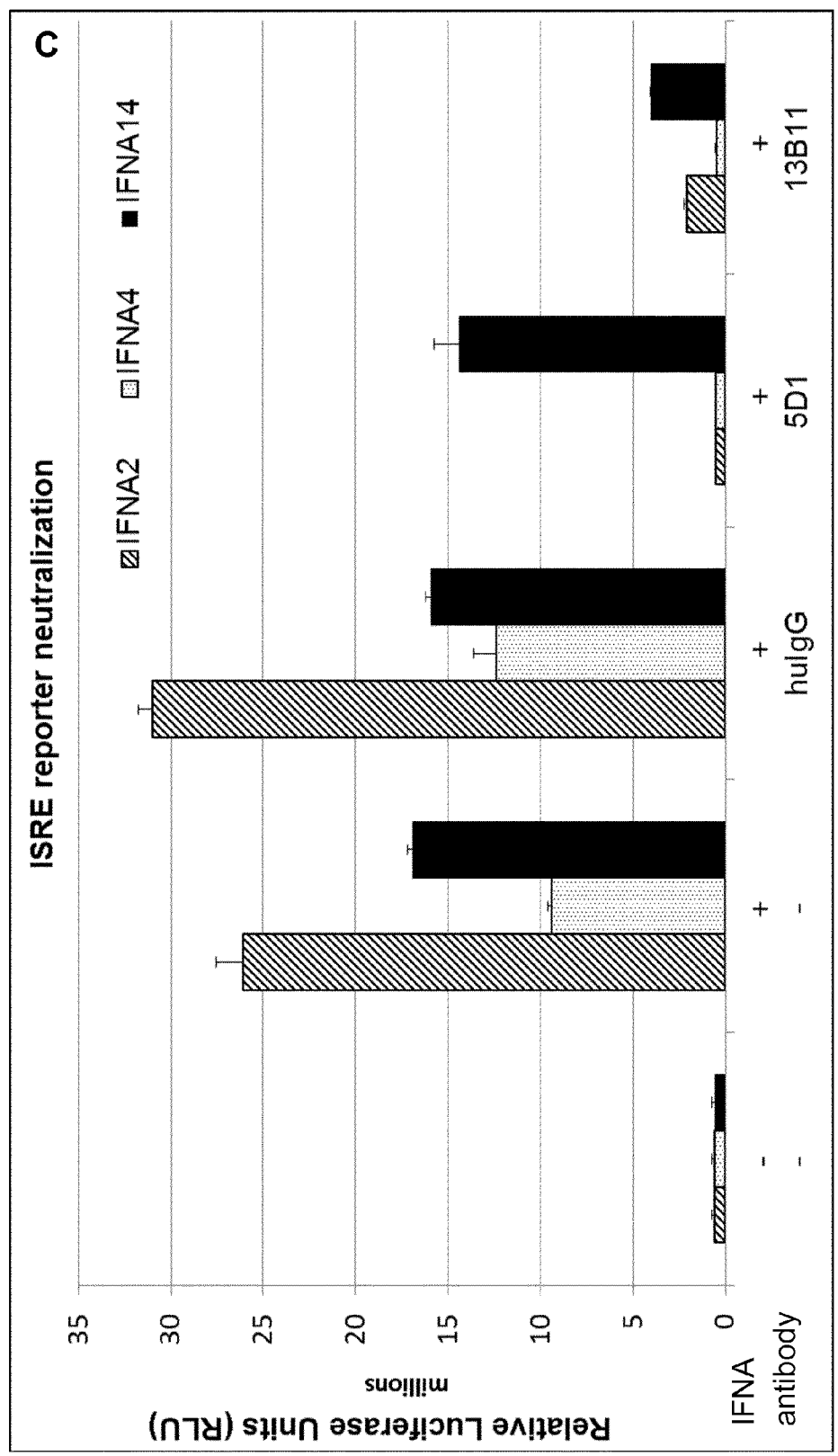
Figure 7:
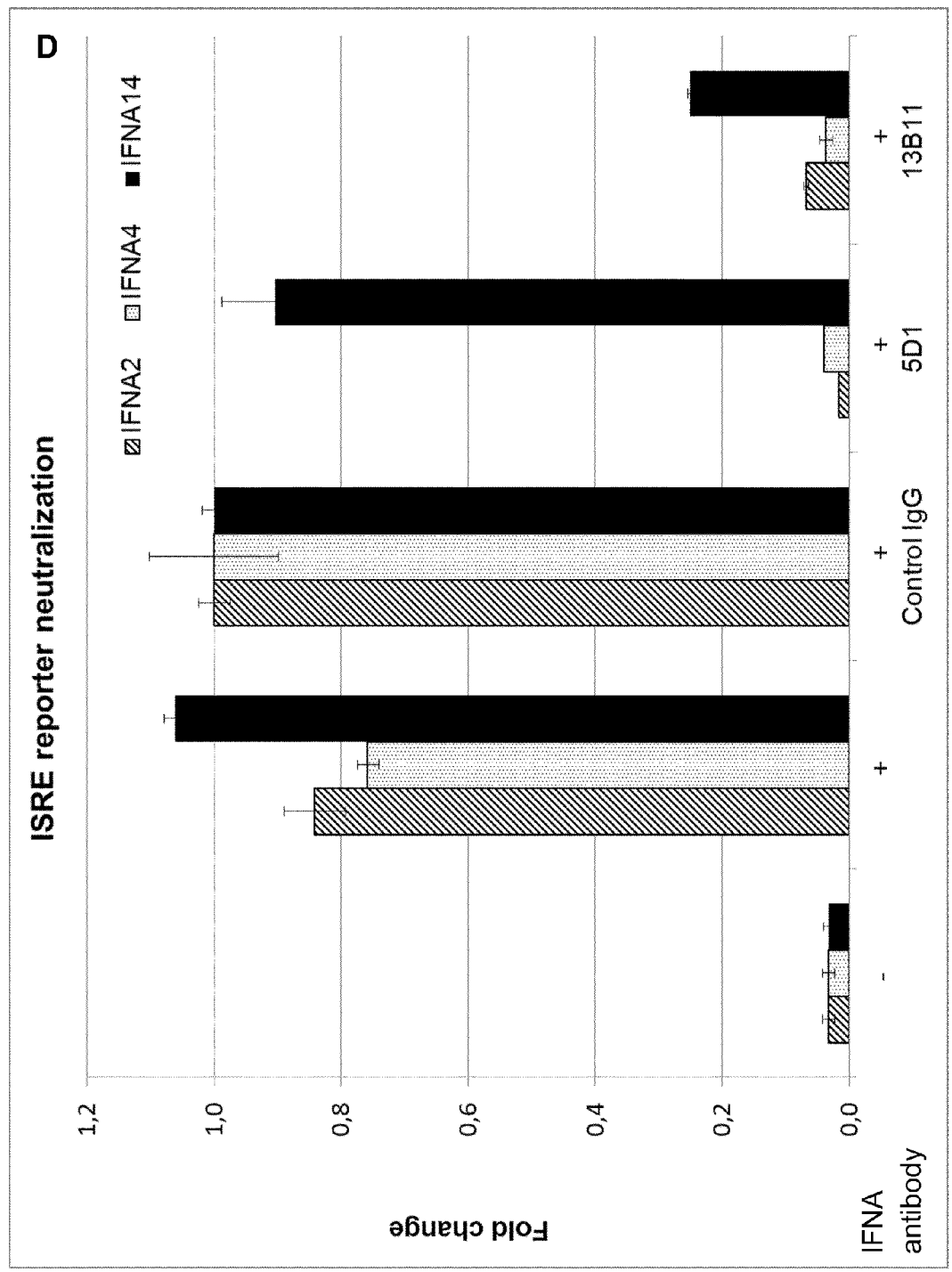
Figure 7:
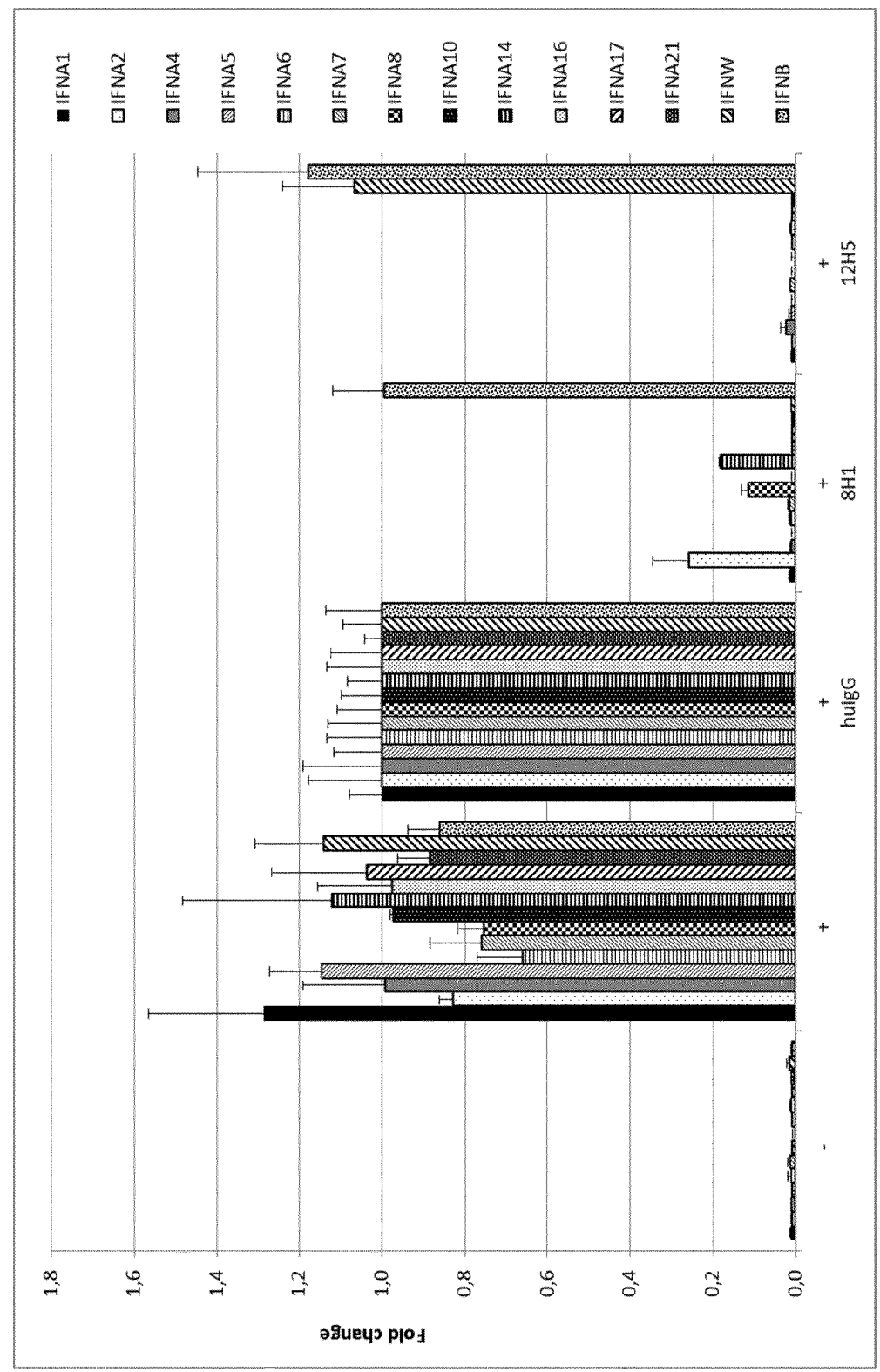

For instance, the exemplary anti-IFN-α antibody 19D11 of the present invention binds to at least human IFN-α subtypes IFN-α1/13, IFN-α2, IFN-α4, IFN-α5, IFN-α6, IFN-α8, IFN-α10, IFN-α14, IFN-α16 and IFN-α21 (see, e.g., FIGS. 13 and 18 to 27) and has neutralization properties as described in the Examples and in FIGS. 5 to 7. Accordingly, in one embodiment, the antibody or IFN-α binding fragment of the present invention in addition to the IFN-α subtypes defined in section (i), supra, binds to at least human IFN-α subtypes IFN-α1/13, IFN-α8, IFN-α16 and IFN-α21. Thus, in one preferred embodiment, the anti-IFN-α antibody or an IFN-α binding fragment, synthetic or biotechnological derivative thereof has the immunological characteristics and/or biological properties of antibody 19D11 as illustrated in the appended Examples and Figures, in particular with respect to its neutralizing activity towards the different IFN-α subtypes.

Exemplary anti-IFN-α antibodies 26B9 and 31B4 of the present invention bind to at least human IFN-α subtypes IFN-α1/13, IFN-α2, IFN-α4, IFN-α5, IFN-α6, IFN-α8, IFN-α10, IFN-α14 and IFN-α21 (see, e.g., FIGS. 13 and 18 to 27) and have neutralization properties as described in the Examples and in FIGS. 5 to 7. Therefore, in one embodiment, the antibody or IFN-α binding fragment of the present invention in addition to the IFN-α subtypes defined in section (i), supra, binds to at least human IFN-α subtypes IFN-α1/13, IFN-α8 and IFN-α21. Thus, in another preferred embodiment, the anti-IFN-α antibody or an IFN-α binding fragment, synthetic or biotechnological derivative thereof has the immunological characteristics and/or biological properties of antibody 26B9 or 31B4 as illustrated in the appended Examples and Figures, in particular with respect to its neutralizing activity towards the different IFN-α subtypes.

Exemplary anti-IFN-α antibody 25C3 of the present invention binds to at least human IFN-α subtypes IFN-α1/13, IFN-α2, IFN-α4, IFN-α5, IFN-α6, IFN-α8, IFN-α10, IFN-α14, IFN-α16 and IFN-α21 (see, e.g., FIGS. 13 and 18 to 19) and has neutralization properties as described in the Examples and in FIGS. 5 to 7, showing in particular a reduced neutralization capability towards IFN-α6, IFN-α8, IFN-α10 and IFN-α16. In one embodiment thus, the antibody or IFN-α binding fragment of the present invention in addition to the IFN-α subtypes defined in section (i), supra, binds to at least human IFN-α subtypes IFN-α1/13, IFN-α8, IFN-α16 and IFN-α21 but shows only weak neutralization of IFN-α16. In a further embodiment, the antibody or IFN-α binding fragment of the present invention shows in addition only weak neutralization of IFN-α6, IFN-α8 and IFN-α10. Thus, in another preferred embodiment, the anti-IFN-α antibody or an IFN-α binding fragment, synthetic or biotechnological derivative thereof has the immunological characteristics and/or biological properties of antibody 25C3 as illustrated in the appended Examples and Figures, in particular with respect to its neutralizing activity towards the different IFN-α subtypes.

Exemplary anti-IFN-α antibody 5D1 of the present invention binds to at least human IFN-α subtypes IFN-α2, IFN-α4, IFN-α5, IFN-α6, IFN-α8, IFN-α10, IFN-α14, IFN-α16 and IFN-α21 but not to IFN-α1/13 and has neutralization properties as described in the Examples and in FIGS. 5 to 7. Accordingly, in one embodiment, the antibody or IFN-α binding fragment of the present invention in addition to the IFN-α subtypes defined in section (i), supra, binds to at least human IFN-α subtypes IFN-α8, IFN-α16 and IFN-α21 but not to IFN-α1/13. Thus, in another preferred embodiment, the anti-IFN-α antibody or an IFN-α binding fragment, synthetic or biotechnological derivative thereof has the immunological characteristics and/or biological properties of antibody 5D1 as illustrated in the appended Examples and Figures, in particular with respect to its neutralizing activity towards the different IFN-α subtypes.

Exemplary anti-IFN-α antibody 13B11 of the present invention binds to at least human IFN-α subtypes IFN-α1/13, IFN-α2, IFN-α4, IFN-α5, IFN-α6, IFN-α10, IFN-α14 and IFN-α16 but not to IFN-α8 and has neutralization properties as described in the Examples and in FIGS. 5 to 7. Therefore, in one embodiment, the antibody or IFN-α binding fragment of the present invention in addition to the IFN-α subtypes defined in section (i), supra, binds to at least human IFN-α subtypes IFN-α1/13 and IFN-α1 6 but not to IFN-α8. Thus, in a further preferred embodiment, the anti-IFN-α antibody or an IFN-α binding fragment, synthetic or biotechnological derivative thereof has the immunological characteristics and/or biological properties of antibody 13B11 as illustrated in the appended Examples and Figures, in particular with respect to its neutralizing activity towards the different IFN-α subtypes.

Exemplary anti-IFN-α antibody antibody 8H1 of the present invention binds to at least human IFN-α subtypes IFN-α1, IFN-α4, IFN-α5, IFN-α6, IFN-α7, IFN-α10, IFN-α16, IFN-α17 and IFN-α21 while showing weaker neutralization of IFN-α2, IFN-α8 and IFN-α14 and has neutralization properties as described in the Examples and in FIG. 7. Therefore, in one embodiment, the antibody or IFN-α binding fragment of the present invention binds in addition to the IFN-α subtypes defined in section (i), supra, to at least human IFN-α subtypes IFN-α1/13, IFN-α17 and IFN-α21. Thus, in a still further preferred embodiment, the anti-IFN-α antibody or an IFN-α binding fragment, synthetic or biotechnological derivative thereof has the immunological characteristics and/or biological properties of antibody 8H1 as illustrated in the appended Examples and Figures, in particular with respect to its neutralizing activity towards the different IFN-α subtypes.

Exemplary anti-IFN-α antibody 12H5 of the present invention binds to and neutralizes all human IFN-α subtypes, namely IFN-α1, IFN-α2, IFN-α4, IFN-α5, IFN-α6, IFN-α7, IFN-α8, IFN-α10, IFN-α14, IFN-α16, IFN-α17 and IFN-α21 and has neutralization properties as described in the Examples and in FIG. 7. Therefore, in one embodiment, the antibody or IFN-a binding fragment of the present invention binds to all human IFN-α subtypes. Thus, in a still further preferred embodiment, the anti-IFN-α antibody or an IFN-α binding fragment, synthetic or biotechnological derivative thereof has the immunological characteristics and/or biological properties of antibody 12H5 as illustrated in the appended Examples and Figures, in particular with respect to its neutralizing activity towards the different IFN-α subtypes.

In one embodiment, the anti-IFN-α antibody and IFN-α binding fragment of the present invention recognize and/or neutralize IFN-α21, preferably with at least substantially the same binding preference/neutralizing activity as for any other IFN-α recognized and/or neutralized by the antibody or fragment thereof.

Figure 25:
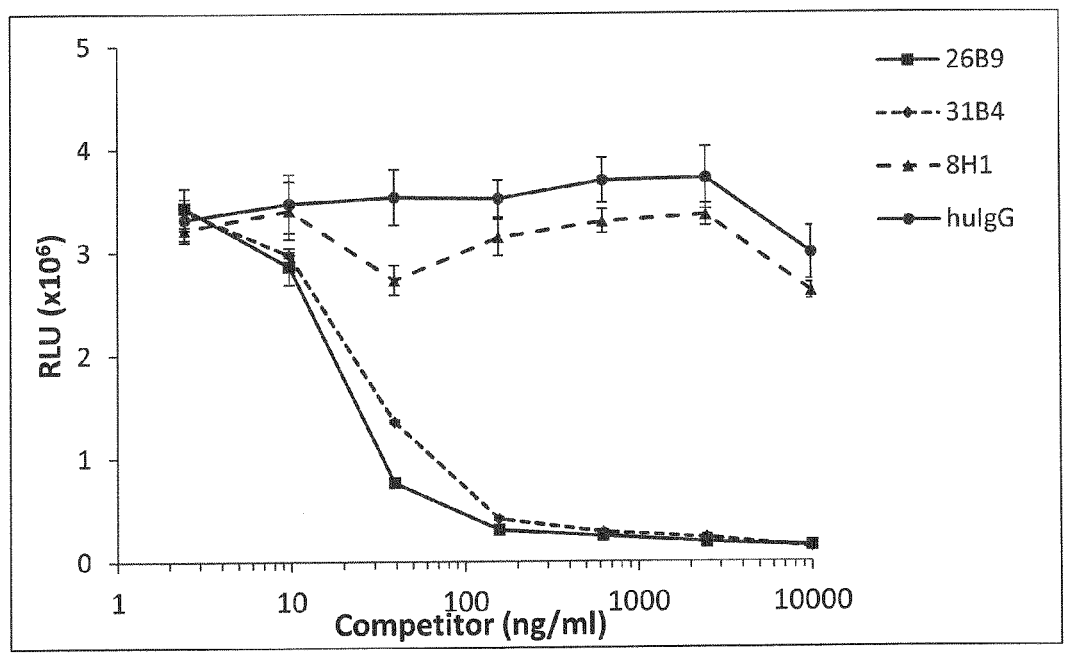
Figure 26:
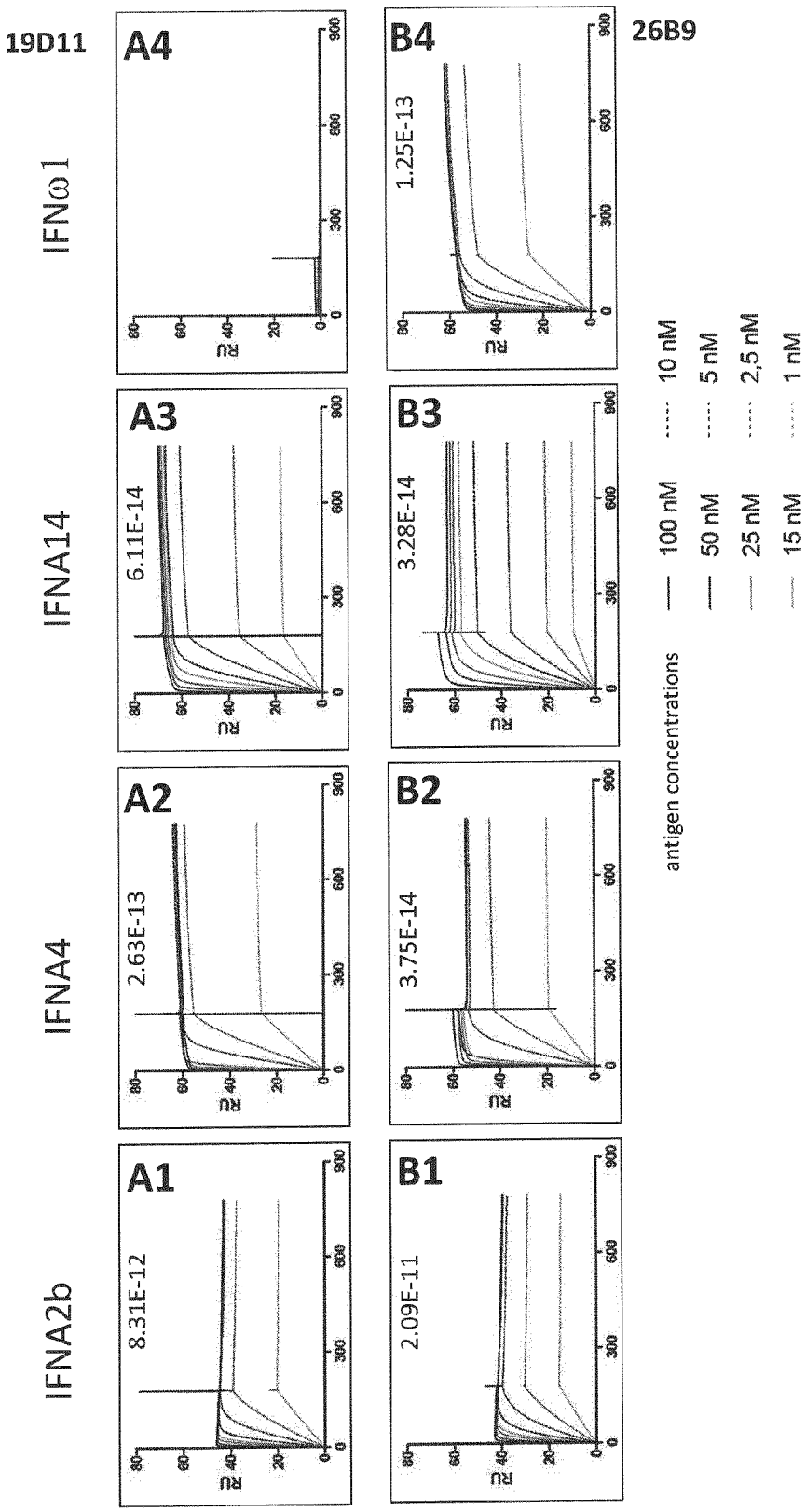
Figure 26:
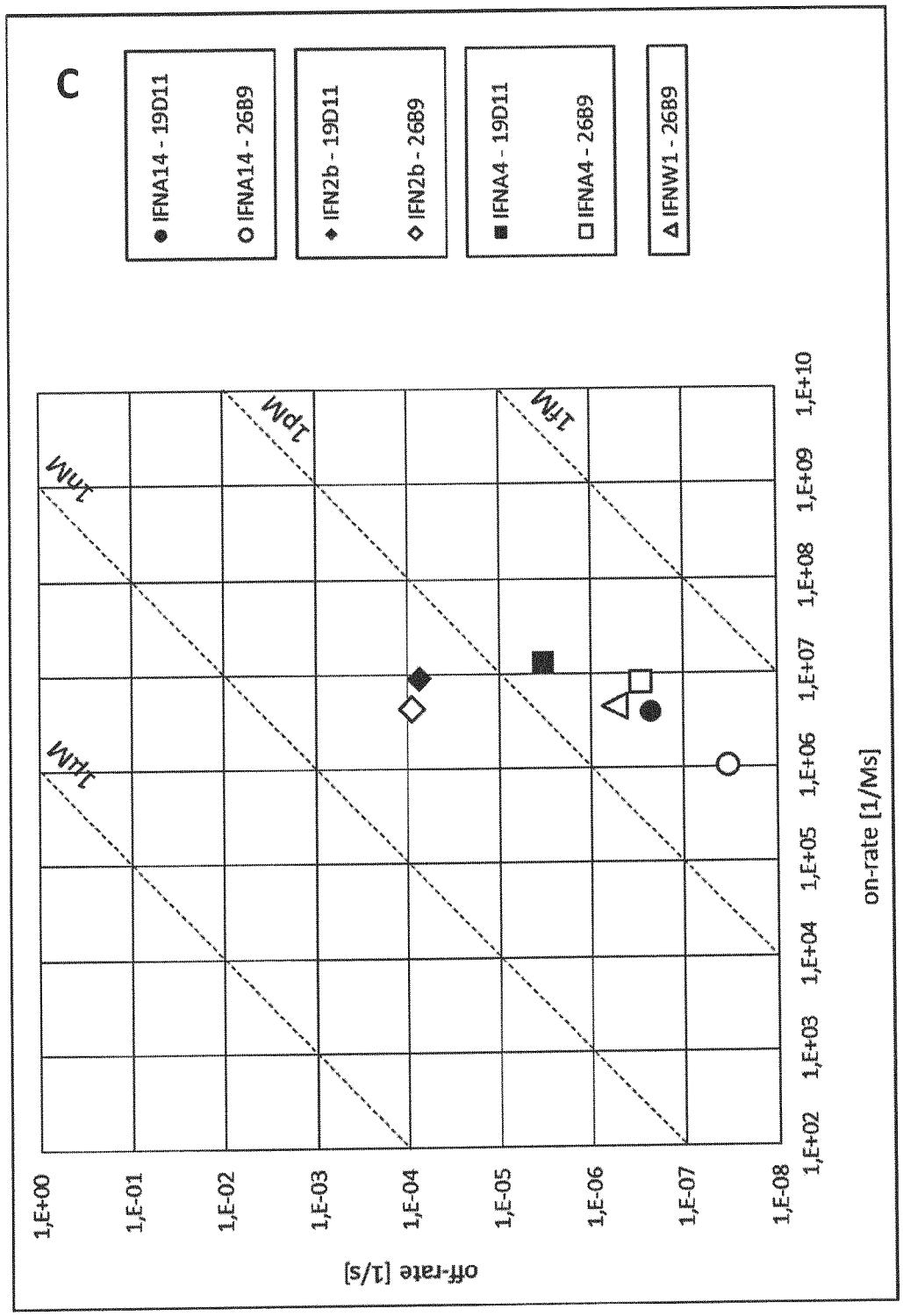
Figure 26:
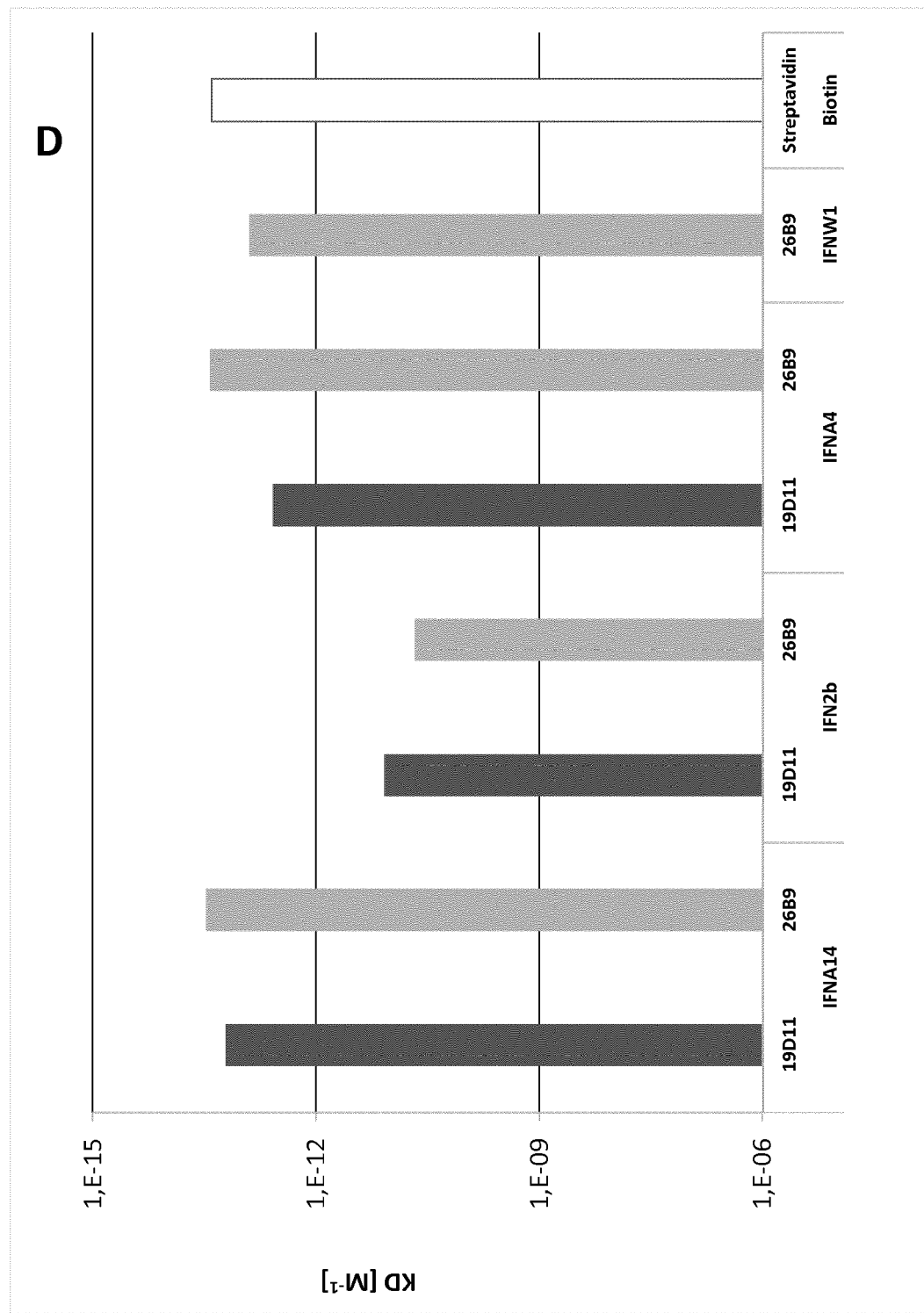

Furthermore, after preliminary results obtained in the experiments performed within the scope of the present invention already indicated that exemplary antibodies provided by the present invention bind in addition to at least one IFN-α subtype to another type I interferon, i.e. IFN-omega (also indicated as IFN-ω or as IFN-ω herein) as exemplarily shown for antibodies 26B9 and 31B4 in FIG. 18, further experiments confirmed the surprising neutralizing properties of some of the subject antibodies towards IFN-ω, i.e. for antibodies 26B9 and 31B4 in FIG. 5 and for antibody 26B9 in comparison to antibody 19D11 in FIG. 24, for antibody 26B9 in FIGS. 25-26, for antibody 31B4 in FIG. 25, for antibody 8H1 in FIGS. 7 and 20 and for antibody 50E1 1 in FIG. 22. Accordingly, in one embodiment the present invention also relates to anti-IFN-a antibodies and IFN-α binding fragments thereof which besides at least one IFN-α subtype bind in addition at least one other type I interferon, wherein preferably the other type I interferon is human IFN-ω (IFN-ω). The corresponding IFN-binding molecules may also be denoted IFN-α/IFN-ω binding molecule or anti-IFN-α/IFN-ω antibody. Preferably, the anti-IFN-α antibody or IFN-α binding fragment of the present invention, in addition to the at least one IFN-a subtype is capable of neutralizing a biological activity of human IFN-ω (IFN-ω). Such an antibody is of particular value for use in the prevention, treatment or diagnosis of patients having a higher titer of IFN-ω and/or for patients showing both, an increased titer of an IFN-α subtype and of IFN-ω. Thus, in a still further preferred embodiment, the anti-IFN-α antibody or an IFN-α binding fragment, synthetic or biotechnological derivative thereof has the immunological characteristics and/or biological properties of antibody 26B9, 31B4, 8H1 or 50E11 as illustrated in the appended Examples and Figures, in particular with respect to its neutralizing activity towards IFN-α.

The IFN-α/IFN-ω binding molecules of the present invention are particularly useful in the prevention, therapy and/or diagnosis of diseases associated with an increased expression or level of activity of IFN-ω in a subject, in particular in case the expression or level of activity of IFN-α is increased as well. For example, IFN-ω is found in the serum of patients with systemic lupus erythematosus (SLE) and renal disease in addition to elevated levels of IFN-α subtypes; see, e.g., M C Dall'Era et al., Ann. Rheum. Dis. 64 (2005), 1692-1697 and Han et al., Genes and Immunity 4 (2003), 177-186. Accordingly, the IFN-α/IFN-ω binding molecules of the present invention broadly blocking multiple type I IFNs may be more advantageous as a potential therapeutic agent than an antibody specific for IFN-α only. In addition, it has been reported that sera of patients with rheumatoid arthritis besides IFN— have an elevated level of IFN-ω relative to normal controls, but not of IFN-α; see Lavoie et al., J. Immunol. 186 (2011), 186, meeting abstract io1.37. Thus, the IFN-α/IFN-ω binding molecules of the present invention may also prove useful in the treatment of autoimmune disorders which do not or not significantly involve IFN-α but IFN-ω. Hence, in a further aspect the present invention relates to IFN-ω binding molecules which are synthetic or biotechnological derivatives of the human-derived anti-IFN-α antibody 26B9, 31B4, 8H1 or 50E1 1 which substantially retain their neutralizing activity towards IFN-ω, but lost their binding specificity to one or more IFN-α subtypes or the capability of binding IFN-α altogether. In addition, the present invention relates to any IFN-ω binding molecule, preferably antibody or antibody fragment which competes with any of the human-derived anti-IFN-α antibodies 26B9, 31B4, 8H1 or 50E11 for binding and/or neutralizing IFN-ω in any of the assays described in the Examples but not necessarily with respect to binding and/or neutralizing IFN-α.

Furthermore, as shown in FIG. 18, the exemplary anti-IFN-α antibodies of the present invention display a much weaker or no affinity towards type I interferon IFN-ε, IFN-β, towards IFN-γ as a type II interferon and/or towards IFN-λ (IL-29, IL-28A and IL-28B in FIG. 18) as type III interferons. Accordingly, in one embodiment the present invention relates to anti-IFN-a antibodies and IFN-α binding fragments thereof which preferably bind type I over type II and/or type III interferons, more preferably anti-IFN-α antibodies and IFN-α binding fragments of the present invention do not substantially recognize type II and type III interferons.

The present invention exemplifies IFN-α binding molecules, i.e. antibodies and IFN-α binding fragments thereof, which may be generally characterized by comprising in their variable region, i.e. binding domain at least one complementarity determining region (CDR) of the VH and/or VL of the variable region comprising the amino acid sequence depicted in FIG. 1 of (VH) (SEQ ID NOs: 2, 10, 18, 22, 30, 38, 76, 84 and 92) and (VL) (SEQ ID NOs: 4, 12, 20, 24, 32, 40, 78, 86 and 94)—see the exemplary CDR sequences underlined in FIG. 1 and identified in Table 1. However, as discussed in the following, the person skilled in the art is well aware of the fact that in addition or alternatively CDRs may be used, which differ in their amino acid sequence from those indicated in FIG. 1 by one, two, three or even more amino acids, in particular in case of CDR2 and CDR3.

In respect of the particular binding preferences and neutralization abilities towards specific IFN-α subtypes and IFN-ω as shown in the Examples and Figures, the general characterization provided above may be subdivided into the following groups of IFN-α binding molecules, i.e. antibodies and binding fragments thereof of the present invention.

In one embodiment, the antibody or IFN-α binding fragment of the present invention is a human-derived antibody and binds to at least one IFN-α subtype selected from the group consisting of IFN-α1/13, IFN-α2, IFN-α4, IFN-α5, IFN-α6, IFN-α8, IFN-α10, IFN-α14, IFN-α16 and IFN-α21, comprising in its variable region:
(a) at least one complementarity determining region (CDR) of the VH and/or VL variable region amino acid sequences depicted in FIG. 1 (VH) (SEQ ID NO: 18); and FIG. 1 (VL) (SEQ ID NO: 20);
(b) an amino acid sequence of the VH and/or VL region as depicted in FIG. 1;
(c) least one CDR consisting of an amino acid sequence resulted from a partial alteration of any one of the amino acid sequences of (a); and/or
(d) heavy chain and/or light variable region comprising an amino acid sequence resulted from a partial alteration of the amino acid sequence of (b).

In addition, or alternatively, the antibody or IFN-α binding fragment of the present invention is characterized by displaying the binding characteristics of exemplary antibody 19D11.

As illustrated in Example 5 and shown in FIG. 27A/B, epitopes in IFN-α2 specifically recognized by exemplary antibody 19D11 have been identified. Accordingly, in one embodiment, the antibody or IFN-α binding fragment, synthetic or biotechnological derivative of the present invention is capable of binding an epitope in IFN-α2 consisting of the amino acid sequence SAAWDETLLDKFYTEL YQ (SEQ ID NO: 99) and/or RITLYLKEKKYSPCAWEV (SEQ ID NO: 100).

In another embodiment, the antibody or IFN-α binding fragment of the present invention is a human-derived antibody and binds to at least one IFN-α subtype selected from the group consisting of IFN-α1/13, IFN-α2, IFN-α4, IFN-α5, IFN-α6, IFN-α8, IFN-α10, IFN-α14 and IFN-α21, comprising in its variable region: at least one complementarity determining region (CDR) of the VH and/or VL variable region amino acid sequences depicted in FIG. 1 (VH) (SEQ ID NO: 30 or SEQ ID NO:38); and FIG. 1 (VL) (SEQ ID NO: 32 or SEQ ID NO: 40);
(a) an amino acid sequence of the VH and/or VL region as depicted in FIG. 1;
(b) at least one CDR consisting of an amino acid sequence resulted from a partial alteration of any one of the amino acid sequences of (a); and/or
(c) a heavy chain and/or light variable region comprising an amino acid sequence resulted from a partial alteration of the amino acid sequence of (b).

In addition, or alternatively, the antibody or IFN-α binding fragment of the present invention is characterized by displaying the binding characteristics of exemplary antibody 26B9 or 31B4. Thus, in this embodiment the anti-IFN-α antibody or IFN-α binding fragment preferably also recognizes and neutralizes IFN-ω; see also supra.

As illustrated in Example 5 and shown in FIG. 27C/D, epitopes in IFN-α2 and IFN-ω specifically recognized by exemplary antibody 26B9 have been identified. Accordingly, in one embodiment, the antibody or IFN-α binding fragment, synthetic or biotechnological derivative of the present invention is capable of binding an epitope of IFN-α2 consisting of the amino acid sequence YTELY-QQLNDLEACVIQG (SEQ ID NO: 101) and/or an epitope of IFN-αW consisting of the amino acid sequence TG1HQQLQHLETCLLQVV (SEQ ID NO: 102).

In another embodiment, the antibody or IFN-α binding fragment of the present invention is a human-derived antibody and binds to at least one IFN-α subtype selected from the group consisting of subtypes IFN-α1/13, IFN-α2, IFN-α4, IFN-α5, IFN-α6, IFN-α8, IFN-α10, IFN-α14, IFN-α16 and IFN-α21, comprising in its variable region:
(a) at least one complementarity determining region (CDR) of the VH and/or VL variable region amino acid sequences depicted in FIG. 1 (VH) (SEQ ID NO: 22); and FIG. 1 (VL) (SEQ ID NO: 24); an amino acid sequence of the VH and/or VL region as depicted in FIG. 1;
(b) at least one CDR consisting of an amino acid sequence resulted from a partial alteration of any one of the amino acid sequences of (a); and/or
(c) a heavy chain and/or light variable region comprising an amino acid sequence resulted from a partial alteration of the amino acid sequence of (b).

In addition, or alternatively, the antibody or IFN-α binding fragment of the present invention is characterized by displaying the binding characteristics of exemplary antibody 25C3.

In another embodiment, the antibody or IFN-α binding fragment of the present invention is a human-derived antibody and binds to at least one IFN-α subtype selected from the group consisting of subtypes IFN-α2, IFN-α4, IFN-α5, IFN-α6, IFN-α8, IFN-α10, IFN-α14, IFN-α16 and IFN-α21 but not to IFN-α1/13, comprising in its variable region:
(a) at least one complementarity determining region (CDR) of the VH and/or VL variable region amino acid sequences depicted in FIG. 1 (VH) (SEQ ID NO: 2); and FIG. 1 (VL) (SEQ ID NO: 4);
(b) an amino acid sequence of the $V_H$ and/or $V_L$ region as depicted in FIG. 1;
(c) least one CDR consisting of an amino acid sequence resulted from a partial alteration of any one of the amino acid sequences of (a); and/or
(d) heavy chain and/or light variable region comprising an amino acid sequence resulted from a partial alteration of the amino acid sequence of (b).

In addition, or alternatively, the antibody or IFN-α binding fragment of the present invention is characterized by displaying the binding characteristics of exemplary antibody 5D1.

In another embodiment, the antibody or IFN-α binding fragment of the present invention is a human-derived antibody and binds to at least one IFN-α subtype selected from the group consisting of IFN-α1/13, IFN-α2, IFN-α4, IFN-α5, IFN-α6, IFN-α10, IFN-α14 and IFN-α16, comprising in its variable region:
(a) at least one complementarity determining region (CDR) of the VH and/or VL variable region amino acid sequences depicted in FIG. 1 (VH) (SEQ ID NO: 10); and FIG. 1 (VL) (SEQ ID NO: 12);
(b) an amino acid sequence of the $V_H$ and/or $V_L$ region as depicted in FIG. 1;
(c) least one CDR consisting of an amino acid sequence resulted from a partial alteration of any one of the amino acid sequences of (a); and/or (d) heavy chain and/or light variable region comprising an amino acid sequence resulted from a partial alteration of the amino acid sequence of (b).

In addition, or alternatively, the antibody or IFN-α binding fragment of the present invention is characterized by displaying the binding characteristics of exemplary antibody 13B11.

In another embodiment, the antibody or IFN-α binding fragment of the present invention is a human-derived antibody and binds to at least one IFN-α subtype selected from the group consisting of IFN-α1, IFN-α4, IFN-α5, IFN-α6, IFN-α7, IFN-α10, IFN-α16, IFN-α1 7 and IFN-α21, comprising in its variable region:

(a) at least one complementarity determining region (CDR) of the VH and/or VL variable region amino acid sequences depicted in FIG. 1 (VH) (SEQ ID NO: 76); and FIG. 1 (VL) (SEQ ID NO: 78);

(b) an amino acid sequence of the $V_H$ and/or $V_L$ region as depicted in FIG. 1;

(c) at least one CDR consisting of an amino acid sequence resulted from a partial alteration of any one of the amino acid sequences of (a); and/or (d) a heavy chain and/or light variable region comprising an amino acid sequence resulted from a partial alteration of the amino acid sequence of (b).

In addition, or alternatively, the antibody or IFN-α binding fragment of the present invention is characterized by displaying the binding characteristics of exemplary antibody 8H1. Thus, in this embodiment the anti-IFN-α antibody or IFN-α binding fragment preferably also recognizes and neutralizes IFN-α; see also supra.

In another embodiment, the antibody or IFN-α binding fragment of the present invention is a human-derived antibody and binds to at least one IFN-α subtype selected from the group consisting of IFN-α1/13, IFN-α2, IFN-α4, IFN-α5, IFN-α6, IFN-α8, IFN-α10, IFN-α14 and IFN-α21, comprising in its variable region:

(a) at least one complementarity determining region (CDR) of the VH and/or VL variable region amino acid sequences depicted in FIG. 1 (VH) (SEQ ID NO: 84); and FIG. 1 (VL) (SEQ ID NO: 86);

(b) an amino acid sequence of the $V_H$ and/or $V_L$ region as depicted in FIG. 1;

(c) at least one CDR consisting of an amino acid sequence resulted from a partial alteration of any one of the amino acid sequences of (a); and/or (d) heavy chain and/or light variable region comprising an amino acid sequence resulted from a partial alteration of the amino acid sequence of (b).

In addition, or alternatively, the antibody or IFN-α binding fragment of the present invention is characterized by displaying the binding characteristics of exemplary antibody 12H5.

In another embodiment, the antibody or IFN-α binding fragment of the present invention is a human-derived antibody and binds to at least one IFN-α subtype selected from the group consisting of IFN-α1/13, IFN-α2, IFN-α4, IFN-α5, IFN-α6, IFN-α8, IFN-α10, IFN-α14 and IFN-α21, comprising in its variable region:

(a) at least one complementarity determining region (CDR) of the VH and/or VL variable region amino acid sequences depicted in FIG. 1 (VH) (SEQ ID NO: 92); and FIG. 1 (VL) (SEQ ID NO: 94);

(b) an amino acid sequence of the $V_H$ and/or $V_L$ region as depicted in FIG. 1;

(c) at least one CDR consisting of an amino acid sequence resulted from a partial alteration of any one of the amino acid sequences of (a); and/or (d) a heavy chain and/or light variable region comprising an amino acid sequence resulted from a partial alteration of the amino acid sequence of (b).

In addition, or alternatively, the antibody or IFN-α binding fragment of the present invention is characterized by displaying the binding characteristics of exemplary antibody SOE11. Thus, in this embodiment the anti-IFN-α antibody or IFN-α binding fragment preferably also recognizes and neutralizes IFN-ω at least to some extent; see also supra.

In summary, in one aspect the present invention relates to human-derived monoclonal antibodies and IFN-α binding fragments as well as synthetic and biotechnological derivatives of the subject antibodies exemplified herein comprising in their variable regions:

(a) at least one complementarity determining region (CDR) of the VH and/or VL variable region amino acid sequences depicted in (i) FIG. 1 (VH) (SEQ ID NOs: 2, 10, 18, 22, 30, 38, 76, 84 and 92); and (ii) FIG. 1 (VL) (SEQ ID NOs: 4, 12, 20, 24, 32, 40, 78, 86 and 94);

(b) an amino acid sequence of the VH and/or VL region as depicted in FIG. 1;

(c) at least one CDR consisting of an amino acid sequence resulted from a partial alteration of any one of the amino acid sequences of (a); and/or (d) a heavy chain and/or light variable region comprising an amino acid sequence resulted from a partial alteration of the amino acid sequence of (b);

preferably wherein the antibody, IFN-α binding fragment or synthetic and biotechnological derivative thereof retains at least one of the immunological characteristics and/or biological activities of any of the subject antibodies described in the Examples, e.g. neutralizing activity towards different IFN-α subtypes and/or IFN-ω.

In addition, in one aspect the present invention relates to an IFN-α neutralizing antibody or IFN-α binding fragment thereof which competes with said antibody or fragment thereof as defined hereinabove for binding to and/neutralizing of at least one IFN-α subtype and/or IFN-ω. Furthermore, in one embodiment the antibody of the present invention or the IFN-α binding fragment thereof contains at least CDR3 of the VH and/or VL variable region depicted in (i) FIG. 1 (VH) (SEQ ID NOs: 2, 10, 18, 22, 30, 38, 76, 84 and 92); and (ii) FIG. 1 (VL) (SEQ ID NOs: 4, 12, 20, 24, 32, 40, 78, 86 and 94);

or a corresponding CDR3 which differs in its amino acid sequence by substitution, deletion and/or addition of 6, 5 or 4, preferably not more than 3 and most preferably red no more than 2 or 1 amino acids.

In order to provide antibodies particularly suitable for therapeutic applications, i.e. to avoid immunological responses to the antibodies of the present invention as observed for foreign antibodies such as mouse antibodies in humans (RAMA-response) the present invention preferably relates to fully human or human-derived antibodies since the exemplary IFN-α antibodies, which are described in the Examples illustrating the present invention, have been derived from a human patient.

In this context, contrary to humanized antibodies and otherwise human-like antibodies, see also the discussion infra, the human-derived antibodies of the present invention are characterized by comprising CDRs which have been seen by the human body and therefore are substantially devoid of the risk of being immunogenic. Therefore, the antibody of the present invention may still be denoted human-derived if at least one, preferably two and most preferably all three CDRs of one or both the variable light and heavy chain of the antibody are derived from the human antibodies illustrated herein.

The human-derived antibodies of the present invention may also be called "human auto-antibodies" in order to emphasize that those antibodies were indeed expressed initially by a human subject and are not in vitro selected constructs generated, for example, by means of human immunoglobulin expressing phage libraries or xenogeneic antibodies generated in a transgenic animal expressing part of the human immunoglobulin repertoire, which hitherto represented the most common method for trying to provide human-like antibodies. On the other hand, the human-derived antibody of the present invention may be denoted synthetic, recombinant, and/or biotechnological in order to distinguish it from human serum antibodies per se, which may be purified via protein A or affinity column.

However, the present invention uses and envisages further studies of the antibodies of the present invention in animal models, e.g., in transgenic mice expressing human IFN-α. To avoid immunogenic effects in the experimental animals analogous to the RAMA-response in humans, in one aspect, the antibody of the present invention may be a humanized, xenogeneic, or chimeric human-murine antibody, preferably a chimeric rodent-human or a rodentized antibody, most preferred a chimeric murine-human or murinized antibody.

As described herein below in more detail, the antibody or antigen-binding fragment thereof of the present invention can be of or derived from any type, class or subclass of an immunoglobulin molecule. However, in a preferred embodiment, the antibody of the present invention is provided, which is of the IgG isotype, most preferably of the IgG1 subclass.

In order to provide such humanized, chimeric and in particular fully human antibodies, fragments and/or native Fab fragments thereof, the antibody of the present invention preferably further comprises a CH and/or CL constant region comprising an amino acid sequence selected from the CH and CL amino acid sequences set forth in Table 1 (SEQ ID NOs.: 6, 8, 14, 16, 26, 28, 34, 36, 42, 44, 72, 74, 80, 82, 88, 90, 96 and 98) or an amino acid sequence with at least 60% identity, preferably 70% identity, more preferably 80% identity, still more preferably 90% identity, and particularly preferred at least 91%, 92%, 93%, 94%, 95%, 96%, 97%, 98% or 99%, identity to the mentioned reference sequences.

In addition, or alternatively, the framework region of the antibody of the present invention comprises an amino acid sequence selected from FIG. 1 (VH) (SEQ ID NOs: 2, 10, 18, 22, 30, 38, 76, 84 and 92); and FIG. 1 (VL) (SEQ ID NOs.: 4, 12, 20, 24, 32, 40, 78, 86 and 94) or an amino acid sequence with at least 60% identity, preferably 70% identity, more preferably 80% identity, still more preferably 90% identity, and particularly preferred at least 91%, 92%, 93%, 94%, 95%, 96%, 97%, 98% or 99%, identity to the mentioned reference sequences.

As mentioned above, the antibodies of the present invention have been isolated from APECED/APS1 patients. In this context, experiments disclosed in applicant's co-pending international application WO2013/098419 surprisingly revealed that APECED/APS1 patients display an auto-immunosome, i.e. an autoantibody profile comprising as well a broad spectrum of binding molecules specific for different IFNα subtypes. APS1 is a rare autoimmune disease caused by mutations in the Autoimmune Regulator (AIRE) gene. The AIRE protein governs the expression in medullary thymic epithelium of many peripheral self-antigens (e.g., insulin) that are presented by MHC to tolerate developing thymocytes. In APS1, AIRE mutations cause aberrant negative selection, which enables autoreactive T cells to escape to the periphery. Accordingly, the patients show an extremely variable spectrum of clinical features in APS1, but usually with several autoimmune disorders of endocrine tissues. The defining APS1 triad comprises chronic mucocutaneous candidiasis, hypoparathyroidism and adrenal failure (Perheentupa, Endocrinol. Metab. Clin. North Am. 31 (2002), 295-320).

Other clinical conditions seen in APECED patients include thyroid autoimmune diseases, diabetes mellitus, gonadal failure, vitiligo, alopecia, chronic hepatitis, chronic gastritis and pernicious anemia and different forms other gastrointestinal symptoms. For further details concerning APECED/APS1 patients and the screening of their auto-immunosome see the description of international application WO2013/098419 and the Examples described therein, in particular the Material and Methods section on pages 112-117; Example 1 on pages 117-118 and Example 7 on page 128 and the following Tables 1 to 14; and Example 17 on pages 168-171, the disclosure content of which is incorporated herein by reference.

As described in detail above and indicated in Example 1, in one preferred embodiment the antibody of the present invention is obtained from a sample of a human subject affected with autoimmune polyendocrinopathy-candidiasis-ectodermal dystrophy (APECED/APS1) or from a patient affected with a similar autoimmune disease as described in international application WO2013/098419 and the Examples therein, in particular the Materials and Methods section on pages 112-117; Example 1 on pages 117-118; in Example 10 on pages 156-161, specifically in section "Patients and controls" on page 156 therein; and Example 17 on pages 168-171, the disclosure content of which is incorporated herein by reference.

In this context it is noted that the subject anti-IFN-α antibodies of the present invention have been cloned by a novel and proprietary method of isolating human antibodies, which is disclosed in applicant's co-pending international application WO2013/098420, the disclosure content of which is incorporated herein by reference.

Briefly, the sample for isolating the antibody of interest comprises or consists of peripheral blood mononuclear cells (PBMC) and serum for the detection of possible antibody reactivities. The sample derived from the subject may either be directly used for, e.g., testing seroreactivity against one or more of the desired antigen(s) or may be further processed, for example enriched for B lymphocytes. In particular, it is preferred that the sample comprises or is derived from B cells that produce the antibody of interest, most preferably memory B-cells. The memory B cells are cultured under conditions allowing only a definite life span of the B cells, typically no more than 1 to 2 weeks until singling out the cells from B cell cultures which are reactive against the desired antigen subsequently followed by RT-PCR of single sorted cells for obtaining the immunoglobulin gene repertoire; see for detailed description Examples 1 and 2 on pages 118 to 120 of WO2013/098419 and in particular Examples 1 to 4 on pages 27 to 31 of WO2013/098420, the disclosure content of which is incorporated herein by reference. Naturally, the present invention extends to the immortalized human B memory lymphocyte and B cell, respectively, that produces the antibody having the distinct and unique characteristics as defined herein above and below.

Thus, besides using a selected patient pool, the anti-IFN-α antibodies have been provided by employing a particular method specifically developed and adapted for isolating human monoclonal antibodies from B cells of patients with an autoimmune disease such as APECED/APS1 patients.

In one embodiment, the antibody or IFN-α binding molecule of the present invention comprises an amino acid sequence of the VH and/or VL region as depicted in FIG. 1 or as encoded by the corresponding nucleic acids as indicated in Table 1. In addition, in another embodiment the present invention relates to an anti-IFN-α antibody or IFN-α binding molecule, which competes with an antibody of the present invention as defined hereinabove for specific binding to at least one human IFN-α subtype and/or human IFN-α.

In particular, anti-IFN-α antibodies are provided which demonstrate the immunological binding characteristics and/or biological properties as outlined for the antibodies illustrated in the Examples and in the Figures. Where present, the term "immunological binding characteristics," or other binding characteristics of an antibody with an antigen, in all of its grammatical forms, refers to the specificity, affinity, cross-reactivity, and other binding characteristics of an antibody.

As demonstrated in the Examples, the antibodies of the present invention are particularly characterized by their high neutralizing activity towards the majority of the IFN-α subtypes as well as in case of the 26B9, 31B4 and 8H1 antibody against IFN-ω in the sub-nanomolar range. Preferably, the human-derived monoclonal antibodies and IFN-α binding fragments as well as synthetic and biotechnological derivatives thereof display the IC50 values as determined in an ISRE (Interferon stimulated response element) reporter gene assay of the subject antibodies exemplified herein for at least one, two, three, four, five, six, seven, eight, nine, ten, eleven, twelve or almost all IFN-α subtypes and optionally for IFN-ω or their IC50 values differ no more than 50%, preferably less than 40%, more preferably less than 30%, still more preferably less than 20% and particularly preferred less than 10% from the IC50 values determined for the subject antibodies illustrated in the Examples and Figures for any of the IFN-α subtypes and optionally for IFN-ω. In a preferred embodiment, the antibody or like IFN-binding molecule of the present invention has an IC 50 value of:S 10 ng for at least 5, preferably 6, more preferably 7, still more preferably 8 or advantageously 9 or 10 human IFN-α subtypes and/or human IFN-α.

In a further embodiment, the antibody of the present invention is an antibody fragment. For example, the antibody or antibody fragment of the present invention may be elected from the group consisting of a single chain Fv fragment (scFv), an F(ab') fragment, an F(ab) fragment, an F(ab')2 fragment and a single domain antibody fragment (sdAB).

A further advantage of the antibodies of the present invention is that due to the fact that the humoral immune response has been elicited against the native antigen in its physiologic and cellular environment, typically autoantibodies are produced and can be isolated which recognize a conformational epitope of the antigen due to its presentation in context for example with other cellular components, presentation on a cell surface membrane and/or binding to a receptor. In contrast, conventional methods of generating monoclonal antibodies such as mouse monoclonals, humanized versions thereof or antibodies obtained from phage display typically employ an antigenic fragment of the target protein for immunizing an non-human mammal and detection, respectively, upon which usually antibodies are obtained which recognize linear epitopes or conformational epitopes limited to a two-dimensional structure of the immunogen rather than the presence of the native protein in its physiological and cellular context. Accordingly, it is prudent to expect that the autoantibodies of the present invention are unique in terms of their epitope specificity. Therefore, the present invention also relates to antibodies and like-binding molecules which display substantially the same binding specificity as the autoantibodies isolated in accordance with the method of the present invention. Such antibodies can be easily tested by for example competitive ELISA or more appropriately in a cell based neutralization assay using an autoantibody and a monoclonal derivative, respectively, thereof of the present invention as a reference antibody and the immunological tests described in the Examples or otherwise known to the person skilled in the art.

As further illustrated in the Examples and in the Figures, e.g., in FIG. 19, the antibodies of the present invention are isolated preferably from human donors and thus bind human IFN-α subtypes. Therefore, in one embodiment the anti-IFN-α antibody and IFN-α binding fragment of the present invention recognize only the human antigen or at least preferentially over the corresponding antigen from other species such as mice. In another embodiment the anti-IFN-α antibody and IFN-α binding fragment of the present invention bind at least one IFN-α subtypes of other species, preferably wherein the other species is mice. Binding characteristics such as specificity and affinity of the antibodies of the present invention have been tested in several experimental assays as described and shown herein, e.g., in Examples 2, 5 and 6 and in FIGS. 2-3 and 8-13, and 18 to 27.

As has been further demonstrated for the antibodies of the present invention, they are capable of neutralizing the biological activity of their target protein; see, e.g., the results of the STAT1 phosphorylation assay and the interferon specific response element reporter-gene assay described in Example 3 and FIGS. 5 to 7. In this context, the term "neutralizing" means that the antibody of the present invention is capable of intervening with the biological activity of its target protein in a biochemical or cell-based assay as can be evaluated by performing the respective assay in the presence of the subject antibody of the present invention, wherein the biological activity of the target protein is reduced concomitantly with increasing level of the antibody of the present invention subjected to the assay compared to the biological activity of the protein without the presence of the antibody of the present invention and in the presence of a compound for example a control antibody which is known to leave the biological activity of the target protein unaffected in kind. Such biochemical and in vitro based assay can also be performed using a reference antibody known to be capable of neutralizing the biological activity of the target protein such as has been shown for the anti-IFN-α antibodies of the present invention and subjecting the candidate antibody to the test sample, wherein either an additive neutralizing effect may be observed resulting from the combined activity of the reference and candidate antibody or a competition of the candidate antibody and reference antibody is observed which may be determined by labelling either antibody. Thus, in a preferred embodiment of the present invention, the antibody obtained by the method of the present invention is capable of neutralizing the biological activity of its antigen, e.g., at least one human IFN-α subtype.

The antibodies or antigen-binding fragments, e.g., peptides, polypeptides or fusion proteins of the present invention may be provided, as indicated above, by expression in a host cell or in an in vitro cell-free translation system, for example. To express the peptide, polypeptide or fusion protein in a host cell, the nucleic acid molecule encoding said peptide, polypeptide or fusion protein may be inserted into appropriate expression vector, i.e. a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., *Molecular Cloning, A Laboratory Manual* (1989), and Ausubel et al., *Current Protocols in Molecular Biology* (1989); see also the sections "Polynucleotides" and "Expressions" further below and literature cited in the Examples section for further details in this respect.

A suitable host cell for expression of the product may be any prokaryotic or eukaryotic cell; e.g., bacterial cells such as *E. coli* or *B. subtilis*, insect cells (baculovirus), yeast cells, plant cell or an animal cell. For efficient processing, however, mammalian cells are preferred. Typical mammalian cell lines useful for this purpose include CHO cells, HEK 293 cells, COS cells and NSO cells.

The isolated antibodies of the present invention may of course not be applied as such to a patient, but usually have to be pharmaceutically formulated to ensure, e.g., their stability, acceptability and bioavailability in the patient. Therefore, in one embodiment, the method of the present invention is provided, further comprising the step of admixing the isolated monoclonal antibody or a fragment thereof with a pharmaceutically acceptable carrier. Pharmaceutically acceptable carriers will be described in detail further below.

As a measure to obtain a stable and permanent source of binding molecules of the present invention, in particular for pharmaceutical use heterologous genes encoding these binding molecules may be isolated by direct cloning, PCR amplification, or artificial synthesis and introduced and expressed in suitable host cells or organisms. Therefore, it is also an object of the present invention to provide a method for preparing a recombinant cell useful for the production of a recombinant human anti-IFN-α antibody or IFN-α binding fragment thereof, comprising the steps of:
(a) preparing a B cell by a method as described above;
(b) sequencing a nucleic acid and/or obtaining from the B cell a nucleic acid that encodes;
(i) at least one of the CH and CL amino acid sequences set forth in Table 1 (SEQ ID NOs.: 6, 8, 14, 16, 26, 28, 34, 36, 42, 44, 72, 74, 80, 82, 88, 92, 96 and 98) or an amino acid sequence with at least 60% identity;
(ii) at least one complementarity determining region (CDR) of the VH and/or VL variable region amino acid sequences depicted in
 FIG. 1 (VH) (SEQ ID NOs: 2, 10, 18, 22, 30, 38, 76, 84 and 92); and
 FIG. 1 (VL) (SEQ ID NOs: 4, 12, 20, 24, 32, 40, 78, 86 and 94);
(iii) an amino acid sequence of the VH and/or VL region as depicted in FIG. 1;
(iv) at least one CDR consisting of an amino acid sequence resulted from a partial alteration of any one of the amino acid sequences of (a);

(v) a heavy chain and/or light variable region comprising an amino acid sequence resulted from a partial alteration of the amino acid sequence of (ii); and/or
(c) inserting the nucleic acid into an expression host in order to permit expression of the antibody of interest in that host.

Host cells as described herein may be used as well in the preceding method and as described in detail in the "Host" section of this specification. In this respect, in one embodiment the above method is provided, where the expression host is a yeast cell, a plant cell or an animal cell.

Furthermore, in one embodiment a method is provided for preparing a pharmaceutical composition for use in the treatment of a disorder associated with the expression and activity of IFN-α and/or IFN-ω, the method comprising:
(a) culturing host cells as defined above;
(b) purifying the antibody, IFN-α binding fragment thereof, biotechnological derivative or immunoglobulin chain(s) thereof of the present invention from the culture to pharmaceutical grade; and
(c) admixing the antibody, IFN-α binding fragment thereof or biotechnological derivative thereof of the present invention with a pharmaceutically acceptable carrier.

In respect of the above described methods for production of the respective antibody of interest, in one embodiment the present invention provides a method, wherein the nucleic acid is manipulated between above steps (b) and (c) to introduce restriction sites, to change codon usage, and/or to add or optimize transcription and/or translation regulatory sequences. As demonstrated in appended Examples 2 and 3 and summarized in Table 4, binding molecules, i.e. antibodies have been identified and cloned, which display a particularly high apparent binding affinity (EC50/ED50) and/or a particularly high in vitro neutralizing activity with low inhibitory concentrations (IC50) for at least one human IFN-α subtype. In this respect, in one embodiment, the anti-IFN-α antibody and IFN-α binding fragment of the present invention thereof have a high affinity for its respective target molecule, e.g., human IFN-α subtypes as defined hereinabove, showing an EC50 at concentrations below 100 ng/ml, preferably below 20 ng/ml and more preferably below 10 ng/ml. Alternatively or in addition, in one embodiment the anti-IFN-α antibody and IFN-α binding fragment thereof have high neutralizing ability for at least one human IFN-α subtype, showing IC50 at concentrations below 500, 400, 300 or 100 ng/ml, preferably below 20 ng/ml, more preferably below 10 ng/ml and most preferred below 5 ng/ml. For more details in respect of the binding affinity of the antibodies of the present invention see, e.g., section "Binding characteristics" further below.

The present invention also relates to polynucleotides encoding at least a variable region of an immunoglobulin chain of the antibody or antigen-binding fragment of the invention. Preferably, said variable region comprises at least one complementarity determining region (CDR) of the VH and/or VL of the variable region as set forth in FIG. 1.

In case of a derived sequence, said sequence shows at least 60% identity, more preferably (in the following order) at least 70%, at least 75%, at least 80%, at least 85%, at least 90%, and most preferably 95%, at least 96-99%, or even 100% identity to a sequence of the group consisting of those sequences referred to above and identified in the Sequence Listing. The percent identity between two sequences is a function of the number of identical positions shared by the sequences, taking into account the number of gaps, and the length of each gap, which need to be introduced for optimal alignment of the two sequences. The comparison of sequences and determination of percent identity between two sequences can be accomplished using a mathematical algorithm, which is well known to those skilled in the art. The identities referred to herein are to be determined by using the BLAST programs as further referred to herein infra.

As mentioned above, in a preferred embodiment, the present invention relates to substantially fully human antibodies, preferably IgG including at least the constant heavy chain I (CHI) and the corresponding light chain of the constant region, i.e. y-I, y-2, y-3 or y-4 in combination with lambda or kappa. In a particularly preferred embodiment, the nucleotide and amino acid sequences of those constant regions isolated for the subject antibodies illustrated in the Examples are used as depicted in Table 1 below and in SEQ ID NOs: 5, 7, 13, 15, 25, 27, 33, 35, 41, 43, 71, 73, 79, 81, 87, 89, 95 and 97 in respect of the nucleotide sequences and/or SEQ ID NOs: 6, 8, 14, 16, 26, 28, 34, 36, 42, 44, 72, 74, 80, 82, 88, 90, 96 and 98 in respect of the amino acid sequences or amino acid sequences with at least 60% identity to these referenced before.

In accordance with the above, the present invention also relates to a polynucleotide, in particular recombinant polynucleotide encoding at least the variable region of one immunoglobulin chain of the anti-IFN-α antibody or IFN-α binding fragment of the present invention. Typically, said variable region encoded by the polynucleotide comprises at least one complementarity determining region (CDR) of the VH and/or VL of the variable region of the said antibody. Variable and constant regions of antibodies are described in more detail in the section "IgG structure" below. In a preferred embodiment of the present invention, the polynucleotide comprises, consists essentially of, or consists of a nucleic acid having a polynucleotide sequence encoding the VH or VL region of an antibody of the present invention as depicted in Table 1 below. In this respect, the person skilled in the art will readily appreciate that the polynucleotides encoding at least the variable domain of the light and/or heavy chain may encode the variable domain of either immunoglobulin chains or only one of them. In a preferred embodiment, the polynucleotide encodes the anti-IFN-α antibody or IFN-α binding fragment as defined hereinabove.

TABLE 1

Nucleotide sequences of the variable and constant regions (VH, VL, CH, CL) regions of IgG1, kappa, IFN-α specific 5D1, 13B11, 19D11, 25C3, 26B9, 31B4, 8H1, 12H5 and 50E11 antibodies of the present invention.

| Antibody | Nucleotide and amino acid sequences of variable heavy (VH) and variable light (VL), constant heavy (CH) and constant light (CL) chains. |
|---|---|
| 5D1-VH | gaagtgcaactggtgcaggccggcgcagaggtgaaagcgcccggggagtctctggaggatctcctgtaaggtgtct ggtatacaccttttacaagttattggatcagttgggtgcgccagattcccgggaaaggcctggagtggatggtgaaaatt gatcctagagactcttataccatctacaacccgtccttccaaggccacgtctccatctcagttgacaagtccatcaccac tgtctacctgcagtggagcagcctgcaggcctcggacaccgccatttattattgtgtgagacattatcttacacagtcat tggtggactac tttgaccactggggccagggaacgctggtcgccgtctcctct<br>SEQ ID NO: 1 |
| 5D1-VH | EVQLVQAGAEVKAPGESLRISCKVSGYTFTSYWISWVRQIPGKG1EWMV<br>KIDPRDSYTIYNPSFQGHVSISVDKSITTVYLQWSSLQASDTAIYYCVRHYL<br>TQSLVDY FDHWGQGTLVAVSS<br>SEQ ID NO: 2 |
| 5D1-VL kappa-type | gacattcagatgacccagtctccatcctccctgtctgcatctgtgggagacagtgtcaccatcacttgccgggcaagtc agagcgtatccaactacttccattggtatcgacagaagcccgggaaagccctgaactcctgatctattctgcatcc aatttgcaaactggggtcccatcaagattcactggcagtgggtctgggacagaatgcactctcaccatcaccagtctg cagcctgatgatttcgcaacttactactgtcaacagactcacggttacccgttcacttttggccaggggaccaagctgg acgtcaga<br>SEQ ID NO: 3 |
| 5D1-VL kappa-type | DIQMTQSPSSLSASVGDSVTITCRASQSVSNYFHWYRQKPGKAPELLIYSA<br>SNLQTGVPSRFTGSGSGTECTLTITSLQPDDFATYYCQQTHGYPFTFGQG<br>TKLDVR<br>SEQ ID NO: 4 |
| 5D1-CH | gcctccaccaagggcccatcggtcttccccctggcaccctcctccaagagcacctctgggggcacagcggccctg ggctgcctggtcaaggactacttccccgaaccggtgacggtgtcgtggaactcaggcgccctgaccagcggcgtg cacaccttcccggctgtcctacagtcctcaggactctactccctcagcagcgtggtgaccgtgccctccagcagcttg ggcacccagacctacatctgcaacgtgaatcacaagcccagcaacaccaaggtggacaagaaagttgagcccaaa tcttgtgacaaaactcacacatgcccaccgtgcccagcacctgaactcctggggggaccgtcagtcttcctcttcccc ccaaaacccaaggacaccctcatgatctcccggacccctgaggtcacatgcgtggtggtggacgtgagccacgaa gaccctgaggtcaagttcaactggtacgtggacggcgtggaggtgcataatgccaagacaaagccgcgggagga gcagtacaacagcacgtaccgtgtggtcagcgtcctcaccgtcctgcaccaggactggctgaatggcaaggagtac aagtgcaaggtctccaacaaagcccTccagccccatcgagaaaaccatctccaaagccaaagggcagccccga gaaccacaggtgtacaccctgccccatcccgggatgagctgaccaagaaccaggtcagcctgacctgcctggtc aaaggcttctatcccagcgacatcgccgtggagtgggagagcaatgggcagccggagaacaactacaagaccac gcctcccgtgctggactccgacggctccttcttcctctacagcaagctcaccgtggacaagagcaggtggcagcag gggaacgtcttctcatgctccgtgatgcatgaggctctgcacaaccactacacgcagaagagcctctccctgtctccg ggtaaatga<br>SEQ ID NO: 5 |
| 5D1-CH | ASTKGPSVFPLAPSSKSTSGGTAALGCLVKDYFPEPVTVSWNSGALTSGV<br>HTFPAVLQSSG1YSLSSWTVPSSSLGTQTYICNVNHKPSNTKVDKKVEPKS<br>CDKTHTCPPCPAPELLGGPSVFLFPPKPKDTLMISRTPEVTCVWDVSHEDP<br>EVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCLV |

TABLE 1-continued

Nucleotide sequences of the variable and constant regions (VH, VL, CH, CL) regions of IgG1, kappa, IFN-α specific 5D1, 13B11, 19D11, 25C3, 26B9, 31B4, 8H1, 12H5 and 50E11 antibodies of the present invention.

| Antibody | Nucleotide and amino acid sequences of variable heavy (VH) and variable light (VL), constant heavy (CH) and constant light (CL) chains. |
|---|---|
| | KGFYPSDIAVEWESNGQPENNYKTTPPVLDSDGSFFLYSKLTVDKSRWQQ<br>GNVFSCSVMHEALHNHYTQKSL SLSPGK<br>SEQ ID NO: 6 |
| 5D1-CL<br>kappa-type | cgaactgtggctgcaccatctgtcttcatcttcccgccatctgatgagcagttgaaatctggaactgcctctgttgtgtgc<br>ctgctgaataacttctatcccagagaggccaaagtacagtggaaggtggataacgccctccaatcgggtaactccca<br>ggagagtgtcacagagcaggacagcaaggacagcacctacagcctcagcagcaccctg<u>acgctgagcaaagca</u><br><u>gactacgagaaacacaaagtctacgcctgcgaagtcacc</u>catcagggcctgagctcgcccgtcacaaagagcttc<br>aacaggggagagtgttag<br>SEQ ID NO: 7 |
| 5D1-CL<br>kappa-type | RTVAAPSVFIFPPSDEQLKSGTASVVCLLNNFYPREAKVQWKVDNALQSG<br>NSQESVTEQDSKDSTYSLSSTLTLSKADYEKHKVYACEVTHQG1SSPVTK<br>SFNRGEC<br>SEQ ID NO: 8 |
| 13B11-VH | Gacgtacagctgttgcagtctggggggaggcttgatacagccggggggtccctg<u>agactctcctgtgcagcctctg</u><br><u>gctttacttttaaggactatgccatgagttgggtccgccaggggaaggggctggagtgggtctcagtaata</u><br><u>agtcgtagtgg</u>taatattgtagactatgtcgactccgtgaagggccggttcaccgtctccaga gacaattccaacaac<br>acactatttctgcaaatggacggcctgagagccgacga<u>acggccatttattactgtgcgaaacccaaggatatgat</u><br><u>tgtcgtggtccctgcg ggctttgactcctggggccagggaaccttgtctccgtctcctca</u><br>SEQ ID NO: 9 |
| 13B11-VH | DVQLLQSGGG1IQPGGSLRLSCAASGFTEKDYAMSWVRQAPGKG1EWVS<br>VISRSGNIVDYVDSVKGRFTVSRDNSNNTLFQMDG1RADDTAIYYCAKP<br>KDMIWYPA <u>GFDSWGQGTLVSVSS</u><br>SEQ ID NO: 10 |
| 13B11-VL<br>kappa-type | gacatccagatgacccagtttccatccaccctgtctgcatctgttggagacagc<u>gtcaccatcacttgccgggccagt</u><br><u>cagagcattagtgcctggttggcctggtat</u><u>cagcagaaaccagggaaagcccctaaactcctgatctataagggg</u><u>t</u><br><u>ctagatta</u>gaaaacggggtcccatcgaggttcagcggcagtggatctgggacagaattcact ctcaccatcggcag<br>cctgcagcctgatgattttgcaacttattactgccaacaa<u>tataagacttggacgttcggccaagggaccaaggtgga</u><br><u>aatcaaa</u><br>SEQ ID NO: 11 |
| 13B11-VL<br>kappa-type | DIQMTQFPSTLSASVGDSVTITCRASQSISAWLAWYQQKPGKAPKLLIYK<br>GSRL<u>ENGVPSRFSGSGSGTEFTLTIGSLQPDDFATYYCQQYKTWTFGQGT</u><br><u>KVEIK</u><br>SEQ ID NO: 12 |
| 13BL1-CH | gcctccaccaagggcccatcggtcttccccctggcaccctcctccaagagcacctctgggggcacagcggccctg<br>ggctgcctggtcaaggactacttccccgaaccggtgacggtgtcgtggaactcaggcgccctgaccagcggcgtg<br>cacaccttcccggctgtcctacagtcctcaggactctactccctcagcagcgtggtgaccgtgccctccagcagcttg<br>ggcacccagacctacatctgcaacgtgaatcacaagcccagcaacaccaaggtggacaagaaagttgagcccaaa<br>tcttgtgacaaaactcacacatgcccaccgtgcccagcacctgaactcctggggggaccgtcagtcttcctcttcccc<br>ccaaaacccaaggacaccctcatgatctcccggacccctgaggtcacatgcgtggtggtggacgtgagccacga<br>gacccctgaggtcaagttcaactggtacgtggacggcgtggaggtgcataatgccaagacaaagccgcggggagga<br>gcagtacaacagcacgtaccgtgtggtcagcgtcctcaccgtcctgcaccaggactggctgaatggcaaggagtac<br>aagtgcaaggtctccaacaaagccctcccagcccccatcgagaaaaccatctccaaagccaaagggcagcccga<br>gaaccacaggtgtacaccctgccccatcccgggatgagctgaccaagaaccaggtcagcctgacctgcctggtc<br>aaaggcttctatcccagcgacatcgccgtggagtgggagagcaatgggcagccggagaacaactacaagaccac<br>gcctcccgtgctggactccgacggctccttcttcctctacagcaagctcaccgtggacaagagcaggtggcagcag<br>gggaacgtcttctcatgctccgtgatgcatgaggctctgcacaaccactacacgcagaagagcctctccctgtctccg<br>ggtaaatga<br>SEQ ID NO: 13 |
| 13B11-CH | ASTKGPSVFPLAPSSKSTSGGTAALGCLVKDYFPEPVTVSWNSGALTSGV<br>HTFPAVLQSSG1YSLSSWTVPSSSLGTQTYICNVNHKPSNTKVDKKVEPKS<br>CDKTHTCPPCPAPELLGGPSVFLFPPKPKDTLMISRTPEVTCVWDVSHEDP<br>EVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCLV<br>KGFYPSDIAVEWESNGQPENNYKTTPPVLDSDGSFFLYSKLTVDKSRWQQ<br>GNVFSCSVMHEALHNHYTQKSLSLSPGK<br>SEQ ID NO: 14 |
| 13B11-CL<br>kappa-type | cgaactgtggctgcaccatctgtcttcatcttcccgccatctgatgagcagttgaaatctggaactgcctctgttgtgtgc<br>ctgctgaataacttctatcccagagaggccaaagtacagtggaaggtggataacgccctccaatcgggtaactccca<br>ggagagtgtcacagagcaggacagcaaggacagcacctacagcctcagcagcaccctgacgctgagcaaagca<br>gactacgagaaacacaaagtctacgcctgcgaagtcacccatcagggcctgagctcgcccgtcacaaagagcttca<br>acaggggagagtgttag<br>SEQ ID NO: 15 |

TABLE 1-continued

Nucleotide sequences of the variable and constant regions (VH, VL, CH, CL) regions of
IgG1, kappa, IFN-α specific 5D1, 13B11, 19D11, 25C3, 26B9, 31B4, 8H1, 12H5 and
50E11 antibodies of the present invention.

| Antibody | Nucleotide and amino acid sequences of variable heavy (VH) and variable light (VL), constant heavy (CH) and constant light (CL) chains. |
|---|---|
| 13B1 1-CL kappa-type | RTVAAPSVFIFPPSDEQLKSGTASVVCLLNNFYPREAKVQWKVDNALQSG<br>NSQESVTEQDSKDSTYSLSSTLTLSKADYEKHKVYACEVTHQG1SSPVTK<br>SFNRGEC<br>SEQ ID NO: 16 |
| 19D11-VH | gaggtgcagctgttggagtctggggctgaggtgaagaggcctggggtcgtcggtgagggtctcctgcagggcttctg<br>gagacaccttcagcagttaccctatcagttgggtgcgacaggcccctggacaaggccttgagtggatgggaaggat<br>cctccctgcccttggtgtcacaaactacgctcagaacttccggggcagaatcacgattaccgcggacaagtcgccc<br>ctcacagcctacttggaactgagtagcctcagatttgaggacacggccgtgtattactgtgcgagtccagtgcgg<br>acataattccttcgattttggggacgaccctctttgccttctggggccagggaagcctggtcaccgtctcctca<br>SEQ ID NO: 17 |
| 19D11-VH | EVQLLESGAEVKRPGSSVRVSCRASGDTFSSYPISWVRQAPGQG1EWMGRI<br>LPALGVTNYAQNFRGRITITADKSPLTAYLELSSLRFEDTAVYYCASPS<br>ADIIPSIL GTTLFAFWGQGSLVTVSS<br>SEQ ID NO: 18 |
| 19D11-VL kappa-type | gaaattgtgttgacgcagtctccaggcacccctgtctctgtctccggggggaaggggccaccctctcctgcagggccag<br>tcagaatgttagcagacactacttaacctggtaccagcagaaacctggccagtctcccggctcctcatctatggtg<br>gctccagcagggccactggcgtcccagacaggttcagtggcggtgggtctgggacagacttcactctcaccatcagc<br>aggctggagcctgaagactttgcagtgttttactgccagagctatcatagcccacctcctgtgtacactttcggccag<br>gggaccaaggtggagatcaaa<br>SEQ ID NO: 19 |
| 19D11-VL kappa-type | EIVLTQSPGTLSLSPGEGATLSCRASQNVSRHYLTWYQQKPGQSPRLLI<br>YGGSSRATGVPDRFSGGGSGTDFTLTISRLEPEDFAVEYCQSYHSPPPV<br>YTFGQGTKVEIK<br>SEQ ID NO: 20 |
| 19D11-CH | gcctccaccaagggcccatcggtcttccccctggcaccctcctccaagagcacctctgggggcacagcggccctg<br>ggctgcctggtcaaggactacttccccgaaccggtgacggtgtcgtggaactcaggcgccctgaccagcggcgtgc<br>acaccttcccggctgtcctacagtcctcaggactctactccctcagcagcgtggtgaccgtgccctccagcagcttggg<br>cacccagacctacatctgcaacgtgaatcacaagcccagcaacaccaaggtggacaagagagttgagcccaaatctt<br>gtgacaaaactcacacatgcccaccgtgcccagccacctgaactcctggggggaccgtcagtcttcctcttccccccaa<br>aacccaaggacaccctcatgatctcccggacccctgaggtcacatgcgtggtggtggacgtgagccacgaagaccct<br>gaggtcaagttcaactggtacgtggacggcgtggaggtgcataatgccaagacaaagccgcgggaggagcagtac<br>aacagcacgtaccgtgtggtcagcgtcctcaccgtcctgcaccaggactggctgaatggcaaggagtacaagtgcaa<br>ggtctccaacaaagcccctcccagcccccatcgagaaaaccatctccaaagccaaagggcagccccgagaaccaca<br>ggtgtacaccctgcccccatcccgggaggagatgaccaagaaccaggtcagcctgacctgcctggtcaaaggcttct<br>atcccagcgacatcgccgtggagtgggagagcaatgggcagccggagaacaactacaagaccacgcctcccgtgc<br>tggactccgacggctccttcttcctctatagcaagctcaccgtggacaagagcaggtggcagcaggggaacgtcttct<br>catgctccgtgatgcatgaggctctgcacaaccactacacgcagaanancctctccctgtccccgggtaaatga<br>SEQ ID NO: 71 |
| 19D11-CH | ASTKGPSVFPLAPSSKSTSGGTAALGCLVKDYFPEPVTVSWNSGALTSGVH<br>TFPAVLQSSG1YSLSSWTVPSSSLGTQTYICNVNHKPSNTKVDKRVEPKSC<br>DKTHTCPPCPAPELLGGPSVFLFPPKPKDTLMISRTPEVTCVVDVSHEDPE<br>VKFNWYVDGVEVHNAKTKPREEQYNSTYRWSVLTVLHQDWLNGKEYKC<br>KVSNKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQQGNV<br>FSCSVMHEALHNHYTQXXLSLSPGK<br>SEQ ID NO: 72 |
| 19D11-CL kappa-type | cgaactgtggctgcaccatctgtcttcatcttcccgccatctgatgagcagttgaaatctggaactgcctctgttgtgtgcc<br>tgctgaataacttctctatcccagagaggccaaagtacagtggaaggtggataacgccctccaatcgggtaactcccagg<br>agagtgtcacagagcaggacagcaaggacagcacctacagcctcagcagcaccctgacgctgagcaaagcagact<br>acgagaaacacaaagtctacgcctgcgaagtcacccatcagggcctgagctcgcccgtcacaaagagcttcaacag<br>gggagagtgttag<br>SEQ ID NO: 73 |
| 19D11-CL kappa-type | RTVAAPSVFIFPPSDEQLKSGTASWCLLNNFYPREAKVQWKVDNALQSGN<br>SQESVTEQDSKDSTYSLSSTLTLSKADYEKHKVYACEVTHQG1SSPVTKSF<br>NRGEC<br>SEQ ID NO: 74 |
| 25C3-VH | gagatgcagctgatggagtctgggggaggtttggtacaaccggggggtccctgagactctcctgtgtagcctctg<br>gtttcacctttaaaagttttcgatgagttgggtccgccaggctccagggaaggggctggagtgggtcgctagtg<br>tcggctctcagggtggcagcaaatactatgcaccctccgtgaagggccggttctccatctctcagagacaattcca<br>acaacactctctatgtgcaaatgaacagcctgggagtcgaggacacggcctttatattgtgttaaagagaccgat<br>gcagtggcgacgatggacgctcttgacatgtgggccaagggaccctggtcatcgtctctacc<br>SEQ ID NO: 21 |

TABLE 1-continued

Nucleotide sequences of the variable and constant regions (VH, VL, CH, CL) regions of IgG1, kappa, IFN-α specific 5D1, 13B11, 19D11, 25C3, 26B9, 31B4, 8H1, 12H5 and 50E11 antibodies of the present invention.

| Antibody | Nucleotide and amino acid sequences of variable heavy (VH) and variable light (VL), constant heavy (CH) and constant light (CL) chains. |
|---|---|
| 25C3-VH | EMQLMESGGG1VQPGGSLRLSCVASGFTFKSFAMSWVRQAPGKG1EWVA SVGSQGGSKYYAPSVKGRFSISRDNSNNTLYVQMNSLGVEDTAFYYCVKE TDAVATMDA LDMWGQGTLVIVST<br>SEQ ID NO: 22 |
| 25C3-VL kappa-type | gacatccgggtgacccagtctccatcctccctgtctgcatctgtcggagacagggtctccatctcttgccagacaagt cagagtgttaacatatatctaaattggtatcaacagagaccagggaaaggcccctcagctcctgatctctgctgcttc cactttgcagagtggggtcccatcaaggttcagtggcagtggatctgggacagacttcatcctcaccatcatcagtctac aacctgaagattctgcatcctactactgtcaacagggttacattacccccgtacacttttggccaggggaccaaggtg gagatcaaa<br>SEQ ID NO: 23 |
| 25C3-VL kappa-type | DIRVTQSPSSLSASVGDRVSISCQTSQSVNIYLNWYQQRPGKGPQLLISAAS TLQSGVPSRFSGSGSGTDFILTIISLQPEDSASYYCQQGYITPYTFGQGTKV EIK<br>SEQ ID NO: 24 |
| 25C3-CH | gcctccaccaagggcccatcggtcttccccctggcaccctcctccaagagcacctctgggggcacagcggccctgg gctgcctggtcaaggactacttccccgaaccggtgacggtgtcgtggaactcaggcgccctgaccagcggcgtgca caccttcccggctgtcctacagtcctcaggactctactccctcagcagcgtggtgaccgtgccctccagcagcttgggc acccagacctacatctgcaacgtgaatcacaagcccagcaacaccaaggtggacaagagagttgagcccaaatcttg tgacaaaactcacacatgcccaccgtgcccagcacctgaactcctggggggaccgtcagtcttcctcttccccccaaa acccaaggacaccctcatgatctcccggacccctgaggtcacatgcgtggtggtggacgtgagccacgaagaccct gaggtcaagttcaactggtacgtggacggcgtggaggtgcataatgccaagacaaagccgcgggaggagcagtac aacagcacgtaccgtgtggtcagcgtcctcaccgtcctgcaccaggactggctgaatggcaaggagtacaagtgcaa ggtctccaacaaagcccttccagcccccatcgagaaaaccatctccaaagccaaagggcagccccgagaaccaca ggtgtacaccctgcccccatcccgggaggagatgaccaagaaccaggtcagcctgacctgcctggtcaaaggcttct atcccagcgacatcgccgtggagtgggagagcaatgggcagccggagaacaactacaagaccacgcctcccgtgc tggactccgacggctccttcttcctctatagcaagctcaccgtggacaagagcaggtggcagcaggggaacgtcttct catgctccgtgatgcatgaggctctgcacaaccactacacgcagaagagcctctccctgtcccccgggtaaatga<br>SEQ ID NO: 25 |
| 25C3-CH | ASTKGPSVFPLAPSSKSTSGGTAALGCLVKDYFPEPVTVSWNSGALTSGVH TFPAVLQSSG1YSLSSWTVPSSSLGTQTYICNVNHKPSNTKVDKRVEPKSC DKTHTCPPCPAPELLGGPSVFLFPPKPKDTLMISRTPEVTCVWDVSHEDPE VKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKG FYPSDIAVEWESNGQPENNYKTTPPVLDSDGSFFLYSKLTVDKSRWQQGN VFSCSVMHEALHNHYTQKSLSLSPGK<br>SEQ ID NO: 26 |
| 25C3-CL kappa-type | cgaactgtggctgcaccatctgtcttcatcttcccgccatctgatgagcagttgaaatctggaactgcctctgttgtgtgcc tgctgaataacctctatcccagagaggccaaagtacagtggaaggtggataacgccctccaatcgggtaactcccag gagagtgtcacagagcaggacagcaaggacagcacctacagcctcagcagcaccctgacgctgagcaaagcaga ctacgagaaacacaaagtctacgcctgcgaagtcacccatcagggcctgagctcgcccgtcacaaagagcttcaac aggggagagtgttag<br>SEQ ID NO: 27 |
| 25C3-CL kappa-type | RTVAAPSVFIFPPSDEQLKSGTASVVCLLNNLYPREAKVQWKVDNALQSG NSQESVTEQDSKDSTYSLSSTLTLSKADYEKHKVYACEVTHQG1SSPVTKS FNRGEC<br>SEQ ID NO: 28 |
| 26B9-VH | cagatactactgcaggagtcgggcccaggactggtgaagcccacggagaccctgtccctcacctgtagtgtctctgg tgactccatcagtgatagtagtcactactgggcctggattcgccagcccccagggaaggggaccagagtggattggca gtgtctatttagttcgatgaccccactacaacccgtccctcaaaagtcgcgtcagcatctccgttgacaagcccaagaa ccagttctccttaaaagtgacctctgtgactgtcgccgacacggccacatattactgtgcgagacaagcccttgcccga gtcggagccatgaattggttcgacccctgggccagggatctctggtcacagtctcctca<br>SEQ ID NO: 29 |
| 26B9-VH | QILLQESGPG1VKPTETLSLTCSVSGDSISDSSHYWAWIRQPPGKGPEWIGS VYFSSMTHYNPSLKSRVSISVDKPKNQFSLKVTSVTVADTATYYCARQALA RVGAM NWFDPWGQGSLVTVSS<br>SEQ ID NO: 30 |
| 26B9-VL kappa-type | gacatcataatgacccagtctccagactcctgcctgtgtctctgggcgaggggtcaccatcaactgcaagtccagc cagagcgtcttttcacctccagtaataagagttgtttagcttggtatcagcagaagccaggaaagtctcccaaattgct catttactgggcatcaacccgccaatccggggtccctgaccgattcagaggcagcgggtctgggacagatttctctctc accatcaccagtctgcaggctgaagatgtggctgtttatttctgtcagcagtgtcagacatcccctccactttcggcgg aggaccaggttggagatcaaa<br>SEQ ID NO: 31 |

TABLE 1-continued

Nucleotide sequences of the variable and constant regions (VH, VL, CH, CL) regions of
IgG1, kappa, IFN-α specific 5D1, 13B11, 19D11, 25C3, 26B9, 31B4, 8H1, 12H5 and
50E11 antibodies of the present invention.

| Antibody | Nucleotide and amino acid sequences of variable heavy (VH) and variable light (VL), constant heavy (CH) and constant light (CL) chains. |
|---|---|
| 26B9-VL kappa-type | DIIMTQSPDSLPVSLGEGVTINCKSSQSVFFTSSNKSCLAWYQQKPGKSPKL LIYWASTRQSGVPDRFRGSGSTDFSLTITSLQAEDVAVYFCQQCQTSPPT FGGGTRLEIK<br>SEQ ID NO: 32 |
| 26B9-CH | gcctccaccaagggcccatcggtcttcccctggcacctcctccaagagcacctctgggggcacagcggccctgg<br>gctgcctggtcaaggactacttccccgaaccggtgacggtgtcgtggaactcaggcgccctgaccagcggcgtgca<br>caccttcccggctgtcctacagtcctcaggactctactccctcagcagcgtggtgaccgtgcctccagcagcttgggc<br>acccagacctacatctgcaacgtgaatcacaagcccagcaacaccaaggtggacaagagagttgagcccaaatcttg<br>tgacaaaactcacacatgcccaccgtgcccagcacctgaactcctggggggaccgtcagtcttcctcttccccccaaa<br>acccaaggacaccctcatgatctcccggacccctgaggtcacatgcgtggtggtggacgtgagccacgaagaccct<br>gaggtcaagttcaactggtacgtggacggcgtggaggtgcataatgccaagacaaagccgcgggaggagcagtac<br>aacagcacgtaccgtgtggtcagcgtcctcaccgtcctgcaccaggactggctgaatggcaaggagtacaagtgcaa<br>ggtctccaacaaagccctcccagcccccatcgagaaaaccatctccaaagccaaagggcagccccgagaaccaca<br>ggtgtacaccctgcccccatcccgggaggagatgaccaagaaccaggtcagcctgacctgcctggtcaaaggcttct<br>atcccagcgacatcgccgtggagtgggagagcaatgggcagccggagaacaactacaagaccacgcctcccgtgc<br>tggactccgacggctccttcttcctctatagcaagctcaccgtggacaagagcaggtggcagcaggggaacgtcttct<br>catgctccgtgatgcatgaggctctgcacaaccactacacgcagaagagcctctccctgtccccgggtaaatga<br>SEQ ID NO: 33 |
| 26B9-CH | ASTKGPSVFPLAPSSKSTSGGTAALGCLVKDYFPEPVTVSWNSGALTSGVH<br>TFPAVLQSSG1YSLSSWTVPSSSLGTQTYICNVNHKPSNTKVDKRVEPKSC<br>DKTHTCPPCPAPELLGGPSVFLFPPKPKDTLMISRTPEVTCVWDVSHEDPE<br>VKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKG<br>FYPSDIAVEWESNGQPENNYKTTPPVLDSDGSFFLYSKLTVDKSRWQQGN<br>VFSCSVMHEALHNHYTQKSLSLSPGK<br>SEQ ID NO: 34 |
| 26B9-CL kappa-type | cgaactgtggctgcaccatctgtcttcatcttcccgccatctgatgagcagttgaaatctggaactgcctctgttgtgtgcc<br>tgctgaataacttctatcccagagaggccaaagtacagtggaaggtggataacgccctccaatcgggtaactcccagg<br>agagtgtcacagagcaggacagcaaggacagcacctacagcctcagcagcaccctgacgctgagcaaagcagact<br>acgagaaacacaaagtctacgcctgcgaagtcacccatcagggcctgagctcgcccgtcacaaagagcttcaacag<br>gggagagtgttag<br>SEQ ID NO: 35 |
| 26B9-CL kappa-type | RTVAAPSVFIFPPSDEQLKSGTASVVCLLNNFYPREAKVQWKVDNALQSG<br>NSQESVTEQDSKDSTYSLSSTLTLSKADYEKHKVYACEVTHQG1SSPVTKS<br>FNRGEC<br>SEQ ID NO: 36 |
| 31B4-VH | cagatacagctgcaggagtcgggcccaggactggtgaggccacggagaccctg<u>tccctcacttgtagtgtctctgg tgactccatcagtcagagtagtcattactgggcctggattcgccagccccagggaagggaccagaatggattggca gtgtctatttt</u>agctcgatgacccactacaaccgtccctcacaagtcgcgtcagcatctccattgacaaggccatgaat aagttctccttaaaagtgacctctgtgactgtcgcc<u>gacacggccacatattactgtgcgagacaggccttgcccgag tcggagccatg</u> aattggttcgacccctggggccagggatctctggtcacagtctcctca<br>SEQ ID NO: 37 |
| 31B4-VH | <u>QIQLQESGPG1VRPTETLSLTCSVSGDSISQSSHYWAWIRQPPGKGPEWIGS VYFSSMTHYNPSLTSRVSISIDKAMNKFSLKVTSVTVADTATYYCARQALA RVGAM</u> NWFDPWGQGSLVTVSS<br>SEQ ID NO: 38 |
| 31B4-VL kappa-type | gacatcataatgacccagtctccagagtccctgcctgtgtctctgggcgagggg<u>gtcaccatcaactgcaagtccagc cagagcgtcttttt</u>cacctccagtaatagg<u>agttgtttagcttggtatcagcagaagccaggacagtctcccaaattgct cattactgggcatcaacccgccaatccgggg</u>tccctgaccgattcacaggcagcggg tctgggacagatttctctctc accatcgccggtctgcaggttgaagatgtggct<u>gtttatttctgtcagcagtgtcacgcatcccctcccactttcggcgg cgggacc</u>aggttggagctcaga<br>SEQ ID NO: 39 |
| 31B4-VL kappa-type | DIIMTQSPESLPVSLGEGVTINCKSSQSVFFTSSNRSCLAWYQQKPGQSPKL LIYWASTRQSGVPDRFTGSGSTDFSLTIAG1QVEDVAVYFCQQCHASPPT FGGGTRLELR<br>SEQ ID NO: 40 |
| 31B4-CH | gcctccaccaagggcccatcggtcttcccctggcacctcctccaagagcacctctgggggcacagcggccctgg<br>gctgcctggtcaaggactacttccccgaaccggtgacggtgtcgtggaactcaggcgccctgaccagcggcgtgca<br>caccttcccggctgtcctacagtcctcaggactctactccctcagcagcgtggtgaccgtgcctccagcagcttgggc<br>acccagacctacatctgcaacgtgaatcacaagcccagcaacaccaaggtggacaagagagttgagcccaaatcttg<br>tgacaaaactcacacatgcccaccgtgcccagcacctgaactcctggggggaccgtcagtcttcctcttccccccaaa<br>acccaaggacaccctcatgatctcccggacccctgaggtcacatgcgtggtggtggacgtgagccacgaagaccct<br>gaggtcaagttcaactggtacgtggacggcgtggaggtgcataatgccaagacaaagccgcgggaggagcagtac |

TABLE 1-continued

Nucleotide sequences of the variable and constant regions (VH, VL, CH, CL) regions of IgG1, kappa, IFN-α specific 5D1, 13B11, 19D11, 25C3, 26B9, 31B4, 8H1, 12H5 and 50E11 antibodies of the present invention.

| Antibody | Nucleotide and amino acid sequences of variable heavy (VH) and variable light (VL), constant heavy (CH) and constant light (CL) chains. |
|---|---|
| | aacagcacgtaccgtgtggtcagcgtcctcaccgtcctgcaccaggactggctgaatggcaaggagtacaagtgcaa<br>ggtctccaacaaagcccctcccagcccccatcgagaaaaccatctccaaagccaaagggcagccccgagaaccaca<br>ggtgtacaccctgcccccatcccgggaggagatgaccaagaaccaggtcagcctgacctgcctggtcaaaggcttct<br>atcccagcgacatcgccgtggagtgggagagcaatgggcagccggagaacaactacaagaccacgcctcccgtgc<br>tggactccgacggctccttcttcctctatagcaagctcaccgtggacaagagcaggtggcagcaggggaacgtcttc<br>tcatgctccgtgatgcatgaggctctgcacaaccactacacgcagaagagcctctccctgtccccgggtaaatga<br>SEQ ID NO: 41 |
| 31B4-CH | ASTKGPSVFPLAPSSKSTSGGTAALGCLVKDYFPEPVTVSWNSGALTSGVH<br>TFPAVLQSSG1YSLSSWTVPSSSLGTQTYICNVNHKPSNTKVDKRVEPKSC<br>DKTHTCPPCPAPELLGGPSVFLFPPKPKDTLMISRTPEVTCVWDVSHEDPE<br>VKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKG<br>FYPSDIAVEWESNGQPENNYKTTPPVLDSDGSFFLYSKLTVDKSRWQQGN<br>VFSCSVMHEALHNHYTQKSLSLSPGK<br>SEQ ID NO: 42 |
| 31B4-CL<br>kappa-type | cgaactgtggctgcaccatctgtcttcatcttcccgccatctgatgagcagttgaaatctggaactgcctctgttgtgtgcc<br>tgctgaataacttctatcccagagaggccaaagtacagtggaaggtggataacgccctccaatcgggtaactcccagg<br>agtgtcacagagcaggacagcaaggacagcacctacagcctcagcagcaccctgacgctgagcaaagcagact<br>acgagaaacacaaagtctacgcctgcgaagtcacccatcagggcctgagctcgcccgtcacaaagagcttcaaca<br>ggggagagtgttag<br>SEQ ID NO: 43 |
| 31B4-CL<br>kappa-type | RTVAAPSVFIFPPSDEQLKSGTASVVCLLNNFYPREAKVQWKVDNALQSGN<br>SQESVTEQDSKDSTYSLSSTLTLSKADYEKHKVYACEVTHQG1SSPVTKSFN<br>RGEC<br>SEQ ID NO: 44 |
| 8H1 VH | caggtgcagctggtgcagtctggggctgaggtgaagaagcctggggcctcagtgaaggtctgccaggcttctgg<br>acagaccttcaccagtgatgatatcaactgggtgcgacaggcccctggacaggggctagagtggatgggatggagg<br>aaccctaacactcaggacacgggctatgcacagaagttccagggcagactcaccttgaccagcaacagttccataagt<br>acatcctatctggagttgagcggcctgagatctgaggacacggccgtgtattactgtgcgagagcggggacttcgacct<br>tgaccggccactacttcgctttggggggtctggggccaggggaccacggtcatcgtctcctca<br>SEQ ID NO: 75 |
| 8H1 VH | QVQLVQSGAEVKKPGASVKVSCKASGQTFTSDDINWVRQAPGQG1EWMG<br>WRNPNTQDTGYAQKFHGRLTLTSNSSISTSYLELSG1RSEDTAVYYCARAG<br>TSTLTGHY FALGVWGQGTTVIVSS<br>SEQ ID NO: 76 |
| 8H1 VL<br>kappa-type | gacatccagctgacccagtctccatcctccctgtctgcatctgtaggagacagagtcaccatcacttgtcaggcgactca<br>ggatattagcaaatatttaaattggtatcagcagaaaccagggaaagtccctaaactcctgatctacgaaacatccaa<br>tttggaagtaggggtcccatcaaggttcagtggaagtgggtctgggacacatttactctctcaccatcagcagcctgcagg<br>ctgaagattttgcaacatattactgtcaacagtatgagaatttcccgttcactttcggcggagggaccaaggtggagatc<br>aaa<br>SEQ ID NO: 77 |
| 8H1 VL<br>kappa-type | DIQLTQSPSSLSASVGDRVTITCQATQDISKYLNWYQQKPGKVPKLLIYETS<br>NLEVGVPSRFSGSGSGTHFTLTISSLQAEDFATYYCQQYENFPFTFGGGTKV<br>EIK<br>SEQ ID NO: 78 |
| 8H1 CH | gcctccaccaagggcccatcggtcttccccctggcaccctcctccaagagcacctctggggcacagcggccctggg<br>ctgcctggtcaaggactacttccccgaaccggtgacggtgtcgtggaactcaggcgccctgaccagcggcgtgcaca<br>ccttcccggctgtcctacagtcctcaggactctactccctcagcagcgtggtgaccgtgccctccagcagcttgggcac<br>ccagacctacatctgcaacgtgaatcacaagcccagcaacaccaaggtggacaagagagttgagcccaaatcttgtga<br>caaaactcacacatgcccaccgtgcccagcacctgaactcctggggggaccgtcagtcttcctcttccccccaaaaccc<br>aaggacaccctcatgatctcccggacccctgaggtcacatgcgtggtggtggacgtgagccacgaagaccctgaggt<br>caagttcaactggtacgtggacggcgtggaggtgcataatgccaagacaaagccgcgggaggagcagtacaac<br>agcacgtaccgtgtggtcagcgtcctcaccgtcctgcaccaggactggctgaatggcaaggagtacaagtgcaaggtc<br>tccaacaaagcccctcccagcccccatcgagaaaaccatctccaaagccaaagggcagccccgagaaccacaggtgt<br>acaccctgcccccatcccgggaggagatgaccaagaaccaggtcagcctgacctgcctggtcaaaggcttctatccca<br>gcgacatcgccgtggagtgggagagcaatgggcagccggagaacaactacaagaccacgcctcccgtgctggactc<br>cgacggctccttcttcctctatagcaagctcaccgtggacaagagcaggtggcagcaggggaacgtcttctcatgctcc<br>gtgatgcatgaggctctgcacaaccactacacgcagaagagcctctccctgtccccgggtaaa<br>SEQ ID NO: 79 |
| 8H1 CH | ASTKGPSVFPLAPSSKSTSGGTAALGCLVKDYFPEPVTVSWNSGALTSGVH<br>TFPAVLQSSG1YSLSSWTVPSSSLGTQTYICNVNHKPSNTKVDKRVEPKSCD<br>KTHTCPPCPAPELLGGPSVFLFPPKPKDTLMISRTPEVTCVWDVSHEDPEVK<br>FNWYVDGVEVHNAKTKPREEQYNSTYRVVSVLTVLHQDWLNGKEYKCK<br>VSNKALPAPIEKTISKAKGQPREPQVYTLPPSREEMTKNQVSLTCLVKGFYP |

TABLE 1-continued

Nucleotide sequences of the variable and constant regions (VH, VL, CH, CL) regions of IgG1, kappa, IFN-α specific 5D1, 13B11, 19D11, 25C3, 26B9, 31B4, 8H1, 12H5 and 50E11 antibodies of the present invention.

| Antibody | Nucleotide and amino acid sequences of variable heavy (VH) and variable light (VL), constant heavy (CH) and constant light (CL) chains. |
|---|---|
| | SDIAVEWESNGQPENNYKTTPPVLDSDGSFFLYSKLTVDKSRWQQGNVFSC<br>SVMHEALHNHYTQKSLSLSPGK<br>SEQ ID NO: 80 |
| 8H1 CL<br>kappa-type | cgaactgtggctgcaccatctgtcttcatcttcccgccatctgatgagcagttgaaatctggaactgcctctgttgtgtgcct<br>gctgaataacttctatcccagagaggccaaagtacagtggaaggtggataacgccctccaatcgggtaactcccagga<br>gagtgtcacagagcaggacagcaaggacagcacctacagcctcagcagcaccctgacgctgagcaaagcagacta<br>cgagaaacacaaagtctacgcctgcgaagtcacccatcagggcctgagctcgcccgtcacaaagagcttcaacaggg<br>gagagtgttag<br>SEQ ID NO: 81 |
| 8H1 CL<br>kappa-type | RTVAAPSVFIFPPSDEQLKSGTASVVCLLNNFYPREAKVQWKVDNALQSGN<br>SQESVTEQDSKDSTYSLSSTLTLSKADYEKHKVYACEVTHQGISSPVTKSFN<br>RGEC<br>SEQ ID NO: 82 |
| 12H5 VH | caagtgcaactgatacagtctgggcctgaggtgaagaggcctggggcctcagtgaaggtctcctgcaaggcgtctga<br>aaacaccttcgacacttcattatattaattgggtgcgacaggcccactggacaagggcttacttggctggctgggatggctgaac<br>cctaccactggtaaaacaggctttccacaaaagtttaagggcagagtcattctgaccagcgacacctccctaaatactg<br>cctatatggaagtgagccgcctgacatctgaggacacggccgtttatttctgtgccagagagttttgaagttgtctgatgagt<br>acaactatggtttcgacgtctggggccaagggaccacggtcatcgtctcctca<br>SEQ ID NO: 83 |
| 12H5 VH | QVQLIQSGPEVKRPGASVKVSCKASENTFDTHYINWVRQAPGQGITWLGW<br>LNPTTGKTGFPQKFKGRVILTSDTSLNTAYMEVSRLTSEDTAVYFCARVLK<br>LSDEYNYGFDVWGQGTTVIVSS<br>SEQ ID NO: 84 |
| 12H5 VL<br>kappa-type | gacatccaggtgacccagtctccatcctcccctgtctgcatctattggggacagagtcaccatcacgtgccgggcaagtc<br>agaacattctcacctttataaaattggtatcagcacaaaccagggaaagcccctaaactcctgatctatgctgcatccgtt<br>ttacaaaatgaagtcccatcaaggttcagtggcagtggatctgggacagatttcactctcaccatcaccagtctgcaacct<br>gacgattttggaacttactactgtcagcagacttaccttaccccctcaatgcagttttggccaggggaccaaggtggagat<br>caaa<br>SEQ ID NO: 85 |
| 12H5 VL<br>kappa-type | DIQVTQSPSSLSASIGDRVTITCRASQNILTFINWYQHKPGKAPKLLIYAASV<br>LQNEVPSRFSGSGSGTDFTLTITSLQPDDFGTYYCQQTYLTPQCSFGQGTK<br>VEIK<br>SEQ ID NO: 86 |
| 12H5 CH | gcctccaccaagggcccatcggtcttccccctggcaccctcctccaagagcacctctgggggcacagcggccctggg<br>ctgcctggtcaaggactacttccccgaaccggtgacggtgtcgtggaactcaggcgccctgaccagcggcgtgcaca<br>ccttcccggctgtcctacagtcctcaggactctactccctcagcagcgtggtgaccgtgccctcagcagcttgggcac<br>ccagacctacatctgcaacgtgaatcacaagcccagcaacaccaaggttgacaagaaagttgagcccaaatcttgtga<br>caaaactcacacatgcccaccgtgcccagcacctgaactcctggggggaccgtcagtcttcctcttccccccaaaaccc<br>aaggacaccctcatgatctcccggacccctgaggtcacatgcgtggtggtggacgtgagccacgaagaccctgaggt<br>caagttcaactggtacgtggacggcgtggaggtgcataatgccaagacaaagccgcgggaggagcagtacaacagc<br>acgtaccgtgtggtcagcgtcctcaccgtcctgcaccaggactggctgaatggcaaggagtacaagtgcaaggtctcc<br>aacaaagccctcccagcccccatcgagaaaatctccaaagccaaagggcagccccgagaaccacaggtgtaca<br>ccctgcccccatcccgggatgagctgaccaagaaccaggtcagcctgacctgcctggtcaaaggcttctatcccagcg<br>acatcgccgtggagtgggagagcaatgggcagccggagaacaactacaagaccacgcctcccgtgctggactccga<br>cggctccttcttcctctacagcaagctcaccgtggacaagagcaggtggcagcaggggaacgtcttctcatgctccgtg<br>atgcatgaggctctgcacaaccactacacgcagaagagcctctccctgtctccgggtaaatga<br>SEQ ID NO: 87 |
| 12H5 CH | ASTKGPSVFPLAPSSKSTSGGTAALGCLVKDYFPEPVTVSWNSGALTSGVH<br>TFPAVLQSSG1YSLSSWTVPSSSLGTQTYICNVNHKPSNTKVDKKVEPKSCD<br>KTHTCPPCPAPELLGGPSVFLFPPKPKDTLMISRTPEVTCVWDVSHEDPEVK<br>FNWYVDGVEVHNAKTKPREEQYNSTYRWSVLTVLHQDWLNGKEYKCKV<br>SNKALPAPIEKTISKAKGQPREPQVYTLPPSRDELTKNQVSLTCLVKGFYPS<br>DIAVEWESNGQPENNYKTTPPVLDSDGSFFLYSKLTVDKSRWQQGNVFSCS<br>VMHEALHNHYTQKSLSLSPGK<br>SEQ ID NO: 88 |
| 12H5 CL<br>kappa-type | cgaactgtggctgcaccatctgtcttcatcttcccgccatctgatgagcagttgaaatctggaactgcctctgttgtgtgcct<br>gctgaataacttctatcccagagaggccaaagtacagtggaaggtggataacgccctccaatcgggtaactcccagga<br>gagtgtcacagagcaggacagcaaggacagcacctacagcctcagcagcaccctgacgctgagcaaagcagacta<br>cgagaaacacaaagtctacgcctgcgaagtcacccatcagggcctgagctcgcccgtcacaaagagcttcaacaggg<br>gagagtgttag<br>SEQ ID NO: 89 |

TABLE 1-continued

Nucleotide sequences of the variable and constant regions (VH, VL, CH, CL) regions of IgG1, kappa, IFN-α specific 5D1, 13B11, 19D11, 25C3, 26B9, 31B4, 8H1, 12H5 and 50E11 antibodies of the present invention.

| Antibody | Nucleotide and amino acid sequences of variable heavy (VH) and variable light (VL), constant heavy (CH) and constant light (CL) chains. |
|---|---|
| 12H5 CL kappa-type | RTVAAPSVFIFPPSDEQLKSGTASVVCLLNNFYPREAKVQWKVDNALQSGN SQESVTEQDSKDSTYSLSSTLTLSKADYEKHKVYACEVTHQG1SSPVTKSFN RGEC<br>SEQ ID NO: 90 |
| 50E11 VH | caggtgcagctggtgcagtctggggcagagatgaagaagcctgggtcctcggtgaaggtctcctgcaaggatttttgaggcaccttcagcgtctatggtgtcaactgggtgcgacaggcccctggacaagggcttgagtggatggggggggctcatccctgtcattgggccagctaactacgcacagaagttccagggcagaatcaccattactgcggacgaatccacgagcac agcctatatggagttgagcagcctgagatttgacgacacggccatttattattgtgtgagagacgacaacgaatattggggccagggaaccctggtcaccgtctcctcg<br>SEQ ID NO: 91 |
| 50E11 VH | QVQLVQSGAEMKKPGSSVKVSCKDFGGTFSVYGVNWVRQAPGQG1EWM GG1IPVIGPANYAQKFQGRITITADESTSTAYMELSSLRFDDTAIYYCVRDDNEYWGQGTLVTVSS<br>SEQ ID NO: 92 |
| 50E11 VL kappa-type | gaaatggtgctgacacagtctccagccacccctgtattgtctccaggagaaagagccaccctctcctgtagggccagtcagactgttagcacccttcttagcctggtaccaacagaaacctggccaggttcccaggctcctcgtctacgatatctcctcc agggccaatggcactccagccaggttcagtggcggtgggtctgggacagacttcactctcaccatcagcagcctaagaa cttgaagattttacggtttattactgtcagtggcgtagcaactggcctccctcgctcactttcggcggagggaccagggtggagatcaaa<br>SEQ ID NO: 93 |
| 50E11 VL kappa-type | EMVLTQSPATLSLSPGERATLSCRASQTVSTFLAWYQQKPGQVPRLLVYDISSRANGTPARFSGGGSGTDFTLTISSLELEDFAVYYCQWRSNWPPSLTEGGGTRVEIK<br>SEQ ID NO: 94 |
| 50E11 CH | gcctccaccaagggcccatcggtcttccccctggcaccctcctccaagagcacctctggggggcacagcggccctggg ctgcctggtcaaggactacttccccgaaccggtgacggtgtcgtggaactcaggcgccctgaccagcggcgtgcaca ccttcccggctgtcctacagtcctcaggactctactccctcagcagcgtggtgaccgtgccctcagcagcttgggcac ccagacctacatctgcaacgtgaatcacaagcccagcaacaccaaggtggacaagaaagttgagcccaaatcttgtga caaaactcacacatgcccaccgtgcccagcacctgaactcctgggggaccgtcagtcttcctcttccccccaaaacc aaggacaccctcatgatctcccggacccctgaggtcacatgcgtggtggtggacgtgagccacgaagaccctgaggt caagttcaactggtacgtggacggcgtggaggtgcataatgccaagacaaagccgcgggaggagcagtacaac agcacgtaccgtgtggtcagcgtcctcaccgtcctgcaccaggactggctgaatggcaaggagtacaagtgcaaggtc tccaacaaagccctcccagcccccatcgagaaaaccatctccaaagccaaagggcagccccgagaaccacaggtgt acaccctgcccccatcccgggatgagctgaccaagaaccaggtcagcctgacctgcctggtcaaaggcttctatccca gcgacatcgccgtggagtgggagagcaatgggcagccggagaacaactacaagaccacgcctcccgtgctggactc cgacggctccttcttcctctacagcaagctcaccgtggacaagagcaggtggcagcaggggaacgtcttctcatgctcc gtgatgcatgagggtctgcacaaccactacacgcagaagagcctctccctgtctccgggtaaatga<br>SEQ ID NO: 95 |
| 50E11 CH | ASTKGPSVFPLAPSSKSTSGGTAALGCLVKDYFPEPVTVSWNSGALTSGVH TFPAVLQSSG1YSLSSWTVPSSSLGTQTYICNVNHKPSNTKVDKKVEPKSCD KTHTCPPCPAPELLGGPSVFLFPPKPKDTLMISRTPEVTCVWDVSHEDPEVK FNWYVDGVEVHNAKTKPREEQYNSTYRVVSVLTVLHQDWLNGKEYKCK VSNKALPAPIEKTISKAKGQPREPQVYTLPPSRDELTKNQVSLTCLVKGFYP SDIAVEWESNGQPENNYKTTPPVLDSDGSFFLYSKLTVDKSRWQQGNVFSC SVMHEG1HNHYTQKSLSLSPGK<br>SEQ ID NO: 96 |
| 50E11 CL kappa-type | cgaactgtggctgcaccatctgtcttcatcttcccgccatctgatgagcagttgaaatctggaactgcctctgttgtgtgcct gctgaataacttctatcccagagaggccaaagtacagtggaaggtggataacgccctccaatcgggtaactcccagga gagtgtcacagagcaggacagcaaggacagcacctacagcctcagcagcaccctgacgctgagcaaagcagacta cgagaaacacaaagtctacgcctgcgaagtcacccatcagggcctgagctcgcccgtcacaaagagcttcaacaggg gagagtgttag<br>SEQ ID NO: 97 |
| 50E11 CL kappa-type | RTVAAPSVFIFPPSDEQLKSGTASVVCLLNNFYPREAKVQWKVDNALQSGN SQESVTEQDSKDSTYSLSSTLTLSKADYEKHKVYACEVTHQG1SSPVTKSFN RGEC<br>SEQ ID NO: 98 |

Underlined, bold nucleotides or amino acids indicate the CDR coding regions in the variable chain sequence. Underlined, italic nucleotides or amino acids indicate sequences which have not been sequenced but obtained from database. In the constant chains, such regions are aligned with and tuned in accordance with the pertinent human germ line variable region sequences in the database; see, e.g., Vbase (http://vbase.mrc-cpe.cam.ac.uk) hosted by the MRC Centre for Protein Engineering (Cambridge, UK).

The person skilled in the art will readily appreciate that the variable domain of the antibody having the above-described variable domain can be used for the construction of other polypeptides or antibodies of desired specificity and biological function. Thus, the present invention also encompasses polypeptides and antibodies comprising at least one CDR of the above-described variable domain and which advantageously have substantially the same or similar binding properties as the antibody described in the appended examples. The person skilled in the art will readily appreciate that using the variable domains or CDRs described herein antibodies can be constructed according to methods known in the art, e.g., as described in European patent applications EP 0 451 216 A1 and EP 0 549 581 A1. Furthermore, the person skilled in the art knows that binding affinity may be enhanced by making amino acid substitutions within the CDRs or within the hypervariable loops (Chothia and Lesk, *J Mol Biol.* 196 (1987), 901-917) which partially overlap with the CDRs as defined by Kabat. Thus, the present invention also relates to antibodies wherein one or more of the mentioned CDRs comprise one or more, preferably not more than two amino acid substitutions. Preferably, the antibody of the invention comprises in one or both of its immunoglobulin chains two or all three CDRs of the variable regions as set forth for VH regions in SEQ ID NOs: 2, 10, 18, 22, 30, 38, 76, 84 and 92, for VL regions and SEQ ID NOs: 4, 12, 20, 24, 32, 40, 78, 86 and 94 or as indicated in FIG. 1.

The polynucleotide of the invention encoding the above described antibody may be, e.g., DNA, cDNA, RNA or synthetically produced DNA or RNA or a recombinantly produced chimeric nucleic acid molecule comprising any of those polynucleotides either alone or in combination. In one embodiment the polynucleotide is a cDNA encoding the variable region and at least part of the constant domain. In a preferred embodiment a vector comprising the above polynucleotide is provided, optionally in combination with said polynucleotide which encodes the variable region of the other immunoglobulin chain of said antibody. Such vectors may comprise further genes such as marker genes which allow for the selection of said vector in a suitable host cell and under suitable conditions.

Preferably, the polynucleotide of the invention is operatively linked to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally associated or heterologous promoter regions.

In this respect, the person skilled in the art will readily appreciate that the polynucleotides encoding at least the variable domain of the light and/or heavy chain may encode the variable domains of both immunoglobulin chains or one chain only.

Likewise, said polynucleotides may be under the control of the same promoter or may be separately controlled for expression. Possible regulatory elements permitting expression in prokaryotic host cells comprise, e.g., the PL, lac, trp or tac promoter in *E. coli*, and examples for regulatory elements permitting expression in eukaryotic host cells are the AOXI or GALI promoter in yeast or the CMV-, SV40-, RSV-promoter, CMV-enhancer, SV40-enhancer or a globin intron in mammalian and other animal cells.

Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the polynucleotide of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including a C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3 (Invitrogen), or pSPORT1 (GIBCO BRL).

Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the immunoglobulin light chains, heavy chains, light/heavy chain dimers or intact antibodies, binding fragments or other immunoglobulin forms may follow; see, Beychok, *Cells of Immunoglobulin Synthesis*, Academic Press, N.Y., (1979).

Furthermore, the present invention relates to vectors, particularly plasmids, cosmids, viruses and bacteriophages used conventionally in genetic engineering that comprise a polynucleotide encoding the antigen or preferably a variable domain of an immunoglobulin chain of an antibody of the invention; optionally in combination with a polynucleotide of the invention that encodes the variable domain of the other immunoglobulin chain of the antibody of the invention. Preferably, said vector is an expression vector and/or a gene transfer or targeting vector.

Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, *Molecular Cloning A Laboratory Manual*, Cold Spring Harbor Laboratory (1989) N.Y. and Ausubel, *Current Protocols in Molecular Biology*, Green Publishing Associates and Wiley Interscience, N.Y. (1994). Alternatively, the polynucleotides and vectors of the invention can be reconstituted into liposomes for delivery to target cells. The vectors containing the polynucleotides of the invention (e.g., the heavy and/or light variable domain(s) of the immunoglobulin chains encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for the transformation of other cellular hosts; see Sambrook, supra.

In respect to the above, the present invention furthermore relates to a host cell comprising said polynucleotide or vector. Said host cell may be a prokaryotic or eukaryotic cell. The polynucleotide or vector of the invention which is present in the host cell may either be integrated into the genome of the host cell or it may be maintained extrachromosomally. The host cell can be any prokaryotic or eukaryotic cell, such as a bacterial, insect, fungal, plant, animal or human cell; suitable host cells and methods for production of the antibodies of the present invention are described in more detail in the section "Host cells" below.

Using the above-mentioned host cells it is possible to produce and prepare an antibody of the present invention for, e.g., a pharmaceutical use or as a target for therapeutic intervention. Therefore, in one embodiment, it is also an object of the present invention to provide a method for preparing an anti-IFN-α antibody or IFN-α binding fragment thereof, said method comprising
(a) culturing the cell as defined hereinabove; and
(b) isolating said antibody or IFN-α binding fragment thereof from the culture.

Accordingly, the present invention relates to recombinant antibody or IFN-α binding fragment thereof immunoglobulin chain(s) thereof encoded by the polynucleotide of the present invention or obtainable by the above-mentioned method for preparing an anti-IFN-α antibody or immunoglobulin chain(s) thereof Means and methods for the recombinant production of antibodies and mimics thereof as well as methods of screening for competing binding molecules, which may or may not be antibodies, are known in the art. However, as described herein, in particular with respect to therapeutic applications in human the antibody of the present invention is a recombinant human antibody in the sense that application of said antibody is substantially free of an immune response directed against such antibody otherwise observed for chimeric and even humanized antibodies.

The binding molecules, antibodies or fragments thereof may be directly used as a therapeutic. However, in one embodiment the antibody or antigen-binding fragment which is provided by the present invention, is detectably labeled or attached to a drug, preferably wherein the detectable label is selected from the group consisting of an enzyme, a radioisotope, a fluorophore, a peptide and a heavy metal. Labeled antibodies or antigen-binding fragments of the present invention may be used to detect specific targets in vivo or in vitro including "immunochemistry/immunolabelling" like assays in vitro. In vivo they may be used in a manner similar to nuclear medicine imaging techniques to detect tissues, cells, or other material expressing the antigen of interest. Labels, their use in diagnostics and their coupling to the binding molecules of the present invention are described in more detail in section "labels and diagnostics" further below.

The antibodies of the present invention are isolated from animals or humans affected by an autoimmune disorder. On the other hand, IFN-α specific antibodies identified in the present invention may be involved in severely impairing the immune system of the affected individual, which is associated with, e.g., symptoms observed in APECED patients. Therefore, it is a further aspect of the present invention, to extinguish or at least relieve the pathological reactions of subjects suffering from autoimmune disorders by providing means and measures to minimize the number of autoantibodies and/or their effects in a diseased human patient or animal. Thus, in one embodiment the present invention also relates to a peptide or peptide-based compound comprising an epitope specifically recognized by an autoantibody of the present invention. A similar effect as by application of competitive antigens, sequestering and preventing thereby the binding of the autoantibodies to their respective targets may be obtained by anti-idiotypic antibodies, as described in detail further below. Therefore, in one embodiment the present invention also provides an anti-idiotypic antibody of an autoantibody of the present invention.

As already indicated above, the present invention also relates to the anti-idiotypic antibody or the peptide or peptide-based compound of the present invention for use in the treatment of a disorder as defined above, i.e. a disorder associated with a disrupted or deregulated genesis of self-tolerance. These isolated antibodies or fragments thereof of the present invention can be used as immunogenes to generate a panel of monoclonal anti-idiotypes. For suitable methods for the generation of anti-idiotypic antibodies see Raychadhuri et al., *J Immunol.* 137 (1986), 1743 and for T-cells see Ertl et al., *J Exp. Med.* 159 (1985), 1776. The anti-idiotypic antibodies will be characterized with respect to the expression of internal image and non-internal image idiotypes using standard assays routinely practiced in the art as described in detail by Raychaudhuri et al., *J Immunol* 137 (1986), 1743. If an anti-idiotypic antibody structurally mimics the antigen of the antibody it is binding to or bound by, it is called the "internal image" of the antigen.

Methods of providing molecules which mimic an idiotype of an autoimmune disease-associated auto-antibody (autoantibodies) are described in the art; see, e.g., international application WO03/099868, the disclosure content of which incorporated herein by reference. For example, such method may comprise the following steps: (a) providing autoantibodies in accordance with the method of the present invention; (b) binding the autoantibodies to a solid phase to form an affinity matrix; (c) contacting pooled plasma or B cells comprising immunoglobulins with the affinity matrix followed by removal of unbound plasma components; (d) eluting bound immunoglobulins, being anti-Idiotypic antibodies (anti-Id) to autoantibodies, from the matrix; (e) providing a molecular library comprising a plurality of molecule members; and (f) contacting the anti-Id with the molecular library and isolating those bound molecules which are bound by the anti-Id, the bound molecules being molecules which mimic an idiotype of autoantibodies. A method of isolating idiotypic autoantibodies in disclosed in international application WO2010/136196, the disclosure content of which incorporated herein by reference, which describes immunoglobulin preparations containing natural polyclonal IgG-reactive antibodies (Abs) isolated from normal human serum (NHS), for the treatment of autoimmune diseases and immune system disorders. The IgG-reactive Abs potently neutralize disease-associated or pathogenic autoantibodies present in sera of patients suffering from autoimmune diseases, by binding to their antigenic determinants located either within or near (e.g. overlapping with) the antigen combining sites.

The present invention also relates to compositions comprising any one of the aforementioned anti-IFN-α antibodies and/or IFN-α binding fragments, the polynucleotide, the vector, the cell, the peptide or peptide-based compound of the present invention and/or a cocktail of antibodies or IFN-α binding fragments thereof which in combination display the features of an antibody or IFN-α binding fragment thereof of the present invention. In addition or alternatively in one embodiment the composition or the kit of the present invention comprises the anti-idiotypic antibody of the present invention. In one embodiment the composition is a pharmaceutical composition and further comprises a pharmaceutically acceptable carrier. Pharmaceutically acceptable carriers, administration routes and dosage regimen can be taken from corresponding literature known to the person skilled in the art and are described as well in more detail in sections "Pharmaceutical carriers" and "Dosage regimen" further below.

Besides biochemical and cell based in vitro assays therapeutic utility of the antibodies of the present invention can be validated in appropriate animal models such as for RA, psoriasis, SLE or TIDM; see the Examples below, e.g., Example 4.

In one embodiment the pharmaceutical composition further comprises an additional agent useful for treating an inflammation or an autoimmune disorder, preferably wherein said agent is selected from the group consisting of Non-Steroidal Antiinflammatory Drugs (NSAIDs), Corticosteroids, Anti-Histamines and combinations thereof. In addition or alternatively, in a further embodiment the pharmaceutical composition further comprises an additional agent useful for treating an inflammation related disease, selected from the group consisting of immunosuppressive and anti-inflammatory or "anti-rheumatic" drugs.

In another embodiment, the composition is a diagnostic composition or kit and further comprises reagents conventionally used in immuno- or nucleic acid based diagnostic methods.

Furthermore, the present invention relates to any one of the aforementioned anti-IFN-a antibodies and IFN-α binding fragment thereof, or the composition as defined hereinabove for use in a method of:
(a) treating or preventing the progression of an immune mediated or autoimmune disease or condition;
(b) amelioration of symptoms associated with an immune mediated or autoimmune disease or condition; and/or
(c) diagnosing or screening a subject for the presence or for determining a subject's risk for developing an immune mediated or autoimmune disease or condition; wherein the disease or condition associated with the expression of IFN-α and/or IFN-ω in a patient In this respect several application routes may be used. In one embodiment of the present invention the aforementioned antibody or antigen-binding fragment, the anti-idiotypic antibody or peptide or peptide-based compound and/or a cocktail of antibodies which in combination display the features of an antibody of the present invention is provided, which is designed to be administered intravenously, intramuscularly, subcutaneously, intraperitoneally, intranasally, parenterally or as an aerosol. As indicated above, due to their binding specificity, the molecules of the present invention such as antibodies and fragments thereof may preferably be used in the above defined method of treatment, amelioration, diagnosing and/or screening of an immune mediated or autoimmune disorder or condition. For example, elevated IFN-α activity has been frequently detected in the sera of patients with SLE (R6nnblom et al., Sem. Immun. 23 (2011), 113-121). A specific expression pattern of interferon-dependent genes (termed the "interferon signature") is further displayed in the leukocytes of patients with various autoimmune disorders such as Sj6gren's syndrome, Dermatomyositis, Multiple Sclerosis (MS), Psoriasis, type 1 or insulin dependent diabetes mellitus (T1DM or IDDM) and a fraction of RA patients (see, e.g., Higgs et al., *Eur Muse Rev* (2012), 22-28). In addition, development of inflammatory arthritis, MS and T1DM has been repeatedly observed during IFN-α therapy indicating that IFN-α at least promotes those diseases (Crow M K., Arthritis Res Ther. (2010), Suppl 1:S5). Further data suggest an involvement of IFN-α in myositis, systemic scleroderma, chronic psoriasis (Higgs et al., Eur Muse Rev (2012), 22-28; Bissonnette et al., J Am Acad Dermatol (2009), 427-436; Greenberg S A, Arth Res Ther (2010): S4) and autoimmune thyroiditis (Prummel and Laurberg, Thyroid (2003), 547-551). Therefore, in one embodiment the antibody or IFN-α binding fragment thereof or the composition as defined hereinabove for use in the above-mentioned method is provided, wherein said disease is an autoimmune disease, preferably selected from the group consisting of Systemic lupus erythematosus (SLE), cutaneous lupus erythematosus (CLE), discoid lupus erythematosus (DLE), type 1 diabetes mellitus (T1DM) Sj6gren's syndrome, dermatomyositis, psoriasis, autoimmune thyroiditis, rheumatoid arthritis, spondyloarthritis, scleroderma and different cancer forms including leukemia, such as breast and ovarian cancer and childhood lymphoblastic leukemia (ALL; Einav et al., Oncogene 24 (2005), 6367-6375). Preliminary results suggested a difference in neutralizing activity of antibodies obtained from APS1-patients suffering or not suffering in addition from T1DM (FIG. 4). However, a more detailed analysis of the patient's sera revealed that the neutralizing activity of individual anti-IFN-α antibodies in both kind of patients may be substantially the same, while the antibody titers and total level of IFN neutralizing activity significantly differ with a very low titer in T1DM patients; see FIGS. 31 and 32. Accordingly, in one embodiment the present invention also relates to the IFN-α and IFN-α/m binding molecules described herein as well as other IFN-a binding molecules for use in the treatment of T1DM in a patient, from whom a sample of sera has been determined to display a lower neutralizing activity against cytokines of at least one IFN-α subtype compared to a control sample, i.e. sera from a healthy subject or from a TD1M patient which is free of disease symptoms.

Due to the multitude of molecules suitable in treatment of, e.g., disorders associated with inflammation presented herein, the present invention also relates to methods of treatment, diagnosing and/or prognosticate the probable course and outcome of such disorders, preferably wherein the immune mediated or autoimmune disease or condition is associated with the expression of IFN-α and/or IFN-w to the use of the molecules of the present invention. In one embodiment a method for treating of such a disorder is provided, which method comprises administering to a subject in need thereof a therapeutically effective amount of the aforementioned antibody or antigen-binding fragment, the cocktail of antibodies which in combination display the features of an antibody of the present invention, the anti-idiotypic antibody or the peptide or peptide-based compound.

Furthermore, in one embodiment the present invention relates to a method of treating an immune mediated or autoimmune disease or condition associated with the expression of IFN-a and/or IFN-ω comprising administering to a subject a therapeutically effective amount of a ligand binding molecule comprising:
(i) at least one CDR of the anti-IFN-α antibodies and IFN-α binding fragment of the present invention; or
(ii) at least one anti-idiotypic antibody and/or peptide or peptide-based compound as defined hereinabove.

Treatment methods based on the use of only one monoclonal antibody specific for an epitope of a particular antigen, which is related or causing a disease may suffer from several shortcomings. For example, difficulties and probably inefficiency of treatment may stem from the multiplicity of the pathogenic mechanisms causing a specific disorder requiring targeting of several antigens simultaneously. Furthermore, the inherent diversity of the patient population has to be taken into account concerning, e.g., polymorphism, heterogeneity of glycosylation or slight denaturation of a given antigen, either in different or in one patient which may lead to a decreased binding efficiency of the monoclonal antibody used at least. Some of these shortcomings may be circumvented by, e.g., pretreatment screenings to determine whether the antigen is immunologically relevant to the patients intended to be treated and whether there are any epitope changes in the particular patients. However, such screenings are often omitted either due to treatment urgency or to cost restraints. Therefore, the present invention further relates to methods based on the application of more than one type of a binding molecule at once to a patient, i.e. to the application of a cocktail of binding molecules. These binding molecules may specifically bind to one IFN-α subtype at different epitopes and/or of an epitope of IFN-ω, each of the binding molecules applied may bind specifically another IFN-α subtype or several binding molecules are used binding to several epitopes of more than one IFN-α subtype and/or IFN-ω. In case the binding molecules of the present invention are directed (bind specifically) towards one IFN-α subtype as antigen, their binding specificity is directed towards distinct epitopes of said antigen. The use of such cocktails is in particular envisaged for the treatment of patients suffering from autoimmune disorders such as APS1, who in view of the presence of autoantibodies against about 3000 endogenous antigens are often not amenable to monotherapy with one particular antibody. In such cases, combination therapy with two or more monoclonal antibodies and/or peptides and peptide-based compounds of the present invention with the same or different antigen specificity are expected to achieve at least some relief of the symptoms.

Therefore, in one embodiment a further method of treating a disorder is provided comprising administering to a subject a therapeutically effective amount of a cocktail consisting essentially of at least two, three, four, five and more components selected from the groups consisting of: an anti-IFN-α antibody and IFN-α binding fragment of the present invention specifically binding the IFN-α subtypes and/or IFN-ω as defined hereinabove; and/or an anti-idiotypic antibody of the present invention, and/or from a peptide or peptide-based compound of the present invention, which peptide or peptide-based compound comprises an epitope specifically recognized by an anti-IFN-α antibodies and IFN-α binding fragment of the present invention.

The present invention naturally extents also to diagnostic and prognostic methods directed towards diagnosing immune mediated or autoimmune conditions and disorders associated with expression of one or more subtypes of IFN-α and/or IFN-ω and/or prognosis of the development of the disease, i.e. its progression, response to treatment or recovery. Therefore, in one embodiment the present invention relates to a method for diagnosing an immune mediated or autoimmune disease or condition in a subject associated with the expression of IFN-α comprising contacting a biological sample of the subject with anti-IFN-α antibody and IFN-a binding fragment of the present invention, and detecting the presence of IFN-α and/or IFN-m. Furthermore, in one embodiment the present invention relates to a method of detecting or determining IFN-α and/or IFN-ω in an isolated biological sample comprising admixing the sample with an anti-IFN-α antibody of the present invention, allowing the antibody to form a complex with any IFN-α subtype and/or IFN-ω present in the mixture, and detecting the complex present in the mixture.

As already mentioned above, in one embodiment the present invention relates to a kit for the diagnosis of an immune mediated or autoimmune disease or condition associated with the expression of IFN-α and/or IFN-ω, said kit comprising the aforementioned anti-IFN-a antibody and IFN-α binding fragment, the anti-idiotypic antibody or the peptide or peptide-based compound, the polynucleotide, the vector or the cell, optionally with reagents and/or instructions for use. Associated with the kits of the present invention, e.g., within a container comprising the kit can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate diagnostic assays. The compositions, i.e. kits of the present invention are of course particularly suitable for the diagnosis, prevention and treatment of a disorder which is accompanied with the expression of IFN-α, in particular applicable for the treatment of diseases as mentioned above. In a particularly preferred embodiment the disorder is associated with expression of one or more of IFN-α subtypes and/or IFN-ω.

In another embodiment the present invention relates to a diagnostic composition comprising any one of the above described binding molecules, antibodies, antigen-binding fragments, peptides or peptide-based compounds, polynucleotides, vectors or cells of the invention and optionally suitable means for detection such as reagents conventionally used in immune- or nucleic acid based diagnostic methods. The antibodies of the invention are, for example, suited for use in immunoassays in which they can be utilized in liquid phase or bound to a solid phase carrier. Examples of immunoassays which can utilize the antibody of the invention are competitive and non-competitive immunoassays in either a direct or indirect format. Examples of such immunoassays are the radioimmunoassay (RIA), the sandwich (immunometric assay), flow cytometry and the Western blot assay. The antigens and antibodies of the invention can be bound to many different carriers and used to isolate cells specifically bound thereto. Examples of well-known carriers include glass, polystyrene, polyvinyl chloride, polypropylene, polyethylene, polycarbonate, dextran, nylon, amyloses, natural and modified celluloses, poly-acrylamides, agaroses, and magnetite. The nature of the carrier can be either soluble or insoluble for the purposes of the invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove. In this context, the present invention also relates to means specifically designed for this purpose. For example, a protein- or antibody-based array may be used, which is for example loaded with either antigens derived from one or more IFN-α subtypes and containing the disease-associated antigen in order to detect autoantibodies which may be present in patients suffering from an autoimmune diseases, in particular SLE or APECED/APS1, or with antibodies or equivalent antigen-binding molecules of the present invention which specifically recognize any one of those inflammation-associated antigens. Design of microarray immunoassays is summarized in Kusnezow et al., *Mal. Cell Proteomics* 5 (2006), 1681-1696. Accordingly, the present invention also relates to microarrays loaded with binding molecules, in particular anti-IFN-α antibody and IFN-α binding fragment of the present invention or antigens identified in accordance with the present invention.

Definitions and Embodiments

Unless otherwise stated, a term and an embodiment as used herein is given the definition as provided and used in international application WO2013/098419 and international application WO2013/098420. Supplementary, a common term as used herein is given the definition as provided in the *Oxford Dictionary of Biochemistry and Molecular Biology*, Oxford University Press, 1997, revised 2000 and reprinted 2003, ISBN 0 19 850673 2.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

The term "neutralizing" and "neutralizing antibody", respectively, is used as common in the art in that an antibody is meant that reduces or abolishes at least some biological activity of an antigen or of a living microorganism. For example, a subtype-specific anti-IFN-α antibody of the present invention is a neutralizing antibody, if, in adequate amounts, it abolishes or reduces the activity of the respective IFN-α subtype(s) for example in an assay as described in the Examples. Neutralization is commonly defined by 50% inhibitory concentrations (IC 50) and can be statistically assessed based on the area under the neutralization titration curves (AUC). IC 50 values of exemplary anti-IFN-α antibodies of the present invention are described and shown herein, e.g., in FIGS. 8-10 and in Table 4.

Central and Peripheral Tolerance

Central and peripheral tolerance are described in more detail in the respective chapter of the international application WO2013/098419 on pages 62-63, the disclosure content of which is incorporated herein by reference.

Peptides and Polypeptides:

The term "peptide" is understood to include the terms "polypeptide" and "protein" (which, at times, may be used interchangeably herein) and any amino acid sequence such as those of the heavy and light chain variable region as well as constant region of the present invention within its meaning. Similarly, fragments of proteins and polypeptides are also contemplated and may be referred to herein as "peptides". Nevertheless, the term "peptide" preferably denotes an amino acid polymer including at least 5 contiguous amino acids, preferably at least 10 contiguous amino acids, more preferably at least 15 contiguous amino acids, still more preferably at least 20 contiguous amino acids, and particularly preferred at least 25 contiguous amino acids. In addition, the peptide in accordance with present invention typically has no more than 100 contiguous amino acids, preferably less than 80 contiguous amino acids and more preferably less than 50 contiguous amino acids.

As used herein, the term "polypeptide" is intended to encompass a singular "polypeptide" as well as plural "polypeptides" such as antibodies of the present invention, and refers to a molecule composed of monomers (amino acids) linearly linked by amide bonds (also known as peptide bonds). The term "polypeptide" refers to any chain or chains of two or more amino acids, and does not refer to a specific length of the product. Thus, "peptides," "dipeptides," "tripeptides, "oligopeptides," "protein," "amino acid chain," or any other term used to refer to a chain or chains of two or more amino acids, are included within the definition of "polypeptide," and the term "polypeptide" may be used instead of, or interchangeably with any of these terms.

The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Nevertheless, the term "polypeptide" preferably denotes an amino acid polymer including at least 100 amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

"Recombinant peptides, polypeptides or proteins" refer to peptides, polypeptides or proteins produced by recombinant DNA techniques, i.e. produced from cells, microbial or mammalian, transformed by an exogenous recombinant DNA expression construct encoding the fusion protein including the desired peptide. Proteins or peptides expressed in most bacterial cultures will typically be free of glycan. Proteins or polypeptides expressed in yeast may have a glycosylation pattern different from that expressed in mammalian cells.

Also included as polypeptides of the present invention are fragments, derivatives, analogs and variants of the foregoing polypeptides and any combination thereof. The terms "fragment," "variant," "derivative" and "analog" include peptides and polypeptides having an amino acid sequence sufficiently similar to the amino acid sequence of the natural peptide. The term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar. Preferably, variants will be sufficiently similar to the amino acid sequence of the preferred peptides of the present invention, in particular to antibodies or antibody fragments, or to synthetic peptide or peptide-based compound comprising epitopes recognized by the antibodies of the present invention or fragments, variants, derivatives or analogs of either of them. Such variants generally retain the functional activity of the peptides of the present invention, i.e. are bound by the antibodies of the present invention. Variants include peptides that differ in amino acid sequence from the native and wt peptide, respectively, by way of one or more amino acid deletion(s), addition(s), and/or substitution(s). These may be naturally occurring variants as well as artificially designed ones. The terms "fragment," "variant," "derivative" and "analog" when referring to antibodies or antibody polypeptides of the present invention include any polypeptides which retain at least some of the antigen-binding properties of the corresponding native binding molecule, antibody, or polypeptide. Fragments of polypeptides of the present invention include proteolytic fragments, as well as deletion fragments, in addition to specific antibody fragments discussed elsewhere herein. Variants of antibodies and antibody polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions or additions. Derivatives of binding molecules of the present invention, e.g., antibodies and antibody polypeptides of the present invention, are polypeptides which have been altered so as to exhibit additional features not found on the native polypeptide. Examples include fusion proteins. Variant polypeptides may also be referred to herein as "polypeptide analogs". As used herein a "derivative" of a binding molecule or fragment thereof, an antibody, or an antibody polypeptide refers to a subject polypeptide having one or more residues chemically derivatized by reaction of a functional side group. Also included as "derivatives" are peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

Anti-Idiotypic Antibodies:

The term "anti-idiotypic antibodies" when referring to antibodies or other binding molecules includes molecules which bind to the unique antigenic peptide sequence located on an antibody's variable region near or at the antigen binding site, inhibiting by this a specific immune response by otherwise caused by the given auto-antibody. In an analogous manner synthetic peptide or peptide-based compound comprising an epitope specifically recognized by an antibody of the present invention may be used.

Anti-idiotypic antibodies may be obtained in a similar fashion as other antibodies. The particular anti-idiotypic antibody is detected by any sort of cross-linking, either by agglutination (in turbidimetric or nephelometric assays), precipitation (radial immunodiffusion), or sandwich immunoassays such as ELISAs. U.S. patent application No. 20020142356 provides a method for obtaining anti-idiotypic monoclonal antibody populations directed to an antibody that is specific for a high-concentration, high-molecular-weight target antigen wherein said anti-idiotypic antibody populations have a wide range of binding affinities for the selected antibody specific to said target antigen and wherein a subset of said anti-idiotypic antibody populations can be selected having the required affinity for a particular application.

U.S. patent application No. 20020142356 describes a competitive immunoassay of an antigen using an antibody as coat and an anti-idiotypic antibody as detection or vice-versa. Other references disclosing use of an anti-idiotypic antibody as a surrogate antigen include Losman et al., *Cancer Research*, 55 (1995) (23 suppl. S):S5978-S5982; Becker et al., *J of Immunol. Methods* 192 (1996), 73-85; Baral et al., *International J of Cancer*, 92 (2001), 88-95; and Kohen et al., *Food and Agriculture Immunology*, 12 (2000), 193-201. Use of anti-idiotypic antibodies in treatment of diseases or against parasites is known in the art; see, e.g., in Sacks et at, *J Exper. Medicine*, 155 (1982), 1108-1119.

Determination of Similarity and/or Identity of Molecules:

"Similarity" between two peptides is determined by comparing the amino acid sequence of one peptide to the sequence of a second peptide. An amino acid of one peptide is similar to the corresponding amino acid of a second peptide if it is identical or a conservative amino acid substitution. Conservative substitutions include those described in Dayhoff, M. O., ed., The Atlas of Protein Sequence and Structure 5, National Biomedical Research Foundation, Washington, D.C. (1978), and in Argos, *EMBO J* 8 (1989), 779-785. For example, amino acids belonging to one of the following groups represent conservative changes or substitutions: -Ala, Pro, Gly, Gln, Asn, Ser, Thr; -Cys, Ser, Tyr, Thr; -Val, Ile, Leu, Met, Ala, Phe; -Lys, Arg, His;-Phe, Tyr, Trp, His; and -Asp, Glu.

The determination of percent identity or similarity between two sequences is preferably accomplished using the mathematical algorithm of Karlin and Altschul (1993) *Proc. Natl. Acad. Sci USA* 90: 5873-5877. Such an algorithm is incorporated into the BLASTn and BLASTp programs of Altschul et al. (1990) *J Mal Biol.* 215: 403-410 available at NCBI (http://www.ncbi.nlm.nih.gov/blast/Blast.cge).

The determination of percent identity or similarity is performed with the standard parameters of the BLASTn and BLASTp programs. BLAST polynucleotide searches are performed with the BLASTn program. For the general parameters, the "Max Target Sequences" box may be set to 100, the "Short queries" box may be ticked, the "Expect threshold" box may be set to 10 and the "Word Size" box may be set to 28. For the scoring parameters the "Match/mismatch Scores" may be set to 1,-2 and the "Gap Costs" box may be set to linear. For the Filters and Masking parameters, the "Low complexity regions" box may not be ticked, the "Species-specific repeats" box may not be ticked, the "Mask for lookup table only" box may be ticked, and the "Mask lower case letters" box may not be ticked.

BLAST protein searches are performed with the BLASTp program. For the general parameters, the "Max Target Sequences" box may be set to 100, the "Short queries" box may be ticked, the "Expect threshold" box may be set to 10 and the "Word Size" box may be set to "3". For the scoring parameters the "Matrix" box may be set to "BLOSUM62", the "Gap Costs" Box may be set to "Existence: 11 Extension: 1", the "Compositional adjustments" box may be set to "Conditional compositional score matrix adjustment". For the Filters and Masking parameters the "Low complexity regions" box may not be ticked, the "Mask for lookup table only" box may not be ticked and the "Mask lower case letters" box may not be ticked.

Polynucleotides:

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or not fused to a nucleic acid encoding a binding molecule, an antibody, or fragment, variant, or derivative thereof. Heterologous coding regions include without limitation specialized elements or motifs, such as a secretory signal peptide or a heterologous functional domain. In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit B-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA), small hairpin RNA (shRNA), small interfering RNA (siRNA) or any other RNA product.

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full-length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse B-glucuronidase. However, intracellular production of the polypeptides, in particular of the immunoglobulins and fragments thereof of the present invention is also possible.

Expression:

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., small interfering RNA (siRNA), a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

To express the peptide, polypeptide or fusion protein (hereinafter referred to as "product") in a host cell, a procedure such as the following can be used. A restriction fragment containing a DNA sequence that encodes said product may be cloned into an appropriate recombinant plasmid containing an origin of replication that functions in the host cell and an appropriate selectable marker. The plasmid may include a promoter for inducible expression of the product (e.g., pTrc (Amann et al, *Gene* 69 (1988), 301 315) and pET1 Id (Studier et al., *Gene Expression Technology: Methods in Enzymology* 185, Academic Press, San Diego, Calif. (1990), 60 89). The recombinant plasmid may be introduced into the host cell by, for example, electroporation and cells containing the recombinant plasmid may be identified by selection for the marker on the plasmid. Expression of the product may be induced and detected in the host cell using an assay specific for the product.

In some embodiments, the DNA that encodes the product/peptide may be optimized for expression in the host cell. For example, the DNA may include codons for one or more amino acids that are predominant in the host cell relative to other codons for the same amino acid.

Alternatively, the expression of the product may be performed by in vitro synthesis of the protein in cell-free extracts which are also particularly suited for the incorporation of modified or unnatural amino acids for functional studies; see also infra. The use of in vitro translation systems can have advantages over in vivo gene expression when the over-expressed product is toxic to the host cell, when the product is insoluble or forms inclusion bodies, or when the protein undergoes rapid proteolytic degradation by intracellular proteases. The most frequently used cell-free translation systems consist of extracts from rabbit reticulocytes, wheat germ and *Escherichia coli*. All are prepared as crude extracts containing all the macromolecular components (70S or 80S ribosomes, tRNAs, aminoacyl-tRNA synthetases, initiation, elongation and termination factors, etc.) required for translation of exogenous RNA. To ensure efficient translation, each extract must be supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors known in the art ($Mg^{2+}$, K+, etc.). Appropriate transcription/translation systems are commercially available, for example from Promega Corporation, Roche Diagnostics, and Ambion, i.e. Applied Biosystems (Anderson, C. et al., *Meth. Enzymol.* 101 (1983), 635-644; Arduengo, M. et al. (2007), *The Role of Cell-Free Rabbit Reticulocyte Expression Systems in Functional Proteomics* in, Kudlicki, Katzen and Bennett eds., *Cell-Free Expression* Vol. 2007. Austin, Tx: *Landes Bioscience*, pp. 1-18; Chen and Zubay, *Meth. Enzymol.* 101 (1983), 674-90; Ezure et al., *Biotechnol. Prag.* 22 (2006), 1570-1577).

Host Cells:

In respect of the present invention, host cell can be any prokaryotic or eukaryotic cell, such as a bacterial, insect, fungal, plant, animal or human cell. Preferred fungal cells are, for example, those of the genus *Saccharomyces*, in particular those of the species *S. cerevisiae*. The term "prokaryotic" is meant to include all bacteria which can be transformed or transfected with a DNA or RNA molecules for the expression of an antibody of the invention or the corresponding immunoglobulin chains. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect and preferably mammalian cells, most preferably HEK 293, NSO, CSO and CHO cells. Depending upon the host employed in a recombinant production procedure, the antibodies or immunoglobulin chains encoded by the polynucleotide of the present invention may be glycosylated or may be non-glycosylated. Antibodies of the invention or the corresponding immunoglobulin chains may also include an initial methionine amino acid residue. A polynucleotide of the invention can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook, Molecular Cloning: *A Laboratory Manual*, Cold Spring Harbor Laboratory, Cold Spring Harbor, N.Y., 1989). The genetic constructs and methods described therein can be utilized for expression of the antibody of the invention or the corresponding immunoglobulin chains in eukaryotic or prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. Suitable source cells for the DNA sequences and host cells for immunoglobulin expression and secretion can be obtained from a number of sources, such as the American Type Culture Collection ("Catalogue of Cell Lines and Hybridomas," Fifth edition (1985) Rockville, Md., U.S.A., which is incorporated herein by reference). Furthermore, transgenic animals, preferably mammals, comprising cells of the invention may be used for the large scale production of the antibody of the invention.

The transformed hosts can be grown in fermentors and cultured according to techniques known in the art to achieve optimal cell growth. Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like; see, Scopes, "*Protein Purification*", Springer Verlag, N.Y. (1982). The antibody or its corresponding immunoglobulin chain(s) of the invention can then be isolated from the growth medium, cellular lysates, or cellular membrane fractions. The isolation and purification of the, e.g., recombinantly expressed antibodies or immunoglobulin chains of the invention may be by any conventional means such as, for example, preparative chromatographic separations and immunological separations such as those involving the use of monoclonal or polyclonal antibodies directed, e.g., against the constant region of the antibody of the invention. It will be apparent to those skilled in the art that the antibodies of the invention can be further coupled to other moieties for, e.g., drug targeting and imaging applications. Such coupling may be conducted chemically after expression of the antibody or antigen to site of attachment or the coupling product may be engineered into the antibody or antigen of the invention at the DNA level. The DNAs are then expressed in a suitable host system, and the expressed proteins are collected and renatured, if necessary.

Substantially pure immunoglobulins of at least about 90 to 95% homogeneity are preferred, and 98 to 99% or more homogeneity most preferred, for pharmaceutical uses. Once purified, partially or to homogeneity as desired, the antibodies may then be used therapeutically (including extracorporally) or in developing and performing assay procedures.

The present invention also involves a method for producing cells capable of expressing an antibody of the invention or its corresponding immunoglobulin chain(s) comprising genetically engineering cells with the polynucleotide or with the vector of the invention. The cells obtainable by the method of the invention can be used, for example, to test the interaction of the antibody of the invention with its antigen.

ELISA-Assays:

Enzyme-linked immunosorbent assays (ELISAs) for various antigens include those based on colorimetry, chemiluminescence, and fluorometry. ELISAs have been successfully applied in the determination of low amounts of drugs and other antigenic components in plasma and urine samples, involve no extraction steps, and are simple to carry out. ELISAs for the detection of antibodies to protein antigens often use direct binding of short synthetic peptides to the plastic surface of a microtitre plate. The peptides are, in general, very pure due to their synthetic nature and efficient purification methods using high-performance liquid chromatography. A drawback of short peptides is that they usually represent linear, but not conformational or discontinuous epitopes. To present conformational epitopes, either long peptides or the complete native protein is used. Direct binding of the protein antigens to the hydrophobic polystyrene support of the plate can result in partial or total denaturation of the bound protein and loss of conformational epitopes. Coating the plate with an antibody, which mediates the immobilization (capture ELISA) of the antigens, can avoid this effect.

However, frequently, overexpressed recombinant proteins are insoluble and require purification under denaturing conditions and renaturation, when antibodies to conformational epitopes are to be analyzed. See, for example, U.S. patent application No. 20030044870 for a generic ELISA using recombinant fusion proteins as coat proteins.

Binding Molecules:

A "binding molecule" as used in the context of the present invention relates primarily to antibodies, and fragments thereof, but may also refer to other non-antibody molecules that bind to the "molecules of interest" of the present invention, wherein the molecules of interest are proteins of the class of glycoproteins known as cytokines, in particular interferons selected from the group of different IFN-α subtypes. The molecules of interest of the present invention are defined in further detail within the description of the particular embodiments of the present invention above and below. The binding molecules of the present invention include but are not limited to hormones, receptors, ligands, major histocompatibility complex (MHC) molecules, chaperones such as heat shock proteins (HSPs) as well as cell-cell adhesion molecules such as members of the cadherin, intergrin, C-type lectin and immunoglobulin (lg) superfamilies. Thus, for the sake of clarity only and without restricting the scope of the present invention most of the following embodiments are discussed with respect to antibodies and antibody-like molecules which represent the preferred binding molecules for the development of therapeutic and diagnostic agents.

Antibodies:

The terms "antibody" and "immunoglobulin" are used interchangeably herein. An antibody or immunoglobulin is a molecule binding to a molecule of interest of the present invention as defined hereinabove and below, which comprises at least the variable domain of a heavy chain, and normally comprises at least the variable domains of a heavy chain and a light chain. Basic immunoglobulin structures in vertebrate systems are relatively well understood; see, e.g., Harlow and Lane, Antibodies: A Laboratory Manual, (Cold Spring Harbor Laboratory Press, 2nd ed. 1988). The terms "binds" and "recognizes" are used interchangeably in respect of the binding affinity of the binding molecules of the present invention, e.g., antibodies.

Any antibody or immunoglobulin fragment which contains sufficient structure to specifically bind to the molecules of interest, as defined hereinabove and below, is denoted herein interchangeably as a "binding molecule", "binding fragment" or an "immunospecific fragment."

Antibodies or antigen-binding fragments, immunospecific fragments, variants, or derivatives thereof of the invention include, but are not limited to, polyclonal, monoclonal, multispecific, human, humanized, primatized, murinized or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies (including, e.g., anti-Id antibodies to antibodies disclosed herein). ScFv molecules are known in the art and are described, e.g., in U.S. Pat. No. 5,892,019. In this respect, antigen-binding fragment of the antibody can be as well domain antibodies (dAb) also known as single domain antibodies (sdAB) or Nanobodies™ (Ablynx, Gent, Belgium), see, e.g., De Haard et al., *J Bacterial* 187 (2005), 4531-4541; Holt et al., *Trends Biotechnol.* 21 (2003), 484-490. As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, a, δ, ε) with some subclasses among them (e.g., γ1-γ4). It is the nature of this chain that determines the "class" of the antibody as IgG, IgE, IgM, IgD, IgA, and IgY, respectively. The immunoglobulin subclasses (isotypes)

e.g., IgG1, IgG2, IgG3, IgG4, IgA1, etc. are well characterized and are known to confer functional specialization. Immunoglobulin or antibody molecules of the invention can be of any type (e.g., IgG, IgE, IgM, IgD, IgA, and IgY), class (e.g., IgG1, IgG2, IgG3, IgG4, IgA1, IgA2, etc.) or subclass of immunoglobulin molecule. Modified versions of each of these classes and isotypes are readily discernable to the skilled artisan in view of the instant disclosure and, Accordingly, are within the scope of the instant invention. Although all immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

As evident from the classification of the exemplary anti-IFNα antibodies of the present invention enlisted in Table 1 above, the exemplary antibodies of the present invention are of the IgG1 class, possibly implicating regulatory T-cell responses and/or epithelia in their initiation in these AIRE-deficiency states. These findings are confirmed by the classification of corresponding autoantibodies found in the AIRE-deficient mice described by Kamer et al., in Clin. Exp. Immunol. (2012); doi: 10.1111/cei.12024, the disclosure content of which is incorporated herein by reference. Accordingly, in a preferred embodiment of the present invention, the antibodies of the present invention are of the IgG type, even more preferred IgG1.

IgG Structure:

Light chains are classified as either kappa or lambda (K, A). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CHI, CH2 or CH3) confer important biological properties such as secretion, transplacental mobility, Fe receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VL chains. Any antibody or immunoglobulin fragment which contains sufficient structure to specifically bind to a molecule of interest of the present invention is denoted herein interchangeably as a "binding fragment" or an "immunospecific fragment."

In naturally occurring antibodies, an antibody comprises six hypervariable regions, sometimes called "complementarity determining regions" or "CDRs" present in each antigen-binding domain, which are short, non-contiguous sequences of amino acids that are specifically positioned to form the antigen-binding domain as the antibody assumes its three dimensional configuration in an aqueous environment. The "CDRs" are flanked by four relatively conserved "framework" regions or "FRs" which show less inter-molecular variability. The framework regions largely adopt a -sheet conformation and the CDRs form loops which connect, and in some cases form part of, the -sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined; see, "Sequences of Proteins of Immunological Interest," Kabat, E., et al., US. Department of Health and Human Services, (1983); and Chothia and Lesk, J Mal. Biol. 196 (1987), 901-917, which are incorporated herein by reference in their entireties.

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., US. Dept. of Health and Human Services, "Sequences of Proteins of Immunological Interest" (1983) and by Chothia and Lesk, J Mal. Biol. 196 (1987), 901-917, which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 2 as a comparison. The exact residue numbers which encompass a particular CDR will vary depending on the sequence and size of the CDR. Those skilled in the art can routinely determine which residues comprise a particular hypervariable region or CDR of the human IgG subtype of antibody given the variable region amino acid sequence of the antibody.

TABLE 2

CDR Definitions[1]

| | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 2 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., US. Dept. of Health and Human Services, "Sequence of Proteins of Immunological Interest" (1983). Unless otherwise specified, references to the numbering of specific amino acid residue positions in an antibody or antigen-binding fragment, variant, or derivative thereof of the present invention are according to the Kabat numbering system, which however is theoretical and may not equally apply to every antibody of the present invention. For example, depending on the position of the first CDR the following CDRs might be shifted in either direction.

In one embodiment, the antibody of the present invention is not IgM or a derivative thereof with a pentavalent structure. Particular, in specific applications of the present invention, especially therapeutic use, IgMs are less useful than IgG and other bivalent antibodies or corresponding binding molecules since IgMs due to their pentavalent structure and lack of affinity maturation often show unspecific cross-reactivities and very low affinity.

In a particularly preferred embodiment, the antibody of the present invention is not a polyclonal antibody, i.e. it substantially consists of one particular antibody species rather than being a mixture obtained from a plasma immunoglobulin sample.

Antibody Fragments, Animalization:

Antibody fragments, including single-chain antibodies, may comprise the variable region(s) alone or in combination with the entirety or a portion of the following: hinge region, CHI, CH2, and CH3 domains. Also included in the invention are fragments binding to a molecule of interest of the present invention, said fragments comprising any combination of variable region(s) with a hinge region, CHI, CH2, and CH3 domains. Antibodies or immunospecific fragments thereof of the present invention equivalent to the monoclonal antibodies isolated in accordance with the method of the present invention, in particular to the human monoclonal antibodies may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

In a particularly preferred embodiment of the present invention, the antibodies are naturally occurring human monoclonal antibodies or binding fragments, derivatives and variants thereof cloned from human subjects, which bind specifically to specific IFNα subtypes of the present invention, as defined in detail above and below, e.g., in Table 1, the Figures, in particular FIGS. 1 to 4 and in the Examples, e.g., in Examples 2 and 6.

Optionally, the framework region of the human antibody is aligned and adopted in accordance with the pertinent human germ line variable region sequences in the database; see, e.g., Vbase (http://vbase.mrc-cpe.cam.ac.uk/) hosted by the MRC Centre for Protein Engineering (Cambridge, UK). For example, amino acids considered to potentially deviate from the true germ line sequence could be due to the PCR primer sequences incorporated during the cloning process. Compared to artificially generated human-like antibodies such as single chain antibody fragments (scFvs) from a phage displayed antibody library or xenogeneic mice the human monoclonal antibody of the present invention is characterized by (i) being obtained using the human immune response rather than that of animal surrogates, i.e. the antibody has been generated in response to natural IFNα subtypes in their relevant conformation in the human body, (ii) having protected the individual from or minimized at least significant the presence of symptoms of a disease, e.g., SLE, and (iii) since the antibody is of human origin the risks of cross-reactivity against self-antigens is minimized. Thus, in accordance with the present invention the terms "human monoclonal antibody", "human monoclonal autoantibody", "human antibody" and the like are used to denote a IFN-α binding molecule of a particular IFN-α subtype specificity which is of human origin, i.e. which has been isolated from a human cell such as a B cell or hybridoma thereof or the cDNA of which has been directly cloned from mRNA of a human cell, for example a human memory B cell. A human antibody is still considered as "human" even if amino acid substitutions are made in the antibody, e.g., to improve its binding characteristics.

Antibodies derived from human immunoglobulin libraries or from animals transgenic for one or more human immunoglobulins and that do not express endogenous immunoglobulins, as described infra and, for example in, U.S. Pat. No. 5,939,598 by Kucherlapati et al., are denoted human-like antibodies in order distinguish them from truly human antibodies of the present invention.

For example, the paring of heavy and light chains of human-like antibodies such as synthetic and semi-synthetic antibodies typically isolated from phage display do not necessarily reflect the original paring as it occurred in the original human B cell. Accordingly Fab and scFv fragments obtained from recombinant expression libraries as commonly used in the prior art can be considered as being artificial with all possible associated effects on immunogenicity and stability.

In contrast, the present invention provides isolated affinity-matured antibodies from selected human subjects, which are characterized by their therapeutic utility.

Grafted Antibodies {Equivalents)

The invention also relates to grafted antibodies (interchangeably referred to as equivalents) containing CDRs derived from the antibodies of the present invention, such as anti-IFN-a antibodies, respectively. Such grafted CDRs include animalized antibodies, in which CDRs from the antibodies of the present invention have been grafted or in which a CDR containing one or more amino acid substitutions is grafted. The CDRs can be grafted directly into a human framework or an antibody framework from animal origin as indicated above. If desired, framework changes can also be incorporated by generating framework libraries. The optimization of CDRs and/or framework sequences can be performed independently and sequentially combined or can be performed simultaneously, as described in more detail below.

To generate grafted antibodies donor CDRs of the antibodies of the present invention are grafted onto an antibody acceptor variable region framework. Methods for grafting antibodies and generating CDR variants to optimize activity have been described previously (see, e.g., international patent applications WO 98/33919; WO 00/78815; WO 01/27160). The procedure can be performed to achieve grafting of donor CDRs and affinity reacquisition in a simultaneous process. The methods similarly can be used, either alone or in combination with CDR grafting, to modify or optimize the binding affinity of a variable region. The methods for conferring donor CDR binding affinity onto an acceptor variable region are applicable to both heavy and light chain variable regions and as such can be used to simultaneously graft and optimize the binding affinity of an antibody variable region.

The donor CDRs can be altered to contain a plurality of different amino acid residue changes at all or selected positions within the donor CDRs. For example, random or biased incorporation of the twenty naturally occurring amino acid residues, or preselected subsets, can be introduced into the donor CDRs to produce a diverse population of CDR species. Inclusion of CDR variant species into the diverse population of variable regions allows for the generation of variant species that exhibit optimized binding affinity for a predetermined antigen. A range of possible changes can be made in the donor CDR positions. Some or all of the possible changes that can be selected for change can be introduced into the population of grafted donor CDRs. A single position in a CDR can be selected to introduce changes or a variety of positions having altered amino acids can be combined and screened for activity.

One approach is to change all amino acid positions along a CDR by replacement at each position with, for example, all twenty naturally occurring amino acids. The replacement of each position can occur in the context of other donor CDR amino acid positions so that a significant portion of the CDR maintains the authentic donor CDR sequence, and therefore, the binding affinity of the donor CDR. For example, an acceptor variable region framework, either a native or altered framework, can be grafted with a population of CDRs containing single position replacements at each position within the CDRs. Similarly, an acceptor variable region framework can be targeted for grafting with a population of CDRs containing more than one position changed to incorporate all twenty amino acid residues, or a subset of amino acids. One or more amino acid positions within a CDR, or within a group of CDRs to be grafted, can be altered and grafted into an acceptor variable region framework to generate a population of grafted antibodies. It is understood that a CDR having one or more altered positions can be combined with one or more other CDRs having one or more altered positions, if desired.

A population of CDR variant species having one or more altered positions can be combined with any or all of the CDRs which constitute the binding pocket of a variable region. Therefore, an acceptor variable region framework can be targeted for the simultaneous incorporation of donor CDR variant populations at one, two or all three recipient CDR locations in a heavy or light chain. The choice of which CDR or the number of CDRs to target with amino acid position changes will depend on, for example, if a full CDR grafting into an acceptor is desired or whether the method is being performed for optimization of binding affinity.

Another approach for selecting donor CDR amino acids to change for conferring donor CDR binding affinity onto an antibody acceptor variable region framework is to select known or readily identifiable CDR positions that are highly variable. For example, the variable region CDR3 is generally highly variable. This region therefore can be selectively targeted for amino acid position changes during grafting procedures to ensure binding affinity reacquisition or augmentation, either alone or together with relevant acceptor variable framework changes.

Murinized Antibodies:

An example of antibodies generated by grafting, as described above, are murinized antibodies. As used herein, the term "murinized antibody" or "murinized immunoglobulin" refers to an antibody comprising one or more CDRs from a human antibody of the present invention; and a human framework region that contains amino acid substitutions and/or deletions and/or insertions that are based on a mouse antibody sequence. The human immunoglobulin providing the CDRs is called the "parent" or "acceptor" and the mouse antibody providing the framework changes is called the "donor". Constant regions need not be present, but if they are, they are usually substantially identical to mouse antibody constant regions, i.e. at least about 85-90%, preferably about 95% or more identical. Hence, in some embodiments, a full-length murinized human heavy or light chain immunoglobulin contains a mouse constant region, human CDRs, and a substantially human framework that has a number of "murinizing" amino acid substitutions. Typically, a "murinized antibody" is an antibody comprising a murinized variable light chain and/or a murinized variable heavy chain. For example, a murinized antibody would not encompass a typical chimeric antibody, e.g., because the entire variable region of a chimeric antibody is non-mouse. A modified antibody that has been "murinized" by the process of "murinization" binds to the same antigen as the parent antibody that provides the CDRs and is usually less immunogenic in mice, as compared to the parent antibody.

Antibody Fragments:

As used herein, the term "heavy chain portion" includes amino acid sequences derived from an immunoglobulin heavy chain. A polypeptide comprising a heavy chain portion comprises at least one of: a CHI domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CHI domain; a polypeptide chain comprising a CHI domain, at least a portion of a hinge domain, and a CH2 domain; a polypeptide chain comprising a CHI domain and a CH3 domain; a polypeptide chain comprising a CHI domain, at least a portion of a hinge domain, and a CH3 domain, or a polypeptide chain comprising a CHI domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain antibodies, or antigen-binding fragments, variants, or derivatives thereof disclosed herein, the heavy chain portions of one polypeptide chain of a multimere are identical to those on a second polypeptide chain of the multimere. Alternatively, heavy chain portion-containing monomers of the invention are not identical. For example, each monomer may comprise a different target binding site, forming, for example, a bispecific antibody or diabody.

In another embodiment, the antibodies, or antigen-binding fragments, variants, or derivatives thereof disclosed herein are composed of a single polypeptide chain such as scFvs and are to be expressed intracellularly (intrabodies) for potential in vivo therapeutic and diagnostic applications.

The heavy chain portions of a binding polypeptide for use in the diagnostic and treatment methods disclosed herein may be derived from different immunoglobulin molecules. For example, a heavy chain portion of a polypeptide may comprise a CHI domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

Thus, as also exemplified in the Examples, in one embodiment the constant region of the antibody of the present invention or part thereof, in particular the CH2 and/or CH3 domain but optionally also the CHI domain is heterologous to the variable region of the native human monoclonal antibody isolated in accordance with the method of the present invention. In this context, the heterologous constant region(s) are preferably of human origin in case of therapeutic applications of the antibody of the present invention but could also be of for example rodent origin in case of animal studies; see also the Examples.

As used herein, the term "light chain portion" includes amino acid sequences derived from an immunoglobulin light chain. Preferably, the light chain portion comprises at least one of a VL or CL domain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CHI domain" includes the first (most amino terminal) constant region domain of an immunoglobulin heavy chain. The CHI domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CHI domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains; see Roux et al., *J Immunol.* 161 (1998), 4083.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CHI and CL regions are linked by a disulfide bond and the two heavy chains are linked by two disulfide bonds at positions corresponding to 239 and 242 using the Kabat numbering system (position 226 or 229, EU numbering system).

As used herein, the terms "linked", "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide. Accordingly, in one embodiment the polynucleotide is a cDNA encoding the variable region and at least part of the constant domain. In one embodiment the polynucleotide is a cDNA encoding the variable region and the constant domain of an antibody of the present invention as defined herein.

Epitopes:

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, a peptide or polypeptide epitope recognized by antibodies of the present invention contains a sequence of at least 4, at least 5, at least 6, at least 7, more preferably at least 8, at least 9, at least 10, at least 15, at least 20, at least 25, between about 15 to about 30 or between about 30 to about 50 contiguous or non-contiguous amino acids of a molecule of interest of the present invention, i.e. at least one IFN-α subtype, or the homologous sequences of the other IFN-α subtypes, in case the antibody recognizes more than one subtype. For mapping of epitopes of IFN-α2 for the exemplary antibodies 19D11 and 26B9 and of epitope of IFN-ω for the exemplary antibody 26B9 of the present invention see FIG. 27.

Binding Characteristics:

By "binding" or "recognizing", used interchangeably herein, it is generally meant that a binding molecule, e.g., an antibody binds to a predetermined epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D". Unrelated epitopes are usually part of a nonspecific antigen (e.g., BSA, casein, or any other specified polypeptide), which may be used for the estimation of the binding specificity of a given binding molecule. In this respect, term "specific binding" refers to antibody binding to a predetermined antigen with a Ko that is at least twofold less than its Ko for binding to a nonspecific antigen. The term "highly specific" binding as used herein means that the relative Ko of the antibody for the specific target epitope is at least 10-fold less than the Ko for binding that antibody to other ligands.

Where present, the term "immunological binding characteristics," or other binding characteristics of an antibody with an antigen, in all of its grammatical forms, refers to the specificity, affinity, cross-reactivity, and other binding characteristics of an antibody.

By "preferentially binding", it is meant that the binding molecule, e.g., antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope. In respect of particular antigens, such as specific IFN-α subtypes the term "preferentially binding" means that the binding molecule, e.g., antibody specifically binds to an IFN-α subtype more readily than it would bind to a related, similar, homologous, or analogous IFN-α subtype.

By way of non-limiting example, a binding molecule, e.g., an antibody may be considered to bind a first epitope preferentially if it binds said first epitope with dissociation constant (Ko) that is less than the antibody's Ko for the second epitope. In another non-limiting example, an antibody may be considered to bind a first antigen preferentially if it binds the first epitope with an affinity that is at least one order of magnitude less than the antibody's Ko for the second epitope. In another non-limiting example, an antibody may be considered to bind a first epitope preferentially if it binds the first epitope with an affinity that is at least two orders of magnitude less than the antibody's Ko for the second epitope.

In another non-limiting example, a binding molecule, e.g., an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

A binding molecule, e.g., an antibody or antigen-binding fragment, variant, or derivative is closed herein may be said to bind a molecule of interest of the present invention, a fragment or variant thereof with an off rate (k(off)) of less than or equal to $5\times10-2$ sec-1, $10-2$ sec-1, $5\times10-3$ sec-1 or $10-3$ sec-1. More preferably, an antibody of the invention may be said to bind a molecule of interest of the present invention or a fragment or variant thereof with an off rate (k(off)) less than or equal to $5\times10^{-4}$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$-^{10}$ or $10^{-7}$ sec$^{-1}$.

A binding molecule, e.g., an antibody or antigen-binding fragment, variant, or derivative disclosed herein may be said to bind a molecule of interest of the present invention or a fragment or variant thereof with an on rate (k(on)) of greater than or equal to $10^3$ M$^{-1}$ sec$^{-1}$, $5\times10^3$ M$^{-1}$ sec$^{-1}$, $10^4$M$^{-1}$ sec$^{-1}$ or $5\times10^4$M$^{-1}$ sec$^{-1}$. More preferably, an antibody of the invention may be said to bind a molecule of interest of the present invention or a fragment or variant thereof with an on rate (k(on)) greater than or equal to $10^5$M$^{-1}$ sec$^{-1}$, $5\times10^5$ M$^{-1}$ sec$^{-1}$, $10^6$ M$^{-1}$ sec$^{-1}$, or $5\times10^6$M$^{-1}$ sec$^{-1}$ or $10^7$M$^{-1}$ sec$^{-1}$. A binding molecule, e.g., an antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of a binding molecule, e.g., an immunoglobulin molecule; see, e.g., Harlow et al., *Antibodies: A Laboratory Manual*, Cold Spring Harbor Laboratory Press, 2nd ed. (1988) at pages 27-28. As used herein, the term "avidity" refers to the overall stability of the complex between a population of immunoglobulins and an antigen, that is, the functional combining strength of an immunoglobulin mixture with the antigen; see, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity. The affinity or avidity of an antibody for an antigen can be determined experimentally using any suitable method; see, for example, Berzofsky et al., "Antibody-Antigen Interactions" In *Fundamental Immunology*, Paul, W. E., Ed., Raven Press New York, N.Y. (1984), Kuby, *Janis Immunology*, W H Freeman and Company New York, N.Y. (1992), and methods described therein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., Ko, ICso, are preferably made with standardized solutions of antibody and antigen, and a standardized buffer.

Binding molecules, e.g., antibodies or antigen-binding fragments, variants or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Binding molecules, e.g., antibodies or antigen-binding fragments, variants or derivatives thereof of the invention may also be described or specified in terms of their binding affinity to a molecule of interest of the present invention. Preferred binding affinities include those with a dissociation constant or $K_D$ less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M. Typically, the antibody binds with a dissociation constant ($K_D$) of $10^{-7}$ M or less to its predetermined antigen. Preferably, the antibody binds its cognate antigen with a dissociation constant ($K_D$) of 10-9 M or less and still more preferably with a dissociation constant ($K_D$) of $10^{-11}$ M or less.

Modifications of Antibodies:

The immunoglobulin or its encoding cDNAs may be further modified. Thus, in a further embodiment the method of the present invention comprises any one of the step(s) of producing a chimeric antibody, humanized antibody, single-chain antibody, Fab-fragment, bi-specific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to the same epitope as that of any one of the antibodies provided by the present invention (Schier, *Human Antibodies Hybridomas* 7 (1996), 97-io5; Malmborg, *J Immunol. Methods* 183 (1995), 7-13). The production of chimeric antibodies is described, for example, in international application WO89/09622. Methods for the production of humanized antibodies are described in, e.g., European application EP-Al O 239 400 and international application WO90/07861. Further sources of antibodies to be utilized in accordance with the present invention are so-called xenogeneic antibodies. The general principle for the production of xenogeneic antibodies such as human antibodies in mice is described in, e.g., international applications WO91/10741, WO94/02602, WO96/34096 and WO 96/33735. As discussed above, the antibody of the invention may exist in a variety of forms besides complete antibodies; including, for example, Fv, Fab and F(ab)2, as well as in single chains; see e.g. international application WO88/09344.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, *Molecular Cloning A Laboratory Manual*, Cold Spring Harbor Laboratory (1989) N.Y. and Ausubel, *Current Protocols in Molecular Biology*, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins which comprise the described antibody or some fragment thereof at the amino terminus fused to heterologous molecule such as a label or a drug. Antigen binding molecules generated this way may be used for drug localization to cells expressing the appropriate surface structures of the diseased cell and tissue, respectively. This targeting and binding to cells could be useful for the delivery of therapeutically or diagnostically active agents and gene therapy/gene delivery. Molecules/particles with an antibody of the invention would bind specifically to cells/tissues expressing the particular antigen of interest, and therefore could have diagnostic and therapeutic use.

Samples:

As used herein, the term "sample" or "biological sample" refers to any biological material obtained from a subject or patient. In one aspect, a sample can comprise blood, cerebrospinal fluid ("CSF"), or urine. In other aspects, a sample can comprise whole blood, plasma, mononuclear cells enriched from peripheral blood (PBMC) such as lymphocytes (i.e. T-cells, NK-cell or B-cells), monocytes, macrophages, dendritic cells and basophils; and cultured cells (e.g., B-cells from a subject). A sample can also include a biopsy or tissue sample including tumor tissue. In still other aspects, a sample can comprise whole cells and/or a lysate of the cells. In one embodiment a sample comprises peripheral blood mononuclear cells (PBMC). Samples can be collected by methods known in the art.

Identification of Anti-IFN-α Antibodies, Isolation of Corresponding B Cells and Recombinant Expression of Anti-IFN-α Antibodies:

Identification of B-cells specific for the anti-IFN-α antibodies of the present invention, as enlisted in Table 1, and as exemplary shown for several IFN-α subtypes and molecular cloning of antibodies displaying specificity of interest as well as their recombinant expression and functional characterization can be generally performed as described in the international applications WO2013/098419 and WO2013/098420; see Examples sections therein, in particular Examples 1 and 2 on pages 118 to 120 of WO2013/098419 and Examples 1 to 4 on pages 27 to 31 of WO2013/098420, the disclosure content of which is incorporated herein by reference.

Briefly, in one embodiment of the present invention cultures of single or oligoclonal B-cells were cultured and the supernatant of the culture, which contains antibodies produced by said B-cells was screened for presence and affinity of antibodies specific for one or more of the IFN-a subtypes, as described in the Examples. In another embodiment, patient sera were first screened for the presence of autoantibodies against IFN-α subtypes and then those with high titer were selected for peripheral blood mononuclear cells isolation; see Example 2 on pages 118-120 of WO2013/098419, the disclosure content of which is incorporated herein by reference. The screening process comprises screening for binding on fragments, peptides or derivatives of IFN-α subtypes. Subsequently, the antibody for which binding is detected or the cell producing said antibody were isolated; see Example 3 on page 120 of WO2013/098419, the disclosure content of which is incorporated herein by reference. Thus, a preliminary screen can be done on a panel of candidate donors, using samples containing antibody secreting cells (such as total peripheral blood or serum). In particular, mononuclear cells can be isolated from blood or lymphatic tissues using standard separation techniques for isolating peripheral blood mononuclear cells (PBMCs), such as gradient centrifugation. After and/or before this separation step, the samples of sera (or plasma), cell culture supernatants, or cells (obtained from different patients, from different tissues, and/or at different time points) can be prescreened using standard technologies for detecting the presence of antibodies and antibody-secreting cells (e.g. ELISA, BIACORE, Western blot, FACS, SERPA, antigen arrays, neutralization of viral infection in a cell culture system, or ELISPOT assays). The literature provides several examples of these technologies showing, for example, the use of ELISPOT for characterizing the immune response in vaccinated donors (Crotty et al., Immunol Meth. 286 (2004), 111-122), the use of antigen microarrays as diagnostic tools for newly infected patients (Mezzasoma et al., Clin Chem. 48 (2002), 121-130, and other technologies for measuring antigen-specific immune responses (Kem et al., Trends Immunol. 26 (2005), 477-484).

After identification of candidate anti-IFN-α antibodies and B cells secreting them, respectively, the nucleic acid sequence that encodes the antibody of interest is obtained, comprising the steps of preparing a B cell and obtaining/sequencing nucleic acid from the B cell that encodes the antibody of interest and further inserting the nucleic acid into or using the nucleic acid to prepare an expression host that can express the antibody of interest, culturing or subculturing the expression host under conditions where the antibody of interest is expressed and, optionally, purifying the antibody of interest. It goes without saying that the nucleic acid may be manipulated in between to introduce restriction sites, to change codon usage, and/or to add or optimize transcription and/or translation regulatory sequences. These techniques are state of the art and can be performed by the person skilled in the art without undue burden. For example, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Once the genetic material is available, design of analogs as described above which retain both their ability to bind the desired target is straightforward. Methods for the cloning of antibody variable regions and generation of recombinant antibodies are known to the person skilled in the art and are described, for example, in Gilliland et al., *Tissue Antigens* 47 (1996), 1-20; Doenecke et al., *Leukemia* 11 (1997), 1787-1792. In a preferred embodiment of the present invention however, B cells are obtained and the corresponding antibody is expressed by the methods described in international application WO2013/098420, in particular in Example 3, on pages 28-30 therein, the disclosure content of which is incorporated herein by reference.

Diseases and Disorders:

Unless stated otherwise, the terms "disorder" and "disease" are used interchangeably herein. The term "autoimmune disorder" as used herein is a disease or disorder arising from and directed against an individual's own tissues or organs or a co-segregate or manifestation thereof or resulting condition therefrom. Autoimmune diseases are primarily caused by dysregulation of adaptive immune responses and autoantibodies or autoreactive T cells against self-structures are formed. Nearly all autoimmune diseases have an inflammatory component, too. Autoinflammatory diseases are primarily inflammatory, and some classic autoinflammatory diseases are caused by genetic defects in innate inflammatory pathways. In autoinflammatory diseases, no autoreactive T cells or autoantibodies are found. In many of these autoimmune and autoinflammatory disorders, a number of clinical and laboratory markers may exist, including, but not limited to, hypergammaglobulinemia, high levels of autoantibodies, antigen-antibody complex deposits in tissues, benefit from corticosteroid or immunosuppressive treatments, and lymphoid cell aggregates in affected tissues. Without being limited to a theory regarding B-cell mediated autoimmune disorder, it is believed that B cells demonstrate a pathogenic effect in human autoimmune diseases through a multitude of mechanistic pathways, including autoantibody production, immune complex formation, dendritic and T-cell activation, cytokine synthesis, direct chemokine release, and providing a nidus for ectopic neo-lymphogenesis. Each of these pathways may participate to different degrees in the pathology of autoimmune diseases.

As used herein, an "autoimmune disorder" can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease that can affect multiple organ systems (for example, systemic lupus erythematosus (SLE), rheumatoid arthritis, polymyositis, autoimmune polyendocrinopathy syndrome type 1 (APS1)/autoimmune polyendocrinopathy-candidiasis-ectodermal dystrophy (APECED) etc. Preferred such diseases include autoimmune rheumatologic disorders (such as, for example, rheumatoid arthritis, Sjogren's syndrome, scleroderma, lupus such as SLE and lupus nephritis, polymyositis/dermatomyositis, and psoriatic arthritis), autoimmune dermatologic disorders (such as, for example, psoriasis, pemphigus group diseases, bullous pemphigoid diseases, and cutaneous lupus erythematosus), and autoimmune endocrine disorders (such as, for example, diabetic-related autoimmune diseases such as type 1 or insulin dependent diabetes mellitus (T1DM or IDDM), autoimmune thyroid disease (e.g., Graves' disease and thyroiditis)) and diseases affecting the generation of autoimmunity such as autoimmune polyendocrinopathy syndrome type 1 (APS1)/autoimmune polyendocrinopathy-candidiasis-ectodermal dystrophy (APECED) Myasthenia Gravis (MG/Thymoma). Preferred diseases include, for example, SLE, RA, T1DM, MS, Sjogren's syndrome, Graves' disease, thyroiditis, and glomerulonephritis, and APS1. Still more preferred are RA, SLE, and MS, and mostly preferred SLE.

Labels and Diagnostics:

Labeling agents can be coupled either directly or indirectly to the antibodies or antigens of the invention. One example of indirect coupling is by use of a spacer moiety.

Furthermore, the antibodies of the present invention can comprise a further domain, said domain being linked by covalent or non-covalent bonds. The linkage can be based on genetic fusion according to the methods known in the art and described above or can be performed by, e.g., chemical cross-linking as described in, e.g., international application WO94/04686. The additional domain present in the fusion protein comprising the antibody of the invention may preferably be linked by a flexible linker, advantageously a polypeptide linker, wherein said polypeptide linker comprises plural, hydrophilic, peptide-bonded amino acids of a length sufficient to span the distance between the C-terminal end of said further domain and the N-terminal end of the antibody of the invention or vice versa. The therapeutically or diagnostically active agent can be coupled to the antibody of the invention or an antigen-binding fragment thereof by various means. This includes, for example, single-chain fusion proteins comprising the variable regions of the antibody of the invention coupled by covalent methods, such as peptide linkages, to the therapeutically or diagnostically active agent. Further examples include molecules which comprise at least an antigen-binding fragment coupled to additional molecules covalently or on-covalently include those in the following non-limiting illustrative list. Traunecker, *Int. J Cancer Surp. SuDP* 7 (1992), 51-52, describe the bispecific reagent janusin in which the Fv region directed to CD3 is coupled to soluble CD4 or to other ligands such as OVCA and IL-7. Similarly, the variable regions of the antibody of the invention can be constructed into Fv molecules and coupled to alternative ligands such as those illustrated in the cited article. Higgins, *J Infect. Disease* 166 (1992), 198-202, described a hetero-conjugate antibody composed of OKT3 cross-linked to an antibody directed to a specific sequence in the V3 region of GP120. Such hetero-conjugate antibodies can also be constructed using at least the variable regions contained in the antibody of the invention methods. Additional examples of specific antibodies include those described by Fanger, *Cancer Treat. Res.* 68 (1993), 181-194 and by Fanger, *Crit. Rev. Immunol.* 12 (1992), 101-124. Conjugates that are immunotoxins including conventional antibodies have been widely described in the art. The toxins may be coupled to the antibodies by conventional coupling techniques or immunotoxins containing protein toxin portions can be produced as fusion proteins. The antibodies of the present invention can be used in a corresponding way to obtain such immunotoxins. Illustrative of such immunotoxins are those described by Byers, *Seminars Cell. Biol.* 2 (1991), 59-70 and by Fanger, *Immunol. Today* 12 (1991), 51-54.

The above described fusion protein may further comprise a cleavable linker or cleavage site for proteinases. These spacer moieties, in turn, can be either insoluble or soluble (Diener et al., *Science* 231 (1986), 148) and can be selected to enable drug release from the antigen at the target site. Examples of therapeutic agents which can be coupled to the antibodies and antigens of the present invention for immunotherapy are chemokines, homing molecules, drugs, radioisotopes, lectins, and toxins. The $^{127}$I, $^{131}$I, $^{111}$In, $^{177}$Lu, $^{15}$O, $^{13}$N, $^{32}$P, $^{33}$P, $^{203}$Pb, $^{186}$Re, $^{188}$Re, $^{105}$Rh, $^{97}$Rh, $^{35}$S, $^{153}$Sm and $^{99m}$Tc. drugs with which can be conjugated to the antibodies and antigens of the present invention depend on the disease context in which the conjugated molecules are intended to be used. For example, antibodies specific for targets useful in treatment of tumor diseases can be conjugated to compounds which are classically referred to as anti-neoplastic drugs such as mitomycin C, daunorubicin, and vinblastine. In using radioisotopically conjugated antibodies or antigens of the invention for, e.g., tumor immunotherapy, certain isotopes may be more preferable than others depending on such factors as leukocyte distribution as well as stability and emission. Depending on the autoimmune response, some emitters may be preferable to others. In general, a and B particle emitting radioisotopes are preferred in immunotherapy. Preferred are short range, high energy a emitters such as $^{212}$Bi. Examples of radioisotopes which can be bound to the antibodies or antigens of the invention for therapeutic purposes are $^{125}$I, $^{131}$I, $^{90}$Y, $^{67}$Cu, $^{212}$Bi, $^{212}$At, $^{211}$Pb, $^{47}$Sc, $^{109}$Pd and $^{188}$Re. Other therapeutic agents which can be coupled to the antibody or antigen of the invention, as well as ex vivo and in vivo therapeutic protocols, are known, or can be easily ascertained, by those of ordinary skill in the art. Non-limiting examples of suitable radionuclides for labeling are $^{198}$Au, $^{212}$Bi, $^{11}$C, $^{14}$C, $^{57}$Co, $^{67}$Cu, $^{18}$F, $^{67}$Ga, $^{3}$H, $^{166}$Ho, $^{111}$In, $^{113m}$In, $^{123}$I, $^{125}$I, $^{127}$I, $^{131}$I, $^{111}$In, $^{177}$Lu, $^{15}$O, $^{13}$N, $^{32}$P, $^{33}$P, $^{203}$Pb, $^{186}$Re, $^{188}$Re, $^{105}$Rh, $^{97}$Ru, $^{35}$S, $^{153}$Sm, and $^{99m}$Tc. Other molecules suitable for labeling are a fluorescent or luminescent dye, a magnetic particle, a metal, and a molecule which may be detected through a secondary enzymatic or binding step such as an enzyme or peptide tag. Commercial fluorescent probes suitable for use as labels in the present invention are listed in the Handbook of Fluorescent Probes and Research Products, 8th Edition, the disclosure contents of which are incorporated herein by reference. Magnetic particles suitable for use in magnetic particle-based assays (MPAs) may be selected from paramagnetic, diamagnetic, ferromagnetic, ferromagnetic and superpara-magnetic materials.

General methods in molecular and cellular biochemistry useful for diagnostic purposes can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996). Reagents, detection means and kits for diagnostic purposes are available from commercial vendors such as Pharmacia Diagnostics, Amersham, Bio-Rad, Stratagene, Invitrogen, and Sigma-Aldrich as well as from the sources given any one of the references cited herein, in particular patent literature.

Treatment and Drugs:

As used herein, the terms "treat" or "treatment" refer to both therapeutic treatment and prophylactic or preventative measures, wherein the object is to prevent or slow down (lessen) an undesired physiological change or disorder, such as the development of an autoimmune and/or autoinflammatory disease. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented.

If not stated otherwise the term "drug," "medicine," or "medicament" are used interchangeably herein and shall include but are not limited to all (A) articles, medicines and preparations for internal or external use, and any substance or mixture of substances intended to be used for diagnosis, cure, mitigation, treatment, or prevention of disease of either man or other animals; and (B) articles, medicines and preparations (other than food) intended to affect the structure or any function of the body of man or other animals; and (C) articles intended for use as a component of any article specified in clause (A) and (B). The term "drug," "medicine," or "medicament" shall include the complete formula of the preparation intended for use in either man or other animals containing one or more "agents," "compounds", "substances" or "(chemical) compositions" as and in some other context also other pharmaceutically inactive excipients as fillers, disintegrants, lubricants, glidants, binders or ensuring easy transport, disintegration, disaggregation, dissolution and biological availability of the "drug," "medicine," or "medicament" at an intended target location within the body of man or other animals, e.g., at the skin, in the stomach or the intestine. The terms "agent," "compound" or "substance" are used interchangeably herein and shall include, in a more particular context, but are not limited to all pharmacologically active agents, i.e. agents that induce a desired biological or pharmacological effect or are investigated or tested for the capability of inducing such a possible pharmacological effect by the methods of the present invention.

Examples of "anti-rheumatic drugs" and immunosuppressive drugs include chloroquine, hydroxycloroquine, myocrisin, auranofin, sulfasalazine, methotrexate, leflunomide, etanercept, infliximab (plus oral and subcutaneous methotrexate), adalimumab etc., azathioprine, D-penicilamine, gold salts (oral), gold salts (intramuscular), minocycline, cyclosporine including cyclosporine A and topical cyclosporine, tacrolimus, mycophenolate mofetil, cyclophosphamide, staphylococcal protein A (Goodyear and Silverman, J. Exp. Med., 197 (2003), 125-39), including salts and derivatives thereof, etc.

Examples of "non-steroidal anti-inflammatory drugs" or "NSAIDs" include aspmn, acetylsalicylic acid, ibuprofen and ibuprofen retard, fenoprofen, piroxicam, flurbiprofen, naproxen, ketoprofen, naproxen, tenoxicam, benorylate, diclofenac, naproxen, nabumetone, indomethacin, ketoprofen, mefenamic acid, diclofenac, fenbufen, azapropazone, acemetacin, tiaprofenic acid, indomethacin, sulindac, tolmetin, phenylbutazone, diclofenac and diclofenac retard, cyclooxygenase (COX)-2 inhibitors such as GR 253035, MK966, celecoxib (CELEBREX®; 4-(5-(4-methylphenyl)-3-(trifluoromethyl)-1H-pyrazol-1-yl), benzenesulfon-amide and valdecoxib (BEXTRA®), and meloxicam (MOBIC®), including salts and derivatives thereof, etc. Preferably, they are aspirin, naproxen, ibuprofen, indomethacin, or tolmetin. Such NSAIDs are optionally used with an analgesic such as codenine, tramadol, and/or dihydrocodinine or narcotic such as morphine.

By "subject" or "individual" or "animal" or "patient" or "mammal," is meant any subject, particularly a mammalian subject, e.g., a human patient, for whom diagnosis, prognosis, prevention, or therapy is desired.

Pharmaceutical Carriers:

Pharmaceutically acceptable earners and administration routes can be taken from corresponding literature known to the person skilled in the art. The pharmaceutical compositions of the present invention can be formulated according to methods well known in the art; see for example Remington: *The Science and Practice of Pharmacy* (2000) by the University of Sciences in Philadelphia, ISBN 0-683-306472, *Vaccine Protocols*. 2nd Edition by Robinson et al., Humana Press, Totowa, N.J., USA, 2003; Banga, *Therapeutic Peptides and Proteins: Formulation, Processing, and Delivery Systems*. 2nd Edition by Taylor and Francis. (2006), ISBN: 0-8493-1630-8. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods. Aerosol formulations such as nasal spray formulations include purified aqueous or other solutions of the active agent with preservative agents and isotonic agents. Such formulations are preferably adjusted to a pH and isotonic state compatible with the nasal mucous membranes. Pharmaceutical compositions for oral administration, such as single domain antibody molecules (e.g., "Nanobodies™") etc are also envisaged in the present invention. Such oral formulations may be in tablet, capsule, powder, liquid or semi-solid form. A tablet may comprise a solid carrier, such as gelatin or an adjuvant. Formulations for rectal or vaginal administration may be presented as a suppository with a suitable carrier; see also O'Hagan et al., *Nature Reviews, Drug Discovery* 2(9) (2003), 727-735. Further guidance regarding formulations that are suitable for various types of administration can be found in *Remington's Pharmaceutical Sciences*, Mace Publishing Company, Philadelphia, Pa., 17th ed. (1985) and corresponding updates. For a brief review of methods for drug delivery see Langer, *Science* 249 (1990), 1527-1533.

Dosage Regimen:

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg (or of nucleic acid for expression or for inhibition of expression in this range); however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per minute, respectively. Progress can be monitored by periodic assessment. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as anti-tumor agents and cytotoxic drugs, depending on the intended use of the pharmaceutical composition.

In addition, co-administration or sequential administration of other agents may be desirable. A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

Preferably, the therapeutic agent in the composition is present in an amount sufficient for preventing inflammation or suppression of the immune response.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, *TIBTECH* 12 (1994), 352-364.

The above disclosure generally describes the present invention. Several documents are cited throughout the text of this specification. Full bibliographic citations may be found at the end of the specification immediately preceding the claims. The contents of all cited references (including literature references, issued patents, published patent applications as cited throughout this application and manufacturer's specifications, instructions, etc.) are hereby expressly incorporated by reference; however, there is no admission that any document cited is indeed prior art as to the present invention. A more complete understanding can be obtained by reference to the following specific examples which are provided herein for purposes of illustration only and are not intended to limit the scope of the invention.

EXAMPLES

The Examples 1 to 9 which follow and corresponding FIGS. 1 to 32 further illustrate the invention, but should not be construed to limit the scope of the invention in any way. Detailed descriptions of conventional methods, such as those employed herein can be found in the cited literature; see also "*The Merck Manual of Diagnosis and Therapy*" Seventeenth Ed. ed. by Beers and Berkow (Merck & Co., Inc., 2003).

The practice of the present invention will employ, unless otherwise indicated, conventional techniques of cell biology, cell culture, molecular biology, transgenic biology, microbiology, recombinant DNA, and immunology, which are within the skill of the art. Methods in molecular genetics and genetic engineering are described generally in the current editions of Molecular Cloning: A Laboratory Manual, (Sambrook et al., (1989) *Molecular Cloning: A Laboratory Manual*, 2nd ed., Cold Spring Harbor Laboratory Press); *DNA Cloning*, Volumes I and II (Glover ed., 1985); *Oligonucleotide Synthesis* (Gait ed., 1984); *Nucleic Acid Hybridization* (Hames and Higgins eds. 1984); *Transcription And Translation* (Hames and Higgins eds. 1984); *Culture Of Animal Cells* (Freshney and Alan, Liss, Inc., 1987); *Gene Transfer Vectors for Mammalian Cells* (Miller and Calos, eds.); *Current Protocols in Molecular Biology and Short Protocols in Molecular Biology*, 3rd Edition (Ausubel et al., eds.); and *Recombinant DNA Methodology* (Wu, ed., Academic Press). *Gene Transfer Vectors For Mammalian Cells* (Miller and Calos, eds., 1987, Cold Spring Harbor Laboratory); *Methods In Enzymology*, Vols. 154 and 155 (Wu et al., eds.); *Immobilized Cells And Enzymes* (IRL Press, 1986); Perbal, *A Practical Guide To Molecular Cloning* (1984); the treatise, *Methods In Enzymology* (Academic Press, Inc., N.Y.); *Immunochemical Methods In Cell And Molecular Biology* (Mayer and Walker, eds., Academic Press, London, 1987); *Handbook Of Experimental Immunology*, Volumes I-IV (Weir and Blackwell, eds., 1986). Reagents, cloning vectors, and kits for genetic manipulation referred to in this disclosure are available from commercial vendors such as BioRad, Stratagene, Invitrogen, and Clontech. General techniques in cell culture and media collection are outlined in Large Scale Mammalian Cell Culture (Hu et al., *Curr. Opin. Biotechnol.* 8 (1997), 148); Serum-free Media (Kitano, *Biotechnology* 17 (1991), 73); Large Scale Mammalian Cell Culture (*Curr. Opin. Biotechnol.* 2 (1991), 375); and Suspension Culture of Mammalian Cells (Birch et al., *Bioprocess Technol.* 19 (1990), 251.

Material and Methods

Patients selection, peripheral blood mononuclear cells (PBMC) isolation from APECED/APS1 patients memory B cell culture and antibody isolation were carried out as described in the international applications WO2013/098419 and WO2013/098420 with the difference that specificity of the antibodies isolated and analyzed was directed towards IFN-α subtypes as defined hereinabove and below instead of IL-17 and IL-22, which were specifically used in the mentioned PCT applications; see Examples sections therein, in particular Examples 1 and 2 on pages 117 to 120 and Example 17 on pages 168-171 of WO2013/098419 and Examples 1 to 4 on pages 27 to 31 of WO2013/098420, the disclosure content of which is incorporated herein by reference.

The molecular cloning of human antibodies of the present invention and subsequent antibody production and purification were performed as described in the international application WO2013/098419, see the Examples section of the application and in particular Examples 1 to 3 on pages 117-120 therein, the disclosure content of which is incorporated herein by reference. Mutation analysis of the AIRE gene was performed as described in the international application WO2013/098419; see the Examples therein, in particular the "Mutation analysis of the AIRE gene" section in Materials and Methods of the Examples, on pages 115-116, the disclosure content of which is incorporated herein by reference, with particular steps performed as described in WO99/15559. In this concern, genotyping of the respective mutations in the AIRE (APECED) gene is performed as described in international application WO99/15559 in Example 2 at pages 12 to 13; a confirmation of the mutations in exons 2 and 6 of the AIRE gene as described in Example 3 of international application WO99/15559 at page 13, line 5 bridging to page 14, line 13, the disclosure content of which is incorporated herein by reference in its entirety. In particular, for the mutation analysis the DNA samples are purified from peripheral blood mononuclear cells from patients with APECED and from suspected carriers of APECED and from normal healthy controls (according to Sambrook et al. 1989, *Molecular Cloning. A Laboratory Manual*. CSH Press) and subjected to PCR using primers specific for all identified exons.

Example 1: Detection of Cytokine Specific Antibodies in the Serum of Patients The general presence of various cytokine and disease specific antibodies in the sera of the patients suffering from the genetic condition APECED (Autoimmune polyendocrinopathy candidiasis epidermal dysplasia, also called Autoimmune polyendocrinopathy type 1 (APS1)) has been determined by protoarray analysis as described in Example 7 on page 128 and indicated Tables 1 and 2 on pages 128-130 of applicant's international application WO2013/098419, the disclosure content of which is incorporated herein by reference. Altogether sera from 23 patients, presented by codes from APS1-1 to APS1-23 were used in the assays. Eight control sera were obtained from healthy laboratory personnel, age matched with the patients and coded as C1-C8. See FIG. 4 indicating the presence of IFN-α subtype specific and dsDNA-specific antibodies in the 23 patients examined. In addition to the seroreactivities shown in FIG. 4, patients APS1-9 and APS1-2 have shown seroreactivity towards IFN-α1/13, IFN-α5, IFN-α6, IFN-α10, IFN-α14, IFN-α16 and IFN-α21.

Anti-dsDNA antibodies are highly specific for SLE and used in the diagnosis of the disease. Surprisingly, no APS1 patients have lupus despite the frequent presence of anti-dsDNA antibodies. However, APS1 patients display pronounced seroreactivity against several interferon-a subtypes which are clinically-relevant drug targets involved in many lupus-implicated molecular mechanisms, implicating the possible suitability of these antibodies in SLE treatment.

ELISA-IFN-α

96 well microplates (Costar, USA) were coated with human IFN-α1, IFN-α2 (ImmunoTools), IFN-α4 (SinoBiological), IFN-α5, IFN-α6, IFN-α8, IFN-α21 (all form PBL) and IFN-α14 (ATGen) or IFN-α8 (Novus Biologicals). Plates were washed with PBS-T and blocked 1h at room temperature with PBS containing 2% BSA (Sigma, Buchs, Switzerland). Patient sera, B cell conditioned medium, or recombinant antibody preparations were incubated for 2h at room temperature. Binding of human IgG to the antigen of interest was determined using a horseradish peroxidase conjugated goat anti human Fc-gamma-specific antibody (Jackson ImmunoResearch, Europe Ltd., Cambridgeshire, UK) followed by measurement of the HRP activity using a TMB substrate solution (TMB, Sigma, Buchs, Switzerland). Binding to human Fc fusion mouse IFN-α2, IFN-α4, IFN-α14 (SinoBiological) was detected with horseradish peroxidase conjugated anti-F(ab')2-specific antibody (see FIG. 19A).

Example 2: ECSO ELISA Determination of the Antibodies of the Present Invention EC50 binding of the hMABs of the present invention to IFN-α2 (ImmunoTools), IFN-α4 (SinoBiological), IFN-α14 (ATGen) was determined by ELISA (see also Table 3 below for details concerning the recombinant proteins used). Serial dilutions of MABs (from 1000 ng/ml down to 0.0169 ng/ml) were incubated for 2 hours with antigen-coated plates (coating overnight at 1 μg/ml in PBS, followed by wash out and blocking with 2% BSA in PBS). The plates were subsequently washed and binding of MABs was detected with anti-human HRP-conjugated secondary antibody. Concentrations of MAB resulting in half of maximal binding to respective antigens (EC50, ng/ml) were calculated using Prism 4 GraphPad software on sigmoidal dose-response curves (variable slope, 4 parameters) obtained by plotting the log of the concentration versus OD 450 nm measurements; see FIG. 3 and Table 4 below.

TABLE 3

List of recombinant proteins used in the Elisa assays.

| Target | Provider | Catalog number |
|---|---|---|
| IFN-alpha 1beta (IFN-α1/13) | Immunotools | 11343596 |
| IFN-α2 | ImmunoTools | 11343516 |
| IFN-α4 | Sino Biological | 10336-H08B |
| IFN-α5 | PBL | 11135 |
| IFN-α6 | PBL | 11165 |
| IFN-α8 | PBL | 11115 |
| IFN-α21 | PBL | 11130 |
| IFN-α14 | ATGen | ATGP1500 |
| IFN-omega 1 | ProSpec | CYT-040 |
| IFN.gamma | Immunotools | 11343536 |
| gIFN-α1, 2, 4, 5, 6, 7, 8, 10, 14, 16, 17,21, B, W | In-house production, Fusion construct with Gaussia luciferase | |

TABLE 4

Summary of IC 50 neutralization values of exemplary anti-IFN-α antibodies 19D11, 26B9, 8H1, 12H5 and 50E11 of the present invention as obtained in the ISRE dual luciferase reporter assay.

| | IC 50 (ng/ml) | | | | |
|---|---|---|---|---|---|
| Antigen | 19D11 | 26B9 | 8H1 | 12H5 | 50E11 |
| IFN-α1 | 3.80 | 8.60 | 28.98 | 51.32 | 97.38 |
| IFN-α2 | 1.62 | 2.83 | 1039.0 | 10.66 | 158.6 |
| IFN-α4 | 0.95 | 2.07 | 5.43 | 0.48 | 20.25 |
| IFN-α5 | 0.85 | 3.74 | 1.78 | 22.61 | 0.91 |
| IFN-α6 | 0.79 | 3.16 | 77.70 | 3.55 | 39.30 |
| IFN-α7 | 0.37 | 1.57 | 0.90 | 0.64 | 1.90 |
| IFN-α8 | 27.69 | 205.0 | 571.0 | 0.86 | 4.02 |
| IFN-α10 | 0.72 | 1.84 | 2.69 | 0.66 | 3.63 |
| IFN-α14 | 0.31 | 2.01 | 784.6 | 2.15 | 9.20 |
| IFN-α16 | 1.86 | 4013.0 | 1.86 | 32.99 | 2.35 |
| IFN-α17 | 0.75 | 2.22 | 2.11 | 0.75 | 2.31 |
| IFN-α21 | 2.22 | 4.65 | 2.78 | 13.02 | 3.05 |
| IFN-ω | — | 0.50 | 2.13 | — | 113.2 |

Previous EC50 binding versus IC50 neutralization assays performed in accordance with the present invention of the exemplary anti-IFN-α antibodies using IFN-α-proteins obtained from commercial suppliers as indicated in Table 3 and IFN-α-proteins gIFN-α2/-4 and -14 generated in accordance with the present invention gave similar results.

In addition, binding of exemplary MABs 19D11, 25C3, 26B9, 5D1 and 13B11 of the present invention to IFN-α1 (ImmunoTools) was compared to the binding of these antibodies to IFN-α2 (ImmunoTools) by ELISA. In this experiment, examined MABs (300 ng/ml) were incubated for 2 hours with antigen-coated plates (coating overnight at 1 μg/ml in PBS, followed by wash out and blocking with 2% BSA in PBS). The plates were subsequently washed and binding of MABs was detected with anti-human HRP-conjugated secondary antibody. Exemplary MABs 19D11, 25C3, 26B9 and 13B1 1 have shown a comparable binding affinity to IFN-α1 and IFN-α2 (see FIG. 11A). However, exemplary anti-IFN-α MAB 5D1 binds IFN-α2 and does not cross-react with IFN-α1 (see FIG. 11A). In a further experiment binding of exemplary MABs 19D11, 25C3, 26B9, 5D1 and 13B11 of the present invention to IFN-α8 was compared by LIPS to the binding of these antibodies to IFN-α14 (both IFN-*Gaussia* luciferase fusion proteins). Herein, exemplary MAB 13B11 did not show cross-reactivity with IFN-α8. The other exemplary antibodies 19D11, 25C3, 26B9 and 5D1 have shown stronger binding of INFA8 than of IFN-α14 (see FIG. 11B). In an additional experiment binding of exemplary MABs 5D1, 13B11 19D11, 25C3, 26B9 and 31B4 of the present invention to IFN-α5, IFN-α6, IFN-α8, IFN-α21 (all from PBL) and IFN-α14 (ATGen) was determined and comparised. Exemplary anti-IFN-α-a antibody 13B1 did not cross-react with IFN-α8 and IFN-α21 and antibody 19D11 cross-reacted with a lower affinity with IFN-α21 than with the other IFN-α subtypes (see FIG. 11C).

Example: 3

Neutralization Assays

The neuralizing assays are carried out on cell lines that respond to the studied cytokine, i.e. carry the necessary receptor. The ligand binding to receptor activates a corresponding signaling pathway, translocation of transcription factors to the nucleus and upregulate responder gene transcription, translation and if applicable product secretion. The cytokine concentration used is selected from the beginning of the linear part of the dose-response curve to maximize the sensitivity of the assay. To test the neutralizing capacity of antibodies the optimal concentration of the target cytokine is preincubated with serial dilutions of serum, supernatant or purified antibody samples. The results are expressed as titer or concentration of antibody that show the value half-way between the positive and negative controls.

Phospho-STATJ Assay 30,000 HEK 293T or HEK 293T MSR cells were seeded into Poly-L-Lysine-coated 96-well plates (BD Biocoat, Bedford, Mass., USA) or into regular tissue culture-treated 96-well plates (Cat. No. 3598, Corning Inc., Corning, N.Y., USA), respectively. The following day, rhIFN-αs or supernatants of HEK 293T cells transiently expressing IFN-*Gaussia* luciferase fusion proteins (g1 IFNs) were mixed with anti-IFN-α mAbs or control IgG (5 mg/ml) and preincubated for one hour at 37° C. After preincubation, the mixtures were used to stimulate HEK 293T or HEK 293T MSR cells for 10 min at 37° C. Following stimulation, cells were lysed with CelLytic™ M lysis buffer supplemented with protease and phosphatase inhibitors (Cat. No. C2978, P5726, P0044, P8340, SIGMA-ALDRICH, St. Louis, Mo., USA) and the collected lysates were cleared at 13,000 RPM, 4° C. in a tabletop centrifuge. Lysates were subjected to reducing SDS-PAGE and blotted onto nitrocellulose membranes. Membranes were blocked with a buffer containing 0.25% bovine gelatin, 150 mM NaCl, 5 mM EDTA, 50 mM Tris/HCl pH 7.5, 0.05% Triton X-100 for one hour at room temperature, followed by incubation with rabbit monoclonal antibodies against phosphorylated STAT1 (Tyr701, diluted 1:1000 in blocking buffer, Cat. No. 9167, Cell Signaling Technology, Danvers, Mass., USA) at 4° C. over night. On the next day, blots were washed three times with blocking buffer followed by incubation with horseradish peroxidase-linked secondary antibodies against rabbit IgG (diluted 1:20,000 in blocking buffer, Cat. No. 111-035-144, Jackson ImmunoResearch, West Grove, Pa., USA). After three additional washing steps, an ECL substrate was added (Cat. No. 34087, Thermo Fisher Scientific, Rockford, Ill., USA) and reactive bands were visualized via autoradiography. Bound antibodies were removed by incubation in Restore Western Blot Stripping Buffer (Cat. No. 21059, Thermo Fisher Scientific) and a rabbit polyclonal anti-STAT1 serum was used to visualize total STAT1 levels (diluted 1:1000 in blocking buffer, Cat. No. 9172, Cell Signaling Technology).

In the following the results of two Phospho-STAT1 assays performed with exemplary anti-IFN-α specific antibodies 5D1, 19D11, 25C3, 26B9, 31B4 and 13B11 are discussed. As may be seen in FIGS. 5B and 5C, addition of exemplary anti-IFN-α specific antibodies 19D11, 25C3, 26B9, 31B4 and 13B11 prohibits the IFN-α2, IFN-α4 and IFN-α14 dependent phosphorylation of STAT1 indicating the IFN-α neutralizing capacity of the antibodies of the present invention. In addition, exemplary anti-IFN-α specific antibodies 19D11, 26B9 and 31B4 also prohibit the IFN-α1, g1 IFN-α5 and IFN-α6 dependent phosphorylation of STAT1, with the neutralization capacity of antibody 26B9 slightly reduced against IFN-α5. Antibody 25C3 showed a slightly weaker neutralization capacity concerning IFN-α6 and IFN-α1 4 activity in comparison to its neutralizing capacity towards IFN-α2 and IFN-α4. Addition of exemplary anti-IFN-α specific antibody 5D1 of the present invention showed neutralizing activity of this antibody against IFN-α2 and IFN-α4, wherein no or very weak neutralization could be observed in respect of IFN-α14 dependent STAT1-phosphorylation (FIG. 5C, right panel) and a slightly weaker neutralization of IFN-α6.

After IFN-α1b or IFN-α16 stimulation exemplary antibodies 19D11, 25C3, 26B9, 31B4 and 13B11 have shown neutralization capacity towards IFN-α1b (IFN-α1/13) activity, wherein no neutralization could be observed in respect of antibody 5D1 (FIG. 5B). Concerning IFN-α16, only antibodies 19D11, 5D1 and 13B11 have shown neutralization capacity, wherein exemplary antibodies 25C3, 26B9 and 31B4 indicated at least severely reduced or even a lack of neutralizing capacity towards IFN-α16 (FIG. 5C). Exemplary antibody 13B11 potently neutralized IFN-α1, IFN-α2, IFN-α4 and g1 IFN-α5, whereas very weak neutralization could be observed in respect of IFN-α6 dependent STAT1 phosphorylation. rhIFN-α concentration as used was: 10 ng/ml (IFN-α1b), 2 ng/ml (IFN-α2, IFN-α4, IFN-α6, IFN-α16). g1 IFN-α5 supernatant was used at its EC 80 dilution.

While all exemplary antibodies except 13B11 neutralized IFN-α21 in this functional assay (FIG. 5D), exemplary antibodies 25C3 and 13B11 did not neutralize IFN-α6 (FIG. 5B). MABs concentration was at 5 mg/ml, rhIFN-αs (PBL) at 2 ng/ml. All antibodies were neutralizing IFN-α5 (g1IFN-α5) (FIG. 5B). Antibodies 25C3 and 13B11 did not neutralize IFN-α8 (g1IFN-α8). None of the exemplary anti-IFN-α antibodies of the present invention antibodies neutralized IFN-γ (IFN-gamma/IFNG) (FIG. 5D). Other than in the above general experimental description, here HEK 293T cells were either left untreated (−) or stimulated with supernatants of HEK 293T cells transiently expressing human IFN-*Gaussia* luciferase fusion proteins (+) in the absence of antibodies or in the presence of 5 mg/ml human-derived exemplary human MABs or a human control IgG (huigG) as indicated in FIG. 5D.

In a second experimental round, additional IFN-α subtypes have been tested. The results of these two experimental rounds have been combined in FIG. 5. After IFN-α7, g1 IFN-α8, IFN-α10, IFN-α1 4 or IFN-α1 6 stimulation exemplary antibody 19D11 has shown neutralization capacity towards all tested IFNs, wherein exemplary antibodies 26B9 and 31B4 could not neutralize IFN-α16 (FIG. 5C). Exemplary antibody 25C3 fully neutralized IFN-α7, but showed weaker neutralization of g1 IFN-α8, IFN-α10, IFN-α1 4 and IFN-α1 6. Exemplary antibody 5D1 neutralized IFN-α7, g1 IFN-α8, IFN-α10 and IFN-α16 but no neutralization of IFN-α14. Exemplary antibody 13B11 showed neutralization of IFN-α7, IFN-α1 0, IFN-α14 and IFN-α16, but no neutralization of g1 IFN-α8. rhIFN-α concentration as used was 2 ng/ml (IFN-α7, IFN-α1 0, IFN-α14, IFN-α16). g1 IFN-α8 supernatant was used at its EC 80 dilution.

All exemplary antibodies neutralized IFN-α1 7 in this functional assay (FIG. 5D). All exemplary antibodies except 13B11 neutralized IFN-α21. Only two exemplary antibodies, 26B9 and 31B4, neutralized IFN-co in this functional assay, while none of the exemplary antibodies neutralized IFNB or g1 IFNG. rhIFN-α concentration was 2 ng/ml, g1 IFNG supernatant was used at its EC 80 dilution.

ISRE-Luciferase Reporter Assay 20,000 HEK 293T or 10,000 HEK 293T MSR cells were seeded in Poly-L-Lysine-coated 96-well plates (BD Biocoat) (in white half-area 96-well plates (Cat. No. 3688, Corning Inc.)—values in brackets indicate the differences in the second experimental option with HEK 293 TMSR cells) and reverse-transfected with 100 ng (50 ng) of premixed ISRE-Firefly luciferase reporter and *Renilla* luciferase constructs (Cat. No. CCS-008L, Qiagen, Hilden, Germany) (see scheme of the constructs in FIG. 6A) using Fugene HD according to the manufacturer's instructions (Promega, Madison, Wis., USA). The *Renilla* luciferase-expressing construct served as an internal normalization control. Cells were incubated overnight in Opti-MEM® I Reduced Serum Medium supplemented with 0.1 mM non-essential amino acids, 1 mM sodium pyruvate, 10% (0.5%) fetal bovine serum (Life Technologies, Carlsbad, Calif., USA) at 37° C., 5% CO2 in a humidified atmosphere. Following overnight incubation, cells were stimulated for 24 hours with medium containing mixtures of rhIFN-αs with or without anti-IFN-α mAbs or control IgG that had been preincubated for one hour at 37° C. After 24 hours of stimulation, dual luciferase reporter assays were performed according to the manufacturer's instructions (Promega).

As may be seen in FIG. 7, addition of exemplary anti-IFN-α specific antibodies 19D11, 25C3, 26B9, 31B4 (FIGS. 7A and B) and 13B11 (FIGS. 7C and D) prohibits the IFN-α2, IFN-α4 and IFN-α14 dependent ISRE-Luciferase reporter activation indicating the IFN-α neutralizing capacity of the antibodies of the present invention. Addition of exemplary anti-IFN-α specific antibody 5D1of the present invention showed neutralizing activity of this antibody against IFN-α2 and IFN-α4, wherein no or very weak neutralization could be observed in respect of IFN-α14 dependent ISRE-Luciferase activation (FIGS. 7C and D). As already seen in the phospho-STAT1-assay, antibody 25C3 showed a slightly weaker neutralization capacity concerning IFN-α14 activity in comparison to its neutralizing capacity towards IFN-α2 and IFN-α4. Similarly, exemplary anti-IFN-α specific antibody 13B11 has shown a slightly weaker neutralization capacity towards IFN-α14 (FIGS. 7C and D). Exemplary antibody 8H1 neutralizes IFN-α, together with IFN-αI, A4, A5, A6, A7, A1 0, A1 6, A1 7 and A21, while showing weaker neutralization of IFN-α2, A8 and A14 (FIG. 7E). Exemplary antibody 12H5 strongly inhibits ISRE-Luciferase reporter induction by all alpha interferons, namely IFN-α1, A2, A4, A5, A6, A7, A8, A10, A14, A16, A1 7 and A21, while virtually not affecting IFN-α-mediated reporter induction. Neither exemplary antibody 8H1 nor 12H5 interfere with IFNB-mediated reporter induction (FIG. 7E).

As shown in FIG. 8, exemplary antibody 26B9 potently neutralizes rhIFN-α1, A2, A4, A5, A6, A8, A10, A14, A1 7, A21 and rhIFN-α, while weakly neutralizing rhIFN-α16. rhIFN concentration was 10 ng/ml (IFN-αI), 1.3 ng/ml (IFN-α16) and 2 ng/ml (all other rhIFNs). A summary of the IC 50 values as determined in the ISRE-Luciferase reporter assay is shown in Table 4.

As may be seen in FIG. 9, exemplary antibody 19D11 neutralizes all rhIFN-α molecules, namely IFN-αI, A2, A4, A5, A6, A7, A8, A10, A14, A16, A1 7 and A21. rhIFN concentration was 10 ng/ml (IFN-α1), 1.3 ng/ml (IFN-α16) and 2 ng/ml (all other rhIFNs). A summary of the IC 50 values as determined in the ISRE-Luciferase reporter assay is shown in Table 4.

Chemiluminescent Cellular Binding Assay 30,000 HEK 293T MSR cells were seeded in white half-area 96-well tissue culture plates (Cat. No. 3688, Corning Inc.). The following day, supernatants of HEK 293T cells transiently expressing human IFN-*Gaussia* luciferase fusion proteins were mixed with anti-IFN mAbs, control IgG or excess concentrations of unlabeled recombinant IFN-α2 and preincubated for one hour at 37° C. After preincubation, the mixtures were used to stimulate HEK 293T MSR cells for 40 minutes at 37° C. Upon binding, cells were washed three times with PBS, and the *Gaussia* luciferase assay was developed using the *Gaussia* Flash Assay Kit according to the manufacturer's instructions (Cat. No. 16159, Thermo Fisher Scientific).

As shown in FIG. 10C, exemplary antibody 19D11 efficiently neutralizes binding of g1 IFN-α2, A4, A5, A6, A7, A8, A10, A14, A16, A17 and A21 to HEK 293T MSR cells endogenously expressing IFN receptors. In contrast, exemplary antibody 19D11 does virtually not interfere with binding of g1 IFNB and g1 IFN-α. Binding of all g1 IFNs showed herein is apparently not affected by a control human antibody (huigG). Antibody concentration: 5 mg/ml.

As may be seen in FIG. 10D, binding of g1 IFN-α16 to HEK 293T MSR cells is more efficiently neutralized by exemplary antibody 19D11 as compared to exemplary antibody 26B9. However, exemplary antibody 26B9 strongly neutralizes binding of g1 IFN-ω to HEK 293T MSR cells, whereas exemplary antibody 19D11 shows no apparent neutralization capacity towards this ligand. Binding of both g1 IFN-α16 and g1 IFN-ω remains unaffected by a control human antibody (huigG). Antibody concentration: 10 mg/ml.

Example 4: Validation of Subject Antibodies

Antibodies provided by the present invention are tested in concern of their neutralizing activity towards human IFN-α in animal disease models. When performing such experiments it has to be ensured that human IFN-α subtypes induce diseased phenotypes in mice and that no cross-reaction occurs between the tested IFN-α antibodies of the present invention and the murine IFN-α homologues. Since no adequate model system for IFN-alpha was available in the prior art, the present Example describes and provides such a system to test IFN-alpha neutralizing antibodies that do not cross react with mouse IFNs. First, the effect of different IFN-α subtypes was tested in vivo for the induction of ear inflammation. In particular the proinflammatory activity of human subtypes IFN-α2a, IFN-α2b, IFN-α4 and IFN-α1 4 have been tested. IFN-α2a differs from IFN-α2b by amino acid 23 (Lys in IFN-α2a and Arg in IFN-α2b)

Ear Inflammation Assay

Ear inflammation phenotype was induced in 8 weeks old C57BL/6J (WT; from Charles River) mice by intradermal injection of human IFN-α2a, IFN-α2b, IFN-α4 and IFN-α14 in 20 µl of PBS, or PBS control into each ear given on alternate days at Day 0, Day 2 and Day 4 (20 µl/ear, 500 ng/ear, 1 µg total/mouse/day) using a 30-gauge needle. The mice were sacrificed at day 6;
see Table 5 below and FIG. 14A for the experimental timeline.

TABLE 5

Group allocation of animals to the different cytokines tested.

| Group | n | Cytokine | ng/20 µl |
|---|---|---|---|
| A | 5 | PBS | Na |
| B | 5 | IFN-α2a | 500 |
| C | 5 | IFN-α2b | 500 |
| D | 5 | IFN-α4 | 500 |
| E | 5 | IFN-α14 | 500 | n—number of animals in the group,
ng/20 µl—amount of cytokine injected per ear.

To test the proinflammatory effect of the injected IFN-α subtypes ear thickness measurements of the animals were taken with a Mitutoyo digital micrometer during the cytokine administration by 2 measurements per ear prior to cytokine injection at Day 0 and at alternate days at Day 1, Day 3, Day 5 (indicated by letter Min FIG. 14A) and alternatively or in addition at Day 6 after sacrifice of the animal.

Furthermore, body weight is monitored during the treatment, to observe any possible weight changes due to the inflammation induction or its respective reduction due to the treatment applied. In addition, after sacrifice of the animals H&E ((hematoxylin and eosin; see Harris, H. F., J. Appl. Microscopy III (1900), 777-781 and Mallory, F. B.: Pathological technique. Philadelphia, Saunders, 1938) histology stainings of the ears are performed.

All four human IFN-α subtypes tested were able to significantly induce ear swelling following cytokine injection; see FIGS. 14-16 and results of the experiment summarized in the table in FIG. 17. All ears were markedly thicker than PBS treated ears, this was significant in all groups after the 2nd intradermal injection, from Day 3 until the end of the experiment. IFN-α14 was the most potent especially at Day 5 in this experiment. IFN-α2a and IFN-α4 induced similar levels of ear thickening. IFN-α2b was most similar to both IFN-α4 and IFN-α1 4 induced swelling. IFN-α2b induced swelling more than the IFN-α2a isoform in this experiment; see FIGS. 14-16 and the experimental results summary in the table in FIG. 17.

The results of this experiment show the applicability of the ear inflammation assay for tests of the therapeutic applicability of the antibodies of the present invention. Since the exemplary anti-IFN-α antibodies 19D11, 26B9, 31B4, 5D1 and 13B11 of the present invention did not show any apparent cross-reaction with at least murine IFN-α subtypes 2, 4 and 14 (see FIG. 19A), they are tested in the above indicated assay in respect of their neutralization properties towards human IFN-α used for induction of inflammation. Apparent binding affinity of exemplary anti-IFN-α antibody 25C3 towards murine INFA2 and the affinity of exemplary anti-IFN-α antibodies 5D1 and 19D1 1 towards murine IFN-α1 is taken into consideration when designing the in vivo CytoEar neutralization experiments described herein.

Such treatment tests are performed with the exemplary anti-IFN-α antibodies of the present invention by injection of the antibodies at different time points during the above drafted experimental timeline (see also FIG. 14A) for testing induction of inflammation by human IFN-α. For example, for testing the preventive and/or therapeutic effect one or more of the exemplary antibodies of the present invention are injected together with or separately to the IFN-α subtype or subtypes at Day 0 of the experiment. In addition or alternatively, one or more of the antibodies of the present invention or IFN-α binding fragments thereof are injected on alternate days with the IFN-α subtype or subtypes. For example, if the IFN-α subtype or subtypes are injected as indicated above at Days 0, 2 and 4 (short arrows in FIG. 14A), the antibodies are injected on the alternate Days 1, 3 and/or 5 (long arrows in FIG. 14A).

The neutralizing potential of the antibodies of the present invention or IFN-α binding fragments thereof to reduce the induced ear inflammation phenotype and/or to prevent such an induction is examined by comparison of ear swelling (thickness) observed in animals obtaining the anti-IFN-α antibody treatment and the control groups obtaining either PBS or human IgGs of a binding specificity directed towards other molecules than human IFN-α subtypes (of IFN-α non-related binding specificity).

Furthermore, or alternatively body weight is monitored during the treatment, to observe any possible weight changes due to the inflammation induction or its respective reduction due to the treatment applied. In addition, after sacrifice of the animals H&E (hematoxylin and eosin; see supra) histology stainings of the ears are performed. This assay is used preferably as a surrogate model for psoriasis.

In a second experimental round, the above indicated assay has been used with some modifications to test neutralization properties of exemplary antibodies 26B9 and 19D11 of the present invention towards inflammation induced in mice ears by injections of human IFN-α14 (FIG. 28), IFN-α5 (FIG. 29) and IFN-ω) (FIG. 30). As may be seen from the time schemes shown in FIGS. 28A, 29A and 30A the experimental time line has been prolonged here to 10 days with tested antibodies and controls injected at experimental day 0 (IP), intradermal cytokine injections at days 1, 3, 6 and 8 and a sacrifice of the test animals at day 10. Group allocations of animals to the different cytokines tested and the respective concentrations and amounts of the cytokines, respective antibodies tested are indicated in tables in panels B of the respective figures. Both antibodies, 26B9 and 19D11 have shown pronounced preventive and/or therapeutic potential due to a significant reduction of the ear thickness on several experimental days after IFN-α14 (FIGS. 28 D and E) and IFN-α5 (FIGS. 29 D and E) induced ear inflammation in comparison to IgG controls. Treatment with the reference IFN-α specific antibody (Ref. A in FIGS. 28, 29, in particular FIGS. 28F and 29F) led also to a significant reduction of ear swelling after IFN-α14 treatment on several experimental days, however with a slightly lower reduction at day 10 compared with antibodies 26B9 and 19D11 of the present invention (compare curves F for 26B9 in FIGS. 28D and G for 19D11 in FIG. 28E with curve H for Ref.A in FIG. 28F and with curve E in each Fig. for the IgG-control). Furthermore, exemplary antibody 26B9 has shown a significant reduction of IFN-ω induced ear swelling at experimental day 9 (FIG. 30D), wherein injections of antibody 19D11 and Ref.A did not show any significant reduction of the ear swelling compared to nonspecific IgG treatment.

Accordingly, antibodies provided with the present invention have a high potential for use in prevention and/or treatment of diseases associated with enhanced IFN-α and/or IFN-ω activity.

CytoAnkle Assay:

In this assay mice cohorts (c57/b16, 7-8 weeks) are intraarticular (IA) injected with 62.5-io00ng cytokine, e.g., at least one IFN-α subtype such as IFN-α2a, IFN-α2b, IFN-α4 or IFN-α1 4 or mixtures of several IFN-α subtypes in lOul of PBS (or PBS control) into ankles every 48-72 hours. Axial ankle thickness measurements are than taken with a Mitutoyo digital micrometer. Animals are weighed each day and respective IFN-α subtype or subtypes are administered while the mice are anaesthetized with isofluorane. The experimental time frame is designed as indicated above for the ear inflammation assay, with injections of the anti-IFN-α antibody or antibodies of the present invention, respective the control groups obtaining either PBS or human IgGs of IFN-α non-related binding specificity as indicated above. Reduction of the ankle swelling is used as readout of the therapeutic effect of the antibodies of the present invention. This assay is used preferably as a surrogate model for arthritis, e.g., rheumatoid arthritis.

Example 5: Epitope Mapping of Exemplary IFN-α Antibodies

As a first step of mapping, differential binding of anti-IFN-α MABs of the present invention to distinct antigen binding sites was examined to determine the number of different binding sites. For this purpose, MABs were expressed either with human (hMAB) or mouse (hmMAB) Fc and cross-competition experiments were carried out by coating antigen on plates and by detecting binding of hmMABs in the presence of large excess of human MABs. Detection of hmMABs bound to the ligand was performed by a HRP-conjugated secondary antibody directed against the Fc portion of the primary antibody.

As may be seen from FIG. 2A and Table 6A below, exemplary anti-IFN-α antibodies 19D11, 26B9, 31B4 and 13B11 of the present invention compete each other for binding of IFN-α2 but not with antibodies 5D1 and 25C3, indicating that 5D1 and 25C3 bind other site(s) of IFN-α2 than 19D11, 26B9, 31B4 and 13B11. The same competition pattern may be seen for IFN-α4 and IFN-α14 with the difference however that 13B1 does not compete for binding of IFN-α4 and only weakly competes for binding of IFN-α1 4 with 19D11, 26B9, 31B4 indicating that the epitope the antibodies are binding to may be not conserved in this IFN-α subtypes and in particular divergent in IFN-α4. The results of the first approach also indicate a weak competition of each other of anti-IFN-α antibodies 5D1 and 25C3 of the present invention for binding of IFN-α2 and IFN-α4 indicating a possible partially overlapping epitope of these antibodies; see FIGS. 2A, 2B and Tables 5A, 5B. Furthermore, a diverging competition pattern on IFN-α1 4 may be observed, where hMAB 25C3 shows strong competition with hmMAB 5D1 but only a weak competition in the reverse situation (hMAB 5D1 against hmMAB 25C3) may be observed, indicating a possible preference of the 25C3 antibody towards an IFN-α14-specific epitope; see FIG. 2C and Table 6C below.

TABLE 6

Results of the cross-competition experiments of exemplary antibodies of the present invention. Human MAB (hMAB) were added in large excess to plates coated with the respective antigens before addition of MABs with mouse Fc (hmMAB).

| | | Human MAB competitor | | | | | |
|---|---|---|---|---|---|---|---|
| | | 19D11 | 25C3 | 26B9 | 31B4 | 5D1 | 13B11 |
| A Human IFNA2 | | | | | | | |
| Competition of binding of hmMAB | 19D11 | +++++ | − | +++++ | +++++ | − | ++++ |
| | 25C3 | − | +++++ | − | − | + | − |
| | 31B4 | +++++ | − | +++++ | +++++ | (+) | ++++ |
| | 5D1 | − | (+) | − | − | +++(+) | − |
| | 13B11 | − | − | − | − | − | +++(+) |
| B Human IFNA4 | | | | | | | |
| Competition of binding of hmMAB | 19D11 | +++++ | − | ++++ | +++(+) | − | − |
| | 25C3 | − | ++++ | − | − | (+) | − |
| | 31B4 | +++++ | − | +++++ | +++++ | − | +++ |
| | 5D1 | − | (+) | − | − | +++(+) | − |
| | 13B11 | − | − | − | − | − | +(+) |
| C Human IFNA14 | | | | | | | |
| Competition of binding of hmMAB | 19D11 | +++++ | − | ++++ | +++(+) | − | ++ |
| | 25C3 | (+) | +++++ | (+) | − | +++ | (+) |
| | 31B4 | +++++ | − | +++++ | +++++ | ++ | ++(+) |
| | 5D1 | +++++ | +++++ | +++++ | +++++ | +++++ | (+) |
| | 13B11 | +++(+) | − | +++(+) | +++ | − | ++++ |

Binding regions of MABs to their respective antigens can be mapped by, e.g., PepStar™ analysis. Therefore, overlapping 20mer peptides (15 amino acid overlap) are designed to cover the IFN-α-a subtypes of interest, e.g., IFN-α2, IFN-α4 and IFN-cd 4 including all known variants. The peptides and full length antigen (as positive control) are spotted on microarray and the peptide microarray is incubated with the primary antibody followed by a fluorescently labelled secondary antibody directed against the Fc portion of the primary antibody. To avoid false negatives caused by steric hindrance, an optimized hydrophilic linker moiety is inserted between the glass surface and the antigen derived peptide sequence.

Figure 27:
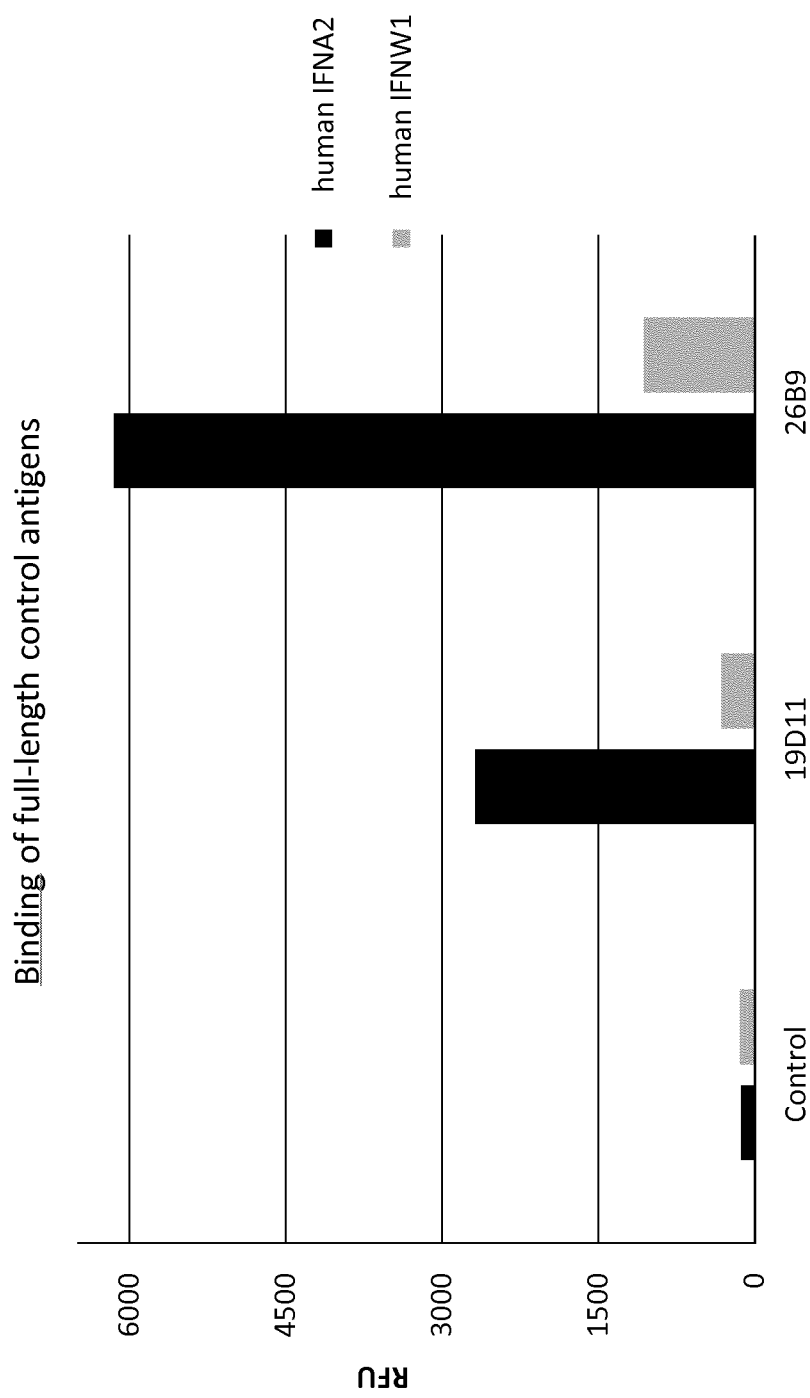
Figure 27:
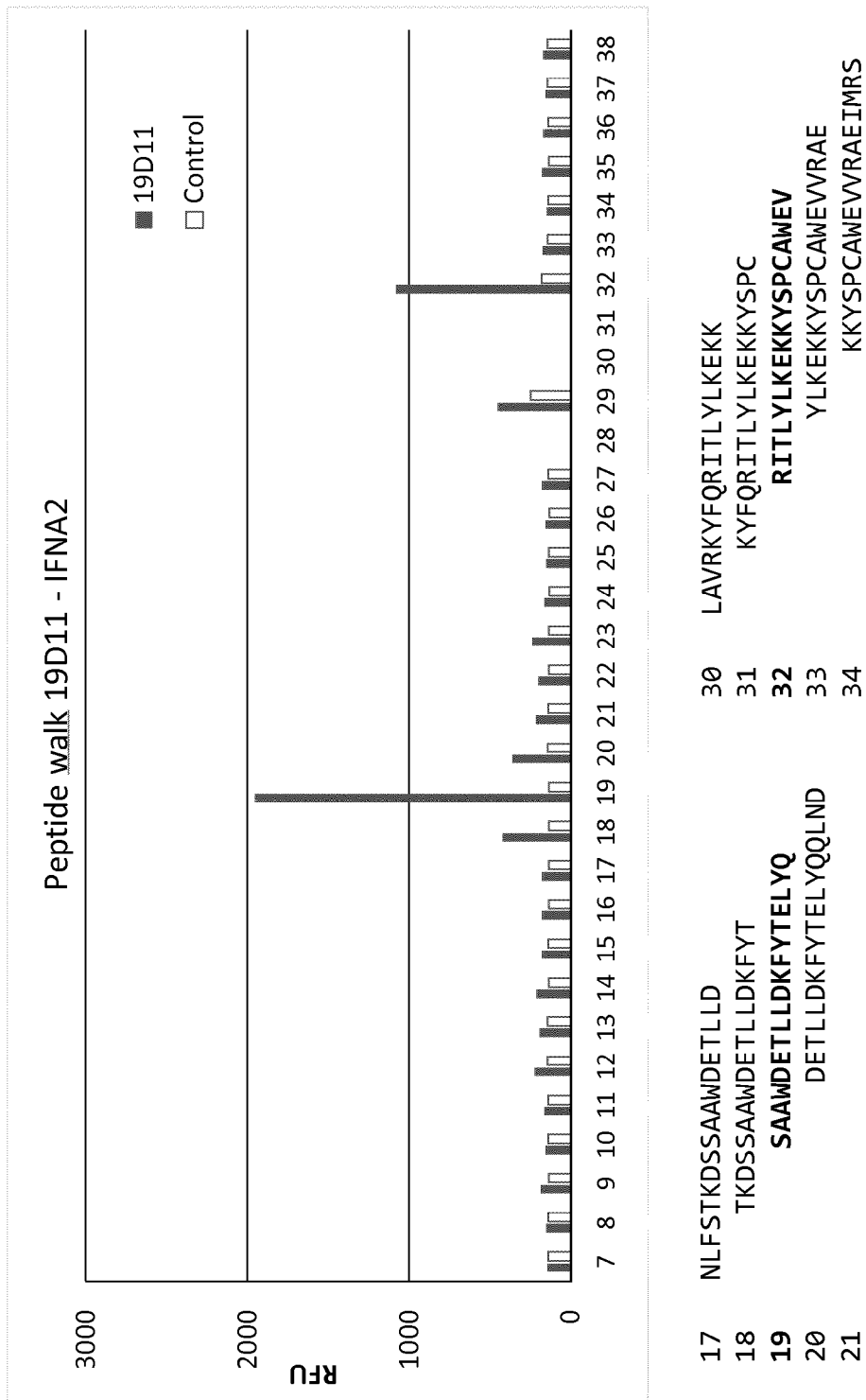
Figure 27:
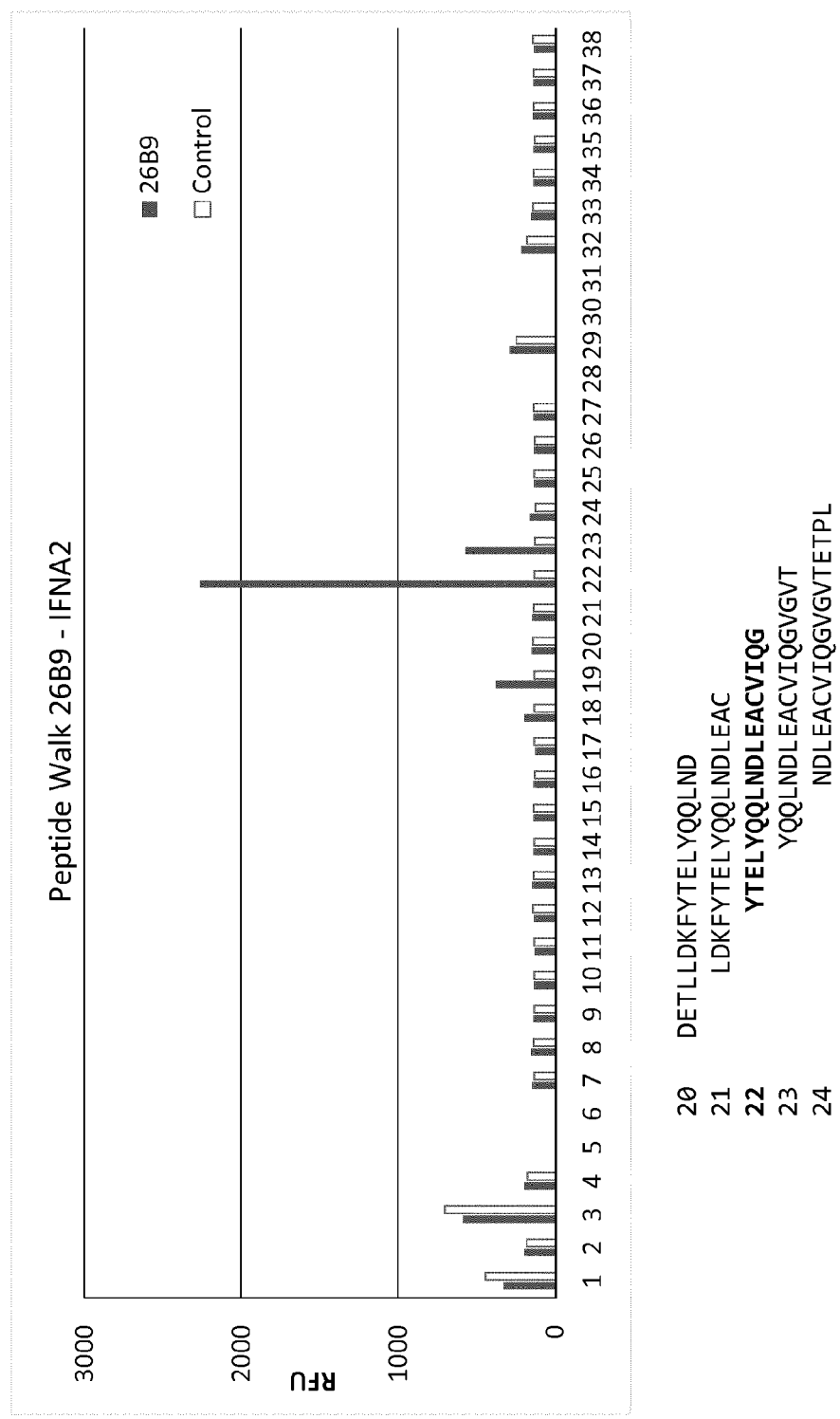
Figure 27:
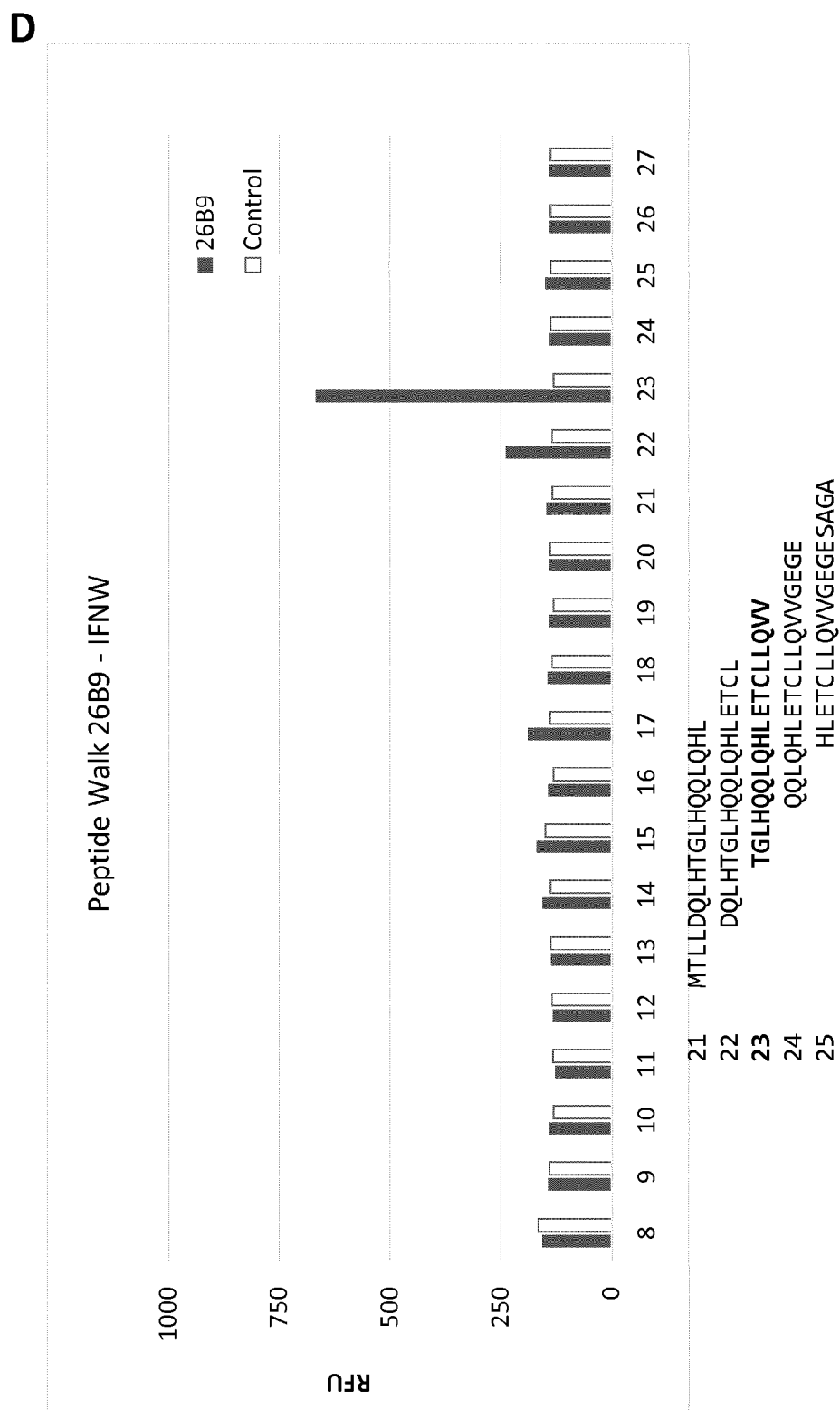
Figure 28:
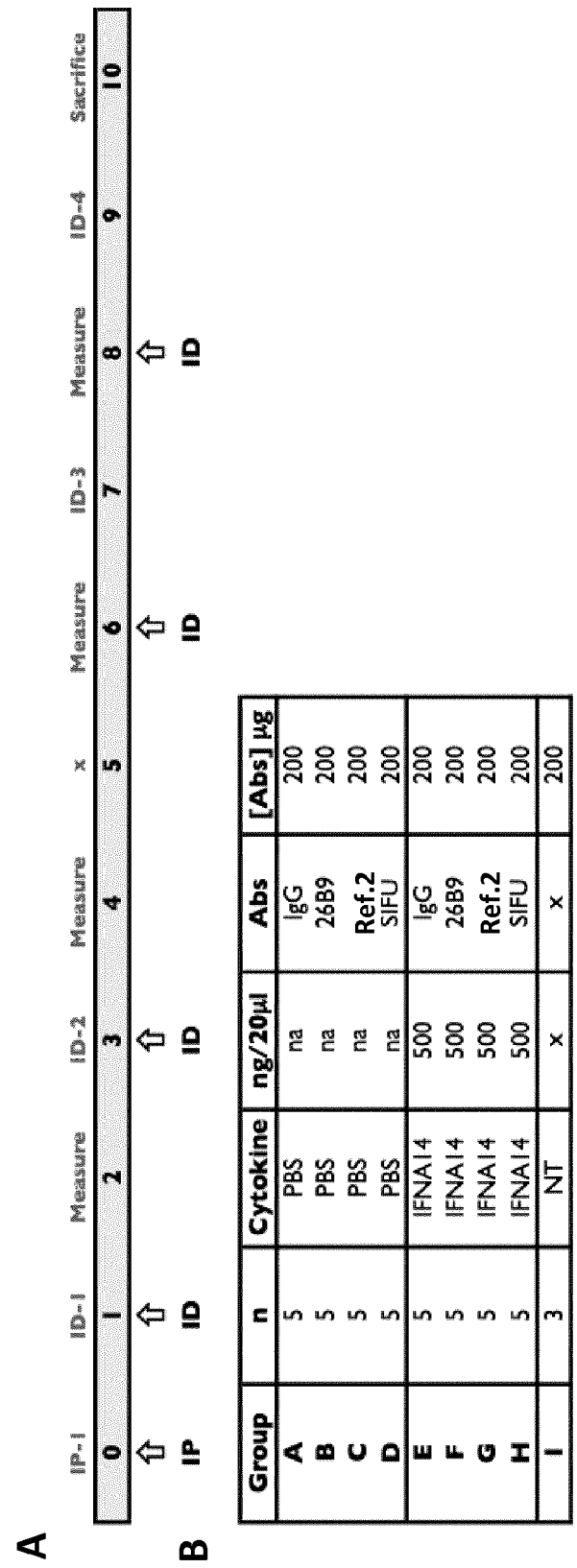
Figure 28:
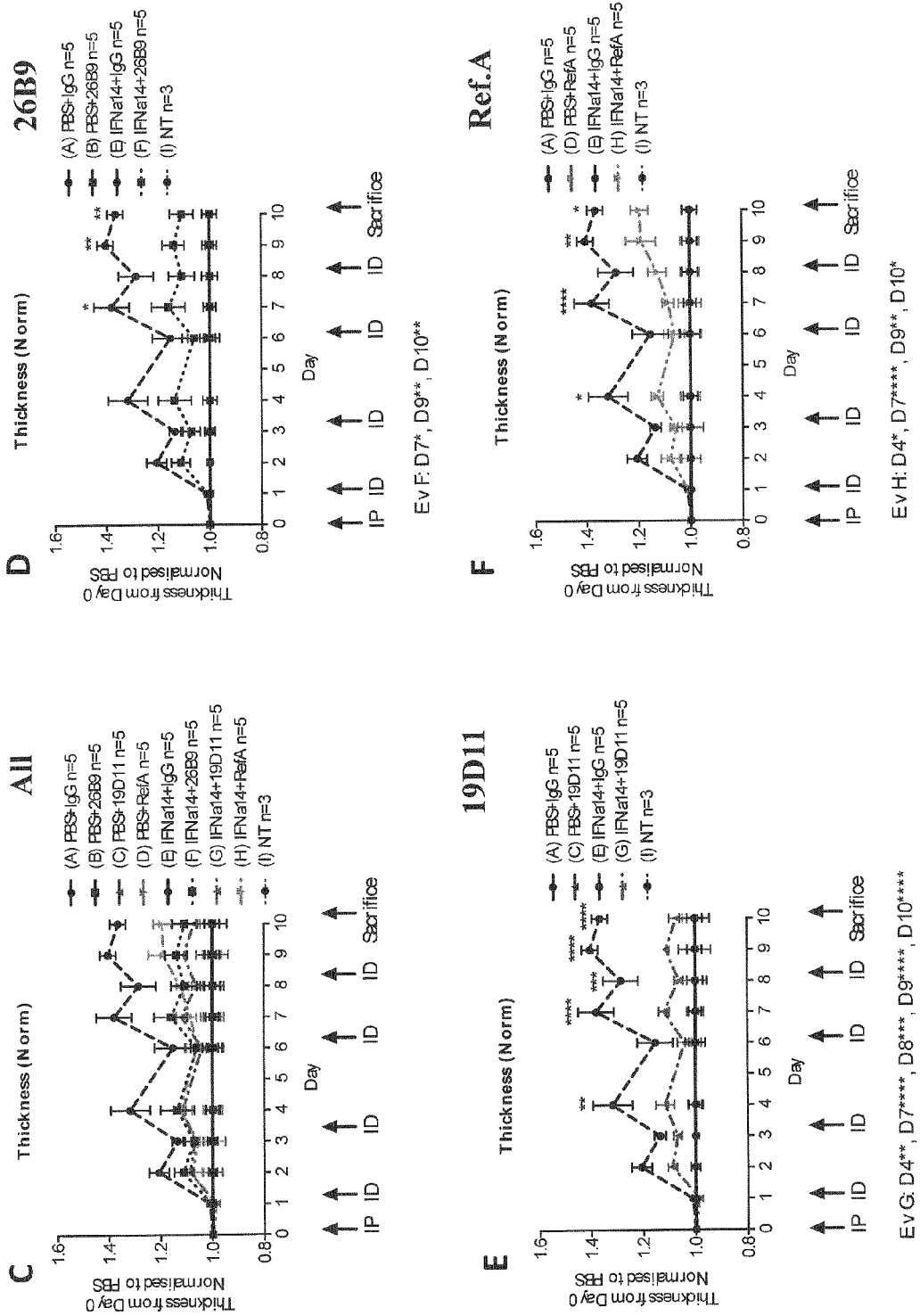

Such peptide mapping has been performed for exemplary antibodies 19D11 and 26B9 of the present invention on peptide arrays of 18mer peptides of human IFN-α2, respective human IFN-αW. The results of the assay are shown in FIG. 27. Exemplary antibody 19D11 binds specifically to peptides 19 (SAAWDETLLDKFYTELYQ SEQ ID NO: 99) and 32 (RITLYLKEKKYSPCA WEV SEQ ID NO: 100) of IFN-α2 (FIG. 27B). The antibody 26B9 binds specifically to peptide 22 (YTELYQQLNDLEACVIQG SEQ ID NO: 101) of IFN-α2 (FIG. 27C) and to peptide 23 (TG1HQQLQHLETCLLQVV SEQ ID NO: 102) of IFN-αW (FIG. 27D).

Example 6: Determination of MABs Binding to IFN-α Subtypes by LIPS Assay

In addition to the ELISA assay, binding of MABs to the different IFN-α subtypes was determined by the LIPS assay. IFN-α5-, IFN-α6- and IFN-α8-*Gaussia* fusion proteins were produced by cloning IFN-α5, IFN-α6 and IFN-α8 each fused with *Gaussia* luciferase at N-terminus and expressing them individually by transient transfection of HEK293 cells (harvest of the supernatant after 2 days) as described in Example 10 on page 158 and Example 15 on pages 165-167 in applicant's international application WO2013/098419, the disclosure content of which is incorporated herein by reference, using primers indicated in Table 8 below. MABs (4 µg/ml) were diluted in Buffer A (50 mM Tris, pH 7.5, 100 mM NaCl, 5 mM MgCl2, 1% Triton X-100) and incubated for 1 hour with an equal Protein A agarose beads (Exalpha) in wells of MultiScreen HTS Filter Plates (Millipore) on rotary shaker. Two volumes of IFN-α5- or IFN-α6- or IFN-α8-*Gaussia* fusion protein (1 million LU) were added and plates incubated for 1 hour. Plates were washed 5 times with Buffer A and 2 additional times with PBS before addition of the substrate (*Gaussia* Luciferase Flash Assay Kit, Pierce). Luminescence (CPS) was read using EnSprire (Perkin Elmer) (see FIGS. 11B, 12A-C and 13). A human antibody binding to an unrelated antigen human MAB has been used as negative control.

As can be seen from the results shown in FIGS. 11 and 12, exemplary MAB 13B11 binds to: IFN-α2, 4, 5, 6, 10 and 14 but not, or weaker to IFN-α1/13 and not to IFN-α8. Furthermore, the results provided in experiments described herein, e.g., in Examples 2 and 3 show that exemplary MAB 13B11 neutralizes: IFN-α2, 4, 5, 14 but not IFN-α6, 8 and IFN-α21. All results concerning the binding and neutralization properties of the exemplary antibodies of the present invention as provided by the experiments described in Examples 2, 3 and 6 are summarized in Table 7 below.

TABLE 7

Binding (B) and neutralization (N) of different IFN subtypes by exemplary antibodies of the present invention as obtained in ELISA, LIPS or neutralization assays described herein. Exemplary human anti-IFN-α antibody of the present invention 19D11 neutralizes all IFN-α subtypes and not IFN-ω. Exemplary antibody 26B9 neutralizes IFN-ω and all IFN-α subtypes except IFN-αI 6. +/++/+++ = binding, respective neutralisation; — = lack of binding/neutralization. nd = not determined; B = binding, determined by ELISA with commercial recombinant proteins or by LIPS with self-produced IFN-Gaussia luciferase fusion proteins; N = neutralization, determined by ISRE-Luciferase reporter assay or by phospho-STAT1 assay.

| Antigen | 19D11 B | 19D11 N | 25C3 B | 25C3 N | 26B9 B | 26B9 N | 31B4 B | 31B4 N | 5D1 B | 5D1 N | 13B11 B | 13B11 N |
|---|---|---|---|---|---|---|---|---|---|---|---|---|
| IFN-α1 | +++ | +++ | +++ | +++ | +++ | +++ | +++ | +++ | — | — | +++ | +++ |
| IFN-α2 | +++ | +++ | +++ | +++ | +++ | +++ | +++ | +++ | +++ | +++ | +++ | +++ |
| IFN-α4 | +++ | +++ | +++ | +++ | +++ | +++ | +++ | +++ | +++ | +++ | +++ | +++ |
| IFN-α5 | +++ | +++ | +++ | +++ | +++ | +++ | +++ | +++ | +++ | +++ | +++ | +++ |
| IFN-α6 | +++ | +++ | +++ | + | +++ | +++ | +++ | +++ | +++ | ++ | +++ | + |
| IFN-α7 | nd | +++ | nd | +++ | nd | +++ | nd | +++ | nd | +++ | nd | +++ |
| IFN-α8 | +++ | +++ | +++ | + | +++ | +++ | +++ | +++ | +++ | +++ | — | — |
| IFN-α10 | +++ | +++ | +++ | + | +++ | +++ | +++ | +++ | +++ | +++ | +++ | +++ |
| IFN-α14 | +++ | +++ | +++ | ++ | +++ | +++ | +++ | +++ | +++ | — | +++ | +++ |
| IFN-α16 | +++ | +++ | +++ | + | +++ | — | +++ | — | +++ | +++ | +++ | +++ |
| IFN-α17 | nd | +++ | nd | +++ | nd | +++ | nd | +++ | nd | +++ | nd | +++ |
| IFN-α21 | +++ | +++ | +++ | +++ | +++ | +++ | +++ | +++ | +++ | +++ | +++ | — |
| IFN-ω | — | — | nd | — | +++ | +++ | nd | +++ | nd | — | nd | — |

Previous experiments on binding and neutralization of different IFN-α subtypes by the exemplary antibodies of the present invention in ELISA, LIPS and neutralization assays gave similar results.

TABLE 8

Overview of all IFN proteins and used primer sequences used for cloning the Gaussia-luciferase-IFN-fusion constructs.

| Gene | AA | Primer Name | Sequence and SEQ ID NO: |
|---|---|---|---|
| IFN-α1 | 24-189 | IFN-α1F | TTTGGATCCTATGTGATCTCCCTGAGACCCACAGCCTGGA SEQ ID NO: 45 |
| | | IFN-α1R | TTTGCGGCCGCGACCAGATGTTATTCCTTCCTCCTTAATCTTTC SEQ ID NO: 46 |
| IFN-α2 | 24-188 | IFN-α2F | TTTGGGATCCTCTGTGATCTGCCTCAAACCCACA SEQ ID NO: 47 |
| | | IFN-α2R | TTTGCGGCCGCTTACTTCTTAAACTTTCTTGCA SEQ ID NO: 48 |
| IFN-α4 | 24-189 | IFN-α4F | TTTGGATCCTATGTGATCTGCCTCAGACCCACAGCCTGG SEQ ID NO: 49 |
| | | IFN-α4R | TTTGCGGCCGCTCAATCCTTCCTCCTTAATCTTTTTTGCAAGTTTGT TGAAAAC SEQ ID NO: 50 |
| IFN-α5 | 22-189 | IFN-α5F | TTTGGATCCTACTGGGCTGTGATCTGCCTCAGACCCACAGCCTGAG SEQ ID NO: 51 |
| | | IFN-α5R | TTTGCGGCCGCTCATTCCTTCCTCCTTAATCTTTCTTGCAAGTTTGC SEQ ID NO: 52 |
| IFN-α6 | 21-189 | IFN-α6F | TTTGGATCCTATCTCTGGACTGTGATCTGCCTCAGACCCACAGCCTG GGTC SEQ ID NO: 53 |
| | | IFN-α6R | TTTGCGGCCGCTTATTCCTTCCTCCTTAACCTTTCTTGCAAGTTTC SEQ ID NO: 54 |
| IFN-α7 | 24-189 | IFN-α7F | TTTGGATCCTATGTGATCTGCCTCAGACCCACAGCCTGC SEQ ID NO: 55 |
| | | IFN-α7R | TTTGCGGCCGCGAACCAGTTTTCAATCCTTCCTCCTTAATCCTTTTT T SEQ ID NO: 56 |
| IFN-α8 | 23-189 | IFN-α8F | TTTGGGATCCTCTGTGATCTGCCTCAGACTCACA SEQ ID NO: 57 |
| | | IFN-α8R | TTTGCGGCCGCTCATTCCTTACTCTTCAATCTT SEQ ID NO: 58 |
| IFN-α10 | 24-189 | IFN-α9F | TTTGGATCCTATGTGATCTGCCTCAGACCCACAGCCTGGG SEQ ID NO: 59 |
| | | IFN-α9R | TTTGCGGCCGCTCAATCCTTCCTCCTTAATCTTTTTTGCAAGTTTGT TGAAAAC SEQ ID NO: 50 |
| IFNA14 | 24-189 | IFN-α14F | TTTGGATCCTATGTAATCTGTCTCAAACCCACAGCCTGAA SEQ ID NO: 60 |
| | | IFN-α14R | TTTGCGGCCGCTCAATCCTTCCTCCTTAATCTTTTTTGCAAGTTTGT SEQ ID NO: 61 |
| IFN-α16 | 24-189 | IFN-α16F | TTTGGATCCTATGTGATCTGCCTCAGACT SEQ ID NO: 62 |
| | | IFN-α16R | TTTGCGGCCGCTCAATCCTTCCTTCTTAATCC SEQ ID NO: 63 |
| IFN-α17 | 24-189 | IFN-α17F | TTTGGATCCTATGTGATCTGCCTCAGACCCACAGCCTGGG SEQ ID NO: 59 |
| | | IFN-α17R | TTTGCGGCCGCGTTGAACCAGTTTTCAATCCTTCCTCCTTAATA SEQ ID NO: 64 |
| IFN-α21 | 24-189 | IFN-α21F | TTTGGATCCTATGTGATCTGCCTCAGACCCACAGCCT SEQ ID NO: 65 |
| | | IFN-α21R | TTTGCGGCCGCTCATTCCTTCCTCCTTAATCTTTCTTGAAAAA SEQ ID NO: 66 |
| IFNB | 22-187 | IFNB1F | TTTGGATCCTAATGAGCTACAACTTGCTTGGATTCCTAC SEQ ID NO: 67 |
| | | IFNB1R | TTTGCGGCCGCTCAGTTTCGGAGGTAACCTGTAAGTCT SEQ ID NO: 68 |
| IFNIG | 24-166 | IFNGF | TTTGGATCCTACAGGACCCATATGTAAAAGAAGCAGAAAAC SEQ ID NO: 69 |
| | | IFNGR | TTTGCGGCCGCCCATTACTGGGATGCTCTTCGACCT SEQ ID NO: 70 |

Cloning Human IFN Subtypes in Fusion to *Gaussia* Luciferase

Coding sequences of IFN-α1, IFN-α6, IFN-α7, IFN-α8, IFN-α10, IFN-α14, IFN-α16, IFN-α17, IFN-α21, IFNB, IFNG, IFNE and IFNK without signal peptides were cloned into modified pPK-CMV-F4 fusion vector (PromoCell GmbH, Heidelberg; Germany) downstream of naturally secreted *Gaussia* luciferase (Gluc) that was replaced to the plasmid instead of Firefly luciferase.

Example: 7

IC 50 Analysis of Exemplary Human-Derived IFN-α mAbs by ISRE Luciferase Reporter Neutralization Assay.

HEK 293T MSR cells (Cat. No. R79507, Invitrogen, Carlsbad, Calif., USA) transiently expressing ISRE-Firefly luciferase reporter and *Renilla* luciferase constructs (Cat. No. CCS-008L, Quiagen, Hilden, Germany) were stimulated with 2 ng/ml rhIFN-α2, rhIFN-α4, rhIFN-α14 or with supernatants of HEK 293T cells transiently expressing human IFN-*Gaussia* luciferase fusion proteins (IFN-α5, IFN-α8), in the presence of human-derived IFN-α mAbs 26B9 (FIG. 8A-E), 25C3 (FIG. 9A-E) or 19D11 (FIG. 10A-E) as indicated. After 24 hours of stimulation, dual luciferase reporter assays were performed according to the manufacturer's instructions (Promega, Madison, Wis., USA).

In a confirmatory experimental round HEK 293T MSR cells transiently expressing ISRE-Firefly luciferase reporter and *Renilla* luciferase constructs as described above were stimulated with 10 ng/ml rhIFN-α1, 2 ng/ml rhIFN-α2, rhIFN-α4, rhIFN-α5, rhIFN-α6, rhIFN-α8, rhIFN-α1 0, rhIFN-α14, rhIFN-α1 7, rhIFN-α21, 1.3 ng/ml rhIFN-α16, in the presence of human-derived IFN-α mAbs 26B9 (FIG. 8F-R) or 19D11 (FIG. 10F-Q) as indicated. After 24 hours of stimulation, dual luciferase reporter assays were performed according to the manufacturer's instructions (Promega, Madison, Wis., USA). The same experimental setup has been further used to perform the IC 50 analysis of human-derived mAbs 8H1 (FIG. 20), 12H5 (FIG. 21) and 50E1 1 (FIG. 22). The results of the assays are summarized in Table 4 above.

Example: 8

Antibody Affinity Measurements Using Surface Plasmon Resonance (SPR) Technology

For affinity determination of the antibodies of the present invention SPR measurements are performed using a ProteOn™ XPR36 instrument, according to the instructions of the manufacturer (Bio-RAD; Hercules Calif., USA) using the molecules of interest of the present invention in an analogous experimental setup as described in Example 14 of international application WO2013/098419 on pages 163-165, the disclosure content of which is incorporated herein by reference. Alternatively or in addition a similar analysis is made using Biacore SPR instruments according to the manufacturer's instructions.

Results for the SPR measurements performed on exemplary antibodies 19D11 and 26B9 of the present invention are shown in FIG. 26, with a 1:1 binding kinetic observed for the antibodies towards IFN-α2b, IFN-α4, IFN-α1 4 and in respect of antibody 26B9 also towards IFN-α. The affinities towards human IFN-α4 and IFN-α14 are in the sub-picomolar range and in sub-nanomolar range for IFN-α2b. 26B9 also binds human IFN-ω with a sub-picomolar affinity.

Example 9: Chemiluminescent Cellular Binding Assays

Interferons-*Gaussia* Luciferase 30,000 HEK 293T MSR cells were seeded in white half area 96-well tissue culture plates (Cat. No. 3688, Corning Inc.). The following day, supernatants of HEK 293T cells transiently expressing human IFN-*Gaussia* luciferase fusion proteins were mixed with anti-IFN mAbs, control IgG or excess concentrations of unlabeled recombinant IFN-α2 and preincubated for one hour at 37° C. After preincubation, the mixtures were used to stimulate HEK 293T MSR cells for 40 minutes at 37° C. Upon binding, cells were washed three times with PBS, and the *Gaussia* luciferase assay was developed using the *Gaussia* Flash Assay Kit according to the manufacturer's instructions (Cat. No. 16159, Thermo Fisher Scientific).

Binding to Transmembrane Antibodies 30,000 HEK 293T MSR cells were seeded in white half area 96-well tissue culture plates (Cat. No. 3688, Corning Inc.). During seeding, cells were transfected with 100 ng cDNA encoding a transmembrane version of anti-IFN mAb 26B9 (26B9-TM) using Fugene HD (Cat. No. E2311, Promega, Madison, Wis., USA). Surface antibody (26B9-TM) expression was analyzed 48 hours after transfection in a cell-based ELISA (FIG. 24A). Forty-eight hours following transfection, supernatants of HEK 293T cells transiently expressing human IFN-ω-*Gaussia* luciferase fusion proteins (g1 IFN-α) were used to stimulate the previously transfected HEK 293T MSR cells for 40 minutes at 37° C. Alternatively, the g1 IFN-ω supernatants were mixed with anti-IFN mAbs or control IgG and preincubated for one hour at 37° C. After preincubation, the mixtures were used to stimulate HEK 293T MSR cells transiently expressing 26B9-TM for 40 minutes at 37° C. Upon binding, cells were washed three times with PBS, and the *Gaussia* luciferase assay was developed using the *Gaussia* Flash Assay Kit according to the manufacturer's instructions (Cat. No. 16159, Thermo Fisher Scientific) showing that g1 IFN-ω was specifically binding to cells expressing 26B9-TM (FIG. 24B).

Crosscompetition Assay of Anti-IFN-ω Antibodies.

Above experimental setup has been also used to test crosscompetition between exemplary antibodies 26B9, 31B4 and 8H1 of the present invention (see FIG. 25). HEK 293T MSR cells were reverse-transfected with cDNA encoding 26B9-TM. Forty-eight hours after transfection, g1 IFN-ω was mixed and preincubated for one hour with soluble anti-IFN-ω antibodies 26B9, 31B4, 8H1 or a control IgG (huIgG). Following incubation, the mixtures were added to the transfected cells and binding was analysed in the chemiluminescent cellular binding assay. Binding of g1 IFN-ω to 26B9-TM is competed dose-dependently by soluble 26B9 and by the clonally related 31B4 antibody. In contrast, binding is not affected by a control IgG or by exemplary anti-IFN-ω antibody 8H1. These results indicate that exemplary antibodies 26B9 and 31B4 share similar epitopes, while 8H1 appears to bind to a distinct epitope.

The invention claimed is:

1. A human monoclonal anti-interferon-alpha (IFN-α) antibody or an IFN-α binding fragment thereof, wherein the antibody or antigen-binding fragment thereof comprises in its variable regions the complementarily determining regions (CDRs) VH CDRs: amino acids 31-35 of SEQ ID NO:18 and amino acids 50-66 of SEQ ID NO: 18 and amino acids 99-115 of SEQ ID NO: 18; and VL CDRs: amino acids 24-35 of SEQ ID NO:20 and amino acids 51-57 of SEC) ID NO:20 and amino acids 90-100 of SEC) ID NO:20 and wherein the antibody has the following properties: (i) binds to human IFN-α subtypes IFNαI/13 (IFNαIb), IFNα2, IFNα4, IFNα5, IFNα6, IFNα7, IFNα8, IFNα10, IFNα14 IFNα16, IFNα17 and IFNα21; and (ii) does not bind to IFN-ω, wherein the IFN-α antibody or IFN-α binding fragment thereof is labeled with a detectable label selected from the group consisting of an enzyme, a radioisotope, a fluorophore, a peptide and a heavy metal, or attached to a drug.

2. The monoclonal IFN-α antibody or IFN-α binding fragment thereof of claim 1, comprising in its variable regions an amino acid sequence of the $V_H$ and $V_L$ region as depicted in SEQ ID NO:18 and 20, respectively.

3. The human monoclonal IFN-α antibody or IFN-α binding fragment thereof of claim 1, which binds an epitope of IFNα2 consisting of the amino acid sequence SAAWDETLLDKFYTELYQ (SEQ ID NO: 99) and/or RITLYLKEKKYSPCAWEV (SEQ ID NO: 100).

4. The human monoclonal IFN-α antibody or IFN-α binding fragment thereof of claim 1, which is an IgG1 isotype.

5. The human monoclonal IFN-α antibody or IFN-α binding fragment thereof of claim 1 comprising a $C_H$ and/or $C_L$ constant region comprising an amino acid sequence selected from SEQ ID NOs.:72 and 74.

6. The human monoclonal IFN-α antibody or IFN-α binding fragment thereof of claim 1, which has an $IC_{50}$ value of ≤10 ng for at least 10 human IFN-α subtypes.

7. The human monoclonal IFN-α antibody or IFN-α binding fragment thereof of claim 1, which is selected from the group consisting of a single chain Fv fragment (scFv), an F(ab') fragment, an F(ab) fragment, and an F(ab')2 fragment and comprises in its variable regions the complementarity determining regions (CDRs)

$V_H$ CDRs: amino acids 31-35 of SEQ ID NO:18 and amino acids 50-66 of SEQ ID NO:18 and amino acids 99-115 of SEQ ID NO:18; and $V_L$ CDRs: amino acids 24-35 of SEQ ID NO:20 and amino acids 51-57 of SEQ ID NO:20 and amino acids 90-100 of SEQ ID NO:20 and wherein the antibody has the following properties:
(i) binds to human IFN-α subtypes IFNα1/13 (IFNα1b), IFNα2, IFNα4, IFNα5, IFNα6, IFNα7, IFNα8, IFNα10, IFNα14, IFNα16, IFNα17 and IFNα21; and
(ii) does not bind to IFN-ω.

8. A method for diagnosing an inflammatory or autoimmune disease or condition associated with the expression of IFN-α in a subject comprising contacting a biological sample of the subject with the monoclonal anti-IFN-α antibody or IFN-α-binding fragment thereof of claim 1, and detecting the presence of IFN-α in the biological sample.

9. A cDNA molecule encoding a monoclonal anti-interferon-alpha (IFN-α) antibody or an IFN-α binding fragment thereof, wherein the antibody or IFN-α binding fragment thereof comprises in its variable regions the complementarity determining regions (CDRs)

$V_H$ CDRs: amino acids 31-35 of SEQ ID NO:18 and amino acids 50-66 of SEQ ID NO:18 and amino acids 99-115 of SEQ ID NO:18; and $V_L$ CDRs: amino acids 24-35 of SEQ ID NO:20 and amino acids 51-57 of SEQ ID NO:20 and amino acids 90-100 of SEQ ID NO:20 and wherein the antibody has the following properties (i) binds to human IFN-α subtypes IFNα1/13 (IFNα1b), IFNα2, IFNα4, IFNα5, IFNα6, IFNα7, IFNα8, IFNα10, IFNα14, IFNα16, IFNα17 and IFNα21; and
(ii) does not bind to IFN-ω.

10. The cDNA molecule of claim 9, wherein the monoclonal antibody or IFN-α binding fragment thereof binds an epitope of IFNα2 consisting of the amino acid sequence SAAWDETLLDKFYTELYQ (SEQ ID NO: 99) and/or RITLYLKEKKYSPCAWEV (SEQ ID NO: 100).

11. The cDNA molecule of claim 9, wherein the monoclonal antibody or IFN-α binding fragment thereof comprises in its variable regions an amino acid sequence of the $V_H$ and $V_L$ region as depicted in SEQ ID NO:18 and 20, respectively.

12. The cDNA molecule of claim 9, wherein the monoclonal antibody or IFN-α binding fragment thereof is an IgG1 isotype.

13. The cDNA molecule of claim 9, wherein the monoclonal antibody or IFN-α binding fragment thereof comprises a $C_H$ and/or $C_L$ constant region comprising an amino acid sequence selected from SEQ ID NOs.:72 and 74.

14. The cDNA molecule of claim 9, wherein the monoclonal antibody or IFN-α binding fragment thereof has an $IC_{50}$ value of ≤10 ng for at least 10 human IFN-α subtypes.

15. The cDNA molecule of claim 9, wherein the monoclonal antibody or IFN-α binding fragment thereof is selected from the group consisting of a single chain Fv fragment (scFv), an F(ab') fragment, an F(ab) fragment, and an F(ab')$_2$ fragment wherein the antibody or IFN-α binding fragment thereof comprises in its variable regions the complementarity determining regions (CDRs)

$V_H$ CDRs: amino acids 31-35 of SEQ ID NO:18 and amino acids 50-66 of SEQ ID NO:18 and amino acids 99-115 of SEQ ID NO:18; and $V_L$ CDRs: amino acids 24-35 of SEQ ID NO:20 and amino acids 51-57 of SEQ ID NO:20 and amino acids 90-100 of SEQ ID NO:20 and wherein the antibody has the following properties (i) binds to human IFN-α subtypes IFNα1/13 (IFNα1b), IFNα2, IFNα4, IFNα5, IFNα6, IFNα7, IFNα8, IFNα10, IFNα14, IFNα16, IFNα17 and IFNα21; and
(ii) does not bind to IFN-ω.

16. The cDNA molecule of claim 9, encoding the variable region and at least part of the constant domain.

17. The cDNA molecule of claim 9, wherein the monoclonal antibody or IFN-α binding fragment thereof is a human monoclonal antibody or IFN-α binding fragment thereof.

18. A vector comprising the cDNA molecule of claim 9.

19. The vector of claim 18, wherein the vector is an expression vector.

20. An isolated host cell comprising the vector of claim 19.

21. The host cell of claim 20, which is a prokaryotic or eukaryotic host cell.

22. A method of producing a monoclonal anti-IFN-α antibody or IFN-α binding fragment thereof encoded by the vector in the host cell of claim 20, comprising:
   (a) culturing in a cell culture the host cell under conditions allowing the expression of the antibody encoded by the cDNA molecule; and
   (b) isolating the antibody from the cell culture.

23. A polynucleotide linked to a heterologous nucleic acid, wherein the polynucleotide is selected from the group consisting of:
   (a) a polynucleotide encoding an immunoglobulin heavy chain or a fragment thereof comprising a heavy chain variable region (VH) comprising the complementarity determining regions (CDRs) of the VH variable region amino acid sequence depicted in SEQ ID NO: 18, wherein the immunoglobulin heavy chain VH when paired with a light chain variable region (VL) comprising the amino acid sequence depicted in SEQ ID NO: 20
      (i) binds to human IFN-α subtypes IFNα1/13 (IFNα1b), IFNα2, IFNα4, IFNα5, IFNα6, IFNα7, IFNα8, IFNα10, IFNα14, IFNα16, IFNα17 and IFNα21; and
      (ii) does not bind to IFN-ω;
   (b) a polynucleotide encoding an immunoglobulin light chain or a fragment thereof comprising a light chain variable region (VL) comprising the complementarity determining regions (CDRs) of the VL variable region amino acid sequence depicted in SEQ ID NO: 20, wherein the immunoglobulin light chain VL when paired with a heavy chain variable region (VH) comprising the amino acid sequence depicted in SEQ ID NO: 18
      i) binds to human IFN-α subtypes IFNα1/13 (IFNα1b), IFNα2, IFNα4, IFNα5, IFNα6, IFNα7, IFNα8, IFNα10, IFNα14, IFNα16, IFNα17 and IFNα21; and
      (ii) does not bind to IFN-ω;
   (c) a polynucleotide encoding
      (i) an immunoglobulin heavy chain or a fragment thereof comprising a heavy chain variable region (VH) comprising the complementarity determining regions (CDRs) of the VH variable region amino acid sequence depicted in SEQ ID NO: 18; and
      (ii) an immunoglobulin light chain or a fragment thereof comprising a light chain variable region (VL) comprising the complementarity determining regions (CDRs) of the VL variable region amino acid sequence depicted in SEQ ID NO: 20;
   (d) a polynucleotide encoding an immunoglobulin heavy chain or a fragment thereof comprising the amino acid sequence of SEQ ID NO: 18;
   (e) a polynucleotide encoding an immunoglobulin light chain or a fragment thereof comprising the amino acid sequence of SEQ ID NO: 20; and
   (f) a polynucleotide encoding an immunoglobulin heavy chain or a fragment thereof comprising the amino acid sequence of SEQ ID NO: 18 and an immunoglobulin light chain or a fragment thereof comprising the amino acid sequence of SEQ ID NO: 20.

24. The polynucleotide of claim 23, wherein the polynucleotide further encodes an amino acid sequence of a $C_H$ and/or $C_L$ constant region comprising an amino acid sequence selected from SEQ ID NOs.:72 and 74.

25. The polynucleotide of claim 23, wherein the heterologous nucleic acid is a regulatory element.

26. The polynucleotide of claim 25, wherein the regulatory element is a promoter, an enhancer, a transcription termination sequence or a leader sequence.

27. A vector comprising one or more of polynucleotides of claim 23.

28. The vector of claim 27, wherein the vector is an expression vector.

29. An isolated host cell comprising one or more vectors of claim 28.

30. The host cell of claim 29, which is a prokaryotic or eukaryotic host cell.

31. A method of producing a monoclonal antibody that binds to human IFN-α subtypes IFNα1/13 (IFNα1b), IFNα2, IFNα4, IFNα5, IFNα6, IFNα7, IFNα8, IFNα10, IFNα14, IFNα16, IFNα17 and IFNα21; and does not bind to IFN-ω or an immunoglobulin chain thereof encoded by the vector in the host cell of claim 29, which comprises:
   (a) culturing in a cell culture the host cell under conditions allowing the expression of the antibody or immunoglobulin chain; and
   (b) isolating the antibody or immunoglobulin chain from the cell culture.

32. The method of claim 31, wherein the monoclonal antibody is a human antibody.

33. A method of treating an inflammatory or autoimmune disease or condition associated with the expression of IFN-α comprising administering to a subject in need of such treatment an effective amount of a human anti-IFN-α antibody or IFN-α binding fragment thereof produced by the method of claim 22 or 31.

34. A method of treating an inflammatory or autoimmune disease or condition associated with the expression of IFN-α comprising administering to a subject in need of such treatment an effective amount of a human anti-IFN-α antibody or IFN-α binding fragment thereof encoded by the cDNA molecule of claim 9 or the polynucleotides of claim 23.

* * * * *

UNITED STATES PATENT AND TRADEMARK OFFICE
CERTIFICATE OF CORRECTION

PATENT NO.          : 10,112,995 B2
APPLICATION NO.     : 14/902409
DATED               : October 30, 2018
INVENTOR(S)         : Syeda F. Y. Haque et al.

Page 1 of 10

It is certified that error appears in the above-identified patent and that said Letters Patent is hereby corrected as shown below:

In Columns 29-44, please delete Table 1 and insert the following:

-- Table 1: Nucleotide sequences of the variable and constant regions ($V_H$, $V_L$, $C_H$, $C_L$) regions of IgG1, kappa, IFN-α specific 5D1, 13B11, 19D11, 25C3, 26B9, 31B4, 8H1, 12H5 and 50E11 antibodies of the present invention.

| Antibody | Nucleotide and amino acid sequences of variable heavy (VH) and variable light (VL), constant heavy (CH) and constant light (CL) chains. |
|---|---|
| 5D1-$V_H$ | gaagtgcaactggtgcaggccggcgcagaggtgaaagcgcccggggagtctctgaggatctcc tgtaaggtgtctggatacacctttacaagttattggatcagttgggtgcgccagattcccggg aaaggcctggagtggatggtgaaaattgatcctagagactcttataccatctacaacccgtcc ttccaaggccacgtctccatctcagttgacaagtccatcaccactgtctacctgcagtggagc agcctgcaggcctcggacaccgccatttattattgtgtgagacattatcttacacagtcattg gtggactactttgaccactggggccagggaacgctggtcgccgtctcctct SEQ ID NO:1 |
| 5D1-$V_H$ | EVQLVQAGAEVKAPGESLRISCKVSGYTFTSYWISWVRQIPGKGLEWMVKIDPRDSYTIYNPS FQGHVSISVDKSITTVYLQWSSLQASDTAIYYCVRHYLTQSLVDYFDHWGQGTLVAVSS SEQ ID NO:2 |
| 5D1-$V_L$ kappa-type | gacattcagatgacccagtctccatcctccctgtctgcatctgtgggagacagtgtcaccatc acttgccgggcaagtcagagcgtatccaactacttccattggtatcgacagaagcccgggaaa gcccctgaactcctgatctattctgcatccaatttgcaaactggggtcccatcaagattcact ggcagtgggtctgggacagaatgcactctcaccatcaccagtctgcagcctgatgatttcgca acttactactgtcaacagactcacggttacccgttcacttttggccaggggaccaagctggac gtcaga SEQ ID NO:3 |

Signed and Sealed this
Nineteenth Day of February, 2019

Andrei Iancu
*Director of the United States Patent and Trademark Office*

| | |
|---|---|
| 5D1-V$_L$<br>kappa-type | DIQMTQSPSSLSASVGDSVTITCRASQSVSNYFHWYRQKPGKAPELLIYSASNLQTGVPSRFT GSGSGTECTLTITSLQPDDFATYYCQQTHGYPFTFGQGTKLDVR<br>SEQ ID NO:4 |
| 5D1-C$_H$ | gcctccaccaagggcccatcggtcttccccctggcaccctcctccaagagcacctctgggggc acagcggccctgggctgcctggtcaaggactacttccccgaaccggtgacggtgtcgtggaac tcaggcgccctgaccagcggcgtgcacaccttcccggctgtcctacagtcctcaggactctac tccctcagcagcgtggtgaccgtgccctccagcagcttgggcacccagacctacatctgcaac gtgaatcacaagcccagcaacaccaaggtggacaagaaagttgagcccaaatcttgtgacaaa actcacacatgcccaccgtgcccagcacctgaactcctggggggaccgtcagtcttcctcttc cccccaaaacccaaggacaccctcatgatctcccggacccctgaggtcacatgcgtggtggtg gacgtgagccacgaagaccctgaggtcaagttcaactggtacgtggacggcgtggaggtgcat aatgccaagacaaagccgcgggaggagcagtacaacagcacgtaccgtgtggtcagcgtcctc accgtcctgcaccaggactggctgaatggcaaggagtacaagtgcaaggtctccaacaaagcc ctcccagcccccatcgagaaaaccatctccaaagccaaagggcagccccgagaaccacaggtg tacaccctgcccccatcccgggatgagctgaccaagaaccaggtcagcctgacctgcctggtc aaaggcttctatcccagcgacatcgccgtggagtgggagagcaatgggcagccggagaacaac tacaagaccacgcctcccgtgctggactccgacggctccttcttcctctacagcaagctcacc gtggacaagagcaggtggcagcaggggaacgtcttctcatgctccgtgatgcatgaggctctg cacaaccactacacgcagaagagcctctccctgtctccgggtaaatga<br>SEQ ID NO:5 |
| 5D1-CH | astkgpsvfplapsskstsggtaalgclvkdyfpepvtvswnsgaltsgvhtfpavlqssgly slssvvtvpsssgtqtyicnvnhkpsntkvdkkvepkscdkthtcppcpapellggpsvflf ppkpkdtlmisrtpevtcvvvdvshedpevkfnwyvdgvevhnaktkpreeqynstyrvvsvl tvlhqdwlngkeykckvsnkalpapiektiskakgqprepqvytlppsrdeltknqvsltclv kgfypsdiavewesngqpennykttppvldsdgsfflysklitvdksrwqqgnvfscsvmheal hnhytqkslslspgk<br>SEQ ID NO:6 |

| | |
|---|---|
| 5D1-C$_L$<br>kappa-type | cgaactgtggctgcaccatctgtcttcatcttcccgccatctgatgagcagttgaaatctgga actgcctctgttgtgtgcctgctgaataacttctatcccagagaggccaaagtacagtggaag gtggataacgccctccaatcgggtaactcccaggagagtgtcacagagcaggacagcaaggac agcacctacagcctcagcagcaccctgacgctgagcaaagcagactacgagaaacacaaagtc tacgcctgcgaagtc*acccatcagggcctgagctcgcccgtcacaaagagcttcaacaggga gagtgttag*<br>SEQ ID NO:7 |
| 5D1-C$_L$<br>kappa-type | RTVAAPSVFIFPPSDEQLKSGTASVVCLLNNFYPREAKVQWKVDNALQSGNSQESVTEQDSKD STYSLSSTLTLSKADYEKHKVYACEV*THQGLSSPVTKSFNRGEC*<br>SEQ ID NO:8 |
| 13B11-V$_H$ | Gacgtacagctgttgcagtctgggggaggcttgatacagccgggggggtccctgagactctcc tgtgcagcctctggctttacttttaaggactatgccatgagttgggtccgccaggctccaggg aagggcctggagtgggtctcagtaataagtcgtagtggtaatattgtagactatgtcgactcc gtgaagggccggttcaccgtctccagagacaattccaacaacacactctttctgcaaatggac ggcctgagagccgacgacacggccatttattactgtgcgaaacccaaggatatgattgtcgtg gtccctgcgggctttgactcctggggccagggaaccctggtctccgtctcctca<br>SEQ ID NO:9 |
| 13B11-V$_H$ | DVQLLQSGGGLIQPGGSLRLSCAASGFTFKDYAMSWVRQAPGKGLEWVSVISRSGNIVDYVDS VKGRFTVSRDNSNNTLFLQMDGLRADDTAIYYCAKPKDMIVVVPAGFDSWGQGTLVSVSS<br>SEQ ID NO:10 |
| 13B11-V$_L$<br>kappa-type | gacatccagatgacccagtttccatccaccctgtctgcatctgttggagacagcgtcaccatc acttgccgggccagtcagagcattagtgcctggttggcctggtatcagcagaaaccagggaaa gcccctaaactcctgatctataaggggtctagattagaaaacggggtcccatcgaggttcagc ggcagtggatctgggacagaattcactctcaccatcggcagcctgcagcctgatgattttgca acttattactgccaacaatataagacttggacgttcggccaagggaccaaggtggaaatcaaa<br>SEQ ID NO:11 |

| 13B11-V_L kappa-type | DIQMTQFPSTLSASVGDSVTITCRASQSISAWLAWYQQKPGKAPKLLIYKGSRLENGVPSRFSGSGSGTEFTLTIGSLQPDDFATYYCQQYKTWTFGQGTKVEIK<br>SEQ ID NO:12 |
|---|---|
| 13B11-C_H | gcctccaccaagggcccatcggtcttccccctggcaccctcctccaagagcacctctgggggcacagcggccctgggctgcctggtcaaggactacttccccgaaccggtgacggtgtcgtggaactcaggcgccctgaccagcggcgtgcacaccttcccggctgtcctacagtcctcaggactctactccctcagcagcgtggtgaccgtgccctccagcagcttgggcacccagacctacatctgcaacgtgaatcacaagcccagcaacaccaaggtggacaagaaagttgagcccaaatcttgtgacaaaactcacacatgcccaccgtgcccagcacctgaactcctggggggaccgtcagtcttcctcttccccccaaaacccaaggacaccctcatgatctcccggacccctgaggtcacatgcgtggtggtggacgtgagccacgaagaccctgaggtcaagttcaactggtacgtggacggcgtggaggtgcataatgccaagacaaagccgcgggaggagcagtacaacagcacgtaccgtgtggtcagcgtcctcaccgtcctgcaccaggactggctgaatggcaaggagtacaagtgcaaggtctccaacaaagccctcccagcccccatcgagaaaaccatctccaaagccaaagggcagccccgagaaccacaggtgtacaccctgcccccatcccgggatgagctgaccaagaaccaggtcagcctgacctgcctggtcaaaggcttctatcccagcgacatcgccgtggagtgggagagcaatgggcagccggagaacaactacaagaccacgcctcccgtgctggactccgacggctccttcttcctctacagcaagctcaccgtggacaagagcaggtggcagcaggggaacgtcttctcatgctccgtgatgcatgaggctctgcacaaccactacacgcagaagagcctctccctgtctccgggtaaatga<br>SEQ ID NO:13 |
| 13B11-C_H | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK<br>SEQ ID NO:14 |

| 13B11-C_L kappa-type | cgaactgtggctgcaccatctgtcttcatcttcccgccatctgatgagcagttgaaatctggaactgcctctgttgtgtgcctgctgaataacttctatcccagagaggccaaagtacagtggaaggtggataacgccctccaatcgggtaactcccaggagagtgtcacagagcaggacagcaaggacagcacctacagcctcagcagcaccctgacgctgagcaaagcagactacgagaaacacaaagtctacgcctgcgaagtcacccatcagggcctgagctcgcccgtcacaaagagcttcaacaggggagagtgttag<br>SEQ ID NO:15 |
|---|---|
| 13B11-C_L kappa-type | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC<br>SEQ ID NO:16 |
| 19D11-V_H | *gaggtgcagctgttggagt*ctgggggctgaggtgaagaggcctggggtcgtcggtgagggtctcctgcagggcttctggagacaccttcagcagttaccctatcagttgggtgcgacaggcccctggacaaggccttgagtggatgggaaggatcctccctgcccttggtgtcacaaactacgctcagaacttccgggcagaatcacgattaccgcggacaagtcgcccctcacagcctacttggaactgagtagcctcagatttgaggacacggccgtgtattactgtgcgagtcccagtgcggacataattcctcgattttggggacgacctctttgccttctggggccagggaagcctggtcaccgtctcctca<br>SEQ ID NO:17 |
| 19D11-V_H | *EVQLLES*GAEVKRPGSSVRVSCRASGDTFSSYPISWVRQAPGQGLEWMGRILPALGVTNYAQNFRGRITITADKSPLTAYLELSSLRFEDTAVYYCASPSADIIPSILGTTLFAFWGQGS*LVTVSS*<br>SEQ ID NO: 18 |
| 19D11-V_L kappa-type | *gaaattgtgttgacgcagt*ctccaggcacctgtctctgtctccgggggaaggggccaccctctcctgcagggccagtcagaatgttagcagacactacttaacctggtaccagcagaaacctggccagtctcccggctcctcatctatggtggctccagcagggccactggcgtcccagacaggttcagtggcggtgggtctgggacagacttcactctcaccatcagcaggctggagcctgaagactttgcagtgttttactgccagagctatcatagcccacctcctgtgtacactttcggccaggg*accaaggtggagatcaaa*<br>SEQ ID NO:19 |

| | |
|---|---|
| 19D11-V<sub>L</sub><br><br>kappa-type | *EIVLTQ*SPGTLSLSPGEGATLSCRASQNVSRHYLTWYQQKPGQSPRLLIYGGSSRATGVPDRF<br>SGGGSGTDFTLTISRLEPEDFAVFYCQSYHSPPPVYTFGQ*GTKVEIK*<br>SEQ ID NO:20 |
| 19D11-C<sub>H</sub> | *gcctccaccaagggcccatcggtcttccccctggc*accctcctccaagagcacctctggggc<br>acagcggccctgggctgcctggtcaaggactacttccccgaaccggtgacggtgtcgtggaac<br>tcaggcgccctgaccagcggcgtgcacaccttcccggctgtcctacagtcctcaggactctac<br>tccctcagcagcgtggtgaccgtgccctccagcagcttgggcacccagacctacatctgcaac<br>gtgaatcacaagcccagcaacaccaaggtggacaagagagttgagcccaaatcttgtgacaaa<br>actcacacatgcccaccgtgcccagcacctgaactcctggggggaccgtcagtcttcctcttc<br>cccccaaaacccaaggacaccctcatgatctcccggacccctgaggtcacatgcgtggtggtg<br>gacgtgagccacgaagaccctgaggtcaagttcaactggtacgtggacggcgtggaggtgcat<br>aatgccaagacaaagccgcgggaggagcagtacaacagcacgtaccgtgtggtcagcgtcctc<br>accgtcctgcaccaggactggctgaatggcaaggagtacaagtgcaaggtctccaacaaagcc<br>ctcccagcccccatcgagaaaaccatctccaaagccaaagggcagccccgagaaccacaggtg<br>tacaccctgcccccatcccgggaggagatgaccaagaaccaggtcagcctgacctgcctggtc<br>aaaggcttctatcccagcgacatcgccgtggagtgggagagcaatgggcagccggagaacaac<br>tacaagaccacgcctcccgtgctggactccgacggctccttcttcctctatagcaagctcacc<br>gtggacaagagcaggtggcagcaggggaacgtcttctcatgctccgtgatgcatgaggctctg<br>cacaaccactacacgcagaananccctctccctgtccccgggtaaatga<br>SEQ ID NO: 71 |
| 19D11-C<sub>H</sub> | *ASTKGPSVFPLA*PSSKSTSGGTAALGCLVKDYFPEPVTVSWNSGALTSGVHTFPAVLQSSGLY<br>SLSSVVTVPSSSLGTQTYICNVNHKPSNTKVDKRVEPKSCDKTHTCPPCPAPELLGGPSVFLF<br>PPKPKDTLMISRTPEVTCVVVDVSHEDPEVKFNWYVDGVEVHNAKTKPREEQYNSTYRVVSVL<br>TVLHQDWLNGKEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNVFSCSVMHEAL<br>HNHYTQXXLSLSPGK<br>SEQ ID NO: 72 |

| | |
|---|---|
| 19D11-C<sub>L</sub><br><br>kappa-type | cgaactgtggctgcaccatctgtcttcatcttcccgccatctgatgagcagttgaaatctgga<br>actgcctctgttgtgtgcctgctgaataacttctatcccagagaggccaaagtacagtggaag<br>gtggataacgccctccaatcgggtaactcccaggagagtgtcacagagcaggacagcaaggac<br>agcacctacagcctcagcagcaccctgacgctgagcaaagcagactacgagaaacacaaagtc<br>tacgcctgcgaagtcacccatcagggcctgagctcgcccgtcacaaagagcttcaacaggggga<br>gagtgttag<br>SEQ ID NO: 73 |
| 19D11-C<sub>L</sub><br><br>kappa-type | RTVAAPSVFIFPPSDEQLKSGTASVVCLLNNFYPREAKVQWKVDNALQSGNSQESVTEQDSKD<br>STYSLSSTLTLSKADYEKHKVYACEVTHQGLSSPVTKSFNRGEC<br>SEQ ID NO: 74 |
| 25C3-V<sub>H</sub> | gagatgcagctgatggagtctgggggaggtttggtacaacgggggggtccctgagactctcc<br>tgtgtagcctctggtttcacctttaaaagttttgcgatgagttgggtccgccaggctccaggg<br>aaggggctggagtgggtcgctagtgtcggctctcagggtggcagcaaatactatgcaccctcc<br>gtgaagggccggttctccatctccagagacaattccaacaacactctctatgtgcaaatgaac<br>agcctgggagtcgaggacacggcctttttattattgtgttaaagagaccgatgcagtggcgacg<br>atggacgctcttgacatgtggggccaagggaccctggtcatcgtctctacc<br>SEQ ID NO: 21 |
| 25C3-V<sub>H</sub> | EMQLMESGGGLVQPGGSLRLSCVASGFTFKSFAMSWVRQAPGKGLEWVASVGSQGGSKYYAPS<br>VKGRFSISRDNSNNTLYVQMNSLGVEDTAFYYCVKETDAVATMDALDMWGQGTLVIVST<br>SEQ ID NO:22 |
| 25C3-V<sub>L</sub><br><br>kappa-type | gacatccgggtgacccagtctccatcctccctgtctgcatctgtcggagacagggtctccatc<br>tcttgcagacaagtcagagtgttaacatatatctaaattggtatcaacagagaccagggaaa<br>gcccctcagctcctgatctctgctgcttccactttgcagagtggggtcccatcaaggttcagt<br>ggcagtggatctgggacagacttcatcctcaccatcatcagtctacaacctgaagattctgca<br>tcctactactgtcaacagggttacattaccccgtacacttttggccaggggaccaaggtggag<br>atcaaa<br>SEQ ID NO:23 |

| 25C3-V_L kappa-type | DIRVTQSPSSLSASVGDRVSISCQTSQSVNIYLNWYQQRPGKGPQLLISAASTLQSGVPSRFS GSGSGTDFILTIISLQPEDSASYYCQQGYITPYTFGQGTKVEIK<br>SEQ ID NO:24 |
|---|---|
| 25C3-C_H | gcctccaccaagggcccatcggtcttccccctggcaccctcctccaagagcacctctgggggc acagcggccctgggctgcctggtcaaggactacttccccgaaccggtgacggtgtcgtggaac tcaggcgccctgaccagcggcgtgcacaccttcccggctgtcctacagtcctcaggactctac tccctcagcagcgtggtgaccgtgcctccagcagcttgggcacccagacctacatctgcaac gtgaatcacaagcccagcaacaccaaggtggacaagagagttgagcccaaatcttgtgacaaa actcacacatgcccaccgtgcccagcacctgaactcctggggggaccgtcagtcttcctcttc cccccaaaacccaaggacaccctcatgatctcccggacccctgaggtcacatgcgtggtggtg gacgtgagccacgaagaccctgaggtcaagttcaactggtacgtggacggcgtggaggtgcat aatgccaagacaaagccgcgggaggagcagtacaacagcacgtaccgtgtggtcagcgtcctc accgtcctgcaccaggactggctgaatggcaaggagtacaagtgcaaggtctccaacaaagcc ctcccagcccccatcgagaaaaccatctccaaagccaaagggcagccccgagaaccacaggtg tacaccctgcccccatcccgggaggagatgaccaagaaccaggtcagcctgacctgcctggtc aaaggcttctatcccagcgacatcgccgtggagtgggagagcaatgggcagccggagaacaac tacaagaccacgcctcccgtgctggactccgacggctccttcttcctctatagcaagctcacc gtggacaagagcaggtggcagcaggggaacgtcttctcatgctccgtgatgcatgaggctctg cacaaccactacacgcagaagagcctctccctgtccccgggtaaatga<br>SEQ ID NO:25 |
| 25C3-C_H | ASTKGPSVFPLAPSSKSTSGGTAALGCLVKDYFPEPVTVSWNSGALTSGVHTFPAVLQSSGLY SLSSVVTVPSSSLGTQTYICNVNHKPSNTKVDKRVEPKSCDKTHTCPPCPAPELLGGPSVFLF PPKPKDTLMISRTPEVTCVVVDVSHEDPEVKFNWYVDGVEVHNAKTKPREEQYNSTYRVVSVL TVLHQDWLNGKEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNVFSCSVMHEAL HNHYTQKSLSLSPGK<br>SEQ ID NO:26 |

| 25C3-C_L kappa-type | cgaactgtggctgcaccatctgtcttcatcttcccgccatctgatgagcagttgaaatctgga actgcctctgttgtgtgcctgctgaataacctctatcccagagaggccaaagtacagtggaag gtggataacgccctccaatcgggtaactcccaggagagtgtcacagagcaggacagcaaggac agcacctacagcctcagcagcaccctgacgctgagcaaagcagactacgagaaacacaaagtc tacgcctgcgaagt*cacccatcagggcctgagctcgcccgtcacaaagagcttcaacagggga gagtgttag*<br>SEQ ID NO:27 |
|---|---|
| 25C3-C_L kappa-type | RTVAAPSVFIFPPSDEQLKSGTASVVCLLNNLYPREAKVQWKVDNALQSGNSQESVTEQDSKD STYSLSSTLTLSKADYEKHKVYACEV*THQGLSSPVTKSFNRGEC*<br>SEQ ID NO:28 |
| 26B9-V_H | cagatactactgcaggagtcgggcccaggactggtgaagcccacggagaccctgtccctcacc tgtagtgtctctggtgactccatcagtgatagtagtcactactgggcctggattcgccagccc ccagggaagggaccagagtggattggcagtgtctatttagttcgatgaccactacaacccg tccctcaaaagtcgcgtcagcatctccgttgacaagcccaagaaccagttctccttaaaagtg acctctgtgactgtcgccgacacggccacatattactgtgcgagacaagcccttgccgagtc ggagccatgaattggttcgacccctggggccagggatctctggtcacagtctcctca<br>SEQ ID NO:29 |
| 26B9-V_H | QILLQESGPGLVKPTETLSLTCSVSGDSISDSSHYWAWIRQPPGKGPEWIGSVYFSSMTHYNP SLKSRVSISVDKPKNQFSLKVTSVTVADTATYYCARQALARVGAMNWFDPWGQGSLVTVSS<br>SEQ ID NO: 30 |
| 26B9-V_L kappa-type | gacatcataatgacccagtctccagactccctgcctgtgtctctgggcgaggggtcaccatc aactgcaagtccagccagagcgtcttttttcacctccagtaataagagttgtttagcttggtat cagcagaagccaggaaagtctcccaaattgctcatttactgggcatcaacccgccaatccggg gtccctgaccgattcagaggcagcgggtctgggacagatttctctctcaccatcaccagtctg caggctgaagatgtggctgtttatttctgtcagcagtgtcagacatcccctccacttt**cggc ggagggaccaggttggagatcaaa<br>SEQ ID NO:31 |

| | |
|---|---|
| 26B9-V_L<br>kappa-type | DIIMTQSPDSLPVSLGEGVTINCKSSQSVFFTSSNKSCLAWYQQKPGKSPKLLIYWASTRQSG VPDRFRGSGSGTDFSLTITSLQAEDVAVYFCQQCQTSPPTFGGGTRLEIK<br>SEQ ID NO:32 |
| 26B9-C_H | gcctccaccaagggcccatcggtcttccccctggcaccctcctccaagagcacctctgggggc acagcggccctgggctgcctggtcaaggactacttccccgaaccggtgacggtgtcgtggaac tcaggcgccctgaccagcggcgtgcacaccttcccggctgtcctacagtcctcaggactctac tccctcagcagcgtggtgaccgtgccctccagcagcttgggcacccagacctacatctgcaac gtgaatcacaagcccagcaacaccaaggtggacaagagagttgagcccaaatcttgtgacaaa actcacacatgcccaccgtgcccagcacctgaactcctggggggaccgtcagtcttcctcttc cccccaaaacccaaggacaccctcatgatctcccggacccctgaggtcacatgcgtggtggtg gacgtgagccacgaagaccctgaggtcaagttcaactggtacgtggacggcgtggaggtgcat aatgccaagacaaagccgcgggaggagcagtacaacagcacgtaccgtgtggtcagcgtcctc accgtcctgcaccaggactggctgaatggcaaggagtacaagtgcaaggtctccaacaaagcc ctcccagcccccatcgagaaaaccatctccaaagccaaagggcagccccgagaaccacaggtg tacaccctgcccccatcccgggaggagatgaccaagaaccaggtcagcctgacctgcctggtc aaaggcttctatcccagcgacatcgccgtggagtgggagagcaatgggcagccggagaacaac tacaagaccacgcctcccgtgctggactccgacggctccttcttcctctatagcaagctcacc gtggacaagagcaggtggcagcaggggaacgtcttctcatgctccgtgatgcatgaggctctg cacaaccactacacgcagaagagcctctccctgtccccgggtaaatga    SEQ ID NO:33 |
| 26B9-C_H | ASTKGPSVFPLAPSSKSTSGGTAALGCLVKDYFPEPVTVSWNSGALTSGVHTFPAVLQSSGLY SLSSVVTVPSSSLGTQTYICNVNHKPSNTKVDKRVEPKSCDKTHTCPPCPAPELLGGPSVFLF PPKPKDTLMISRTPEVTCVVVDVSHEDPEVKFNWYVDGVEVHNAKTKPREEQYNSTYRVVSVL TVLHQDWLNGKEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNVFSCSVMHEAL HNHYTQKSLSLSPGK<br>SEQ ID NO:34 |

| | |
|---|---|
| 26B9-C_L<br>kappa-type | cgaactgtggctgcaccatctgtcttcatcttcccgccatctgatgagcagttgaaatctgga actgcctctgttgtgtgcctgctgaataacttctatcccagagaggccaaagtacagtggaag gtggataacgccctccaatcgggtaactcccaggagagtgtcacagagcaggacagcaaggac agcacctacagcctcagcagcaccctgacgctgagcaaagcagactacgagaaacacaaagtc tacgcctgcgaagtcacccatcagggcctgagctcgcccgtcacaaagagcttcaacaggggagagtgttag<br>SEQ ID NO:35 |
| 26B9-C_L<br>kappa-type | RTVAAPSVFIFPPSDEQLKSGTASVVCLLNNFYPREAKVQWKVDNALQSGNSQESVTEQDSKD STYSLSSTLTLSKADYEKHKVYACEVTHQGLSSPVTKSFNRGEC<br>SEQ ID NO:36 |
| 31B4-V_H | cagatacagctgcaggagtcggggcccaggactggtgaggcccacggagaccctgtccctcact tgtagtgtctctggtgactccatcagtcagagtagtcattactgggcctggattcgccagccc ccaggaaagggaccagaatggattggagtgtctatttttagctcgatgacccactacaaccog tocctcacaagtcgcgtcagcatctccattgacaaggccatgaataagttctccttaaaagtg acctctgtgactgtcgccgacacggccacatattactgtgcgagacaggcccttgcccgagtc ggagccatgaattggttcgacccctggggccagggatctctggtcacagtctcctca<br>SEQ ID NO:37 |
| 31B4-V_H | QIQLQESGPGLVRPTETLSLTCSVSGDSISQSSHYWAWIRQPPGKGPEWIGSVYFSSMTHYNP SLTSRVSISIDKAMNKFSLKVTVTVADTATYYCARQALARVGAMNWFDPWGQGSLVTVSS<br>SEQ ID NO:38 |
| 31B4-V_L<br>kappa-type | gacatcataatgacccagtctccagagtccctgcctgtgtctctgggcgaggggtcaccatc aactgcaagtccagccagagcgtcttttttcacctccagtaataggagttgtttagcttggtat cagcagaagccaggacagtctcccaaattgctcatttactgggcatcaaccgccaatccggg gtccctgaccgattcacaggcagcgggtctgggacagatttctctctcaccatcgccggtctg caggttgaagatgtggctgtttatttctgt**cagcagtgtcacgcatcccctccactttcggc ggcgggaccaggttggagctcaga<br>SEQ ID NO:39 |

| | |
|---|---|
| 31B4-V<sub>L</sub><br><br>kappa-type | DIIMTQSPESLPVSLGEGVTINCKSSQSVFFTSSNRSCLAWYQQKPGQSPKLLIYWASTRQSG<br>VPDRFTGSGSGTDFSLTIAGLQVEDVAVYFCQQCHASPPTFGGGTRLELR<br>SEQ ID NO:40 |
| 31B4-C<sub>H</sub> | gcctccaccaagggcccatcggtcttccccctggcaccctcctccaagagcacctctgggggc<br>acagcggccctgggctgcctggtcaaggactacttccccgaaccggtgacggtgtcgtggaac<br>tcaggcgccctgaccagcggcgtgcacaccttcccggctgtcctacagtcctcaggactctac<br>tccctcagcagcgtggtgaccgtgccctccagcagcttgggcacccagacctacatctgcaac<br>gtgaatcacaagcccagcaacaccaaggtggacaagagagttgagcccaaatcttgtgacaaa<br>actcacacatgcccaccgtgcccagcacctgaactcctggggggaccgtcagtcttcctcttc<br>cccccaaaacccaaggacaccctcatgatctcccggacccctgaggtcacatgcgtggtggtg<br>gacgtgagccacgaagaccctgaggtcaagttcaactggtacgtggacggcgtggaggtgcat<br>aatgccaagacaaagccgcgggaggagcagtacaacagcacgtaccgtgtggtcagcgtcctc<br>accgtcctgcaccaggactggctgaatggcaaggagtacaagtgcaaggtctccaacaaagcc<br>ctcccagcccccatcgagaaaaccatctccaaagccaaagggcagccccgagaaccacaggtg<br>tacaccctgcccccatcccgggaggagatgaccaagaaccaggtcagcctgacctgcctggtc<br>aaaggcttctatcccagcgacatcgccgtggagtgggagagcaatgggcagccggagaacaac<br>tacaagaccacgcctcccgtgctggactccgacggctccttcttcctctatagcaagctcacc<br>gtggacaagagcaggtggcagcaggggaacgtcttctcatgctccgtgatgcatgaggctctg<br>cacaaccactacacgcagaagagcctctccctgtccccgggtaaatga<br>SEQ ID NO:41 |
| 31B4-C<sub>H</sub> | ASTKGPSVFPLAPSSKSTSGGTAALGCLVKDYFPEPVTVSWNSGALTSGVHTFPAVLQSSGLY<br>SLSSVVTVPSSSLGTQTYICNVNHKPSNTKVDKRVEPKSCDKTHTCPPCPAPELLGGPSVFLF<br>PPKPKDTLMISRTPEVTCVVVDVSHEDPEVKFNWYVDGVEVHNAKTKPREEQYNSTYRVVSVL<br>TVLHQDWLNGKEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNVFSCSVMHEAL<br>HNHYTQKSLSLSPGK SEQ ID NO:42 |
| 31B4-C<sub>L</sub><br><br>kappa-type | cgaactgtggctgcaccatctgtcttcatcttcccgccatctgatgagcagttgaaatctgga<br>actgcctctgttgtgtgcctgctgaataacttctatcccagagaggccaaagtacagtggaag<br>gtggataacgccctccaatcgggtaactcccaggagagtgtcacagagcaggacagcaaggac<br>agcacctacagcctcagcagcaccctgacgctgagcaaagcagactacgagaaacacaaagtc<br>tacgcctgcgaagtc*acccatcagggcctgagctcgcccgtcacaaagagcttcaacaggga*<br>*gagtgttag*<br>SEQ ID NO:43 |
| 31B4-C<sub>L</sub><br><br>kappa-type | RTVAAPSVFIFPPSDEQLKSGTASVVCLLNNFYPREAKVQWKVDNALQSGNSQESVTEQDSKD<br>STYSLSSTLTLSKADYEKHKVYACEV*THQGLSSPVTKSFNRGEC*<br>SEQ ID NO:44 |
| 8H1 V<sub>H</sub> | caggtgcagctggtgcagtctggggctgaggtgaagaagcctggggcctcagtgaaggtctcc<br>tgcaaggcttctggacagaccttcaccagtgatgatatcaactgggtgcgacaggcccctgga<br>caggggctagagtggatgggatggaggaacccaacactcaggacacgggctatgcacagaag<br>ttccacggcagactcaccttgaccagcaacagttccataagtacatcctatctggagttgagc<br>ggcctgagatctgaggacacggccgtgtattactgtgcgagagcggggacttcgaccttgacc<br>ggccactacttcgctttggggtctgggggccaggggaccacgtcatcgtctcctca<br>SEQ ID NO:75 |
| 8H1 V<sub>H</sub> | QVQLVQSGAEVKKPGASVKVSCKASGQTFTSDDINWVRQAPGQGLEWMGWRNPNTQDTGYAQK<br>FHGRLTLTSNSSISTSYLELSGLRSEDTAVYYCARAGTSTLTGHYFALGVWGQGTTVIVSS<br>SEQ ID NO:76 |

| 8H1 V_L kappa-type | gacatccagctgacccagtctccatcctccctgtctgcatctgtaggagacagagtcaccatc acttgtcaggcgactcaggatattagcaaatatttaaattggtatcagcagaaaccagggaaa gtccctaaactcctgatctacgaaacatccaatttggaagtagggtcccatcaaggttcagt ggaagtgggtctgggacacattttactctcaccatcagcagcctgcaggctgaagattttgca acatattactgtcaacagtatgagaatttcccgttcactttcggcggagggaccaaggtggag atcaaa<br>SEQ ID NO: 77 |
|---|---|
| 8H1 V_L kappa-type | DIQLTQSPSSLSASVGDRVTITCQATQDISKYLNWYQQKPGKVPKLLIYETSNLEVGVPSRFS GSGSGTHFTLTISSLQAEDFATYYCQQYENFPFTFGGGTKVEIK<br>SEQ ID NO: 78 |
| 8H1 C_H | gcctccaccaagggcccatcggtcttccccctggcacctcctccaagagcacctctggggc acagcggccctgggctgcctggtcaaggactacttccccgaaccggtgacggtgtcgtggaac tcaggcgccctgaccagcggcgtgcacaccttcccggctgtcctacagtcctcaggactctac tccctcagcagcgtggtgaccgtgccctccagcagcttgggcacccagacctacatctgcaac gtgaatcacaagcccagcaacaccaaggtggacaagagagttgagcccaaatcttgtgacaaa actcacacatgcccaccgtgcccagcacctgaactcctggggggaccgtcagtcttcctcttc cccccaaaacccaaggacaccctcatgatctcccggacccctgaggtcacatgcgtggtggtg gacgtgagccacgaagaccctgaggtcaagttcaactggtacgtggacggcgtggaggtgcat aatgccaagacaaagccgcgggaggagcagtacaacagcacgtaccgtgtggtcagcgtcctc accgtcctgcaccaggactggctgaatggcaaggagtacaagtgcaaggtctccaacaaagcc ctcccagcccccatcgagaaaaccatctccaaagccaaaggtcagccccgagaaccacaggtg tacaccctgcccccatcccgggaggagatgaccaagaaccaggtcagcctgacctgcctggtc aaaggcttctatcccagcgacatcgccgtggagtgggagagcaatgggcagccggagaacaac tacaagaccacgcctcccgtgctggactccgacggctccttcttcctctatagcaagctcacc gtggacaagagcaggtggcagcaggggaacgtcttctcatgctccgtgatgcatgaggctctg cacaaccactacacgcagaagagcctctccctgtccccgggtaaa<br>SEQ ID NO:79 |
| 8H1 C_H | ASTKGPSVFPLAPSSKSTSGGTAALGCLVKDYFPEPVTVSWNSGALTSGVHTFPAVLQSSGLY SLSSVVTVPSSSLGTQTYICNVNHKPSNTKVDKRVEPKSCDKTHTCPPCPAPELLGGPSVFLF PPKPKDTLMISRTPEVTCVVVDVSHEDPEVKFNWYVDGVEVHNAKTKPREEQYNSTYRVVSVL TVLHQDWLNGKEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNVFSCSVMHEAL HNHYTQKSLSLSPGK<br>SEQ ID NO: 80 |
| 8H1 C_L kappa-type | cgaactgtggctgcaccatctgtcttcatcttcccgccatctgatgagcagttgaaatctgga actgcctctgttgtgtgcctgctgaataacttctatcccagagaggccaaagtacagtggaag gtggataacgccctccaatcgggtaactcccaggagagtgtcacagagcaggacagcaaggac agcacctacagcctcagcagcaccctgacgctgagcaaagcagactacgagaaacacaaagtc tacgcctgcgaagtcacccatcagggcctgagctcgcccgtcacaaagagcttcaacaggggaa gagtgttag<br>SEQ ID NO: 81 |
| 8H1 C_L kappa-type | RTVAAPSVFIFPPSDEQLKSGTASVVCLLNNFYPREAKVQWKVDNALQSGNSQESVTEQDSKD STYSLSSTLTLSKADYEKHKVYACEVTHQGLSSPVTKSFNRGEC<br>SEQ ID NO: 82 |
| 12H5 V_H | caagtgcaactgatacagtctgggcctgaggtgaagaggcctgggcctcagtgaaggtctcc tgcaaggcgtctgaaaacaccttcgacactcattatattaattgggtgcgacaggcccctgga caagggcttacttggctggatggctgaacccaccactggtaaaacaggctttccacaaaag tttaagggcagagtcattctgaccagcgacacctccctaaatactgcctatatggaagtgagc cgcctgacatctgaggacacggccgtttatttctgtgccagagttttgaagttgtctgatgag tacaactatggtttcgacgtctggggccaagggaccacggtcatcgtctcctca<br>SEQ ID NO:83 |
| 12H5 V_H | QVQLIQSGPEVKRPGASVKVSCKASENTFDTHYINWVRQAPGQGLTWLGWLNPTTGKTGFPQK FKGRVILTSDTSLNTAYMEVSRLTSEDTAVYFCARVLKLSDEYNYGFDVWGQGTTVIVSS<br>SEQ ID NO:84 |

| 12H5 V_L kappa-type | gacatccaggtgacccagtctccatcctccctgtctgcatctattggggacagagtcaccatc acgtgccgggcaagtcagaacattctcaccttataaattggtatcagcacaaaccagggaaa gcccctaaactcctgatctatgctgcatccgttttacaaaatgaagtcccatcaaggttcagt ggcagtggatctgggacagatttcactctcaccatcaccagtctgcaacctgacgattttgga acttactactgtcagcagacttaccttacccctcaatgcagttttggccaggggaccaaggtg gagatcaaa<br>SEQ ID NO: 85 |
|---|---|
| 12H5 V_L kappa-type | DIQVTQSPSSLSASIGDRVTITCRASQNILTFINWYQHKPGKAPKLLIYAASVLQNEVPSRFS GSGSGTDFTLTITSLQPDDFGTYYCQQTYLTPQCSFGQGTKVEIK<br>SEQ ID NO: 86 |
| 12H5 C_H | gcctccaccaagggcccatcggtcttccccctggcaccctcctccaagagcacctctggggc acagcggccctgggctgcctggtcaaggactacttccccgaaccggtgacggtgtcgtggaac tcaggcgccctgaccagcggcgtgcacaccttcccggctgtcctacagtcctcaggactctac tccctcagcagcgtggtgaccgtgccctccagcagcttgggcacccagacctacatctgcaac gtgaatcacaagcccagcaacaccaaggtggacaagaaagttgagcccaaatcttgtgacaaa actcacacatgcccaccgtgcccagcacctgaactcctggggggaccgtcagtcttcctcttc cccccaaaacccaaggacaccctcatgatctcccggacccctgaggtcacatgcgtggtggtg gacgtgagccacgaagaccctgaggtcaagttcaactggtacgtggacggcgtggaggtgcat aatgccaagacaaagccgcgggaggagcagtacaacagcacgtaccgtgtggtcagcgtcctc accgtcctgcaccaggactggctgaatggcaaggagtacaagtgcaaggtctccaacaaagcc ctcccagcccccatcgagaaaaccatctccaaagccaaagggcagccccgagaaccacaggtg tacaccctgcccccatcccgggatgagctgaccaagaaccaggtcagcctgacctgcctggtc aaaggcttctatcccagcgacatcgccgtggagtgggagagcaatgggcagccggagaacaac tacaagaccacgcctcccgtgctggactccgacggctccttcttcctctacagcaagctcacc gtggacaagagcaggtggcagcaggggaacgtcttctcatgctccgtgatgcatgaggctctg cacaaccactacacgcagaagagcctctccctgtctccgggtaaatga<br>SEQ ID NO: 87 |
| 12H5 C_H | ASTKGPSVFPLAPSSKSTSGGTAALGCLVKDYFPEPVTVSWNSGALTSGVHTFPAVLQSSGLY SLSSVVTVPSSSLGTQTYICNVNHKPSNTKVDKKVEPKSCDKTHTCPPCPAPELLGGPSVFLF PPKPKDTLMISRTPEVTCVVVDVSHEDPEVKFNWYVDGVEVHNAKTKPREEQYNSTYRVVSVL TVLHQDWLNGKEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNVFSCSVMHEAL HNHYTQKSLSLSPGK<br>SEQ ID NO: 88 |
| 12H5 C_L kappa-type | cgaactgtggctgcaccatctgtcttcatcttcccgccatctgatgagcagttgaaatctgga actgcctctgttgtgtgcctgctgaataacttctatcccagagaggccaaagtacagtggaag gtggataacgccctccaatcgggtaactcccaggagagtgtcacagagcaggacagcaaggac agcacctacagcctcagcagcaccctgacgctgagcaaagcagactacgagaaacacaaagtc tacgcctgcgaagtcacccatcagggcctgagctcgcccgtcacaaagagcttcaacagggga gagtgttag<br>SEQ ID NO: 89 |
| 12H5 C_L kappa-type | RTVAAPSVFIFPPSDEQLKSGTASVVCLLNNFYPREAKVQWKVDNALQSGNSQESVTEQDSKD STYSLSSTLTLSKADYEKHKVYACEVTHQGLSSPVTKSFNRGEC<br>SEQ ID NO: 90 |
| 50E11 V_H | caggtgcagctggtgcagtctggggcagagatgaagaagcctggggcctcggtgaaggtctcc tgcaaggattttggaggcaccttcagcgtctatggtgtcaactgggtgcgacaggcccctgga caagggcttgagtggatgggggggctcatccctgtcattgggccagctaactacgcacagaag ttccagggcagaatcaccattactgcggacgaatccacgagcacagcctatatggagttgagc agcctgagatttgacgacacggccatttattattgtgtgagagacgacaacgaatatgggc cagggaaccctggtcaccgtctcctcg<br>SEQ ID NO:91 |
| 50E11 V_H | QVQLVQSGAEMKKPGSSVKVSCKDFGGTFSVYGVNWVRQAPGQGLEWMGGLIPVIGPANYAQK FQGRITITADESTSTAYMELSSLRFDDTAIYYCVRDDNEYWGQGTLVTVSS<br>SEQ ID NO:92 |

| | |
|---|---|
| 50E11 V$_L$ kappa-type | gaaatggtgctgacacagtctccagccaccctgtctttgtctccaggagaaagagccaccctc<br>tcctgtagggccagtcagactgttagcaccttcttagcctggtaccaacagaaacctggccag<br>gttcccaggctcctcgtctacgatatctcctccagggccaatggcactccagccaggttcagt<br>ggcggtgggtctgggacagacttcactctcaccatcagcagcctagaacttgaagattttgcg<br>gtttattactgtcagtggcgtagcaactggcctcctcgctcactttcggcggagggaccagg<br>gtggagatcaaa<br>SEQ ID NO: 93 |
| 50E11 V$_L$ kappa-type | EMVLTQSPATLSLSPGERATLSCRASQTVSTFLAWYQQKPGQVPRLLVYDISSRANGTPARFS<br>GGGSGTDFTLTISSLELEDFAVYYCQWRSNWPPSLTFGGGTRVEIK<br>SEQ ID NO: 94 |
| 50E11 C$_H$ | gcctccaccaagggcccatcggtcttccccctggcaccctcctccaagagcacctctggggc<br>acagcggccctgggctgcctggtcaaggactacttccccgaaccggtgacggtgtcgtggaac<br>tcaggcgccctgaccagcggcgtgcacaccttcccggctgtcctacagtcctcaggactctac<br>tccctcagcagcgtggtgaccgtgccctccagcagcttgggcacccagacctacatctgcaac<br>gtgaatcacaagcccagcaacaccaaggtggacaagaaagttgagcccaaatcttgtgacaaa<br>actcacacatgcccaccgtgcccagcacctgaactcctggggggaccgtcagtcttcctcttc<br>cccccaaaacccaaggacaccctcatgatctcccggacccctgaggtcacatgcgtggtggtg<br>gacgtgagccacgaagaccctgaggtcaagttcaactggtacgtggacggcgtggaggtgcat<br>aatgccaagacaaagccgcgggaggagcagtacaacagcacgtaccgtgtggtcagcgtcctc<br>accgtcctgcaccaggactggctgaatggcaaggagtacaagtgcaaggtctccaacaaagcc<br>ctcccagcccccatcgagaaaaccatctccaaagccaaagggcagccccgagaaccacaggtg<br>tacaccctgcccccatcccgggatgagctgaccaagaaccaggtcagcctgacctgcctggtc<br>aaaggcttctatccagcgacatcgccgtggagtgggagagcaatgggcagccggagaacaac<br>tacaagaccacgcctcccgtgctggactccgacggctccttcttcctctacagcaagctcacc<br>gtggacaagagcaggtggcagcaggggaacgtcttctcatgctccgtgatgcatgagggtctg<br>cacaaccactacacgcagaagagcctctccctgtctccgggtaaatga<br>SEQ ID NO: 95 |

| | |
|---|---|
| 50E11 C$_H$ | ASTKGPSVFPLAPSSKSTSGGTAALGCLVKDYFPEPVTVSWNSGALTSGVHTFPAVLQSSGLY<br>SLSSVVTVPSSSLGTQTYICNVNHKPSNTKVDKKVEPKSCDKTHTCPPCPAPELLGGPSVFLF<br>PPKPKDTLMISRTPEVTCVVVDVSHEDPEVKFNWYVDGVEVHNAKTKPREEQYNSTYRVVSVL<br>TVLHQDWLNGKEYKCKVSNKALPAPIEKTISKAKGQPREPQVYTLPPSRDELTKNQVSLTCLV<br>KGFYPSDIAVEWESNGQPENNYKTTPPVLDSDGSFFLYSKLTVDKSRWQQGNVFSCSVMHEGL<br>HNHYTQKSLSLSPGK<br>SEQ ID NO: 96 |
| 50E11 C$_L$ kappa-type | cgaactgtggctgcaccatctgtcttcatcttcccgccatctgatgagcagttgaaatctgga<br>actgcctctgttgtgtgcctgctgaataacttctatcccagagaggccaaagtacagtggaag<br>gtggataacgccctccaatcgggtaactcccaggagagtgtcacagagcaggacagcaaggac<br>agcacctacagcctcagcagcaccctgacgctgagcaaagcagactacgagaaacacaaagtc<br>tacgcctgcgaagtcacccatcagggcctgagctcgcccgtcacaaagagcttcaacaggga<br>gagtgttag<br>SEQ ID NO: 97 |
| 50E11 C$_L$ kappa-type | RTVAAPSVFIFPPSDEQLKSGTASVVCLLNNFYPREAKVQWKVDNALQSGNSQESVTEQDSKD<br>STYSLSSTLTLSKADYEKHKVYACEVTHQGLSSPVTKSFNRGEC<br>SEQ ID NO: 98 |

Underlined, bold nucleotides or amino acids indicate the CDR coding regions in the variable chain sequence. Underlined, italic nucleotides or amino acids indicate sequences which have not been sequenced but obtained from database. In the constant chains, such regions are aligned with and tuned in accordance with the pertinent human germ line variable region sequences in the database; see, e.g., Vbase (http://vbase.mrc-cpe.cam.ac.uk) hosted by the MRC Centre for Protein Engineering (Cambridge, UK). --